US008410336B2

(12) United States Patent
Lutfiyya

(10) Patent No.: US 8,410,336 B2

(45) Date of Patent: Apr. 2, 2013

(54) TRANSGENIC PLANTS WITH ENHANCED AGRONOMIC TRAITS

(75) Inventor: Linda L. Lutfiyya, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/299,402

(22) Filed: Nov. 18, 2011

(65) Prior Publication Data

US 2012/0066787 A1 Mar. 15, 2012

Related U.S. Application Data

(63) Continuation of application No. 12/316,385, filed on Dec. 11, 2008, now abandoned.

(60) Provisional application No. 61/013,179, filed on Dec. 12, 2007.

(51) Int. Cl.

| | |
|---|---|
| ***A01H 5/00*** | (2006.01) |
| ***A01H 1/00*** | (2006.01) |
| ***A01H 5/10*** | (2006.01) |
| ***C12N 15/82*** | (2006.01) |

(52) U.S. Cl. ........ 800/284; 800/295; 800/266; 435/468; 435/419

(58) Field of Classification Search ........................ None
See application file for complete search history.

(56) References Cited

U.S. PATENT DOCUMENTS

| | | | | |
|---|---|---|---|---|
| 6,781,034 | B2 | 8/2004 | Palatnik et al. | |
| 2006/0179511 | A1 * | 8/2006 | Chomet et al. ................ | 800/278 |
| 2009/0165165 | A1 | 6/2009 | Madappa et al. | |

OTHER PUBLICATIONS

Friedberg (Brief. Bioinformatics (2006) 7: 225-242).*

Guo et al (PNAS 2004 (101)25,9205-9210).*

"U.S. Appl. No. 12/316,385, Non Final Office Action mailed Aug. 25, 2011", 13 pgs.

"U.S. Appl. No. 12/316,385, Response filed Jul. 22, 2011 to Restriction Requirement mailed May 5, 2011", 7 pgs.

"U.S. Appl. No. 12/316,385, Restriction Requirement mailed May 5, 2011", 9 pgs.

Fillat, Maria F, et al., "Isolation and overexpression in *Escherichia coli* of the flavodoxin gene from *Anabaena* PCC 7119", Biochem J. 280, (1991), 187-191.

Guo, et al., "Protein Tolerance to Random Amino Acid Change", PNAS, 101(25), 101: 9205-9210, (Jun. 2004), 9205-9210.

Avonce, Nelson, et al., "Additional File 2: alignment of about 60 TPS domains spanning over about 420 amino acid residues", Insights on the evolution of trehalose biosynthesis, BMC Ecol. Biol., 6:109 (2006), (Dec. 19, 2006), 4 pgs.

Avonce, Nelson, et al., "Additional File 4: alignment of about 60 TPP domains spanning over about 230 amino acid residues", Insights on the evolution of trehalose biosynthesis; BMC Ecol. Biol., 6:109 (2006), (Dec. 19, 2006), 3 pgs.

Avonce, Nelson, et al., "Insights on the evolution of trehalose biosynthesis", BMC Ecol. Biol., 6:109 (2006), (Dec. 19, 2006), 15 pgs.

Bouche, N., et al., "*Arabidopsis* Gene Knockout: Phenotypes Wanted", Curr Opin Plant Biol. Apr. 2001;4(2):111-7 (abstract only), (Apr. 4, 2001), 1 pg.

Eastmond, P. J., et al., "Abstract: Trehalose-6-phosphate synthase 1, which catalyses the first step in trehalose synthesis, is essential for *Arabidopsis* embryo maturation", Plant J., 29:225 (2002), 1 pg.

Glinski, Mirko, et al., "Differential Multisite Phosphorylation of the Trehalose-6-phosphate Synthase Gene Family in *Arabidopsis thaliana*", Mol. & Cell. Proteomics, 4:1614 (2005), 1614-1625.

Greene, Elizabeth A., et al., "Spectrum of Chemically Induced Mutations From a Large-Scale Reverse-Genetic Screen in *Arabidopsis*", Genetics 164: 731-740 (Jun. 2003), 731-740.

Lu, C., et al., "A High-Throughput Screen for Genes from Castor that Boost Hydroxy Fatty Acid Accumulation in Seed Oils of Transgenic *Arabidoopsis*", Plant J. Mar. 2006;45(5):847-56 (abstract only), 1 pg.

Rama Devi, S., et al., "A Novel High-Throughput Genetic Screen for Stress-Responsive Mutants of *Arabidopsis thaliana* Reveals New Loci Involving Stress Responses", Plant J. Aug. 2006;47(4):652-63 (abstract only), 1 pg.

Skandalis, A., et al., "Enzymatic Properties of Rat DNA Polymerase Beta Mutants Obtained by Randomized Mutagenesis", Nucleic Acids Res. Jun. 1, 2001;29(11):2418-26 (abstract only), 1 pg.

Stoop, A. A., et al., "High-Density Mutagenesis by Combined DNA Shuffling and Phage Display to Assign Essential Amino Acid Residues in Protein-Protein Interactions: Application to Study Structure-Function of Plasminogen Activation Inhibitor 1 (PAI-I)", J Mol Biol. Sep. 1, 2000: 301(5):1135-47 (abstract only), 1 pg.

Takahashi, Y., et al., "A High-Throughput Screen of Cell-Death-Inducing Factors in *Nicotiana bentharniana* Identifies a Novel MAPKK that Mediates INF1-induced Cell Death Signaling and non-Host Resistance to *Pseudomonas cichorii*", Plant J. Mar. 2007;49(6):1030-40 (abstract only), 1 pg.

Vogel, Guido, et al., "Trehalose metabolism in *Arabidopsis*: occurrence of trehalose and molecular cloning and characterization of trehalose-6-phosphate synthase homologues", J. Exp. Botany, 52:1817, (Sep. 2001), 1817-1826.

Yeh, T. C., et al., "A Dual Role for the Kinase-like Domain of the Tyrosine Kinase Tyk2 in Interferon-alpha Signaling", Proc Nati Acad Sci USA Aug. 1, 2000;97(16):8991-6 (abstract only), 1 pg.

*Primary Examiner* — Anne Kubelik
*Assistant Examiner* — Lee A Visone
(74) *Attorney, Agent, or Firm* — Schwegman Lundberg & Woessner, P.A.

(57) ABSTRACT

This invention provides transgenic plant cells with recombinant DNA for expression of proteins that are useful for imparting enhanced agronomic trait(s) to transgenic crop plants. This invention also provides transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein and enhanced seed oil. Also disclosed are methods for manufacturing transgenic seed and plants with enhanced traits.

15 Claims, 4 Drawing Sheets

TRANSGENIC PLANTS WITH ENHANCED AGRONOMIC TRAITS

CROSS REFERENCE TO RELATED APPLICATIONS

This application is a continuation under 35 U.S.C. §120 of U.S. application Ser. No. 12/316,385 filed on Dec. 11, 2008 (pending), which is incorporated by reference in its entirety including sequence listing and Pfam tables. Application Ser. No. 12/316,385 claims benefit under 35 USC §119(e) of U.S. provisional application Ser. No. 61/013,179, filed Dec. 12, 2007, which is also incorporated herein by reference in its entirety.

INCORPORATION OF SEQUENCE LISTING

A computer readable form (CRF) of the sequence listing file named "55579C_seqListing.txt", which is 5,484,279 bytes (measured in MS-WINDOWS), was created on Nov. 15, 2011, filed herewith, and are incorporated herein by reference in its entirety.

INCORPORATION Of LARGE TABLE

A large table containing a folder "pfamdir" on CD-Rs were previously submitted in the parent U.S. application Ser. No. 12/316,385 on Dec. 11, 2008. The content of which are incorporated herein by reference in their entirety. Folder "pfamdir" contains 10 Pfam Hidden Markov Models. The CD-Rs were created on Dec. 8, 2008, having a total size of 864,256 bytes (measured in MS-WINDOWS).

FIELD OF THE INVENTION

Disclosed herein are recombinant DNA useful for providing enhanced traits to transgenic plants, seeds, pollen, plant cells and plant nuclei of such transgenic plants, methods of making and using such recombinant DNA, plants, seeds, pollen, plant cells and plant nuclei. Also disclosed are methods of producing hybrid corn seed comprising such recombinant DNA.

SUMMARY OF THE INVENTION

An aspect of this invention provides recombinant DNA constructs comprising polynucleotides characterized by an encoded protein having amino acids representing a protein family domain module as described in Table 10. Another aspect of this invention provides recombinant DNA constructs comprising polynucleotides characterized by an encoded protein with an amino acid sequence that is at least 90% identical to a corresponding consensus sequence defined in table 8. Yet another aspect of this invention provides recombinant DNA constructs comprising polynucleotides characterized by reference to SEQ ID NO:1-10 and the cognate proteins with amino acid sequences having reference to SEQ ID NO:11-20. The recombinant DNA constructs are useful for providing enhanced traits when stably integrated into the chromosomes and expressed in the nuclei of transgenic plants cells. In most aspects of the invention the recombinant DNA constructs, when expressed in a plant cell, provide for expression of cognate proteins. In particular aspects of the invention the recombinant DNA constructs for expressing cognate proteins are characterized by cognate amino acid sequence that have at least 95% identity over at least 95% of the length of a reference sequence in the group of SEQ ID NOs: 12-16, and 20 when the amino acid sequence is aligned to the reference sequence. In particularly specific embodiments of the invention, the recombinant DNA constructs comprise polynucleotide stacks characterized by cognate proteins having amino acid sequences that have at least 95% identity over at least 95% of the length of reference sequences 13-14 when the amino acid sequences are aligned to the reference sequences. In some aspects of the invention, i.e. the recombinant DNA constructs are characterized as being constructed with sense-oriented and anti-sense-oriented polynucleotides from SEQ ID NOs: 1, and 7-9 which, when expressed in a plant cell, provide for the suppression of cognate proteins having amino acid sequences that have at least 95% identity over at least 95% of the length of a reference sequence in the group consisting of SEQ ID NOs: 11 and 17-19.

In practical aspects of this invention the recombinant DNA constructs of the invention are stably integrated into the chromosome of a plant cell nucleus.

This invention also provides transgenic plant cells comprising the stably integrated recombinant DNA constructs of the invention, transgenic plants and seeds comprising a plurality of such transgenic plant cells and transgenic pollen of such plants. Such transgenic plants are selected from a population of transgenic plants regenerated from plant cells transformed with recombinant DNA constructs by screening transgenic plants for an enhanced trait as compared to control plants. The enhanced trait is one or more of enhanced water use efficiency, enhanced cold tolerance, increased yield, enhanced nitrogen use efficiency, enhanced seed protein and enhanced seed oil.

In another aspect of the invention the plant cells, plants, seeds, and pollen further comprise DNA expressing a protein that provides tolerance from exposure to an herbicide applied at levels that are lethal to a wild type plant cell.

This invention also provides methods for manufacturing non-natural, transgenic seed that can be used to produce a crop of transgenic plants with an enhanced trait resulting from expression of a stably-integrated recombinant DNA construct. More specifically, the method comprises (a) screening a population of plants for an enhanced trait and a recombinant DNA construct, where individual plants in the population can exhibit the trait at a level less than, essentially the same as or greater than the level that the trait is exhibited in control plants, (b) selecting from the population one or more plants that exhibit the trait at a level greater than the level that said trait is exhibited in control plants, (c) collecting seed from a selected plant, (d) verifying that the recombinant DNA is stably integrated in said selected plants, (e) analyzing tissue of a selected plant to determine the production or suppression of a protein having the function of a protein encoded by nucleotides in a sequence of one of SEQ ID NOs:1-10. In one aspect of the invention, the plants in the population further comprise DNA expressing a protein that provides tolerance to exposure to a herbicide applied at levels that are lethal to wild type plant cells and the selecting is affected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, canola, alfalfa, wheat, rice, sugarcane or sugar beet seed.

Another aspect of the invention provides a method of producing hybrid corn seed comprising acquiring hybrid corn seed from a herbicide tolerant corn plant which also has stably-integrated, recombinant DNA construct comprising a promoter that is (a) functional in plant cells and (b) is operably linked to DNA that encodes or suppresses a protein having the function of a protein encoded by nucleotides in a sequence of one of SEQ ID NOs:1-10. The methods further comprise producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising plant cells of the invention by using an immunoreactive antibody to detect the presence or absence of protein expressed or suppressed by recombinant DNA in seed or plant tissue. Yet another aspect of the invention provides anti-counterfeit milled seed having, as an indication of origin, plant cells of this invention.

Still other aspects of this invention relate to transgenic plants with enhanced water use efficiency or enhanced nitrogen use efficiency. For instance, this invention provides methods of growing a corn, cotton, soybean, or canola crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton, soybean or canola crop without added nitrogen fertilizer comprising planting seed having plant cells of the invention which are selected for enhanced nitrogen use efficiency.

Another aspect of the invention provides a mixture comprising plants cells and an antibody to a protein produced in the cells where the protein has an amino acid sequence that has at least 95% identity over at least 95% of the length of a reference sequence selected from the group consisting of SEQ ID NO: 11-20 when the sequence is aligned to the reference sequence.

DETAILED DESCRIPTION OF THE INVENTION

Figure 1:
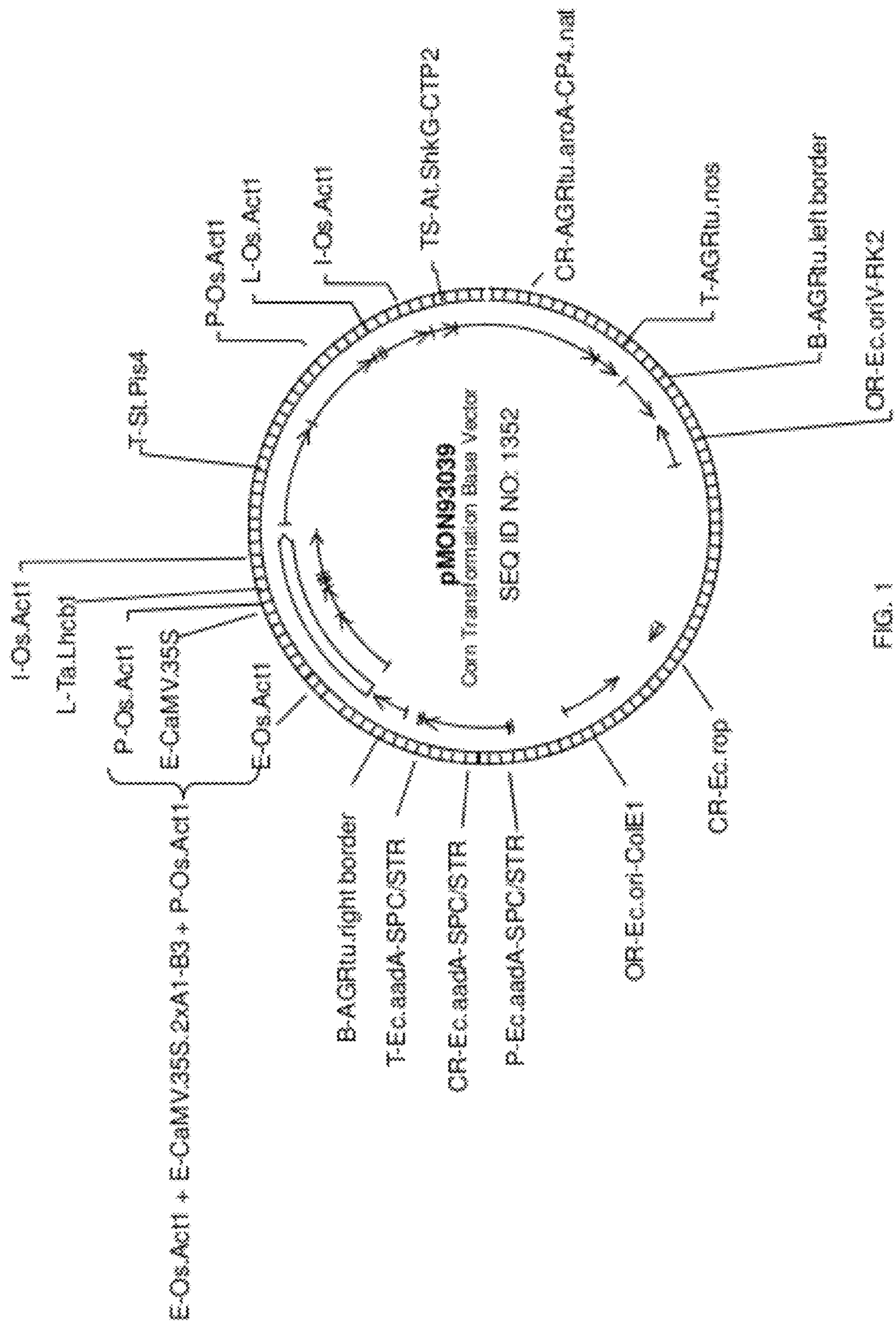
FIGS. 1-4 are plasmid maps.

In the attached sequence listing:

SEQ ID NO:1-10 are nucleotide sequences of the coding strand of DNA for "genes" used in the recombinant DNA imparting an enhanced trait in plant cells, i.e. each represents a coding sequence for a protein;

SEQ ID NO: 11-20 are amino acid sequences of the cognate protein of the "genes" with nucleotide coding sequences 1-10;

SEQ ID NO: 21-1351 are amino acid sequences of homologous proteins;

SEQ ID NO: 1352 is a nucleotide sequence of a base plasmid vector useful for corn transformation;

SEQ ID NO: 1353 is a nucleotide sequence of a base plasmid vector useful for soybean and canola transformation;

SEQ ID NO: 1354 is a nucleotide sequence of a base plasmid vector useful for cotton transformation;

SEQ ID NO: 1355 is a nucleotide sequence of a base plasmid vector useful for co-transformation to produce gene stacks in corn;

SEQ ID NO: 1356-1358 are consensus sequences. Table 8 lists the protein SEQ ID NOs and their corresponding consensus SEQ ID NOs.

As used herein a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. With reference to homologous genes, homologs include orthologs, i.e. genes expressed in different species that evolved from a common ancestral genes by speciation and encode proteins retain the same function, but do not include paralogs, i.e. genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have at least 60% identity, more preferably about 65% or higher, more preferably about 70% or higher, more preferably at least 75%, more preferably at least 80%, more preferably at least 85%, and even more preferably at least 90% identity over the full length of a protein identified as being associated with imparting an enhanced trait when expressed in plant cells. In one aspect of the invention homolog proteins have an amino acid sequence that has at least 90% identity to a consensus amino acid sequence of proteins and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. Because a protein hit with the best E-value for a particular organism may not necessarily be an ortholog, i.e. have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

"Percent identity" describes the extent to which the sequences of DNA or protein segments are invariant throughout a window of alignment of sequences, for example nucleotide sequences or amino acid sequences. An "identity fraction" for a sequence aligned with a reference sequence is the number of identical components which are shared by the sequences, divided by the length of the alignment not including gaps introduced by the alignment algorithm. "Percent identity" ("% identity") is the identity fraction times 100. Percent identity is calculated over the aligned length preferably using a local alignment algorithm, such as BLASTp. As used herein, sequences are "aligned" when the alignment produced by BLASTp has a minimal e-value.

"Pfam" is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

Protein domains are identified by querying the amino acid sequence of a protein against Hidden Markov Models which characterize protein family domains ("Pfam domains") using HMMER software, which is available from the Pfam Consortium. The HMMER software is also disclosed in patent application publication US 2008/0148432 A1 incorporated herein by reference. A protein domain meeting the gathering cutoff for the alignment of a particular Pfam domain is considered to contain the Pfam domain.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by candidate DNA against the Hidden Markov Models which characterizes the Pfam domains using HMMER software. Candidate proteins meeting the same Pfam domain module are in the protein family and have cognate DNA that is useful in constructing recombinant DNA for the use in the plant cells of this invention. Hidden Markov Model databases for use with HMMER software in identifying DNA expressing protein with a common Pfam domain module for recombinant DNA in the plant cells of this invention are included in the large table incorporated into this application.

The HMMER software and Pfam databases (version 19.0) were used to identify known domains in the proteins corresponding to amino acid sequence of SEQ ID NO: 11 through SEQ ID NO: 16 and SEQ ID NO: 20. All DNA encoding proteins that have scores higher than the gathering cutoff disclosed in Table 11 by Pfam analysis disclosed herein can be used in recombinant DNA of the plant cells of this invention, e.g. for selecting transgenic plants having enhanced agronomic traits. The relevant Pfams modules for use in this invention, as more specifically disclosed below, are Cu-oxidase_3::Cu-oxidase::Cu-oxidase_2, Flavodoxin_1, Glyco_transf_20::Trehalose_PPase, Aminotran_1_2, and B3::Auxin_resp::AUX_IAA, for which the databases are included in the appended computer listing.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a recombinant DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein a "control plant" means a plant that does not contain the recombinant DNA that imparts an enhanced trait. A control plant is used to identify and select a transgenic plant that has an enhanced trait. A suitable control plant can be a non-transgenic plant of the parental line used to generate a transgenic plant, i.e. devoid of recombinant DNA. A suitable control plant may in some cases be a progeny of a hemizygous transgenic plant line that does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tons per acre, or kilo per hectare. For example, corn yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as protein and starch, oil components as may be manifest by an alterations in the ratios of seed components.

Recombinant DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164,316 and 5,322,938. Useful promoters derived from plant genes are found in U.S. Pat. No. 5,641,876 which discloses a rice actin promoter, U.S. Pat. No. 7,151,204 which discloses a maize chloroplast aldolase promoter and a maize aldolase (FDA) promoter, and US Patent Application Publication 2003/0131377 A1 which discloses a maize nicotianamine synthase promoter. These and numerous other promoters that function in plant cells are known to those skilled in the art and available for use in recombinant polynucleotides of the present invention to provide for expression of desired genes in transgenic plant cells.

Furthermore, the promoters may be altered to contain multiple "enhancer sequences" to assist in elevating gene expression. Such enhancers are known in the art. By including an enhancer sequence with such constructs, the expression of the selected protein may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene. See also US Patent Application Publication 2002/0192813A1 which discloses 5', 3' and intron elements useful in the design of effective plant expression vectors.

In other aspects of the invention, sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252), zein Z27 as disclosed by Russell et al. (1997) *Transgenic Res.* 6(2):157-166), globulin 1 as disclosed by Belanger et al (1991) *Genetics* 129:863-872), glutelin 1 as disclosed by Russell (1997) supra), and peroxiredoxin antioxidant (Per1) as disclosed by Stacy et al. (1996) *Plant Mol Biol.* 31(6):1205-1216.

Recombinant DNA constructs useful in this invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in US Patent Application Publication 2002/0192813

A1; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. No. 5,188,642 and U.S. Pat. No. 5,728,925. For description of the transit peptide region of an *Arabidopsis* EPSPS gene useful in the present invention, see Klee, H. J. et al (*MGG* (1987) 210:437-442).

Recombinant DNA constructs for gene suppression can be designed for any of a number the well-known methods for suppressing transcription of a gene, the accumulation of the mRNA corresponding to that gene or preventing translation of the transcript into protein. Posttranscriptional gene suppression can be practically effected by transcription of RNA that forms double-stranded RNA (dsRNA) having homology to mRNA produced from a gene targeted for suppression.

Gene suppression can also be achieved by insertion mutations created by transposable elements may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Transgenic plants may comprise a stack of one or more polynucleotides disclosed herein resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene, and co-transformation of genes into a single plant cell. Co-transformation of genes can be carried out using single transformation vectors comprising multiple genes or genes carried separately on multiple vectors.

Transgenic plants comprising or derived from plant cells of this invention transformed with recombinant DNA can be further enhanced with stacked traits, e.g. a crop plant having an enhanced trait resulting from expression of DNA disclosed herein in combination with herbicide and/or pest resistance traits. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in US Patent Application Publication 2003/0083480 A1 also for imparting glyphosate tolerance; dicamba monooxygenase disclosed in US Patent Application Publication 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in US Patent Application Publication 2003/010609 A1 for imparting N-amino methyl phosphonic acid tolerance; polynucleotide molecules disclosed in U.S. Pat. No. 6,107,549 for impartinig pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and US Patent Application Publication 2002/0112260. Molecules and methods for imparting insect/nematode/virus resistance are disclosed in U.S. Pat. Nos. 5,250,515; 5,880,275; 6,506,599; 5,986,175 and US Patent Application Publication 2003/0150017 A1.

Plant Cell Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. Nos. 5,015,580 (soybean); 5,550,318 (corn); 5,538,880 (corn); 5,914,451 (soybean); 6,160,208 (corn); 6,399,861 (corn); 6,153,812 (wheat) and 6,365,807 (rice) and *Agrobacterium*-mediated transformation is described in U.S. Pat. Nos. 5,159,135 (cotton); 5,824,877 (soybean); 5,463,174 (canola); 5,591,616 (corn); 5,846,797 (cotton); 6,384,301 (soybean), 7,026,528 (wheat) and 6,329,571 (rice), US Patent Application Publication 2004/0087030 A1 (cotton), and US Patent Application Publication 2001/0042257 A1 (sugar beet), all of which are incorporated herein by reference for enabling the production of transgenic plants. Transformation of plant material is practiced in tissue culture on a nutrient media, i.e. a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line In the practice of transformation DNA is typically introduced into only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or a herbicide. Any of the herbicides to which plants of this invention may be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (val), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047. Markers which provide an ability to visually screen transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from transgenic plant cells having a transgenic nucleus of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Table 1 provides a list of protein encoding DNA ("genes") that are useful as recombinant DNA for production of transgenic plants with enhanced agronomic trait, the elements of Table 1 are described by reference to:

"PEP SEQ ID NO" identifies an amino acid sequence from SEQ ID NO: 11 to 20.

"NUC SEQ ID NO" identifies a DNA sequence from SEQ ID NO:1 to 10.

"Gene ID" refers to an arbitrary identifier.

"Gene Name" denotes a common name for protein encoded by the recombinant DNA.

"Annotation" refers to a description of the top hit protein obtained from an amino acid sequence query of each PEP SEQ ID NO to GENBANK database of the National Center for Biotechnology Information (ncbi).

TABLE 1

| NUC SEQ ID NO | PEP SEQ ID NO | Gene ID | Gene Name | Annotation |
|---|---|---|---|---|
| 1 | 11 | Mnom000034 | Corn ZmLac | gb\|AAX83113.1\| laccase 1 [*Zea mays*] |
| 2 | 12 | Mnom000037 | *Anabaena* FLD | gb\|AAB20462.1\| flavodoxin [*Anabaena*] |
| 3 | 13 | Mnom000048 | Corn TPS1 | gb\|EAY98715.1\| hypothetical protein OsI_019948 [*Oryza sativa* (*indica* cultivar-group)] |
| 4 | 14 | Mnom000049 | Corn TPP1 | gb\|EAY75823.1\| hypothetical protein OsI_003670 [*Oryza sativa* (*indica* cultivar-group)] |
| 5 | 15 | Mnom000067 | *Lycopersicon* AlaT | gb\|AAZ43369.1\| AlaT1 [*Vitis vinifera*] |
| 6 | 16 | Mnom000068 | *Lycopersicon* AlaT | gb\|AAZ43369.1\| AlaT1 [*Vitis vinifera*] |

TABLE 1-continued

| NUC SEQ ID NO | PEP SEQ ID NO | Gene ID | Gene Name | Annotation |
|---|---|---|---|---|
| 7 | 17 | Mnom000090 | Corn ZmGS3 | gb\|ABC84855.1\| grain length and weight protein [*Oryza sativa* (*indica* cultivar-group)] |
| 8 | 18 | Mnom000091 | Corn ZmGS3 | gb\|ABC84855.1\| grain length and weight protein [*Oryza sativa* (*indica* cultivar-group)] |
| 9 | 19 | Mnom000092 | Corn ZmBB | gb\|EAZ25768.1\| hypothetical protein OsJ_009251 [*Oryza sativa* (*japonica* cultivar-group)] |
| 10 | 20 | Mnom000095 | Corn OSJNBa0064D 20.11 Protein | ref\|NP_001052879.1\| Os04g0442000 [*Oryza sativa* (*japonica* cultivar-group)] [Mendel G471-like ner] |

Selection Methods for Transgenic Plants with Enhanced Agronomic Trait

Within a population of transgenic plants each regenerated from a plant cell having a nucleus with recombinant DNA many plants that survive to fertile transgenic plants that produce seeds and progeny plants will not exhibit an enhanced agronomic trait. Selection from the population is necessary to identify one or more transgenic plant cells having a transgenic nucleus that can provide plants with the enhanced trait. Transgenic plants having enhanced traits are selected from populations of plants regenerated or derived from plant cells transformed as described herein by evaluating the plants in a variety of assays to detect an enhanced trait, e.g. enhanced water use efficiency, enhanced cold tolerance, increased yield, enhanced nitrogen use efficiency, enhanced seed protein and enhanced seed oil. These assays also may take many forms including, but not limited to, direct screening for the trait in a greenhouse or field trial or by screening for a surrogate trait. Such analyses can be directed to detecting changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy, green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates useful screening assays for corn traits using hybrid corn plants. The assays can be readily adapted for screening other plants such as canola, cotton and soybean either as hybrids or inbreds.

Transgenic corn plants having nitrogen use efficiency are identified by screening in fields with three levels of nitrogen (N) fertilizer being applied, e.g. low level (0 N), medium level (80 lb/ac) and high level (180 lb/ac). Plants with enhanced nitrogen use efficiency provide higher yield as compared to control plants.

Transgenic corn plants having enhanced yield are identified by screening using progeny of the transgenic plants over multiple locations with plants grown under optimal production management practices and maximum weed and pest control. A useful target for improved yield is a 5% to 10% increase in yield as compared to yield produced by plants grown from seed for a control plant. Selection methods may be applied in multiple and diverse geographic locations, for example up to 16 or more locations, over one or more planting seasons, for example at least two planting seasons, to statistically distinguish yield improvement from natural environmental effects.

Transgenic corn plants having enhanced water use efficiency are identified by screening plants in an assay where water is withheld for a period to induce stress followed by watering to revive the plants. For example, a useful selection process imposes 3 drought/re-water cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

Transgenic corn plants having enhanced cold tolerance are identified by screening plants in a cold germination assay and/or a cold tolerance field trial. In a cold germination assay trays of transgenic and control seeds are placed in a growth chamber at 9.7° C. for 24 days (no light). Seeds having higher germination rates as compared to the control are identified as having enhanced cold tolerance. In a cold tolerance field trial plants with enhanced cold tolerance are identified from field planting at an earlier date than conventional Spring planting for the field location. For example, seeds are planted into the ground around two weeks before local farmers begin to plant corn so that a significant cold stress is exerted onto the crop, named as cold treatment. Seeds also are planted under local optimal planting conditions such that the crop has little or no exposure to cold condition, named as normal treatment. At each location, seeds are planted under both cold and normal conditions preferably with multiple repetitions per treatment.

Transgenic corn plants having seeds with increased protein and/or oil levels are identified by analyzing progeny seed for protein and/or oil. Near-infrared transmittance spectrometry is a non-destructive, high-throughput method that is useful to determine the composition of a bulk seed sample for properties listed in table 2.

TABLE 2

| Typical sample(s): | Whole grain corn and soybean seeds |
|---|---|
| Typical analytical range: | Corn-moisture 5-15%, oil 5-20%, protein 5-30%, starch 50-75%, and density 1.0-1.3%. Soybean-moisture 5-15%, oil 15-25%, and protein 35-50%. |

Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, wheat, rice, sugarcane, and sugar beet plants. In many cases the invention is applied to corn plants that are inherently resistant to disease from the Mal de Rio Cuarto virus or the *Puccina sorghi* fungus or both.

The following examples are included to demonstrate aspects of the invention, those of skill in the art should, in light of the present disclosure, appreciate that many changes can be made in the specific aspects which are disclosed and still obtain a like or similar results without departing from the spirit and scope of the invention.

EXAMPLE 1

Plant Expression Constructs

This example illustrates the construction of plasmids for transferring recombinant DNA into a plant cell nucleus that can be regenerated into transgenic plants.

A. Plant Expression Constructs for Corn Transformation

A base corn transformation vector pMON93039, as set forth in SEQ ID NO:1352, illustrated in Table 3 and FIG. 1, is fabricated for use in preparing recombinant DNA for *Agrobacterium*-mediated transformation into corn tissue.

TABLE 3

| Function | Name | Annotation | Coordinates of SEQ ID NO: 1352 |
|---|---|---|---|
| *Agrobacterium* T-DNA transfer | B-AGRtu.right border | Agro right border sequence, essential for transfer of T-DNA. | 11364-11720 |
| Gene of interest expression cassette | E-Os.Act1 | Upstream promoter region of the rice actin 1 gene | 19-775 |
| | E-CaMV.35S.2xA1-B3 | Duplicated35S A1-B3 domain without TATA box | 788-1120 |
| | P-Os.Act1 | Promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | First intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | First exon of the rice actin 1 gene | 3671-3750 |
| | I-Os.Act1 | First intron and flanking UTR exon sequences from the rice actin 1 gene | 3751-4228 |
| | TS-At.ShkG-CTP2 | Transit peptide region of *Arabidopsis* EPSPS | 4238-4465 |
| | CR-AGRtu.aroA-CP4.nat | Coding region for bacterial strain CP4 native aroA gene. | 4466-5833 |
| | T-AGRtu.nos | A 3' non-translated region of the nopaline synthase gene of *Agrobacterium tumefaciens* Ti plasmid which functions to direct polyadenylation of the mRNA. | 5849-6101 |
| *Agrobacterium* T-DNA transfer | B-AGRtu.left border | Agro left border sequence, essential for transfer of T-DNA. | 6168-6609 |
| Maintenance in *E. coli* | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the *E. coli* plasmid ColE1. | 9220-9808 |
| | P-Ec.aadA-SPC/STR | Promoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of *E. coli*. | 11170-11227 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the intron element (coordinates 1287-1766) and the polyadenylation element (coordinates 1838-2780).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein. In the embodiments of this invention the proteins that are suppressed are ZmLac, ZmGS3, and ZmBB.

B. Plant Expression Constructs for Soy and Canola Transformation

Figure 2:
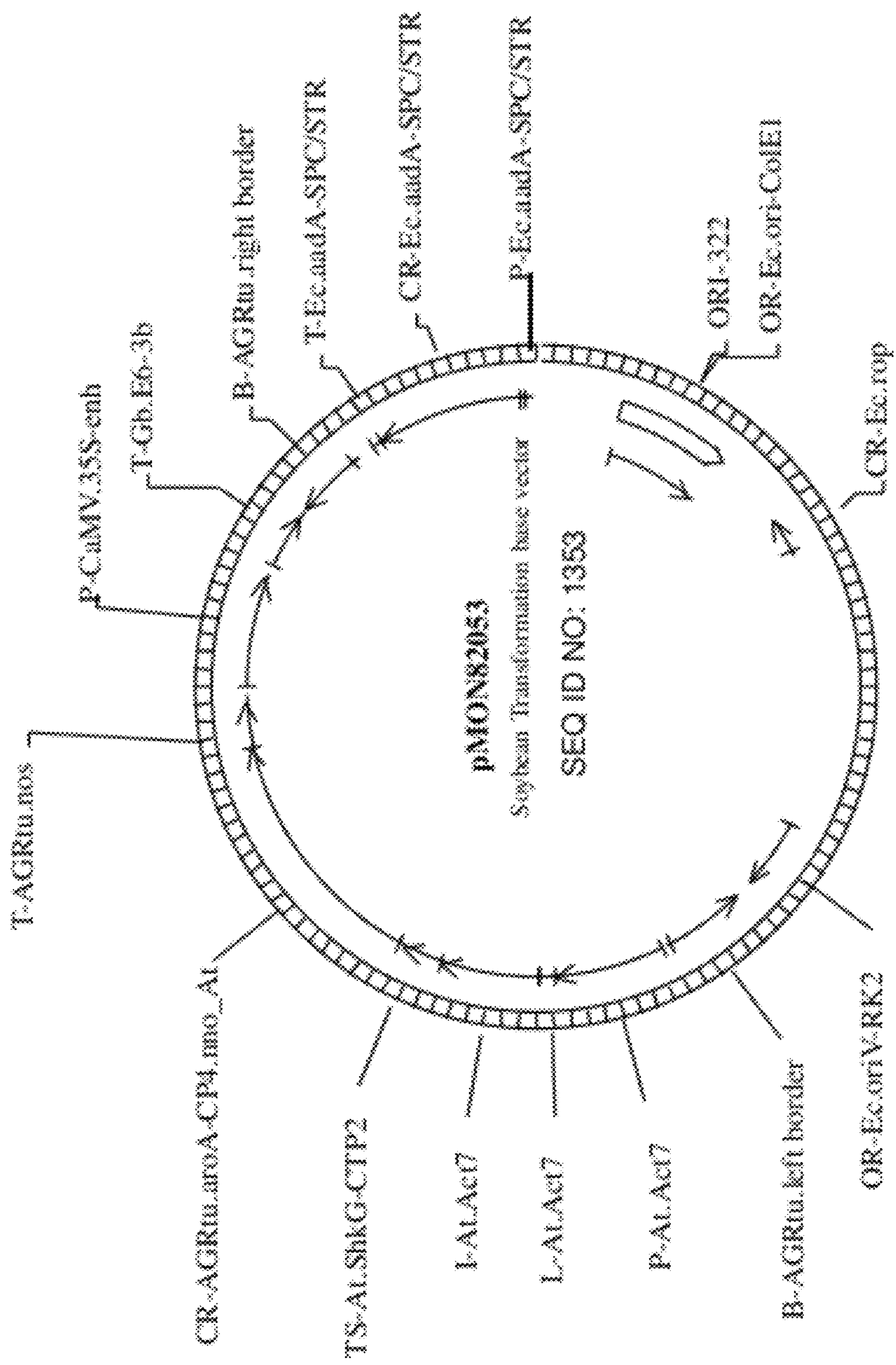

Vectors for use in transformation of soybean and canola tissue are prepared having the elements of expression vector pMON82053 (SEQ ID NO: 1353) as shown in Table 4 below and FIG. 2.

TABLE 4

| Function | Name | Annotation | Coordinates of SEQ ID NO: 1353 |
|---|---|---|---|
| *Agrobacterium* T-DNA transfer | B-AGRtu.left border | Agro left border sequence, essential for transfer of T-DNA. | 6144-6585 |
| Plant selectable marker expression cassette | P-At.Act7 | Promoter from the *Arabidopsis* actin 7 gene | 6624-7861 |
| | L-At.Act7 | 5'UTR of *Arabidopsis* Act7 gene | |
| | I-At.Act7 | Intron from the *Arabidopsis* actin7 gene | |
| | TS-At.ShkG-CTP2 | Transit peptide region of *Arabidopsis* EPSPS | 7864-8091 |
| | CR-AGRtu.aroA-CP4.nno_At | Synthetic CP4 coding region with dicot preferred codon usage. | 8092-9459 |
| | T-AGRtu.nos | A 3' non-translated region of the nopaline synthase gene of *Agrobacterium tumefaciens* Ti plasmid which functions to direct polyadenylation of the mRNA. | 9466-9718 |
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton. | 688-1002 |
| *Agrobacterium* T-DNA transfer | B-AGRtu.right border | Agro right border sequence, essential for transfer of T-DNA. | 1033-1389 |
| Maintenance in *E. coli* | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the *E. coli* plasmid ColE1. | 2945-3533 |
| | P-Ec.aadA-SPC/STR | Promoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of *E. coli*. | 1526-1583 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the promoter element (coordinates 1-613) and the polyadenylation element (coordinates 688-1002).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein. In the embodiments of this invention the proteins that are suppressed are ZmLac, ZmGS3, and ZmBB.

C. Cotton Transformation Vector

Figure 3:
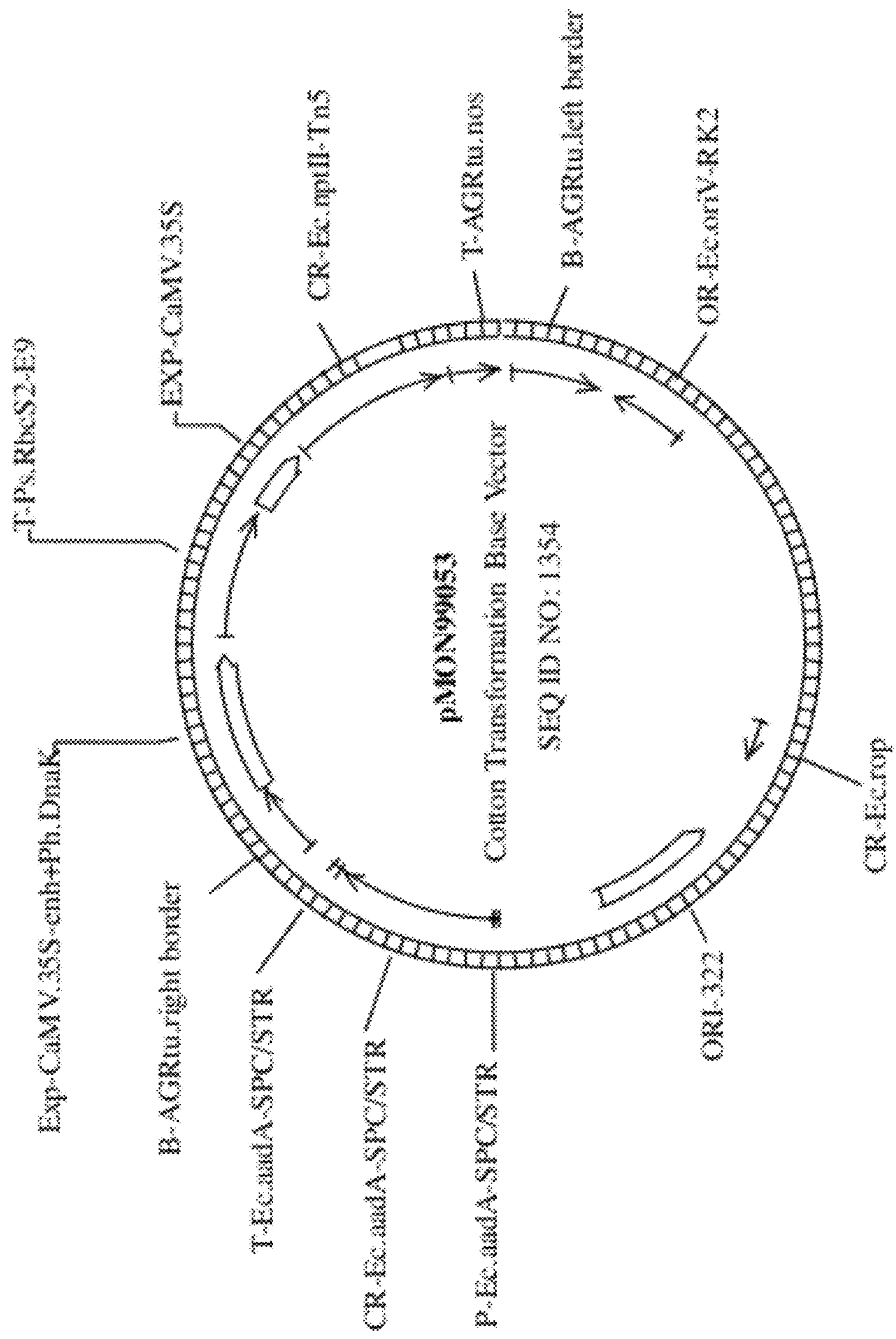

Plasmids for use in transformation of cotton tissue are prepared with elements of expression vector pMON99053 (SEQ ID NO: 1354) as shown in Table 5 below and FIG. 3.

TABLE 5

| Function | Name | Annotation | Coordinates of SEQ ID NO: 1354 |
|---|---|---|---|
| Agrobacterium T-DNA transfer | B-AGRtu.right border | Agro right border sequence, essential for transfer of T-DNA. | 1-357 |
| Gene of interest expression cassette | Exp-CaMV.35S-enh + Ph.DnaK | Enhanced version of the 35S RNA promoter from CaMV plus the petunia hsp70 5' untranslated region | 388-1091 |
| | T-Ps.RbcS2-E9 | The 3' non-translated region of the pea RbcS2 gene which functions to direct polyadenylation of the mRNA. | 1165-1797 |
| Plant selectable marker expression cassette | Exp-CaMV.35S | Promoter and 5' untranslated region from the 35S RNA of CaMV | 1828-2151 |
| | CR-Ec.nptII-Tn5 | Coding region for neomycin phosphotransferase gene from transposon Tn5 which confers resistance to neomycin and kanamycin. | 2185-2979 |
| | T-AGRtu.nos | A 3' non-translated region of the nopaline synthase gene of *Agrobacterium tumefaciens* Ti plasmid which functions to direct polyadenylation of the mRNA. | 3011-3263 |
| Agrobacterium T-DNA transfer | B-AGRtu.left border | Agro left border sequence, essential for transfer of T-DNA. | 3309-3750 |
| Maintenance in *E. coli* | OR-Ec.oriV-RK2 | The vegetative origin of replication from plasmid RK2. | 3837-4233 |
| | CR-Ec.rop | Coding region for repressor of primer from the ColE1 plasmid. Expression of this gene product interferes with primer binding at the origin of replication, keeping plasmid copy number low. | 5742-5933 |
| | OR-Ec.ori-ColE1 | The minimal origin of replication from the *E. coli* plasmid ColE1. | 6361-6949 |
| | P-Ec.aadA-SPC/STR | Promoter for Tn7 adenylyltransferase (AAD(3")) | 7480-7521 |
| | CR-Ec.aadA-SPC/STR | Coding region for Tn7 adenylyltransferase (AAD(3")) conferring spectinomycin and streptomycin resistance. | 7522-8310 |
| | T-Ec.aadA-SPC/STR | 3' UTR from the Tn7 adenylyltransferase (AAD(3")) gene of *E. coli*. | 8311-8368 |

To construct transformation vectors for expressing a protein identified in Table 1, primers for PCR amplification of the protein coding nucleotides are designed at or near the start and stop codons of the coding sequence, in order to eliminate most of the 5' and 3' untranslated regions. The protein coding nucleotides are inserted into the base vector in the gene of interest expression cassette at an insertion site, i.e. between the promoter element (coordinates 388-1091) and the polyadenylation element (coordinates 1165-1797).

To construct transformation vectors for suppressing a protein identified in Table 1, the amplified protein coding nucleotides are assembled in a sense and antisense arrangement and inserted into the base vector at the insertion site in the gene of interest expression cassette to provide transcribed RNA that will form a double-stranded RNA for RNA interference suppression of the protein. In the embodiments of this invention the proteins that are suppressed are ZmLac, ZmGS3, and ZmBB.

D. Plant Expression Constructs for Gene Stacking in Corn.

Figure 4:
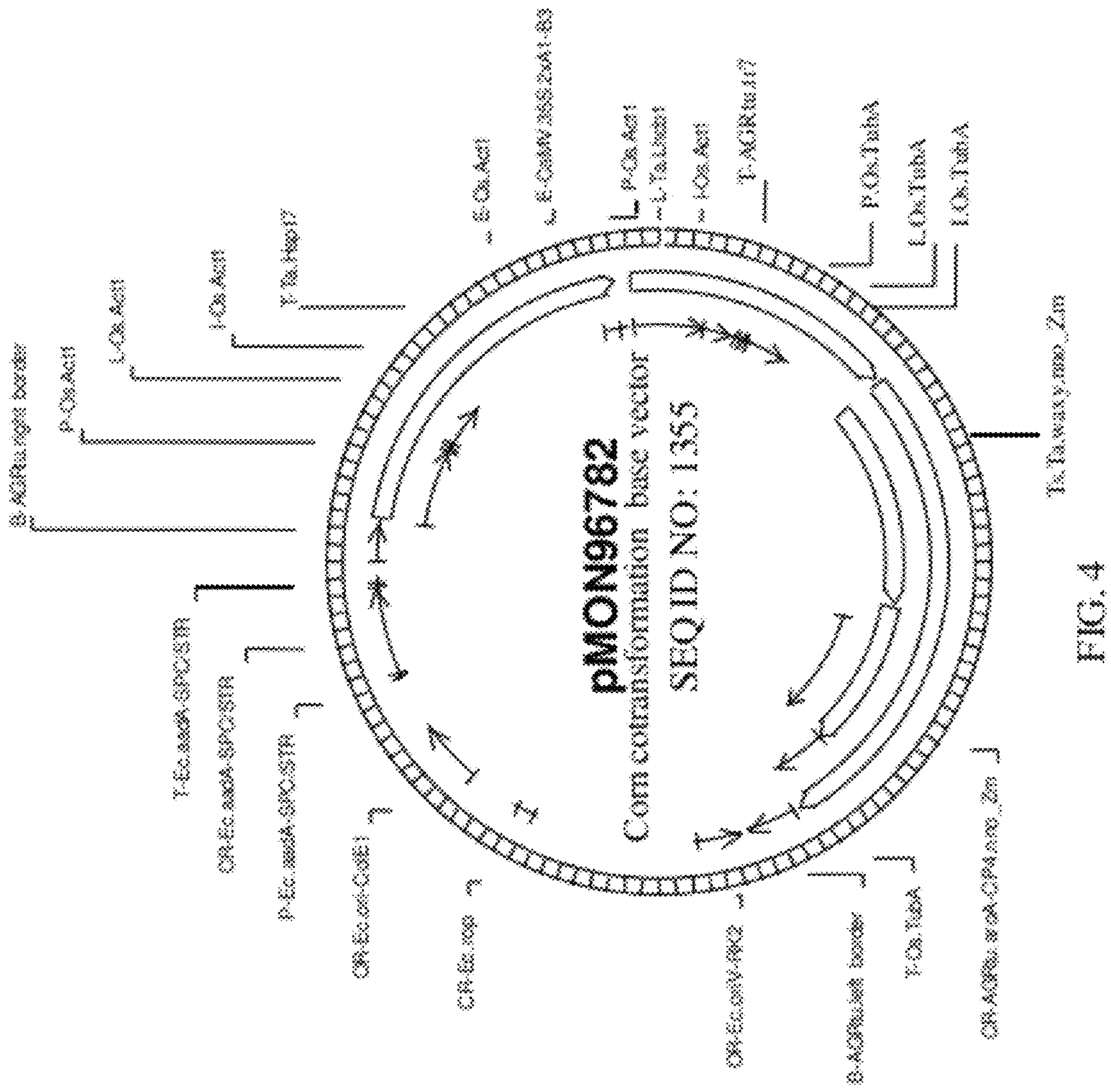

A base corn transformation vector pMON96782, as set forth in SEQ ID NO: 1355, illustrated in Table 6 and FIG. 4, is fabricated for use in preparing recombinant DNA for *Agrobacterium*-mediated transformation into corn tissue.

TABLE 6

| Function | Name | Annotation | Coordinates of SEQ ID NO: 1355 |
|---|---|---|---|
| Agrobacterium T-DNA transfer | B-AGRtu.right border | Agro right border sequence, essential for transfer of T-DNA. | 1-357 |
| Gene of interest expression cassette 1 | P-Os.Act1 | Promoter region of the rice actin 1 gene | 403-1243 |
| | L-Os.Act1 | 5' untranslated leader of rice actin 1 gene | 1244-1323 |
| | I-Os.Act1 | First intron and flanking UTR exon sequences from the rice actin 1 gene | 1324-1801 |
| | T-Ta.Hsp17 | 3' un-translated region of wheat low molecular weight heat shock protein gene | 1834-2043 |

TABLE 6-continued

| Function | Name | Annotation | Coordinates of SEQ ID NO: 1355 |
|---|---|---|---|
| Gene of interest expression cassette 2 | E-Os.Act1 | Upstream Promoter region of rice actin 1 | 2136-2892 |
| | E-CaMV.35S.2xA1-B3 | 35S A1-B3 Domain | 2905-2937 |
| | P-Os.Act1 | Promoter from rice actin gene | 3242-3321 |
| | L-Ta.Lhcb1 | 5' untranslated leader from wheat chlorophyll protein | 3327-3387 |
| | I-Os.Act1 | Intron and 5' untranslated region from rice actin 1 gene | 3404-3883 |
| | T-AGRtu.tr7 | 3' untranslated region from "transcript 7" of Agrobacterium | 3918-4425 |
| Plant selectable marker expression cassette | P.Os.TubA | Promoter of alpha-tubulin gene of rice | 4452-5650 |
| | L.Os.TubA | 5' untranslated region of an alpha tubulin from rice | 5651-5736 |
| | I.Os.TubA | Intron 1 of an alpha tubulin from rice. | 5737-6632 |
| | Ts.Ta.waxy.nno_Zm | Chloroplast transit peptide from wheat starch synthase | 6637-6846 |
| | Cr.AGRtu.aroA-CP4.nno_Zm | CP4 EPSPS gene | 6847-8214 |
| | T.Os.TubA | 3' untranslated region of alpha tubulin from rice | 8219-8800 |
| Agrobacterium T-DNA transfer | B-AGRtu.left border | Left border sequence for T-DNA transfer | 8828-9269 |
| Maintenance in *E. coli* | OR-Ec.oriV-RK2 | Origin of replication from the *E. coli* plasmid RK2. | 9356-9752 |
| | Cr-Ec.rop | Coding region for repressor of primer from ColE1 plasmid | 11261-11452 |
| | OR-Ec.ori-ColE1 | Minimum origin of replication from *E. coli* colE1 plasmid. | 11880-12468 |
| | P-Ec.aadA-SPC/STR | Promoter for Tn7 adenylyltransferase gene | 12999-13040 |
| | CR-Ec.aadA-SPC/STR | Coding region for Tn7 adenylyltransferase gene | 13041-13829 |
| | T-Ec.aadA-SPC/STR | 3' untranslated region from Tn7 adenylyltransferase gene | 13830-13887 |

Primers for PCR amplification of protein coding nucleotides of the genes of interest are designed at or near the start and stop codons of the coding sequence, in order to eliminate most of the 5' and 3' untranslated regions. Protein coding regions of genes encoding a first and second protein of interest are amplified. The amplified region from the first gene of interest is cloned between nucleotides 1801 and 1834 of the base vector and the amplified region from the second gene of interest is cloned between nucleotides 3883 and 3918 of the base vector.

EXAMPLE 2

Corn Transformation

This example illustrates transformation methods useful in producing a transgenic nucleus in a corn plant cell, and the plants, seeds and pollen produced from a transgenic cell with such a nucleus having an enhanced trait, i.e. enhanced water use efficiency, enhanced cold tolerance, increased yield, enhanced nitrogen use efficiency, enhanced seed protein and enhanced seed oil. A plasmid vector is prepared by cloning the DNA of SEQ ID NO:1 into the gene of interest expression cassette in the base vector for use in corn transformation of corn tissue provided in Example 1, Table 3.

For *Agrobacterium*-mediated transformation of corn embryo cells corn plants of a readily transformable line are grown in the greenhouse and ears are harvested when the embryos are 1.5 to 2.0 mm in length. Ears are surface sterilized by spraying or soaking the ears in 80% ethanol, followed by air drying. Immature embryos are isolated from individual kernels on surface sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For *Agrobacterium*-mediated transformation of maize callus immature embryos are cultured for approximately 8-21 days after excision to allow callus to develop. Callus is then incubated for about 30 minutes at room temperature with the *Agrobacterium* suspension, followed by removal of the liquid by aspiration. The callus and *Agrobacterium* are co-cultured without selection for 3-6 days followed by selection on paromomycin for approximately 6 weeks, with biweekly transfers to fresh media. Paromomycin resistant calli are identified about 6-8 weeks after initiation of selection.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

The above process is repeated to produce multiple events of transgenic corn plant cells that are transformed with recombinant DNA from each of the genes identified in Table 1. Events are designed to produce in the transgenic cells one of the proteins identified in Table 1, except the proteins of SEQ ID NOs: 11 and 17-19 which are suppressed. Progeny transgenic plants and seed of the transformed plant cells are screened for enhanced water use efficiency, enhanced cold tolerance, increased yield, enhanced nitrogen use efficiency, enhanced seed protein and enhanced seed oil. From each group of multiple events of transgenic plants with a specific recombinant DNA from Table 1 the event that produces the greatest enhancement in yield, water use efficiency, nitrogen use efficiency, enhanced cold tolerance, enhanced seed protein and enhanced seed oil is identified and progeny seed is selected for commercial development.

EXAMPLE 3

Soybean Transformation

This example illustrates plant transformation useful in producing a transgenic nucleus in a soybean plant cell, and the plants, seeds and pollen produced from a transgenic cell with such a nucleus having an enhanced trait, i.e. enhanced water use efficiency, enhanced cold tolerance, increased yield, enhanced nitrogen use efficiency, enhanced seed protein and enhanced seed oil.

For *Agrobacterium* mediated transformation, soybean seeds are imbided overnight and the meristem explants excised. The explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

The above process is repeated to produce multiple events of transgenic soybean plant cells that are transformed with recombinant DNA from each of the genes identified in Table 1. Events are designed to produce in the transgenic cells one of the proteins identified in Table 1, except the proteins of SEQ ID NOs: 11, and 17-19 which are suppressed. Progeny transgenic plants and seed of the transformed plant cells are screened for enhanced water use efficiency, enhanced cold tolerance, increased yield, enhanced seed protein and enhanced seed oil. From each group of multiple events of transgenic plants with a specific recombinant DNA from Table 1 the event that produces the greatest enhancement in yield, water use efficiency, nitrogen use efficiency, enhanced cold tolerance, enhanced seed protein and enhanced seed oil is identified and progeny seed is selected for commercial development.

EXAMPLE 4

Cotton Transgenic Plants with Enhanced Agronomic Traits

This example illustrates plant transformation useful in producing a transgenic nucleus in a cotton plant cell, and the plants, seeds and pollen produced from a transgenic cell with such a nucleus having an enhanced trait, i.e. enhanced water use efficiency, increased yield, enhanced nitrogen use efficiency and enhanced seed oil.

Transgenic cotton plants containing each recombinant DNA having a sequence of SEQ ID NO: 1 through SEQ ID NO: 10 are obtained by transforming with recombinant DNA from each of the genes identified in Table 1 using *Agrobacterium*-mediated transformation. The above process is repeated to produce multiple events of transgenic cotton plant cells that are transformed with recombinant DNA from each of the genes identified in Table 1. Events are designed to produce in the transgenic cells one of the proteins identified in Table 1, except the proteins of SEQ ID NOs: 11, and 17-19 which are suppressed.

From each group of multiple events of transgenic plants with a specific recombinant DNA from Table 1 the event that produces the greatest enhancement in yield, water use efficiency, nitrogen use efficiency, enhanced cold tolerance, enhanced seed protein and enhanced seed oil is identified and progeny seed is selected for commercial development.

Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA.

Transgenic cotton plants with enhanced yield and water use efficiency are identified by growing under variable water conditions. Specific conditions for cotton include growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

EXAMPLE 5

Canola Transformation

This example illustrates plant transformation useful in producing the transgenic canola plants of this invention and the production and identification of transgenic seed for transgenic canola having enhanced water use efficiency, enhanced cold tolerance, increased yield, enhanced nitrogen use efficiency, enhanced seed protein and enhanced seed oil.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterizations are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant.

Transgenic canola plant cells are transformed with each of the recombinant DNA identified in Table 1. The above process is repeated to produce multiple events of transgenic canola plant cells that are transformed with recombinant DNA from each of the genes identified in Table 1. Events are designed to produce in the transgenic cells one of the proteins identified in Table 1, except the proteins of SEQ ID NOs: 11, and 17-19 which are suppressed. Progeny transgenic plants and seed of the transformed plant cells are screened for enhanced water use efficiency, enhanced cold tolerance, increased yield, enhanced seed protein and enhanced seed oil. From each group of multiple events of transgenic plants with a specific recombinant DNA from Table 1 the event that produces the greatest enhancement in yield, water use efficiency, nitrogen use efficiency, enhanced cold tolerance, enhanced seed protein and enhanced seed oil is identified and progeny seed is selected for commercial development.

EXAMPLE 6

Homolog Identification

This example illustrates the identification of homologs of proteins encoded by the DNA identified in Table 1 which is used to provide transgenic seed and plants having enhanced agronomic traits. From the sequence of the homologs, homologous DNA sequence can be identified for preparing additional transgenic seeds and plants of this invention with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database" was constructed of known protein sequences of the organism; it is a subset of the All Protein Database based on the NCBI taxonomy ID for the organism.

The All Protein Database was queried using amino acid sequences provided herein as SEQ ID NO: 11 through SEQ ID NO: 20 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided herein as SEQ ID NO: 11 through SEQ ID NO: 20 using NCBI "blastp" program with E-value cutoff of 1e-4. Up to 1000 top hits were kept. A BLAST searchable database was constructed based on these hits, and is referred to as "SubDB". SubDB is queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs from a large number of distinct organisms were identified and are reported below in table 7 with the SEQ ID NO of the original query sequence and the identified homologs as [SEQ ID NO]: [Homolog SEQ ID NOs].

TABLE 7

| Protein Sequences and their Homologs |
|---|
| 11: 24 28 32 34 40 44 46 47 49 50 51 52 53 60 68 71 72 74 75 80 81 85 87 90 118 120 121 129 135 143 153 154 157 159 164 168 173 176 182 184 194 197 200 202 203 213 214 228 237 246 248 249 251 253 255 258 261 268 274 277 292 294 299 303 306 313 314 320 325 326 328 333 347 348 349 354 355 357 360 361 362 363 364 365 366 370 374 383 389 390 391 395 397 425 426 431 434 436 456 457 459 463 467 469 470 471 472 473 474 477 480 488 490 492 499 508 515 522 529 530 532 540 541 555 568 574 577 578 579 581 585 587 588 589 595 596 598 600 610 616 618 621 623 626 633 638 639 640 643 644 645 651 652 658 661 662 663 666 674 677 691 692 693 694 695 709 717 718 720 728 729 745 746 753 756 757 774 775 784 787 791 793 799 801 810 825 831 837 850 851 856 857 865 866 868 871 873 875 876 879 881 886 888 891 892 896 899 904 905 906 908 916 917 919 929 935 940 943 946 948 950 962 963 964 969 974 |

TABLE 7-continued

| Protein Sequences and their Homologs |
|---|
| 982 993 997 1005 1009 1011 1013 1015 1027 1028 1031 1032 1035 1049 1050 1059 1066 1068 1069 1076 1083 1085 1088 1090 1093 1095 1097 1098 1100 1107 1108 1110 1111 1117 1118 1120 1131 1134 1136 1137 1145 1146 1147 1149 1150 1153 1155 1156 1158 1168 1169 1170 1176 1184 1188 1193 1196 1205 1207 1212 1216 1226 1229 1230 1232 1233 1236 1241 1242 1243 1244 1248 1249 1252 1254 1256 1257 1260 1262 1265 1267 1269 1280 1283 1287 1292 1306 1307 1334 1335 1345 1350 |
| 12: 36 38 43 45 48 56 61 62 65 73 78 79 82 83 84 89 100 107 109 124 126 131 132 142 144 146 148 152 167 171 196 204 206 212 215 218 219 224 233 235 242 243 254 260 264 265 267 279 290 291 295 297 305 311 316 321 322 324 331 332 340 342 358 369 375 398 410 413 414 417 435 437 438 441 462 468 475 485 493 496 498 500 502 504 509 511 516 518 521 525 531 534 538 539 542 546 556 563 580 606 607 611 620 629 632 636 656 664 665 678 683 705 706 710 711 725 738 742 743 762 788 795 798 802 803 812 822 835 838 839 845 846 852 860 863 869 872 877 883 887 894 930 931 936 939 942 944 971 977 979 983 992 999 1007 1010 1030 1046 1048 1065 1075 1087 1091 1112 1113 1119 1124 1133 1135 1181 1182 1192 1195 1197 1206 1211 1213 1217 1219 1220 1223 1234 1235 1237 1239 1246 1247 1251 1258 1259 1261 1266 1300 1310 1317 1321 1328 1331 |
| 13: 23 30 33 42 54 55 63 64 66 88 92 93 94 95 96 97 99 103 104 106 114 115 117 119 127 128 130 138 147 150 151 155 158 160 165 166 175 178 190 191 195 198 208 210 211 221 229 230 238 247 252 256 257 259 262 263 266 272 283 287 317 327 329 330 353 356 368 378 379 385 387 394 399 404 409 411 419 427 428 433 439 440 444 446 449 458 460 461 481 487 503 505 507 510 513 527 537 545 548 550 552 553 557 558 559 564 565 569 572 584 593 602 605 608 609 612 617 619 625 637 647 650 660 672 690 696 703 716 722 726 730 731 735 747 749 750 755 761 766 771 776 779 786 790 794 804 806 811 817 821 824 826 827 828 829 836 841 847 848 854 867 870 878 884 893 895 897 907 909 910 914 918 923 925 928 933 934 951 952 954 955 957 958 959 965 975 985 987 988 991 1012 1019 1020 1022 1029 1033 1034 1036 1039 1041 1043 1044 1052 1056 1057 1060 1061 1063 1071 1072 1073 1084 1086 1094 1102 1115 1122 1126 1128 1144 1148 1151 1159 1161 1162 1173 1174 1177 1179 1189 1190 1201 1202 1203 1208 1221 1225 1227 1228 1231 1255 1270 1273 1278 1279 1291 1296 1301 1302 1318 1322 1324 1330 1338 1346 1348 |
| 14: 23 30 33 54 55 63 64 66 88 91 92 93 94 95 96 97 99 103 104 106 112 115 117 119 127 128 130 137 138 147 150 151 158 160 162 165 174 175 178 181 186 189 190 191 198 201 217 221 229 230 238 244 247 252 256 257 259 262 263 266 269 272 276 283 286 317 318 319 327 329 330 344 353 356 368 379 385 387 393 394 399 404 408 409 411 419 423 427 440 445 446 449 450 458 460 461 482 487 489 503 505 507 510 513 526 527 535 537 545 548 550 551 552 553 557 558 559 569 572 575 584 590 593 603 605 608 609 612 619 625 628 631 637 642 647 650 653 660 668 672 675 688 690 696 700 703 707 716 722 726 730 731 732 735 747 749 750 754 755 761 766 771 776 778 779 780 781 782 786 790 794 804 806 811 817 820 821 824 826 828 836 841 847 848 854 867 870 878 882 884 893 895 897 907 909 910 913 914 918 920 921 923 924 932 933 934 949 951 952 954 955 957 959 960 965 975 985 987 988 991 1012 1019 1020 1022 1026 1029 1033 1034 1036 1039 1041 1043 1044 1052 1057 1060 1061 1063 1071 1072 1073 1077 1084 1086 1094 1102 1109 1126 1128 1132 1138 1144 1148 1157 1159 1161 1162 1173 1174 1177 1179 1189 1190 1202 1203 1208 1221 1222 1225 1228 1231 1255 1270 1271 1273 1276 1284 1289 1291 1293 1301 1302 1318 1322 1324 1346 1348 |
| 15: 21 26 27 31 35 37 41 57 58 59 69 70 76 77 86 98 101 102 108 110 111 113 116 122 123 125 133 136 139 140 145 149 156 161 163 169 170 172 177 180 183 185 187 188 192 193 199 209 216 220 222 223 225 226 227 231 232 234 236 239 240 241 245 250 270 271 273 275 278 280 281 282 284 285 288 289 293 296 298 300 301 302 307 308 309 310 312 315 323 335 336 337 338 339 341 343 345 346 351 352 359 367 371 372 373 376 377 380 381 382 384 386 392 396 400 401 402 403 406 407 412 415 416 418 420 421 422 424 429 430 432 442 443 447 448 452 453 455 464 465 466 476 478 479 483 484 486 491 494 495 497 501 506 517 519 520 523 524 528 533 536 543 547 549 554 560 561 562 566 567 570 571 573 576 582 583 594 597 599 601 604 613 614 615 622 624 627 630 634 635 641 646 648 649 654 655 657 659 667 669 670 671 673 679 681 682 684 685 686 687 689 697 698 699 701 702 704 708 712 714 715 719 721 723 724 727 733 734 736 739 741 744 748 751 752 758 759 760 763 764 765 767 768 769 770 772 773 783 785 789 792 796 800 805 807 808 809 813 814 815 816 818 823 830 832 833 834 840 842 843 844 849 853 855 858 859 861 862 864 874 880 889 890 898 900 901 903 911 915 922 926 927 937 945 947 953 956 961 966 967 968 970 972 973 976 980 981 984 986 989 990 994 995 996 998 1000 1001 1002 1003 1004 1006 1008 1014 1016 1017 1018 1021 1023 1024 1025 1037 1040 1042 1045 1047 1051 1053 1054 1055 1058 1067 1070 1074 1078 1079 1080 1081 1082 1092 1096 1099 1101 1103 1104 1105 1106 1114 1116 1123 1125 1127 1129 1130 1139 1141 1143 1152 1154 1160 1163 1164 1165 1166 1167 1171 1172 1175 1178 1180 1183 1185 1186 1187 1194 1198 1199 1204 1209 1210 1214 1215 1218 1224 1238 1240 1245 1250 1253 1263 1264 1268 1272 1274 1275 1277 1281 1282 1285 1288 1294 1295 1297 1298 1299 1303 1304 1305 1308 1309 1311 1312 1313 1314 1315 1316 1319 1320 1323 1325 1326 1327 1329 1332 1333 1336 1337 1339 1340 1341 1342 1343 1347 1349 1351 |
| 16: 21 26 27 31 35 37 41 57 58 59 69 70 76 77 86 98 101 102 108 110 111 113 116 122 123 125 133 136 139 140 145 149 156 161 163 169 170 172 177 180 183 185 187 188 192 193 199 209 216 220 222 223 225 226 227 231 232 234 236 239 240 241 245 250 270 271 273 275 278 280 281 282 284 285 288 289 293 296 298 300 301 302 307 308 309 310 312 315 323 335 336 337 338 339 341 343 345 346 351 352 359 367 371 372 373 376 377 380 381 382 384 386 392 396 400 401 402 403 406 407 412 415 416 418 420 421 422 424 429 430 432 442 443 447 448 452 453 455 464 465 466 476 478 479 483 484 486 491 494 495 497 501 506 517 519 520 523 524 528 533 536 543 547 549 554 560 561 562 566 567 570 571 573 576 582 583 594 597 599 601 604 613 614 615 622 624 627 630 634 635 641 646 648 649 654 655 657 659 667 669 670 671 673 679 681 682 684 685 686 687 689 697 698 699 701 702 704 708 712 714 715 719 721 723 |

TABLE 7-continued

| Protein Sequences and their Homologs |
|---|
| 724 727 733 734 736 739 741 744 748 751 752 758 759 760 763 764 765 767 768 769 770 772 773 783 785 789 792 796 800 805 807 808 809 813 814 815 816 818 823 830 832 833 834 840 842 843 844 849 853 855 858 859 861 862 864 874 880 889 890 898 900 901 903 911 915 922 926 927 937 945 947 953 956 961 966 967 968 970 972 973 976 980 981 984 986 989 990 994 995 996 998 1000 1001 1002 1003 1004 1006 1008 1014 1016 1017 1018 1021 1023 1024 1025 1037 1040 1042 1045 1047 1051 1053 1054 1055 1058 1067 1070 1074 1078 1079 1080 1081 1082 1092 1096 1099 1101 1103 1104 1105 1106 1114 1116 1123 1125 1127 1129 1130 1139 1141 1143 1152 1154 1160 1163 1164 1165 1166 1167 1171 1172 1175 1178 1180 1183 1185 1186 1187 1194 1198 1199 1204 1209 1210 1214 1215 1218 1224 1238 1240 1245 1250 1253 1263 1264 1268 1272 1274 1275 1277 1281 1282 1285 1288 1294 1295 1297 1298 1299 1303 1304 1305 1308 1309 1311 1312 1313 1314 1315 1316 1319 1320 1323 1325 1326 1327 1329 1332 1333 1336 1337 1339 1340 1341 1342 1343 1347 1349 1351 |
| 17: 179 207 514 586 591 902 1200 1286 |
| 18: 179 207 514 586 591 902 1200 1286 |
| 19: 22 29 141 592 |
| 20: 25 39 67 105 134 205 304 334 350 388 405 451 454 512 544 676 680 713 737 740 777 797 819 885 912 938 941 978 1038 1062 1064 1089 1121 1140 1142 1191 1290 1344 |

Recombinant DNA constructs are prepared using the DNA encoding each of the identified homologs and the constructs are used to prepare multiple events of transgenic corn, soybean, canola and cotton plants as illustrated in Examples 2-5. Plants are regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. From each group of multiple events of transgenic plants with a specific recombinant DNA for a homolog the event that produces the greatest enhancement in yield, water use efficiency, nitrogen use efficiency, enhanced cold tolerance, enhanced seed protein and enhanced seed oil is identified and progeny seed is selected for commercial development.

EXAMPLE 7

Consensus Sequence

This example illustrates the identification of consensus amino acid sequence for the proteins and homologs encoded by DNA that is used to prepare the transgenic seed and plants of this invention having enhanced agronomic traits.

ClustalW program was selected for multiple sequence alignments of the amino acid sequence of SEQ ID NO: 17-19 and their homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of 1 were chosen for multiple sequence alignment.

The consensus amino acid sequence can be used to identify DNA corresponding to the full scope of this invention that is useful in providing transgenic plants, for example corn and soybean plants with enhanced agronomic traits, for example improved nitrogen use efficiency, improved yield, improved water use efficiency and/or improved growth under cold stress, due to the expression in the plants of DNA suppressing a protein with amino acid sequence identical to the consensus amino acid sequence.

The SEQ ID NOs for the identified consensus sequences are reported in table 8 below and the full consensus sequences are provided in the attached sequence listing.

TABLE 8

| Gene ID | PEP SEQ ID NO | Consensus SEQ ID NO |
|---|---|---|
| Mnom000090 | 17 | 1356 |
| Mnom000091 | 18 | 1357 |
| Mnom000092 | 19 | 1358 |

EXAMPLE 9

Identification of Amino Acid Domain by Pfam Analysis

This example illustrates the identification of domain and domain module by Pfam analysis.

The amino acid sequence of the expressed proteins that are shown to be associated with an enhanced trait were analyzed for Pfam protein family against the current Pfam collection of multiple sequence alignments and hidden Markov models using the HMMER software in the appended computer listing. The Pfam protein domains and modules for the proteins of SEQ ID NO: 11 through 16 and 20 are shown in Tables 9, 10 and 11. The Hidden Markov model databases for the identified patent families are also in the appended computer listing allowing identification of other homologous proteins and their cognate encoding DNA to enable the full breadth of the invention for a person of ordinary skill in the art. Certain proteins are identified by a single Pfam domain and others by multiple Pfam domains.

TABLE 9

| Pfam annotation | | | | | | |
|---|---|---|---|---|---|---|
| PEP SEQ ID NO | Gene ID | Pfam domain name | Begin | Stop | Score | E-value |
| 11 | Mnom000034 | Cu-oxidase__3 | 30 | 146 | 237 | 4.10E−68 |
| 11 | Mnom000034 | Cu-oxidase | 156 | 310 | 158.7 | 1.50E−44 |
| 11 | Mnom000034 | Cu-oxidase__2 | 409 | 532 | 169.9 | 6.30E−48 |
| 12 | Mnom000037 | Flavodoxin__1 | 7 | 160 | 197.3 | 3.70E−56 |
| 13 | Mnom000048 | Glyco__transf__20 | 3 | 470 | 933.9 | 6.70E−278 |
| 13 | Mnom000048 | Trehalose__PPase | 504 | 748 | 256.4 | 6.20E−74 |
| 14 | Mnom000049 | Glyco__transf__20 | 76 | 578 | 841.5 | 4.40E−250 |
| 14 | Mnom000049 | Trehalose__PPase | 627 | 862 | 339.1 | 7.70E−99 |
| 15 | Mnom000067 | Aminotran__1__2 | 60 | 441 | 33.4 | 8.00E−09 |
| 16 | Mnom000068 | Aminotran__1__2 | 60 | 441 | 33.4 | 8.00E−09 |
| 20 | Mnom000095 | B3 | 312 | 417 | 118.5 | 2.00E−32 |
| 20 | Mnom000095 | Auxin__resp | 439 | 524 | 160.7 | 3.80E−45 |
| 20 | Mnom000095 | AUX__IAA | 681 | 826 | −74.9 | 0.00043 |

TABLE 10

| Pfam module annotation | | | |
|---|---|---|---|
| PEP SEQ ID NO | Gene ID | Pfam domain module | Position |
| 11 | Mnom000034 | Cu-oxidase_3::Cu-oxidase::Cu-oxidase_2 | 30-146::156-310::409-532 |
| 12 | Mnom000037 | Flavodoxin_1 | 7-160 |
| 13 | Mnom000048 | Glyco_transf_20::Trehalose_PPase | 3-470::504-748 |
| 14 | Mnom000049 | Glyco_transf_20::Trehalose_PPase | 76-578::627-862 |
| 15 | Mnom000067 | Aminotran_1_2 | 60-441 |
| 16 | Mnom000068 | Aminotran_1_2 | 60-441 |
| 20 | Mnom000095 | 83::Auxin_resp::AUX_IAA | 312-417::439-524::681-826 |

TABLE 11

| Description of Pfam domains | | | |
|---|---|---|---|
| Pfam domain name | Accession number | Gathering cutoff | Domain description |
| AUX_IAA | PF02309.8 | −83.0000; | AUX/IAA family |
| Aminotran_1_2 | PF00155.13 | −57.5000; | Aminotransferase class I and II |
| Auxin_resp | PF06507.5 | 25.0000; | Auxin response factor |
| B3 | PF02362.13 | 26.5000; | B3 DNA binding domain |
| Cu-oxidase | PF00394.14 | −18.9000; | Multicopper oxidase |
| Cu-oxidase_2 | PF07731.6 | −5.8000; | Multicopper oxidase |
| Cu-oxidase_3 | PF07732.7 | 10.0000; | Multicopper oxidase |
| Flavodoxin_1 | PF00258.17 | 6.3000; | Flavodoxin |
| Glyco_transf_20 | PF00982.13 | −243.6000; | Glycosyltransferase family 20 |
| Trehalose_PPase | PF02358.8 | −49.4000; | Trehalose-phosphatase |

HMMER2.0 [2.3.2]
NAME Aminotran_1_2
ACC PF00155.13
DESC Aminotransferase class I and II
LENG 413
ALPH Amino
RF no
CS yes
MAP yes
COM hmmbuild-F HMM_ls.ann SEED.ann
COM hmmcalibrate--seed 0 HMM_ls.ann
NSEQ 48
DATE Wed Jun 4 12:41:51 2008
CKSUM 5427
GA −57.5000 −57.5000;
TC −57.5000 −57.5000;
NC −57.6000 −57.6000;
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −212.832108 0.112804

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −35 | * | −5392 | | | | | | | | | | | | | | | | | | |
| 1 | 384 | −4120 | 12 | 570 | −4439 | −1698 | −2284 | 498 | 915 | −4135 | −3209 | −554 | 901 | −1824 | 813 | 250 | 917 | 298 | −4304 | −385 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | −35 | * | | | | | | | | | | | | |
| 2 | −2650 | −4123 | 1971 | 552 | −4444 | −198 | 1098 | 914 | 1158 | −4139 | −382 | 592 | 363 | −328 | −1015 | −1280 | −157 | −734 | −4306 | −3624 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 3 | −2896 | 567 | −1147 | −1357 | −571 | −676 | −3254 | 799 | 1757 | 207 | 1073 | −3928 | −976 | 1299 | −3869 | −3471 | −2836 | 1527 | 1087 | −313 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 4 | −3740 | −3485 | −6136 | −1671 | −464 | −5430 | −4361 | 2501 | −5177 | 1229 | 2607 | −5079 | −5398 | −4771 | −4988 | −4546 | 121 | 1441 | −4111 | −3808 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 5 | −2664 | −4004 | 1304 | −2017 | −4272 | 968 | −2324 | −1512 | 1015 | −186 | −3107 | 2717 | −756 | −1883 | −703 | −1108 | −2603 | −798 | 822 | −3571 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 6 | −6226 | −5561 | −8547 | −7962 | 1608 | −8401 | −6727 | −3026 | −7769 | 3021 | 248 | −8082 | −7277 | −6383 | −7165 | −7815 | −6037 | −1618 | 2137 | −5272 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 7 | 1299 | 2232 | −264 | −5671 | −6629 | 2106 | −5515 | −6437 | −5715 | −6634 | −5683 | 1058 | −5145 | −5375 | −5792 | 1703 | −62 | −5259 | −6789 | −6576 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 8 | 1079 | −3220 | −3617 | 703 | −3286 | −4113 | −2929 | 1166 | −2924 | −3135 | −2439 | −3170 | −4215 | 389 | −3236 | 1715 | 740 | 1344 | −3665 | −3235 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | −3839 | −4536 | −4390 | −4781 | −6161 | 2644 | −5311 | −6799 | −5903 | −6911 | −6087 | 3381 | −5311 | −5279 | −6157 | −454 | −4274 | −5624 | −6543 | −339 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 10 | 190 | −3905 | 1832 | 1879 | −698 | −3692 | −2363 | −236 | −1989 | −1911 | −3020 | 1391 | −3783 | 1633 | −2477 | −2609 | −1401 | 132 | −4147 | −3526 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 11 | −3090 | 394 | −5376 | −4763 | 441 | −4617 | −3365 | −2413 | −4365 | 247 | 447 | 1605 | 1583 | −3976 | −4169 | −1480 | −3032 | −2337 | −3163 | 3680 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −42 | −10521 | −5148 | −894 | −1115 | −701 | −1378 | * | * | | | | | | | | | | | | |
| 12 | −553 | 1072 | 1339 | −2010 | −4173 | −3638 | −2306 | −3874 | 523 | 1170 | −3032 | −2306 | 1439 | −1873 | 1178 | 228 | 178 | −3506 | −4151 | −557 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10480 | −11522 | −894 | −1115 | −1531 | −613 | * | * | | | | | | | | | | | | |
| 13 | −2762 | −3129 | 1253 | −2894 | 1755 | 1451 | 1051 | −2726 | −2745 | 139 | −2307 | −863 | −4091 | −357 | −3068 | −1794 | 643 | −568 | −3523 | 2072 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −35 | −10480 | −5433 | −894 | −1115 | −1531 | −613 | * | * | | | | | | | | | | | | |
| 14 | 344 | −3875 | 1998 | 822 | 229 | 965 | −2306 | −3803 | −1930 | 760 | 639 | −623 | 574 | −1880 | −2421 | −996 | −2566 | −3451 | −4113 | −3485 | 14 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −824 | −10446 | −1203 | −894 | −1115 | −1962 | −428 | * | * | | | | | | | | | | | | |
| 15 | 1093 | −3375 | 458 | 588 | −3695 | 532 | −1535 | −3445 | 89 | −3390 | −2464 | 572 | −2970 | 878 | −1623 | 1141 | 305 | −564 | 1471 | −2876 | 15 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9625 | −10667 | −894 | −1115 | −4498 | −65 | * | * | | | | | | | | | | | | |
| 16 | −330 | −3373 | −1752 | 4 | −3693 | 2015 | 922 | −3443 | −1118 | −1414 | −2463 | 1429 | −2971 | 1547 | 494 | 184 | −182 | −2995 | −3558 | −2876 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −3 | −9625 | −10667 | −894 | −1115 | −4498 | −65 | * | * | | | | | | | | | | | | |
| 17 | −1905 | −3349 | −77 | −1214 | −56 | −2883 | 2651 | −655 | 1592 | 240 | −2442 | 1208 | −2976 | 824 | −156 | −324 | 499 | −2965 | −3540 | −2864 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −139 | −9625 | −3468 | −894 | −1115 | −4498 | −65 | * | * | | | | | | | | | | | | |
| 18 | −1915 | −2364 | −2497 | −50 | −2406 | −3137 | −1877 | −222 | −29 | −649 | −1540 | −2088 | 3079 | −1690 | −2142 | −382 | 1270 | −220 | −2750 | −2301 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −902 | −9490 | −1109 | −894 | −1115 | −4632 | −59 | * | * | | | | | | | | | | | | |
| 19 | −1317 | −1190 | −3389 | −2773 | −1138 | 192 | −1687 | −689 | −2425 | 393 | −392 | −2386 | 2450 | −2099 | −2321 | −1904 | 594 | 477 | 2075 | 1780 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −6 | −8593 | −9635 | −894 | −1115 | −121 | −3639 | * | * | | | | | | | | | | | | |
| 20 | −1329 | 559 | −74 | −1138 | −3467 | −3819 | −2528 | 69 | −1038 | 345 | −538 | −2648 | 1727 | 863 | −800 | −1226 | 1833 | 834 | −3724 | −3223 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10449 | −11491 | −894 | −1115 | −1931 | −439 | * | * | | | | | | | | | | | | |
| 21 | −986 | 1639 | −1111 | −4552 | 793 | −4393 | −3264 | 523 | −4148 | 1350 | −51 | −4038 | 1636 | −3771 | −3949 | 447 | −983 | 1321 | −3130 | −2788 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10449 | −11491 | −894 | −1115 | −875 | −1136 | * | * | | | | | | | | | | | | |
| 22 | −1149 | −4091 | 367 | 1318 | −4411 | −3593 | −158 | 838 | 684 | −1244 | −3180 | −826 | 2117 | 866 | −158 | −2500 | 470 | −1964 | −4274 | −3592 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −34 | −10485 | −5458 | −894 | −1115 | −1452 | −657 | * | * | | | | | | | | | | | | |
| 23 | 1189 | 1358 | 921 | 893 | −669 | −3566 | 1028 | −4127 | 49 | −4074 | −3149 | 602 | −3659 | −1765 | 841 | 703 | −2530 | 734 | −4244 | −3562 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −35 | −10452 | −5425 | −894 | −1115 | −1898 | −451 | * | * | | | | | | | | | | | | |
| 24 | 1666 | −2652 | −5120 | −4487 | −2607 | −1386 | −3232 | 1176 | −1177 | −548 | −1855 | −3994 | −4413 | −597 | −3908 | −3445 | −1132 | 2273 | 3051 | −2767 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10419 | −11461 | −894 | −1115 | −2238 | −344 | * | * | | | | | | | | | | | | |
| 25 | 1114 | −2654 | −5077 | −4446 | −2609 | −1385 | −3220 | 1265 | 1372 | 191 | 1424 | −3972 | −4404 | −3698 | 1316 | −3435 | −842 | 974 | 958 | −2767 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10419 | −11461 | −894 | −1115 | −2238 | −344 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −458 | −4035 | 5 | 1675 | −4356 | −3535 | −30 | −4106 | 2165 | −368 | −3124 | −2171 | −720 | 1540 | 386 | −1419 | −841 | −1264 | −4218 | −3535 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10419 | −11461 | −894 | −1115 | −2238 | −344 | * | * | | | | | | | | | | | | |
| 27 | 2757 | −4029 | −2420 | 643 | −4345 | −3543 | −2201 | −4092 | 882 | −1827 | −3119 | −1044 | −3636 | −242 | 118 | −1030 | −700 | −904 | −4214 | −3535 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10419 | −11461 | −894 | −1115 | −2238 | −344 | * | * | | | | | | | | | | | | |
| 28 | 1215 | −2992 | −3583 | 1614 | 265 | 67 | −505 | 462 | −2849 | 272 | 272 | 1048 | −4092 | −523 | −3128 | −1138 | −131 | −756 | −3400 | −2984 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −82 | −10419 | −4199 | −894 | −1115 | −2238 | −344 | * | * | | | | | | | | | | | | |
| 29 | 391 | −3510 | −2654 | −2102 | −3659 | −3620 | −2306 | 994 | 1462 | −10 | 192 | 763 | 1459 | 1374 | 458 | −1227 | −2488 | −1000 | −3807 | −3249 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −38 | −10338 | −5291 | −894 | −1115 | −2808 | −222 | * | * | | | | | | | | | | | | |
| 30 | −2477 | −3948 | 2013 | 1870 | −4271 | −3448 | −167 | −4020 | 680 | −1003 | −3038 | −2083 | −3541 | 1637 | 1528 | −940 | −2415 | −3571 | −4130 | −668 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −982 | −10302 | −1020 | −894 | −1115 | −3002 | −192 | * | * | | | | | | | | | | | | |
| 31 | 1546 | −3053 | −1562 | −1013 | −3335 | −1134 | 860 | −300 | 959 | −372 | −2152 | 525 | −2758 | 1370 | 285 | −153 | −186 | −347 | −3260 | −2602 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −125 | −9323 | −3619 | −894 | −1115 | −4766 | −54 | * | * | | | | | | | | | | | | |
| 32 | −555 | 1302 | −3880 | −281 | 569 | −3293 | 2019 | −1135 | −2906 | −577 | −838 | −2859 | −3345 | −2573 | −2790 | 1194 | −1713 | 319 | 1995 | 2929 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −97 | −9202 | −3974 | −894 | −1115 | −3995 | −93 | * | * | | | | | | | | | | | | |
| 33 | −2274 | −2862 | −4953 | −5244 | −5187 | 2991 | −4651 | 2038 | −5203 | −5186 | −4371 | −3850 | −3953 | −4728 | −4958 | 1216 | −2734 | −3733 | −5493 | −5332 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1402 | −9175 | −690 | −894 | −1115 | −4865 | −50 | * | * | | | | | | | | | | | | |
| 34 | −1053 | 4440 | −3262 | −2744 | 1190 | 872 | −1540 | −523 | −2386 | 412 | −271 | −2205 | −2628 | −2034 | −2258 | −1575 | −1087 | −467 | −1404 | −891 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −10 | −7783 | −8825 | −894 | −1115 | −5329 | −36 | * | * | | | | | | | | | | | | |
| 35 | −890 | −2239 | −768 | −219 | −2598 | −1834 | −465 | −2305 | 1003 | −2262 | −1374 | 1443 | −1933 | −20 | 922 | 269 | 2281 | −1894 | −2425 | −1809 | 35 |
| — | −149 | −500 | 232 | 42 | −377 | 398 | 105 | −627 | 210 | −465 | −721 | 277 | 395 | 45 | 98 | 359 | 117 | −370 | −295 | −250 | |
| . | −2264 | −341 | −8825 | −38 | −5258 | −5329 | −36 | * | * | | | | | | | | | | | | |
| 36 | −1602 | −3257 | 1762 | 2595 | −3518 | −1991 | −1048 | −3334 | 700 | −3247 | −2420 | −595 | 1376 | −654 | −1555 | −1374 | −1597 | −2857 | −3425 | −2604 | 37 |
| — | −149 | −500 | 233 | 43 | −381 | 400 | 106 | −626 | 210 | −466 | −721 | 275 | 394 | 45 | 96 | 359 | 117 | −369 | −294 | −249 | |
| . | −160 | −3280 | −8825 | −979 | −1021 | −5329 | −36 | * | * | | | | | | | | | | | | |
| 37 | −1104 | −1724 | −2972 | −3274 | −4155 | 3334 | −3201 | −4056 | −3613 | −4271 | −3372 | −2416 | −2706 | −3181 | −3549 | 1317 | −1561 | −2862 | −4294 | −4154 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7783 | −8825 | −894 | −1115 | −341 | −2249 | * | * | | | | | | | | | | | | |
| 38 | 1671 | −2983 | −3134 | −69 | 430 | −3769 | 1287 | 1197 | −1161 | 595 | 28 | −640 | −3845 | −250 | 156 | −1093 | −709 | −245 | −3368 | −2919 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10247 | −11289 | −894 | −1115 | −322 | −2323 | * | * | | | | | | | | | | | | |
| 39 | 697 | −4040 | −726 | −41 | −1223 | 1271 | 797 | −1182 | −1136 | 1030 | −3135 | 453 | −3694 | −246 | −511 | 189 | −886 | −606 | −4236 | −501 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10480 | −11522 | −894 | −1115 | −1531 | −613 | * | * | | | | | | | | | | | | |
| 40 | 1535 | −4038 | 1694 | 1009 | −4336 | −3602 | −2263 | −185 | −288 | −277 | 886 | −2247 | −3695 | 61 | −1238 | 714 | −858 | −1823 | −4235 | −3566 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10480 | −11522 | −894 | −1115 | −1531 | −613 | * | * | | | | | | | | | | | | |
| 41 | 57 | 581 | −137 | −1942 | 1249 | 1192 | −58 | −214 | 178 | −1833 | 815 | 837 | −1118 | 824 | −988 | 375 | 264 | −3642 | −4232 | −3564 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10480 | −11522 | −894 | −1115 | −352 | −2208 | * | * | | | | | | | | | | | | |
| 42 | −2650 | −4124 | −367 | 20 | −4445 | 1542 | 1114 | −4195 | −46 | −4140 | −698 | −16 | 533 | 1741 | 1406 | 586 | −1003 | −1444 | −4307 | −3624 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −382 | −4122 | 729 | 386 | −4443 | 845 | −2283 | −1617 | 291 | −1503 | 100 | 83 | 3 | −267 | −661 | 843 | 1562 | −1360 | −4306 | −3623 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 44 | −489 | 528 | −796 | −752 | 1099 | −1472 | −3228 | 492 | −3861 | 858 | −1997 | 602 | −4438 | −3567 | 1659 | −1537 | 0 | 410 | 1085 | 533 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 45 | 978 | −3946 | −2601 | −2052 | 248 | −1231 | 2259 | −3890 | 1201 | −78 | −374 | 2043 | −3768 | −1914 | −93 | −458 | 533 | −3527 | −4177 | −3544 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 46 | −1352 | −3965 | −2589 | 690 | 218 | 495 | −2337 | 584 | 188 | 502 | −3073 | 1053 | −3762 | 464 | 1167 | −537 | −933 | 83 | −4191 | −3552 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 47 | −2974 | 491 | −5311 | −4685 | 1333 | −1706 | −3358 | −735 | −4281 | −1215 | −2014 | −4157 | −4567 | −3900 | −4081 | −245 | 332 | −2224 | −3201 | 4215 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 48 | −1231 | −2766 | −5031 | −4410 | −529 | 1763 | −3288 | −414 | −4053 | 804 | −1968 | −3999 | 2007 | 1298 | −3930 | −359 | 551 | −1000 | −3221 | −2874 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 49 | −1408 | −4126 | 2230 | −743 | −4447 | −293 | −119 | −4198 | −632 | −4142 | −3215 | 720 | 2357 | −1825 | −542 | −439 | 804 | −3748 | −4309 | −459 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10521 | −11563 | −894 | −1115 | −701 | −1378 | * | * | | | | | | | | | | | | |
| 50 | −1228 | 542 | −5145 | −4516 | 837 | −628 | −3308 | 1125 | −4135 | −1045 | 801 | −332 | 704 | 280 | −5 | 280 | 1292 | −1046 | 1149 | 1648 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 51 | −613 | −4120 | 1796 | 467 | −810 | −770 | 2742 | −344 | −508 | −2162 | −3209 | −1056 | −237 | 863 | 532 | −1320 | −959 | −141 | −4304 | −375 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −355 | −10521 | −2201 | −894 | −1115 | −701 | −1378 | * | * | | | | | | | | | | | | |
| 52 | −2598 | −2433 | −4902 | −4270 | −2388 | 3079 | 69 | 261 | −3875 | 48 | −1637 | −3774 | −4192 | −3506 | −3690 | −1074 | −473 | 213 | −2892 | −288 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10167 | −11209 | −894 | −1115 | −81 | −4198 | * | * | | | | | | | | | | | | |
| 53 | 243 | −3189 | −375 | −2879 | −642 | −4034 | 3088 | 438 | −2734 | 1213 | −2365 | −519 | −996 | 181 | −814 | 306 | −1175 | −886 | −3580 | 590 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 54 | 899 | −4079 | 602 | −783 | −4380 | −1588 | 173 | −369 | 874 | −170 | −3174 | −706 | 2232 | −335 | −2389 | −2545 | −133 | −141 | −4275 | −278 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 55 | 1200 | 195 | 971 | 2479 | −720 | −3635 | −2295 | −4127 | 123 | −1255 | −3179 | −2277 | −3728 | −337 | −2387 | 348 | −788 | −1524 | −4279 | −3607 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 56 | 75 | −2937 | −5462 | −4830 | 2870 | −4674 | −3523 | −2331 | −4428 | 2223 | −104 | −4318 | −4707 | −4030 | −4222 | −1385 | −3060 | −230 | −3346 | 290 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 57 | −1350 | −57 | −2517 | 1763 | −4394 | −1734 | −2295 | −273 | 1224 | −943 | −3182 | 513 | −3727 | −364 | 2482 | −2542 | −457 | −1682 | −4282 | −3609 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 58 | −455 | 351 | −324 | 1922 | −4445 | −3624 | 39 | −4196 | 1536 | −4140 | −3213 | 1056 | −3717 | 1280 | −287 | −56 | 620 | −3746 | −4307 | −280 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 59 | 2188 | 896 | −679 | 872 | −4444 | −2006 | −2283 | −4195 | 387 | −86 | −3212 | 168 | −3717 | 268 | 1072 | −1036 | −1167 | −3745 | −4306 | −3624 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −559 | −2774 | −5299 | −4665 | −2732 | −4506 | −3381 | 2107 | −4262 | 1993 | 135 | −4152 | −4553 | −3886 | −4064 | −603 | 308 | 954 | −3244 | −270 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 61 | 3052 | 392 | −4894 | −4280 | −2741 | −1553 | −3255 | −52 | −1612 | −1595 | 180 | −3930 | −4456 | −1096 | −1328 | −668 | −500 | −1242 | 648 | −2882 | 64 |
| — | −149 | −500 | 232 | 42 | −381 | 398 | 105 | −627 | 210 | −467 | −721 | 277 | 393 | 45 | 98 | 359 | 119 | −370 | −267 | −250 | |
| H | −37 | −5320 | −11563 | −2194 | −356 | −701 | −1378 | * | * | | | | | | | | | | | | |
| 62 | 250 | −4125 | 1305 | 1569 | −4446 | −3625 | 885 | −4197 | 1866 | −2051 | −3214 | −2260 | −1152 | 1295 | 675 | −117 | −2591 | −3747 | −4308 | −3625 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 63 | −6568 | −5769 | −7371 | −7455 | 2910 | −7149 | 253 | −5623 | 502 | 1668 | −5097 | −5889 | −7035 | −5898 | −166 | −6372 | −6438 | −5707 | 2100 | 2473 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 64 | 382 | −2737 | −5254 | −4618 | 1706 | −4457 | 1714 | 493 | −1273 | 1193 | 2114 | −4103 | −4507 | −3836 | −267 | −3542 | −2850 | 230 | 952 | 1630 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 65 | −1599 | −4117 | −2501 | −775 | 1270 | 1989 | 1572 | −4183 | 684 | −498 | −3207 | 1009 | −3719 | 273 | 0 | 27 | −864 | −3737 | −4302 | −836 | 73 |
| — | −149 | −500 | 232 | 43 | −381 | 398 | 105 | −627 | 212 | −466 | −721 | 275 | 393 | 45 | 95 | 361 | 119 | −370 | −295 | −245 | |
| C | −1456 | −5471 | −706 | −2181 | −359 | −701 | −1378 | * | * | | | | | | | | | | | | |
| 66 | −316 | −3938 | −2281 | 403 | −4484 | 2693 | −1933 | −4104 | 2190 | −3937 | −3126 | −2078 | −3542 | −1504 | −30 | −2565 | −2598 | −3712 | −3970 | −3504 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −81 | −9152 | −4239 | −894 | −1115 | −4879 | −50 | * | * | | | | | | | | | | | | |
| 67 | 1559 | −2955 | 1153 | 1329 | −3273 | −2462 | −1122 | −670 | 808 | −2970 | −2045 | 500 | −2556 | 434 | −1211 | −1370 | 692 | −829 | −3140 | −2459 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −4 | −9075 | −10117 | −894 | −1115 | −1498 | −630 | * | * | | | | | | | | | | | | |
| 68 | −692 | −3466 | 1886 | −1295 | −3786 | −263 | −1629 | −3535 | −2 | −1277 | −2555 | 481 | −239 | −1169 | 2440 | −495 | 630 | −3087 | −3650 | −2968 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9739 | −10781 | −894 | −1115 | −3291 | −155 | * | * | | | | | | | | | | | | |
| 69 | −2041 | 1927 | 226 | 1172 | −3833 | 940 | 1393 | −538 | −1254 | −3529 | −2602 | −261 | −497 | 483 | −109 | 1511 | −254 | −3135 | −3696 | −3014 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −9798 | −10840 | −894 | −1115 | −3347 | −149 | * | * | | | | | | | | | | | | |
| 70 | −917 | −3569 | −397 | 1431 | −3884 | 92 | 997 | −788 | −1327 | −3583 | −2661 | 1496 | 2051 | −1283 | −1835 | −500 | −2047 | −3188 | −3756 | 1942 | 83 |
| — | −149 | −500 | 232 | 42 | −373 | 399 | 105 | −627 | 210 | −467 | −721 | 275 | 395 | 48 | 95 | 359 | 117 | −370 | −295 | −250 | |
| H | −56 | −4732 | −10887 | −2187 | −358 | −4216 | −80 | * | * | | | | | | | | | | | | |
| 71 | 41 | −3367 | −2031 | −215 | −638 | 940 | −1773 | −3307 | 670 | −58 | −2477 | 662 | −3196 | 150 | 638 | −2019 | 262 | 1028 | −3599 | 1170 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9845 | −10887 | −894 | −1115 | −4216 | −80 | * | * | | | | | | | | | | | | |
| 72 | −645 | −2190 | −4633 | −4003 | −2153 | −3904 | 761 | 1500 | 732 | 1485 | −1393 | −3526 | −3953 | −3254 | −3439 | −2987 | 1077 | 1645 | −2662 | −2318 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9845 | −10887 | −894 | −1115 | −4216 | −80 | * | * | | | | | | | | | | | | |
| 73 | 541 | −3551 | 403 | 837 | −3872 | −3053 | −1711 | −1351 | 1373 | −1456 | −2641 | −314 | 1364 | 1281 | −775 | −57 | 506 | −1305 | −3735 | −3052 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9845 | −10887 | −894 | −1115 | −1820 | −481 | * | * | | | | | | | | | | | | |
| 74 | −2408 | −2624 | −182 | 794 | 1709 | −3728 | 486 | 458 | −2617 | 1378 | −1810 | −2839 | −3797 | −307 | −723 | −461 | −506 | 185 | −3039 | 1260 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10047 | −11089 | −894 | −1115 | −2070 | −392 | * | * | | | | | | | | | | | | |
| 75 | −830 | −3805 | 1765 | 770 | −4126 | −447 | −1964 | −911 | 1626 | −3821 | −2894 | 1209 | −3399 | 965 | −2052 | −941 | 944 | −957 | −3988 | −3305 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10150 | −11192 | −894 | −1115 | −78 | −4251 | * | * | | | | | | | | | | | | |
| 76 | 844 | −4036 | −2546 | −1997 | −4318 | −3649 | −14 | −4041 | 620 | −2076 | −19 | −430 | 2001 | −507 | 1979 | −271 | −92 | 61 | −4243 | −452 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | 13 | 352 | 719 | 2363 | −4439 | −1193 | −2284 | −574 | 221 | −4135 | −3209 | −122 | −1231 | 590 | −2372 | 140 | −2590 | 568 | −4304 | −837 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −819 | −10521 | −1210 | −894 | −1115 | −701 | −1378 | * | * | | | | | | | | | | | | |
| 78 | 1353 | −3303 | 1494 | −1687 | −3806 | 123 | −1975 | −3512 | −1607 | −3556 | −2678 | −1944 | −3287 | −1553 | 1305 | 651 | 938 | 1004 | −3796 | −3178 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −3 | −9704 | −10747 | −894 | −1115 | −43 | −5085 | * | * | | | | | | | | | | | | |
| 79 | 1397 | −4121 | −789 | 606 | −897 | −204 | −2284 | −4191 | −1864 | −1653 | −3210 | 1624 | −3718 | 1172 | 571 | −309 | 1275 | −3742 | −4305 | −540 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10521 | −11563 | −894 | −1115 | −701 | −1378 | * | * | | | | | | | | | | | | |
| 80 | −957 | −3941 | −6899 | −6444 | −4375 | −6425 | −5756 | 1973 | −6226 | 942 | −3275 | −6089 | −860 | −5997 | −6188 | −5644 | −106 | 2826 | −5464 | −5053 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 81 | −1168 | 1315 | −5268 | −4633 | −627 | −4472 | −3344 | 1420 | −4228 | 1035 | −1949 | −4118 | −4521 | 2315 | −4029 | −3557 | −243 | 1754 | 1912 | −2866 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 82 | −1199 | 891 | −5255 | −4619 | 2213 | −1095 | −3329 | −824 | −4214 | 477 | 2013 | −4103 | −843 | −3837 | −4014 | −1727 | 1198 | 1461 | −3194 | 1264 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 83 | −82 | 537 | −5198 | −4566 | −447 | 1589 | −3320 | −212 | −4174 | 631 | −1948 | −900 | 142 | −3807 | −3994 | 1530 | 1053 | −710 | −3202 | −2859 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 84 | −1001 | −3967 | −2616 | −2068 | −4239 | 1511 | −2364 | −3943 | −1977 | −3974 | 71 | 1025 | 982 | −225 | −743 | 2052 | 182 | −43 | −4214 | −3577 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 85 | −3631 | 1866 | −926 | −6083 | −6922 | 3647 | −5972 | −6773 | −6605 | −7006 | −6055 | −5047 | −5279 | −5980 | −6447 | −1096 | −4104 | −5461 | −7115 | −7019 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 86 | 1655 | 543 | −5439 | −4870 | 1419 | −24 | −3649 | −2617 | −4483 | −2971 | −2319 | −4276 | −4644 | −4111 | −4301 | 1258 | 1771 | −763 | −3568 | 1775 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 87 | −96 | 545 | 1701 | −1972 | −4382 | 1669 | 180 | −993 | 921 | −1838 | −3175 | 256 | −3729 | −176 | −2389 | −108 | 648 | −813 | −4276 | −3605 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −21 | −10521 | −6155 | −894 | −1115 | −701 | −1378 | * | * | | | | | | | | | | | | |
| 88 | 2212 | −4114 | −2489 | 1541 | −4433 | 284 | 1030 | −4181 | −1870 | −4131 | −3208 | −2260 | −955 | 720 | −2377 | 738 | −856 | −3736 | −4303 | −170 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10501 | −11543 | −894 | −1115 | −471 | −1845 | * | * | | | | | | | | | | | | |
| 89 | 1211 | 118 | −5249 | −4614 | −2699 | 467 | −3334 | 637 | −4212 | 1076 | 465 | 2020 | −4512 | −3838 | −4017 | −563 | −2856 | 916 | −3203 | −2861 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 90 | −487 | −3851 | −343 | −2115 | −4060 | −1403 | −522 | 2077 | −841 | 805 | −2971 | 556 | −846 | −374 | 1648 | −1033 | −2620 | −316 | 428 | −3498 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 91 | 160 | −3576 | 756 | 1013 | 508 | 369 | −2513 | −136 | −2240 | 356 | −2722 | −612 | −3903 | 958 | −2682 | 148 | −1115 | 409 | −3893 | 513 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 92 | 1309 | −2790 | −4836 | −1088 | −896 | 221 | 3 | −31 | −3903 | 869 | 248 | −289 | −4447 | −623 | −3845 | −534 | 1199 | 839 | −3240 | −238 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 93 | 1742 | 1506 | −5264 | −4629 | 304 | −1002 | −3340 | 1070 | −4224 | 1889 | −1948 | −4113 | −4516 | −3847 | −4024 | −1457 | −1552 | 107 | −3205 | −2863 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |

-continued

| 94 | −233 | 531 | 1027 | 435 | 1333 | −1743 | −2835 | 1393 | −1049 | −30 | 1338 | −712 | 573 | −2723 | −3155 | −671 | 199 | −1024 | −3527 | −3101 | 112 |
|---|---|---|---|---|---|---|---|---|---|---|---|---|---|---|---|---|---|---|---|---|---|
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 95 | 697 | −2785 | −4873 | −4260 | 2638 | −1473 | −3250 | −758 | −3931 | −221 | 1430 | −3919 | −4453 | 1157 | 1656 | −1373 | 834 | −2202 | −3236 | −2884 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 96 | 1205 | 2847 | −5256 | −4620 | 396 | −1360 | −3330 | 810 | −4215 | 1643 | 227 | −4105 | −4509 | 165 | −4016 | −3544 | −174 | 261 | −3196 | −2854 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 97 | 1152 | 398 | −5205 | −1751 | 1489 | −912 | −3319 | −79 | −141 | 1266 | 1054 | −4080 | −4501 | −1102 | −3995 | −162 | 310 | −800 | 1150 | −267 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −898 | −10521 | −1112 | −894 | −1115 | −701 | −1378 | * | * | | | | | | | | | | | | |
| 98 | −459 | 2585 | −14 | −1202 | −3695 | 199 | 736 | −3445 | 1316 | −3390 | −2464 | −1513 | −60 | 194 | 2190 | −592 | 320 | −2996 | −3558 | −2876 | 116 |
| — | −149 | −500 | 232 | 43 | −381 | 399 | 105 | −627 | 210 | −466 | −721 | 277 | 393 | 45 | 95 | 359 | 119 | −370 | −285 | −246 | |
| H | −711 | −4865 | −1495 | −2153 | −368 | −40 | −5175 | * | * | | | | | | | | | | | | |
| 99 | 1288 | 1592 | −3961 | −950 | 1191 | −1111 | 597 | 563 | −350 | 1222 | −1827 | −84 | −4058 | −746 | −3277 | −833 | −2528 | −727 | −3068 | 562 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10216 | −11258 | −894 | −1115 | −2422 | −298 | * | * | | | | | | | | | | | | |
| 100 | −1041 | −3505 | 1338 | 473 | 1065 | −1093 | −2196 | −1214 | −1866 | −907 | 891 | 2637 | 601 | −1809 | −2334 | −1199 | −304 | −3044 | −3786 | −824 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10251 | −11293 | −894 | −1115 | −100 | −3902 | * | * | | | | | | | | | | | | |
| 101 | 544 | −4123 | −753 | −827 | −4444 | 276 | 1136 | −1307 | 980 | −4139 | −3212 | −2261 | 2828 | −1824 | 172 | −621 | −42 | −3745 | −4307 | −3624 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 102 | −1485 | −4137 | 250 | 483 | −1246 | 2780 | 371 | −4208 | 1245 | −4153 | −3227 | −2270 | −3730 | 97 | −2387 | −424 | −2605 | −1713 | −4321 | −3638 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −42 | −10521 | −5148 | −894 | −1115 | −701 | −1378 | * | * | | | | | | | | | | | | |
| 103 | −1419 | 1762 | 2916 | 382 | −4409 | −3591 | −2250 | −4159 | −886 | −2094 | −3178 | −2227 | −3685 | 282 | 986 | 936 | −249 | −3711 | −4273 | −3590 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10480 | −11522 | −894 | −1115 | −1531 | −613 | * | * | | | | | | | | | | | | |
| 104 | 875 | −4079 | −816 | 868 | −4397 | 343 | −2250 | −41 | 274 | −407 | −3170 | 619 | 274 | 162 | 723 | −2497 | −103 | 102 | −4265 | −385 | 127 |
| — | −149 | −500 | 235 | 43 | −381 | 399 | 106 | −626 | 210 | −466 | −720 | 275 | 394 | 45 | 96 | 359 | 117 | −369 | −294 | −249 | |
| E | −28 | −5741 | −11522 | −205 | −2913 | −352 | −2208 | * | * | | | | | | | | | | | | |
| 105 | 0 | −4038 | −7058 | −6631 | 1332 | −6667 | −6090 | 2831 | −6452 | −892 | −3362 | −6318 | −6523 | −6252 | −6450 | −5914 | −1105 | 2323 | −5738 | −5313 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 106 | −443 | −3026 | −5560 | −4933 | 851 | −4782 | −3616 | 1350 | −4534 | 1897 | −2066 | −4422 | −4806 | −4131 | −4327 | −3873 | −3157 | 1302 | 3142 | 1078 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 107 | 41 | −2737 | −5252 | −1314 | −625 | −1399 | −3328 | 1967 | −4211 | 317 | 968 | −4102 | −4507 | −3835 | −4013 | 998 | −897 | 1846 | −3194 | −265 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 108 | −1200 | 1375 | 1997 | −3160 | 893 | −1610 | 386 | −3181 | −3053 | −1711 | −2738 | −3253 | 2974 | −2926 | −3387 | 605 | −2955 | −2997 | −3944 | −3504 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 109 | 1151 | −4123 | 1494 | 393 | −4444 | −1193 | −2283 | −767 | −180 | −2025 | −3212 | 397 | 364 | −300 | 11 | 536 | 1001 | −1693 | −4306 | −3624 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 110 | −2979 | −2807 | −5291 | −4661 | −2700 | −1709 | −3368 | −841 | −4254 | 544 | −1987 | −4154 | 3717 | −551 | −4063 | −3606 | −2920 | −929 | 866 | −300 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111 | −1059 | −3138 | −4757 | −4218 | −528 | 490 | −3538 | −2850 | −3970 | −3185 | −2516 | 1431 | −4565 | −3724 | −4035 | 1258 | 2316 | −190 | −3750 | 2290 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 112 | −7183 | −6090 | −7545 | −7907 | 1944 | −7429 | 3149 | −6066 | −7462 | −5368 | −5466 | −6034 | −7282 | −6176 | −6820 | −1393 | −7030 | −6223 | 4459 | 3377 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 113 | 1463 | −3883 | 101 | −372 | −4105 | 884 | −2382 | −3787 | −2016 | −1624 | −3004 | −2394 | 2063 | −1965 | −2501 | 1065 | −264 | −640 | −4135 | −398 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 114 | 131 | −3797 | −2705 | −36 | 29 | −374 | 195 | −1363 | −2058 | −1721 | 1855 | 2006 | −848 | 453 | −2533 | 1854 | −2627 | −3348 | −4065 | −353 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 115 | −4184 | −3916 | −6345 | −5834 | 1730 | −5671 | 3377 | 398 | −5438 | −698 | 1765 | −5160 | −5630 | −4884 | −5170 | −4785 | −4112 | −989 | −3347 | 3507 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 116 | −2 | −4121 | 385 | −193 | −4442 | −1312 | −170 | 1260 | 1127 | −937 | −3211 | 682 | 531 | −197 | −695 | 341 | −29 | −569 | −4305 | −189 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 117 | −731 | −4123 | 1033 | 802 | −4444 | −1698 | 252 | −1346 | −134 | −1773 | 60 | 892 | 270 | 150 | 1432 | −521 | 674 | 363 | −4306 | −3624 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 118 | 461 | 392 | 879 | −4281 | −2741 | 1267 | −3255 | 1698 | −3949 | −755 | −36 | 124 | −4456 | −795 | −3870 | −19 | −2836 | 973 | −3233 | 477 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 119 | 1290 | 2679 | −5526 | −4901 | 2214 | −4751 | −3638 | 1490 | −4507 | 800 | −2106 | −4398 | −4783 | −4126 | −4310 | −3844 | −3108 | 1067 | 459 | −3142 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 120 | −228 | −4123 | −2498 | 1257 | −4444 | −1456 | −2283 | −1617 | 1497 | −4139 | −3213 | 935 | −3718 | 831 | 2432 | −1122 | −363 | −1276 | −4307 | −3624 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 121 | 732 | −2858 | −82 | −3854 | −2829 | 63 | −231 | 656 | −3596 | 1758 | 309 | −905 | −4376 | −3355 | −1237 | −697 | −925 | −2281 | 2951 | 443 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 122 | 1650 | 2229 | −3418 | −1016 | −3234 | −1735 | 202 | −933 | −2712 | −1510 | 157 | 1009 | −4101 | −2600 | 1197 | 1115 | −883 | −1346 | −3590 | 1022 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 123 | −2667 | −4141 | −154 | −951 | −4462 | 2661 | 249 | −4213 | 297 | −4156 | −3230 | −2272 | −1012 | 858 | 1128 | −778 | 675 | −3763 | −4323 | −3640 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 124 | 926 | 1264 | −5253 | −4617 | 1104 | 1616 | −3328 | 750 | −4212 | 281 | 675 | −4102 | −4507 | −3836 | 173 | −466 | −899 | 709 | −3194 | −2852 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 125 | 131 | −4123 | −112 | 1879 | −4444 | −486 | −2283 | −1994 | 1493 | −4139 | −3212 | −2260 | 880 | 235 | −751 | −1540 | 836 | 311 | −4306 | −3624 | 149 |
| — | −150 | −501 | 234 | 46 | −381 | 398 | 105 | −627 | 211 | −467 | −721 | 278 | 393 | 50 | 95 | 358 | 116 | −370 | −295 | −250 | |
| E | −230 | −2766 | −11563 | −31 | −5557 | −701 | −1378 | * | * | | | | | | | | | | | | |
| 126 | −1199 | 544 | −5251 | −4615 | 741 | −4457 | −3328 | 1220 | −655 | 386 | 261 | −4101 | 671 | −1105 | −326 | −3541 | −969 | 2303 | 1689 | −2852 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 127 | −1398 | −2953 | −907 | −3475 | 126 | −4223 | 139 | 1282 | −72 | −1969 | 1027 | −3440 | −4288 | 402 | 1635 | −251 | −2787 | 1690 | −3380 | 1550 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128 | −2662 | −4012 | −2560 | 751 | −31 | −3656 | −18 | −634 | −130 | −1099 | −3115 | −665 | 1163 | 375 | 1309 | −148 | 1022 | −56 | −4226 | 1677 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 129 | −1229 | 399 | −5257 | −4621 | 1726 | −1399 | −3330 | 901 | −4216 | −2586 | 338 | −4105 | −4509 | −3839 | −4016 | −3543 | −966 | 1867 | 525 | 3324 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 130 | 1053 | −4123 | −972 | 309 | −4444 | −3624 | 1890 | −4195 | 243 | −1935 | −772 | 1101 | 2255 | −1823 | 1201 | −754 | −1416 | −3745 | −4307 | −3624 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −426 | −10521 | −1972 | −894 | −1115 | −701 | −1378 | * | * | | | | | | | | | | | | |
| 131 | −951 | 3398 | −4877 | −4241 | −348 | −4079 | −2950 | −300 | −3835 | 1423 | −1560 | −3725 | −4129 | −3458 | −607 | −3164 | 96 | 201 | 1089 | 2740 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10097 | −11139 | −894 | −1115 | −3719 | −114 | * | * | | | | | | | | | | | | |
| 132 | −1236 | −3728 | 453 | 534 | −693 | −3269 | 612 | −3775 | 51 | −592 | −2821 | 308 | −3362 | −1474 | 799 | 42 | 846 | −1165 | 736 | 2730 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −361 | −10097 | −2182 | −894 | −1115 | −3719 | −114 | * | * | | | | | | | | | | | | |
| 133 | −231 | −3465 | 1999 | −33 | −3785 | −2968 | 488 | −3535 | 761 | −3481 | −2555 | −1604 | 1146 | 124 | −1715 | 1632 | −1934 | −785 | 1473 | −2967 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −3 | −9738 | −10781 | −894 | −1115 | −4365 | −72 | * | * | | | | | | | | | | | | |
| 134 | 885 | 76 | −97 | 1765 | −3772 | −2992 | −1662 | −794 | −1252 | −3475 | −2559 | −1635 | 1647 | 524 | −1758 | 1604 | −1963 | −3078 | −3657 | −2982 | 159 |
| — | −148 | −502 | 235 | 46 | −383 | 398 | 104 | −628 | 211 | −466 | −722 | 276 | 392 | 47 | 102 | 357 | 118 | −371 | −296 | −251 | |
| T | −279 | −2511 | −10781 | −1801 | −488 | −1288 | −760 | * | * | | | | | | | | | | | | |
| 135 | −15 | −3893 | 1846 | 1391 | −4210 | −1108 | −2029 | −3965 | 1126 | −3907 | −2986 | 2118 | 724 | −56 | −2143 | −991 | −2351 | −3513 | −4075 | −3384 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10097 | −11139 | −894 | −1115 | −3719 | −114 | * | * | | | | | | | | | | | | |
| 136 | −2610 | −4114 | 2136 | −370 | −4426 | 1186 | −2209 | −4187 | −670 | −4126 | −3214 | 2278 | −3616 | −1761 | −777 | 569 | 970 | −3733 | −4295 | −3589 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −42 | −10097 | −5187 | −894 | −1115 | −3719 | −114 | * | * | | | | | | | | | | | | |
| 137 | −2450 | 497 | −3792 | −3208 | 3092 | −134 | 110 | −701 | −274 | −2368 | 521 | −574 | −3915 | −421 | 243 | −2883 | −2390 | −1936 | 3633 | 979 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10057 | −11099 | −894 | −1115 | −208 | −2898 | * | * | | | | | | | | | | | | |
| 138 | −1444 | −4088 | −2462 | 393 | −541 | 725 | 3060 | −4159 | 1127 | −1698 | −3177 | 153 | −3682 | 1560 | 178 | 63 | 307 | −3709 | −4271 | −3588 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10480 | −11522 | −894 | −1115 | −1531 | −613 | * | * | | | | | | | | | | | | |
| 139 | −460 | 1607 | −5206 | −4571 | −840 | −1369 | 202 | 1773 | −4168 | 1388 | 177 | 1693 | −896 | −611 | −3973 | −3503 | −2813 | 887 | −3158 | −2816 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10480 | −11522 | −894 | −1115 | −352 | −2208 | * | * | | | | | | | | | | | | |
| 140 | −3545 | −4834 | 3599 | −2630 | −5125 | −4273 | −3036 | −1459 | −1106 | −1960 | −3982 | 53 | −4472 | −2629 | −970 | −3421 | 1523 | −4447 | −5008 | −4393 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 141 | 572 | −2737 | −5247 | −4612 | 2143 | −4456 | −3327 | 155 | −598 | 724 | 2379 | −4100 | −1297 | −1311 | −1637 | −2096 | −1047 | 1403 | 441 | −298 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 142 | −815 | −4124 | 2081 | 1826 | −4445 | −1142 | −36 | −4196 | 423 | −4140 | −3213 | 189 | −349 | 1437 | −2371 | −827 | −335 | −41 | −4308 | −3625 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 143 | 1892 | −4143 | 1569 | −120 | −4464 | 1034 | 1808 | −4215 | 446 | −1775 | −3233 | −743 | −3733 | 892 | −2391 | −999 | −2608 | −3765 | −4327 | −3643 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 144 | −350 | −3050 | −5587 | −4952 | 175 | −4805 | −3668 | 956 | −4553 | 2475 | 1709 | −4452 | −4821 | −4142 | −4342 | −3895 | −3177 | 439 | 828 | 475 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145 | −536 | 1226 | 626 | 2225 | −4228 | −3668 | −2334 | 286 | 151 | 785 | −378 | −2332 | −3759 | 137 | −741 | −1107 | −38 | −1490 | −4196 | −3556 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 146 | 1140 | 542 | 799 | 1278 | −4444 | −1456 | −2283 | −752 | 37 | −4139 | −3212 | 823 | −893 | 46 | 1106 | −185 | 187 | −3745 | −66 | −421 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −110 | −10521 | −3785 | −894 | −1115 | −701 | −1378 | * | * | | | | | | | | | | | | |
| 147 | 2120 | −3826 | 1153 | −1973 | −4061 | −1479 | −2260 | −1211 | 995 | 814 | −2939 | −2266 | −3681 | −298 | −689 | −1324 | −193 | −963 | −4063 | −3437 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10412 | −11454 | −894 | −1115 | −2293 | −329 | * | * | | | | | | | | | | | | |
| 148 | −4599 | −4218 | −7029 | −6476 | −3493 | −6492 | −5400 | 2205 | −1200 | 2405 | −2418 | −6139 | −6235 | −5596 | −5931 | −5678 | −4530 | −196 | −4785 | 2087 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10412 | −11454 | −894 | −1115 | −2293 | −329 | * | * | | | | | | | | | | | | |
| 149 | 69 | −4030 | 1490 | 1155 | −4351 | −434 | −2189 | −4102 | 1670 | −1639 | −3120 | 186 | −3624 | −1729 | 833 | 301 | 649 | −3652 | −4214 | −3531 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −81 | −10412 | −4215 | −894 | −1115 | −2293 | −329 | * | * | | | | | | | | | | | | |
| 150 | −740 | −3962 | 660 | 1834 | −4283 | −1398 | −2120 | −4033 | 1749 | −3978 | −3051 | 422 | −265 | 388 | 326 | 702 | −97 | −3584 | −4145 | −3462 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −396 | −10333 | −2062 | −894 | −1115 | −2839 | −217 | * | * | | | | | | | | | | | | |
| 151 | 2243 | 912 | 271 | −2000 | −270 | −1679 | 720 | −17 | −1883 | 50 | −2090 | −192 | 523 | 96 | −2296 | −71 | −2180 | −2423 | −3278 | −2779 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −125 | −9939 | −3613 | −894 | −1115 | −4060 | −89 | * | * | | | | | | | | | | | | |
| 152 | −8 | 957 | −489 | −1427 | −3656 | −3066 | 1629 | −565 | −551 | −1785 | −2499 | −1727 | 2293 | 1841 | −177 | 457 | −193 | −714 | −3613 | −2968 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −109 | −9817 | −3801 | −894 | −1115 | −4259 | −77 | * | * | | | | | | | | | | | | |
| 153 | 369 | −3418 | −1830 | 2165 | −3727 | 138 | −1610 | −3470 | 472 | −1441 | −2510 | −1590 | 1189 | 644 | −1700 | −86 | −675 | −599 | −3608 | 182 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −3 | −9710 | −10752 | −894 | −1115 | −4401 | −70 | * | * | | | | | | | | | | | | |
| 154 | 207 | −3443 | 319 | −90 | −546 | 1945 | 562 | −3514 | 407 | −1099 | −2532 | 688 | −3037 | 1006 | 752 | −401 | −1909 | −3065 | −3626 | −2943 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9710 | −10752 | −894 | −1115 | −4401 | −70 | * | * | | | | | | | | | | | | |
| 155 | −222 | −3441 | 1177 | 24 | −164 | 685 | −1605 | −3510 | −1187 | −3457 | −2531 | 1949 | −3040 | 352 | 437 | 1221 | −1912 | −93 | −3626 | −2944 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −3 | −9710 | −10752 | −894 | −1115 | −4401 | −70 | * | * | | | | | | | | | | | | |
| 156 | 622 | −2145 | −441 | −3168 | 594 | −3615 | −2440 | 1589 | 176 | 123 | −1342 | −2990 | 823 | 1478 | −2965 | −2661 | −2107 | 1353 | −2588 | −2222 | 191 |
| — | −149 | −503 | 230 | 45 | −383 | 396 | 103 | −625 | 214 | −464 | −723 | 282 | 398 | 46 | 96 | 356 | 117 | −372 | −283 | −252 | |
| E | −1940 | −2913 | −721 | −2692 | −243 | −43 | −5078 | * | * | | | | | | | | | | | | |
| 157 | −804 | −3752 | −2174 | 952 | −4096 | 48 | −1886 | −3828 | 2419 | −1418 | −2844 | −1905 | 983 | 233 | 1858 | −2191 | −2242 | −3388 | −3903 | −3256 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −9909 | −10951 | −894 | −1115 | −3057 | −185 | * | * | | | | | | | | | | | | |
| 158 | −646 | 1937 | −2306 | −345 | −3374 | −3285 | 1622 | 396 | −257 | −3161 | −2352 | −235 | 376 | −1594 | 533 | −2214 | 2058 | 1253 | −3507 | −2941 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9960 | −11003 | −894 | −1115 | −1810 | −484 | * | * | | | | | | | | | | | | |
| 159 | −838 | 653 | −418 | −1629 | −4041 | −130 | −1954 | −841 | 3136 | −3747 | −2833 | −1937 | −3386 | 70 | 250 | −840 | −578 | −1006 | −3934 | −3263 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10121 | −11163 | −894 | −1115 | −73 | −4332 | * | * | | | | | | | | | | | | |
| 160 | −496 | 537 | −5270 | −4635 | 1378 | 1026 | −3345 | 1138 | −4230 | 840 | 1624 | −4119 | −4522 | −3852 | −4030 | −3558 | −2864 | 1858 | 1504 | −2867 | 202 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 161 | −5585 | −5013 | −8106 | −7619 | 52 | −7928 | −6972 | 2097 | −7484 | 1535 | 1736 | −7624 | −7165 | −6517 | −7147 | −7308 | −5490 | 2447 | −5598 | −5721 | 203 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 162 | 126 | 572 | −5302 | −4667 | 1409 | −4507 | −3377 | 1677 | −4263 | 1583 | −1966 | −4152 | −4554 | −3884 | −4063 | −3592 | −2895 | 1652 | 956 | 629 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 163 | −524 | −2751 | −5268 | −4633 | 1246 | −4474 | 3060 | 1471 | −4229 | 570 | −1951 | −4119 | −4523 | −1368 | −4030 | −3559 | 1283 | 1401 | −3212 | −2869 | 205 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 164 | 1238 | 2407 | −68 | 1462 | −4501 | −412 | −2402 | −4243 | −2000 | −4209 | −3296 | 1734 | −1154 | −1951 | −2507 | −2631 | 1709 | −1153 | −4394 | −3721 | 206 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 165 | −3522 | 3531 | −6496 | −6709 | −6660 | 867 | −5985 | −6475 | −6528 | −6733 | −5796 | 2463 | −5216 | −6035 | −6280 | 2094 | 462 | −5272 | −6901 | −295 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 166 | 380 | 2749 | −6712 | −6252 | −4217 | −5950 | −5396 | −457 | −5985 | −872 | −3180 | −5770 | 3373 | −5699 | −5890 | −5168 | −4138 | 1348 | −5169 | −4790 | 208 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 167 | −2799 | −564 | −914 | −2156 | 1913 | −643 | 3653 | −3991 | −2108 | −4032 | −3174 | 1652 | −3884 | −177 | −2602 | 1400 | −2742 | −3636 | −4210 | 143 | 209 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 168 | −610 | −4432 | −4572 | −4949 | −6846 | −4492 | 286 | −6780 | −5902 | −6952 | −6058 | 3954 | −5265 | −5350 | −6083 | 1483 | −4187 | −5550 | −7038 | −6688 | 210 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 169 | −1352 | −4234 | −5864 | −6213 | −6776 | −4467 | −5933 | −6637 | −6392 | −6854 | 2889 | −682 | 3923 | −5947 | −6221 | −3854 | −4081 | −5399 | −7002 | −6858 | 211 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 170 | −3020 | 1899 | 1467 | −1156 | −3249 | −4288 | −3241 | −835 | −3484 | 204 | −2448 | −3534 | −4438 | −3275 | −3691 | −124 | 3114 | −2661 | −3685 | −3292 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 171 | −663 | −4957 | −7140 | −7507 | −7496 | 3782 | −6740 | −7514 | −7451 | −7655 | −6800 | −6036 | −5964 | −6951 | −7058 | −4710 | −4922 | −6247 | −7264 | −7640 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 172 | 488 | −3322 | 1044 | −2657 | −901 | −1612 | −2673 | 359 | 407 | −898 | 14 | −2841 | −4028 | −462 | −704 | 596 | 1853 | 721 | −3689 | −3217 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 173 | 1133 | −2774 | 1767 | −4329 | −2733 | −4411 | −3266 | 1021 | −1334 | 456 | −411 | −859 | −4464 | −3666 | −3892 | −1373 | −386 | 1731 | −3227 | −233 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10521 | −11563 | −894 | −1115 | −701 | −1378 | * | * | | | | | | | | | | | | |
| 174 | 1520 | 573 | −5255 | −4619 | 1239 | −4457 | −3329 | −78 | −4214 | 1269 | 405 | −4103 | 1545 | −3837 | −4014 | −1882 | −897 | −797 | 1151 | 1139 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 175 | −1076 | −4228 | 1404 | −2027 | −4561 | −3698 | −2388 | −4313 | −145 | −4257 | −3335 | 1229 | 2004 | −1932 | −1064 | 1214 | 1925 | −3861 | −4425 | −3738 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 176 | −41 | 698 | −3166 | 69 | −1319 | −3930 | 769 | −530 | 547 | 1388 | −2520 | −845 | 1441 | −2395 | 1574 | −2888 | −1022 | −1113 | −3716 | −3237 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 177 | 954 | −4138 | 1394 | 2285 | −4458 | −1309 | −2294 | −4210 | 946 | −4154 | −3227 | −106 | 508 | −299 | −725 | −467 | −2603 | −3760 | −4321 | −3637 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 178 | −1430 | −4128 | 1567 | 2148 | −724 | −1391 | 1075 | −4199 | −15 | −1935 | −3217 | −2264 | −3722 | 2348 | −2377 | −2536 | 774 | −3750 | −4311 | −3629 | 220 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 179 | −5029 | −4639 | −7259 | −6734 | −525 | −6709 | −4962 | 1405 | −6397 | 2191 | −2443 | −6239 | −6401 | −5626 | −6059 | −5878 | −4931 | 895 | 4069 | 517 | 221 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 180 | −1117 | 2062 | −933 | 1498 | −4432 | −3626 | 174 | −4180 | 1319 | −339 | −222 | −1020 | −3720 | 1052 | 1111 | −2533 | 229 | 697 | −4301 | −3620 | 222 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 181 | 611 | −4123 | 1406 | 1372 | −4444 | −3624 | −2283 | −1002 | 1898 | −2359 | −698 | −1124 | −1287 | 1005 | −903 | −1663 | 861 | −3745 | −4307 | −3624 | 223 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 182 | −1471 | −4643 | −7625 | −7121 | −583 | −7259 | −6333 | 2471 | −6915 | 2086 | 1048 | −6931 | −6804 | −6215 | −6677 | −6526 | −5048 | 1419 | −5402 | −5360 | 224 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −373 | −10521 | −2139 | −894 | −1115 | −701 | −1378 | * | * | | | | | | | | | | | | |
| 183 | 1913 | −2405 | −4917 | −4281 | −717 | −1027 | −2995 | 195 | −3877 | 1576 | −71 | −3768 | −4174 | −3501 | −509 | −808 | −867 | 889 | −2862 | 103 | 225 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10150 | −11192 | −894 | −1115 | −3574 | −127 | * | * | | | | | | | | | | | | |
| 184 | 903 | −3811 | 1984 | 1667 | −4132 | −3309 | −1969 | −3883 | 207 | −3827 | −2901 | −175 | −3403 | 1182 | 410 | −224 | 348 | −3433 | −3994 | −3311 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10150 | −11192 | −894 | −1115 | −3574 | −127 | * | * | | | | | | | | | | | | |
| 185 | −866 | −2422 | −4768 | −4142 | 1957 | −4103 | 312 | 1089 | −1001 | 1409 | −1624 | −671 | −4155 | −3421 | 329 | −976 | −667 | 1402 | −2877 | −2532 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10150 | −11192 | −894 | −1115 | −78 | −4251 | * | * | | | | | | | | | | | | |
| 186 | 1506 | 2123 | −5154 | −4524 | −881 | −4443 | −3309 | 600 | 283 | −445 | −85 | −988 | −1162 | 264 | −3976 | −276 | 345 | 1423 | 760 | −2859 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 187 | 64 | −4123 | 614 | 430 | −4444 | −3624 | −36 | −4195 | 1688 | −1187 | −312 | 967 | −124 | 1146 | 1166 | −2531 | −119 | −614 | −4306 | −500 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −100 | −10521 | −3910 | −894 | −1115 | −701 | −1378 | * | * | | | | | | | | | | | | |
| 188 | 917 | −4042 | −700 | 1834 | −4364 | −1259 | −2201 | −4114 | 1722 | −4058 | −3132 | −2178 | −3636 | 978 | 1506 | 84 | −2508 | −3665 | 746 | −3543 | 230 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −160 | −10422 | −3266 | −894 | −1115 | −2211 | −351 | * | * | | | | | | | | | | | | |
| 189 | −935 | −3854 | −2345 | −1793 | −612 | −3447 | 3248 | −3872 | 1533 | −768 | −2952 | 1050 | −3539 | −93 | 843 | −760 | −2401 | −3461 | −4051 | 2345 | 231 |
| — | −149 | −500 | 232 | 43 | −381 | 398 | 105 | −627 | 212 | −466 | −721 | 275 | 399 | 45 | 95 | 359 | 117 | −370 | −295 | −250 | |
| T | −159 | −3263 | −11306 | −51 | −4844 | −104 | −3850 | * | * | | | | | | | | | | | | |
| 190 | −2653 | 392 | −356 | −271 | −1226 | 1540 | 1409 | −4197 | 1436 | −4141 | −3215 | 2563 | −935 | −1825 | 325 | −959 | −2592 | −3747 | −4309 | −3626 | 233 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 191 | 966 | 573 | −5254 | −4618 | −398 | 387 | 612 | 1602 | −4213 | 692 | 191 | −4103 | −4507 | −3836 | −1145 | −554 | −133 | 1140 | 1381 | −2852 | 234 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 192 | −2915 | −2741 | −5260 | −4624 | 412 | −4462 | 2443 | 1374 | −4219 | 1587 | 953 | −4108 | −88 | −3841 | 73 | −3547 | −2855 | 278 | 2186 | 1133 | 235 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 193 | −1000 | −3706 | −6513 | −5990 | −3918 | −5888 | −5024 | 900 | −5693 | 1967 | −2929 | −5563 | 1816 | −5381 | −5575 | −5053 | −13 | 1883 | −4791 | −4427 | 236 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 194 | −5210 | −4777 | −7597 | −7005 | 2492 | −7100 | −5883 | 1388 | −6717 | 1524 | 1628 | −6771 | −6627 | −5876 | −6368 | −6309 | −5103 | 1801 | −4975 | 379 | 237 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 195 | −476 | 1508 | −5261 | −4625 | 1641 | −4464 | 207 | 1004 | −4220 | −41 | −1945 | −4110 | −4514 | −3843 | −4021 | 1138 | −1201 | 2302 | −3201 | −2859 | 238 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 196 | −5803 | −7089 | 4177 | −3842 | −7724 | −5441 | −5063 | −7999 | −5571 | −7753 | −7293 | −885 | −6032 | −4820 | −6485 | −5471 | −5945 | −7410 | −7366 | −6829 | 239 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 197 | −2930 | −3007 | 929 | 3182 | 939 | −4317 | −3124 | −965 | −3413 | −1559 | 1290 | −3556 | −4381 | −3212 | −3575 | −569 | −2871 | −1193 | −3441 | −3059 | 240 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 198 | 2874 | −3559 | −6292 | −5795 | −3871 | −5337 | −4734 | 2016 | −5463 | −3399 | 712 | −5216 | −5502 | −5132 | −5312 | −1509 | −942 | 537 | −4590 | −4229 | 241 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 199 | −7184 | −6092 | −7544 | −7906 | 642 | −7428 | 3344 | −6069 | −7462 | −5370 | −5469 | −6035 | −7283 | −6177 | −6821 | −6679 | −7033 | −6226 | −2853 | 4446 | 242 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 200 | 1422 | −3783 | −842 | 500 | −3969 | 1010 | −2412 | 604 | −2070 | −3740 | 287 | −2443 | −3822 | 2323 | −2544 | 369 | −2631 | −528 | −4055 | −349 | 243 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 201 | 245 | −4046 | 1571 | 712 | −4332 | 1829 | 1426 | −221 | −757 | −1825 | −3145 | −565 | −3740 | −1862 | −2407 | −2557 | 129 | 557 | −4251 | −3590 | 244 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 202 | −3291 | −3098 | −5626 | −4998 | 3170 | 1630 | −3670 | −1028 | −4599 | 598 | 1719 | −4488 | −4864 | −4181 | −4386 | −3940 | 853 | −2447 | −3453 | −239 | 245 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 203 | 1330 | 1393 | −5216 | 194 | −562 | 533 | −3321 | −2233 | −4186 | −807 | 741 | −4086 | −4502 | −3816 | −3999 | −562 | −1199 | 2383 | −3198 | −193 | 246 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 204 | −129 | −3103 | −1248 | −1069 | 2217 | −656 | 195 | −929 | −2898 | −706 | 209 | −1142 | 10 | −2764 | 226 | 701 | −884 | −1020 | 1119 | 2237 | 247 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −42 | −10521 | −5148 | −894 | −1115 | −701 | −1378 | * | * | | | | | | | | | | | | |
| 205 | −345 | −4183 | 198 | 679 | −4502 | 2887 | −2327 | −4256 | −260 | −4199 | −3275 | 208 | −1072 | −280 | −2433 | −658 | −814 | −3805 | −4366 | −3678 | 248 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −584 | −10480 | −1591 | −894 | −1115 | −1531 | −613 | * | * | | | | | | | | | | | | |
| 206 | 672 | −3625 | 1707 | 811 | −3945 | 736 | 27 | −3696 | −1364 | −3640 | −2715 | −93 | −405 | 288 | −1873 | 1507 | −24 | −3246 | −3808 | −3123 | 249 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −61 | −9898 | −4627 | −894 | −1115 | −1712 | −525 | * | * | | | | | | | | | | | | |
| 207 | −168 | 1738 | −442 | −1947 | 249 | −696 | −2108 | −2894 | 817 | 1105 | 1230 | −2191 | 1444 | 194 | −2280 | 501 | −604 | −2663 | −3472 | −2941 | 250 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1358 | −10046 | −716 | −894 | −1115 | −3843 | −104 | * | * | | | | | | | | | | | | |
| 208 | −117 | −3397 | 2295 | 1976 | −3684 | −2521 | −1406 | −3460 | −1145 | −363 | −2525 | 614 | 1395 | −983 | −1713 | −1689 | −1826 | −3006 | −3585 | −2840 | 251 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −5 | −8693 | −9735 | −894 | −1115 | −5096 | −43 | * | * | | | | | | | | | | | | |
| 209 | 840 | −2870 | −1296 | 2103 | −3223 | −2386 | 1908 | −2947 | 1671 | −2869 | −1962 | −1022 | −2472 | 960 | 488 | −1319 | −1367 | −2511 | −3007 | −2373 | 252 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | −8693 | −9735 | −894 | −1115 | −846 | −1173 | * | * | | | | | | | | | | | | |
| 210 | −674 | −3632 | 2606 | −355 | −3946 | −651 | −1812 | −524 | 163 | −461 | 498 | −1791 | −417 | −421 | 207 | 578 | −975 | −3250 | −3820 | 102 | 253 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −297 | −9963 | −2435 | −894 | −1115 | −4016 | −92 | * | * | | | | | | | | | | | | |
| 211 | 2296 | −2945 | −5113 | −4640 | 2846 | −4516 | 832 | −2514 | −4269 | −2751 | −2194 | −3983 | 1424 | −3806 | −4078 | −3630 | −3089 | −525 | −2262 | 724 | 254 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −142 | −9668 | −3433 | −894 | −1115 | −4450 | −68 | * | * | | | | | | | | | | | | |
| 212 | 556 | −2242 | −2801 | 941 | 115 | −3255 | −2017 | 488 | −486 | −2118 | −1424 | 97 | −3326 | 479 | −2355 | −2248 | −4 | 1268 | 2870 | 1723 | 255 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −3 | −9529 | −10571 | −894 | −1115 | −1243 | −792 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 213 | 1453 | −3690 | −2072 | 294 | −4008 | 69 | −1857 | −3757 | −1438 | −1453 | −2780 | −163 | 1320 | 106 | −230 | 1532 | 596 | −3311 | −3875 | −3194 | 256 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −309 | −10018 | −2382 | −894 | −1115 | −2852 | −215 | * | * | | | | | | | | | | | | |
| 214 | −369 | −2746 | −327 | −1917 | −2819 | −777 | 474 | 1461 | −1796 | 390 | −1907 | 748 | −3347 | 165 | 313 | −2220 | 1064 | 1356 | −3100 | −2612 | 257 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −575 | −9770 | −1609 | −894 | −1115 | −4323 | −74 | * | * | | | | | | | | | | | | |
| 215 | 1219 | −1816 | −3679 | −3089 | 588 | 2773 | −2217 | −1350 | −2739 | −647 | 817 | −2800 | −3387 | −2502 | 74 | −2366 | −1819 | −1265 | −2290 | −1926 | 258 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | −9199 | −10241 | −894 | −1115 | −4850 | −51 | * | * | | | | | | | | | | | | |
| 216 | 340 | 1442 | −1533 | 1691 | −3133 | −595 | −1275 | −2832 | −884 | 92 | −1994 | −1278 | −2699 | 220 | 2269 | −1523 | 178 | −2467 | −3113 | −2480 | 259 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −488 | −9199 | −1809 | −894 | −1115 | −4850 | −51 | * | * | | | | | | | | | | | | |
| 217 | −1792 | −2401 | −4580 | −4891 | −4961 | 3507 | −4265 | −4718 | −4829 | −5039 | −4116 | −3398 | −3478 | −4326 | −4561 | 469 | −2264 | −230 | −5200 | −5101 | 260 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −134 | −8716 | −3536 | −894 | −1115 | −5088 | −43 | * | * | | | | | | | | | | | | |
| 218 | −1841 | −1607 | −4203 | −3618 | −1693 | −3518 | −2494 | 2021 | −3267 | 1021 | −832 | −3162 | −3539 | −2928 | −3118 | 1080 | 600 | 1819 | −2342 | −1989 | 261 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −6 | −8587 | −9629 | −894 | −1115 | −5134 | −42 | * | * | | | | | | | | | | | | |
| 219 | 2480 | 3297 | −3710 | −3318 | −2547 | −2591 | 1869 | −2109 | −3050 | −2452 | −1754 | −2711 | −3104 | −2778 | −3062 | 615 | −1723 | 573 | −2978 | −2646 | 262 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −6 | −8587 | −9629 | −894 | −1115 | −5134 | −42 | * | * | | | | | | | | | | | | |
| 220 | −2042 | −3514 | 944 | 3034 | −3384 | −260 | −1531 | −3521 | −1386 | −3486 | −2672 | −1210 | −2885 | −1164 | −1974 | −1862 | −2022 | −3111 | 2572 | 1292 | 263 |
| — | −147 | −502 | 235 | 43 | −382 | 397 | 108 | −625 | 208 | −465 | −722 | 275 | 394 | 46 | 94 | 360 | 119 | −371 | −296 | −243 | |
| H | −111 | −3784 | −9629 | −3929 | −98 | −26 | −5811 | * | * | | | | | | | | | | | | |
| 221 | 3 | 446 | −4713 | −1335 | −2773 | −4371 | 268 | 1342 | −1512 | 371 | −2008 | −3834 | −441 | −487 | 2394 | −3430 | −2828 | 834 | 1144 | 551 | 282 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 222 | 1303 | 478 | 81 | −1626 | 867 | −703 | 705 | −190 | −3734 | 616 | −346 | −3782 | 833 | −685 | −3745 | 453 | −1043 | 214 | −3271 | −654 | 283 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 223 | −2654 | −4091 | 213 | −191 | 1963 | 748 | −2293 | −1401 | 56 | 833 | −3184 | 1419 | −3726 | −398 | −970 | −972 | 663 | −3705 | 818 | −3610 | 284 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 224 | 327 | −2754 | −1051 | −52 | −524 | −2055 | −3347 | 254 | −4221 | 1816 | 382 | −4115 | −4524 | −3847 | −4028 | −3559 | −2867 | 2236 | −3216 | −2874 | 285 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 225 | 1072 | −4123 | 895 | 1348 | −4444 | −350 | −2283 | −1259 | 699 | −4139 | 1738 | 102 | −3717 | −48 | −1173 | 1091 | −1003 | −2011 | −4306 | −3624 | 286 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 226 | 203 | −4124 | 1345 | 1449 | −4445 | 445 | −36 | −4195 | 707 | −4140 | −422 | −379 | 1209 | −592 | 535 | −1507 | 142 | −1535 | −4307 | −3624 | 287 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −41 | −10521 | −5202 | −894 | −1115 | −701 | −1378 | * | * | | | | | | | | | | | | |
| 227 | −386 | −550 | 545 | 986 | −4337 | 1336 | 1433 | −1932 | −71 | −1978 | −831 | −2248 | −3696 | −1812 | 747 | −596 | −864 | −1486 | −4236 | 2404 | 288 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −37 | −10481 | −5344 | −894 | −1115 | −1507 | −625 | * | * | | | | | | | | | | | | |
| 228 | −1015 | −2968 | 1470 | −1594 | −895 | −1164 | −197 | 1244 | −575 | −129 | −99 | −3202 | 1970 | −2830 | −3232 | −703 | −339 | 1030 | −3383 | −2978 | 289 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −20 | −10446 | −6293 | −894 | −1115 | −820 | −1205 | * | * | | | | | | | | | | | | |
| 229 | −322 | −4077 | 1250 | 1386 | −4398 | −1231 | 1577 | −4149 | −146 | −4093 | −3167 | 2217 | 440 | −1778 | −2325 | −491 | −1122 | −1241 | 1969 | −79 | 290 |
| — | −149 | −482 | 232 | 44 | −381 | 398 | 105 | −627 | 210 | −467 | −721 | 275 | 393 | 45 | 95 | 360 | 117 | −367 | −282 | −250 | |
| T | −5633 | −3231 | −195 | −318 | −2336 | −1075 | −929 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 230 | −1642 | −3350 | 1246 | 1147 | −3592 | −1915 | −1042 | −3428 | 802 | −3330 | −2532 | 3284 | −2319 | −662 | −1649 | −1388 | −1651 | −2943 | −3509 | −2651 | 293 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −11 | −7624 | −8666 | −894 | −1115 | −4175 | −82 | * | * | | | | | | | | | | | | |
| 231 | −1262 | −2460 | −1252 | −620 | −2828 | 1681 | −673 | −2466 | 1826 | −2418 | −1582 | −850 | −2246 | 1148 | 919 | −1172 | −1163 | 955 | −2556 | −2046 | 294 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1386 | −7896 | −706 | −894 | −1115 | −3591 | −125 | * | * | | | | | | | | | | | | |
| 232 | −1632 | −2633 | −1862 | −962 | −3200 | −2392 | −562 | −2717 | 2055 | −2511 | −1751 | −1051 | −2388 | 2350 | 2097 | −1521 | −1437 | −2415 | 2869 | −2175 | 295 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −13 | −7382 | −8424 | −894 | −1115 | −2216 | −350 | * | * | | | | | | | | | | | | |
| 233 | 123 | −2828 | 2416 | 900 | −3145 | 235 | −965 | −2899 | 343 | −2842 | −1920 | 274 | −2391 | 1164 | −1079 | −1218 | 576 | −2448 | −3010 | −2320 | 296 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −5 | −8735 | −9777 | −894 | −1115 | −3923 | −98 | * | * | | | | | | | | | | | | |
| 234 | −1531 | −1427 | −3468 | −2855 | 859 | −3030 | −1875 | 732 | −2516 | 1599 | −611 | 714 | −3082 | 603 | 1715 | −2097 | −1471 | 597 | −1875 | −1524 | 297 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −5 | −8864 | −9906 | −894 | −1115 | −453 | −1891 | * | * | | | | | | | | | | | | |
| 235 | −413 | 111 | 136 | −4348 | −605 | −1098 | −3070 | 981 | −3947 | 1794 | −1685 | −3841 | −4250 | −3573 | −771 | −3284 | 833 | 1599 | −2940 | −2598 | 298 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10234 | −11276 | −894 | −1115 | −95 | −3968 | * | * | | | | | | | | | | | | |
| 236 | 727 | 118 | −5264 | −4628 | 986 | −1850 | 2131 | 1784 | −4223 | 1452 | 300 | −4113 | −4516 | −3846 | −4023 | −3551 | −2859 | 1091 | −3203 | −2861 | 299 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 237 | −1203 | 137 | −5270 | −1270 | −2709 | −4477 | −3350 | 2220 | −4232 | 628 | −1956 | −4122 | −4526 | −3856 | −4033 | −1355 | 1194 | 2154 | −3215 | −269 | 300 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 238 | 637 | 2257 | −5256 | −1719 | −367 | −4459 | −3330 | −830 | −4215 | 1097 | 962 | −4105 | −4509 | −3838 | −4015 | 182 | 576 | 2093 | −3196 | −2854 | 301 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 239 | −2734 | −4069 | −2639 | −2093 | −4371 | 1746 | −2392 | −4086 | −1972 | −4088 | −3198 | 1164 | −3818 | 2282 | 1247 | −42 | −48 | −576 | −4300 | 1762 | 302 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 240 | −3542 | −4154 | −6751 | −7107 | −6886 | 977 | −6190 | −6718 | −6861 | −6976 | −5999 | −5251 | −5248 | −6283 | −6480 | 2673 | 2755 | −5378 | −7099 | −7087 | 303 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 241 | −1169 | 1205 | −5259 | −4623 | 2884 | −1213 | −3332 | −2229 | −4218 | 1631 | 1671 | −4107 | −4511 | −3841 | −4018 | −3546 | −935 | 76 | −3197 | 1548 | 304 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 242 | 1145 | −4136 | −6889 | −7241 | −6877 | 1417 | −6207 | −6705 | −6891 | −6966 | −5985 | −5262 | −5237 | −6309 | −6485 | 3082 | −1018 | −5361 | −7098 | −7091 | 305 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 243 | −5679 | −6012 | −6638 | −6016 | −7635 | −6027 | −5171 | −7416 | 4009 | −7100 | −6492 | −5723 | −6410 | −4866 | −3903 | −5788 | −1028 | −6876 | −6601 | −6815 | 306 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 244 | 1939 | −4015 | 941 | −2055 | −616 | −1388 | −2364 | −1377 | −1970 | −4033 | −3144 | 2033 | −3781 | −1924 | −746 | 1448 | −98 | −3628 | −4257 | −3609 | 307 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10521 | −11563 | −894 | −1115 | −701 | −1378 | * | * | | | | | | | | | | | | |
| 245 | −4245 | −3969 | −6293 | −5848 | 3287 | −5643 | 37 | −1042 | −5438 | 1104 | 2640 | −5049 | −5645 | −4877 | −232 | −4757 | −4176 | −3435 | 990 | 1774 | 308 |
| — | −149 | −500 | 233 | 43 | −381 | 400 | 106 | −626 | 210 | −466 | −720 | 275 | 394 | 45 | 96 | 359 | 117 | −369 | −294 | −249 | |
| T | −36 | −5370 | −11563 | −163 | −3229 | −701 | −1378 | * | * | | | | | | | | | | | | |
| 246 | 882 | −4115 | −6568 | −6801 | −6568 | 3244 | −5991 | −6322 | −6590 | −1898 | −5696 | 302 | −5216 | −6074 | −6301 | 381 | −3983 | −1335 | −6831 | −6736 | 310 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 247 | 888 | 172 | −5339 | −4705 | −515 | −4546 | −3420 | −565 | −4302 | 2265 | 2333 | −4193 | −4590 | −3921 | −4102 | 31 | −2931 | 573 | −3275 | −2938 | 311 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 248 | 1726 | −3176 | −3496 | −1106 | −3206 | −4053 | −2810 | −2780 | −2786 | −3064 | 843 | −3055 | 1761 | −550 | −3109 | −503 | 1192 | −551 | −3575 | 2631 | 312 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10521 | −11563 | −894 | −1115 | −701 | −1378 | * | * | | | | | | | | | | | | |
| 249 | 33 | −4321 | −5417 | −5717 | −6915 | 3564 | −5669 | −6738 | −5679 | −6918 | −5999 | 230 | −5283 | −5573 | −334 | −3906 | −4135 | −5484 | −7007 | −6874 | 313 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −373 | −10521 | −2139 | −894 | −1115 | −701 | −1378 | * | * | | | | | | | | | | | | |
| 250 | −2804 | −2708 | −1051 | 1748 | 1672 | −4277 | −3062 | 642 | −3743 | 1276 | −1796 | −3729 | −4324 | −745 | −3709 | −3353 | −2744 | −2101 | 4107 | −2588 | 314 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10150 | −11192 | −894 | −1115 | −3574 | −127 | * | * | | | | | | | | | | | | |
| 251 | −5207 | −5528 | −6771 | −6054 | −7239 | −5624 | −5066 | −7153 | −3875 | −6875 | −6263 | −5597 | −6076 | −4801 | 4192 | −5370 | −554 | −6516 | −6330 | −6575 | 315 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −10150 | −11192 | −894 | −1115 | −3574 | −127 | * | * | | | | | | | | | | | | |
| 252 | −1268 | 875 | −5797 | −5228 | −3232 | −902 | −4128 | 1913 | −4889 | 1212 | 599 | −4771 | −5116 | −4556 | −4740 | −4251 | −3318 | 2626 | −3944 | −3584 | 316 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10150 | −11192 | −894 | −1115 | −78 | −4251 | * | * | | | | | | | | | | | | |
| 253 | 499 | −4823 | −7095 | −7460 | −7401 | 3687 | −6659 | −7382 | −7363 | −7546 | −6667 | −5909 | −5848 | −6848 | −6970 | −4554 | −4769 | −6099 | −7242 | −7556 | 317 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 254 | 1349 | 119 | −5253 | −4617 | 2003 | −1623 | −3328 | 506 | −4212 | −2585 | 141 | −1271 | −4507 | −3836 | −4013 | −861 | −2851 | −906 | 2465 | 3193 | 318 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 255 | 999 | 1164 | −5363 | −4734 | −120 | −384 | −3459 | 2067 | −4334 | 917 | −2035 | −4222 | −4621 | −3961 | −4138 | −3664 | 308 | 1602 | −3321 | −2977 | 319 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 256 | 975 | 581 | −5253 | −4617 | 135 | −1763 | −3328 | 478 | −4212 | 1046 | −1939 | −1271 | −4507 | −3836 | −4013 | 413 | 809 | 719 | −3194 | 2133 | 320 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 257 | 1460 | 1426 | −5255 | −4621 | −2702 | 1674 | −3338 | 592 | −4218 | −1000 | −1950 | −4107 | −4513 | −3842 | −4021 | 800 | −225 | 1292 | −3206 | −271 | 321 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2300 | −10521 | −329 | −894 | −1115 | −701 | −1378 | * | * | | | | | | | | | | | | |
| 258 | 155 | −1009 | −2736 | 780 | 1770 | −2517 | −1342 | 993 | −1865 | 536 | −206 | 397 | −2574 | −1606 | −1894 | −1569 | −996 | −429 | −1442 | 2167 | 322 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −7 | −8228 | −9270 | −894 | −1115 | −24 | −5915 | * | * | | | | | | | | | | | | |
| 259 | −2653 | 133 | 1063 | −1961 | −4411 | −3630 | 1097 | −4154 | −661 | −2173 | −166 | 2147 | 252 | −390 | −100 | 1168 | 347 | 966 | −4290 | −3614 | 323 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 260 | 1291 | 2198 | 1311 | 1211 | −4444 | −3624 | −2283 | −4195 | −85 | −2103 | −3212 | −2260 | 404 | 427 | −110 | 913 | −410 | −3745 | −4307 | −3624 | 324 |
| — | −147 | −501 | 231 | 47 | −382 | 397 | 104 | −628 | 213 | −467 | −722 | 274 | 394 | 47 | 97 | 360 | 117 | −371 | −296 | −251 | |
| H | −5685 | −1906 | −486 | −17 | −6389 | −701 | −1378 | * | * | | | | | | | | | | | | |
| 261 | −1327 | −2808 | 1923 | 426 | −3125 | −2262 | 1644 | −2879 | −545 | −2822 | −1901 | 1331 | −2374 | −493 | 689 | 1396 | 455 | −2428 | −2991 | −2301 | 326 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −5 | −8717 | −9759 | −894 | −1115 | −5087 | −43 | * | * | | | | | | | | | | | | |
| 262 | 2253 | −2874 | 701 | 225 | −3282 | 140 | −1144 | −3033 | −777 | −2995 | −2087 | −1041 | 998 | −701 | −1295 | −3 | 338 | −2574 | −3176 | −2491 | 327 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −134 | −8717 | −3538 | −894 | −1115 | −3873 | −102 | * | * | | | | | | | | | | | | |
| 263 | 40 | −2816 | 1732 | 2054 | −3131 | −2277 | −963 | 192 | 460 | −2830 | −1909 | 790 | −2389 | −508 | −1074 | 471 | −1282 | −2435 | −3000 | −2312 | 328 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | −8741 | −9783 | −894 | −1115 | −4004 | −93 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 264 | 608 | −2611 | −1282 | 276 | 538 | −2355 | −1023 | −267 | 471 | −2593 | −1722 | 1477 | −2446 | 695 | −1132 | 1296 | 96 | 225 | −2845 | −2214 | 329 |
| — | −150 | −501 | 231 | 42 | −378 | 399 | 104 | −628 | 213 | −463 | −722 | 279 | 394 | 50 | 94 | 359 | 116 | −371 | −296 | −251 | |
| H | −114 | −3744 | −9899 | −3400 | −144 | −5030 | −45 | * | * | | | | | | | | | | | | |
| 265 | 2073 | −1773 | −2196 | −1630 | −1796 | 847 | −1467 | 146 | −1470 | −293 | −956 | −1735 | −2784 | 773 | 676 | −396 | −1382 | 53 | −2175 | −1748 | 342 |
| — | −150 | −501 | 238 | 41 | −382 | 398 | 104 | −628 | 211 | −466 | −722 | 276 | 394 | 47 | 94 | 360 | 119 | −369 | −296 | −251 | |
| H | −4021 | −93 | −9899 | −16 | −6535 | −28 | −5707 | * | * | | | | | | | | | | | | |
| 266 | 1458 | −4119 | 335 | 1523 | −4438 | −3625 | −91 | −362 | −208 | −4134 | −609 | 186 | −60 | −1825 | 1354 | −679 | −344 | −702 | 848 | −3622 | 344 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 267 | −170 | −2747 | −5268 | −4632 | −522 | −4470 | −3342 | 1513 | −4227 | 1173 | 384 | −4116 | −4519 | −3849 | −4027 | −1730 | −2862 | 2576 | 953 | −53 | 345 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 268 | 315 | 1362 | −1234 | −499 | −913 | −4398 | −3248 | 1937 | 407 | 803 | −1988 | −3913 | −4452 | −3615 | 696 | −3465 | −2836 | 1530 | −3239 | −2887 | 346 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 269 | −110 | −4124 | 1652 | 639 | −4445 | −1514 | −499 | −4196 | −272 | −1685 | −3213 | 1195 | −3717 | 465 | 281 | 1852 | −394 | −3746 | −4307 | −3624 | 347 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 270 | 1416 | 1971 | −3089 | −2533 | −1035 | −20 | 1611 | −331 | −855 | −1588 | −2571 | −876 | −3980 | 2353 | −325 | −1055 | −621 | −2898 | 800 | 1094 | 348 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 271 | 777 | −2932 | −5463 | −4828 | −374 | −4675 | −3543 | 254 | −4427 | 2239 | 2519 | −4322 | −4705 | −557 | −4221 | −3763 | −3055 | 714 | −3374 | −247 | 349 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 272 | 815 | −4100 | −1042 | −231 | −4410 | −1347 | −2290 | −357 | 1557 | −661 | 25 | 637 | −3723 | 274 | 1897 | −2538 | −73 | −514 | −4290 | −538 | 350 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 273 | −225 | −4117 | 450 | −692 | −1064 | −492 | −2285 | 150 | 1649 | −337 | −312 | 660 | −932 | 981 | 959 | 411 | −2590 | −1613 | −4302 | −3621 | 351 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 274 | −67 | −2742 | −1135 | −4574 | 738 | −1303 | −3319 | 1042 | −4179 | 1116 | 2370 | −913 | −4501 | −719 | −17 | −3533 | −244 | 1359 | 1091 | −2855 | 352 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 275 | 1496 | −4054 | −614 | −1987 | −4343 | −635 | 283 | 529 | 648 | −846 | −5 | −533 | −3736 | 732 | 64 | 1240 | −2597 | 133 | −4256 | −3593 | 353 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 276 | 301 | −4122 | −40 | −718 | −4443 | 70 | −2283 | −4193 | −1864 | −1773 | 17 | 216 | −412 | −300 | 2557 | 1118 | 407 | −3744 | −4306 | −3624 | 354 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 277 | −574 | −3751 | −2741 | −2190 | 1233 | 130 | 1588 | −1487 | −2092 | −784 | −2881 | 68 | 2550 | 93 | 473 | −21 | 161 | −3293 | −4030 | −3449 | 355 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −44 | −10521 | −5086 | −894 | −1115 | −701 | −1378 | * | * | | | | | | | | | | | | |
| 278 | −1440 | −2698 | −5212 | −4576 | 2231 | 572 | −3289 | 53 | −4172 | 24 | 2129 | −239 | −4468 | −979 | −3974 | −660 | −1215 | 729 | 1130 | 2117 | 356 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10478 | −11520 | −894 | −1115 | −1559 | −598 | * | * | | | | | | | | | | | | |
| 279 | −338 | 2140 | −5202 | −4567 | −406 | −4417 | 201 | 1420 | −4165 | 768 | −1902 | 1258 | −977 | −3790 | −3970 | −1282 | 150 | −2113 | 1554 | 2605 | 357 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10478 | −11520 | −894 | −1115 | −1559 | −598 | * | * | | | | | | | | | | | | |
| 280 | −1161 | −2700 | −5215 | −4579 | 2270 | −494 | −3292 | −104 | −4175 | −309 | −1903 | −4065 | −4470 | −3799 | −3976 | 2019 | −77 | 1329 | −3158 | 642 | 358 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1059 | −10478 | −945 | −894 | −1115 | −1559 | −598 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 281 | 510 | 1061 | −2322 | −1770 | −2648 | 326 | −1824 | −2248 | −1648 | −2484 | 829 | 2349 | 863 | −1559 | −2043 | 711 | 386 | −2047 | −2931 | 1364 | 359 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −162 | −9422 | −3252 | −894 | −1115 | −4690 | −57 | * | * | | | | | | | | | | | | |
| 282 | −350 | −2898 | −5264 | −5520 | −5380 | −3190 | −4759 | −5143 | −5289 | −5411 | 1392 | −3933 | 3960 | −4828 | −5015 | 14 | −2763 | −4003 | −5637 | −5540 | 360 |
| — | −149 | −500 | 233 | 43 | −381 | 398 | 105 | −623 | 210 | −464 | −721 | 275 | 394 | 45 | 96 | 359 | 117 | −369 | −295 | −250 | |
| . | −166 | −3215 | −10305 | −94 | −3979 | −33 | −5485 | * | * | | | | | | | | | | | | |
| 283 | −825 | 1467 | 359 | −3264 | −651 | −4089 | −3447 | −4500 | −3190 | −4646 | −3815 | −3368 | 2127 | −582 | −3613 | 2574 | 840 | −4053 | −4961 | −4441 | 362 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 284 | 490 | −4072 | −981 | 325 | −4369 | 88 | −2300 | −402 | −1890 | −2163 | −3167 | 93 | −3731 | −1848 | −7 | 1666 | 2161 | −1660 | −4270 | −3601 | 363 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 285 | 509 | 675 | −5050 | −4427 | 219 | −505 | 2509 | −165 | −4065 | 72 | −1962 | −1278 | 1277 | 1515 | −3935 | 292 | −2843 | 604 | −3215 | −348 | 364 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 286 | 856 | −2909 | −5402 | −4812 | −2956 | 1728 | −3561 | −2485 | −4417 | 1269 | 1085 | −4237 | −4612 | −4041 | −4225 | −35 | 1365 | 650 | −3458 | −3119 | 365 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 287 | 1711 | 589 | −5166 | −4739 | −4468 | −1779 | −4302 | −4057 | −4529 | −1576 | −3646 | −4320 | 1623 | 3211 | −4661 | 362 | −3490 | −990 | −4861 | −4510 | 366 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 288 | 1190 | −4093 | −789 | 260 | −1550 | −1351 | 235 | −1338 | −662 | −1145 | −3186 | −2273 | 1667 | 753 | 1188 | −469 | −760 | −1419 | 450 | 1115 | 367 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 289 | 2131 | −2737 | −5250 | −4614 | −79 | −1558 | −3328 | 1423 | −4210 | 266 | 363 | −4101 | −986 | −958 | −4012 | −708 | −307 | 710 | −3194 | 612 | 368 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 290 | 2000 | 618 | −5047 | −4424 | −2718 | −1555 | −3288 | −326 | −4063 | 993 | −1963 | −893 | −4479 | −717 | −1280 | −569 | −223 | 1743 | −3216 | −2869 | 369 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 291 | 1989 | −3104 | −3623 | −1203 | −3117 | −655 | −2856 | 337 | −118 | 343 | −150 | −822 | −4167 | −2761 | −1120 | 81 | −77 | 1243 | −3509 | −3088 | 370 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 292 | 2438 | −4123 | −895 | 573 | −1743 | −655 | −2283 | −4195 | −64 | −4139 | −3212 | 75 | −3717 | 410 | −1015 | −357 | 1110 | −1391 | −4306 | −3624 | 371 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 293 | 2285 | −2740 | −5218 | −4584 | −2695 | −335 | 355 | 1328 | −4187 | −487 | 1693 | −4086 | −4503 | −654 | −4000 | 45 | −1254 | 403 | 875 | −2855 | 372 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 294 | 462 | −2746 | −5266 | −4630 | −518 | −4469 | −3340 | 119 | −4226 | 2550 | 415 | −4115 | −4518 | −3848 | −4025 | −1394 | −138 | 548 | −3205 | −391 | 373 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 295 | −1010 | 392 | 705 | 210 | −4441 | −407 | 182 | 105 | −535 | −1091 | −103 | 1511 | −3718 | 448 | 480 | 1597 | −1209 | −3742 | −4305 | −375 | 374 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 296 | 570 | −4124 | 2819 | −773 | −846 | 616 | 249 | −4196 | 29 | −4140 | −3213 | 360 | −154 | −1824 | −722 | −539 | −291 | −3746 | −4308 | −3625 | 375 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −42 | −10521 | −5148 | −894 | −1115 | −701 | −1378 | * | * | | | | | | | | | | | | |
| 297 | 494 | −4076 | 832 | 929 | 122 | −1352 | −2251 | −1220 | −990 | −4090 | −3167 | −2229 | 1317 | 914 | −516 | 770 | 404 | 25 | −4263 | −153 | 376 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10480 | −11522 | −894 | −1115 | −1531 | −613 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 298 | 239 | −4084 | 1320 | 1032 | −809 | −1309 | 135 | −1 | 39 | 746 | −3174 | −629 | 525 | 1555 | −2336 | −1156 | −1160 | −3705 | −4268 | −3587 | 377 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −190 | −10480 | −3025 | −894 | −1115 | −1531 | −613 | * | * | | | | | | | | | | | | |
| 299 | −1011 | −3798 | 406 | 537 | 1719 | −1156 | −2126 | −173 | 264 | 1206 | 580 | −2121 | −3553 | 1932 | −808 | −939 | −2404 | −3390 | −4016 | −3368 | 378 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −155 | −10291 | −3310 | −894 | −1115 | −3052 | −185 | * | * | | | | | | | | | | | | |
| 300 | −2457 | −2842 | −787 | 54 | 164 | −846 | 145 | 1085 | 1105 | −1062 | 456 | −2693 | −3780 | −2300 | 1168 | −2686 | 334 | 1429 | −3234 | 836 | 379 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −241 | −10138 | −2711 | −894 | −1115 | −3606 | −124 | * | * | | | | | | | | | | | | |
| 301 | 828 | −3556 | 204 | −218 | −3858 | −51 | −1769 | 999 | −392 | −40 | 689 | 658 | −3201 | 1159 | 551 | −212 | −2066 | −79 | −3750 | −3079 | 380 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −61 | −9900 | −4629 | −894 | −1115 | −4128 | −85 | * | * | | | | | | | | | | | | |
| 302 | −853 | −3549 | 1083 | 1138 | −3870 | −1012 | −1708 | −1081 | 694 | −714 | −2638 | 32 | 597 | 1317 | 300 | 1207 | −2015 | −3171 | −3732 | −3049 | 381 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1033 | −9841 | −971 | −894 | −1115 | −4222 | −79 | * | * | | | | | | | | | | | | |
| 303 | −2236 | −2807 | −4512 | −4788 | −4054 | 370 | −4086 | −4982 | −4725 | −5109 | −4325 | −3649 | −3833 | −4387 | −4550 | 1074 | −2689 | −3909 | 5801 | −3796 | 382 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | −8813 | −9855 | −894 | −1115 | −5049 | −44 | * | * | | | | | | | | | | | | |
| 304 | −20 | −2710 | 523 | 1457 | 465 | −2295 | −958 | −2729 | 434 | 580 | −1807 | −943 | −2389 | 865 | −1054 | −1206 | 1582 | −2315 | −2912 | −2248 | 383 |
| — | −149 | −488 | 233 | 43 | −381 | 398 | 105 | −623 | 210 | −466 | −721 | 275 | 396 | 45 | 96 | 359 | 117 | −370 | −295 | −250 | |
| H | −371 | −3574 | −2810 | −1511 | −624 | −5049 | −44 | * | * | | | | | | | | | | | | |
| 305 | 780 | −2627 | −1009 | 1203 | −2943 | 826 | 1326 | 456 | 1293 | −2640 | −1717 | 608 | −2231 | 886 | −884 | −1046 | −1103 | −2246 | −2812 | −2132 | 387 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −6 | −8593 | −9635 | −894 | −1115 | −26 | −5809 | * | * | | | | | | | | | | | | |
| 306 | 264 | 441 | 20 | 1865 | 1590 | −3624 | 1658 | −4193 | −122 | −4138 | −3211 | 10 | −3718 | 427 | −988 | −380 | −864 | −3744 | 1862 | 1141 | 388 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 307 | −2909 | −2739 | −5229 | −476 | 294 | 337 | −248 | −426 | −4195 | 1634 | 1836 | −731 | −4504 | −3823 | −4004 | −1660 | −14 | 1766 | −3196 | −271 | 389 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 308 | −48 | −4123 | 869 | 1757 | −4445 | −1638 | 1007 | −2093 | 1107 | −1773 | −766 | 269 | −286 | 218 | −307 | −113 | 517 | −1215 | −4307 | −3624 | 390 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 309 | 797 | −4123 | −138 | 2054 | −104 | −430 | −2283 | −4194 | 1054 | −4139 | −382 | −558 | −3717 | 1196 | −966 | −1033 | 500 | −1693 | 768 | −3624 | 391 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 310 | −1090 | −3593 | −1181 | −344 | −3719 | −3810 | −2504 | −146 | −2224 | 25 | 3462 | 1196 | −3895 | −2158 | 1346 | 585 | −202 | −3107 | −3906 | 482 | 392 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 311 | 1042 | −3641 | −2846 | −2293 | −3780 | −3795 | −2484 | −1198 | 146 | −861 | −2781 | −593 | −1024 | −854 | 2659 | −440 | −1159 | 1466 | −3944 | −3394 | 393 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 312 | 634 | −4123 | 1315 | 1244 | −4444 | −1698 | −2283 | −360 | 1030 | −2025 | −875 | −2260 | −3717 | 1933 | 525 | 11 | −236 | −3745 | −4306 | −3624 | 394 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 313 | 227 | −4052 | −2537 | −709 | −805 | −397 | 179 | 110 | 705 | −1117 | −3150 | −2293 | −3737 | 903 | 2768 | −507 | −788 | −3657 | −4255 | −184 | 395 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 314 | −1205 | −2761 | −5281 | −4645 | 1019 | −4485 | 714 | 2553 | −4241 | 1795 | 53 | −4130 | −4532 | −1050 | −4040 | −3570 | −2876 | −217 | −3216 | 691 | 396 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 315 | 332 | −3974 | −2583 | 284 | −1522 | −1339 | 130 | 1310 | 1641 | 181 | −84 | −685 | −3759 | 1939 | −299 | −2581 | −1082 | −3560 | 767 | −3556 | 397 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 316 | 575 | −4123 | −59 | 1134 | −778 | −317 | 136 | −1987 | 1094 | −2130 | −3213 | −25 | −3717 | 1555 | 455 | 445 | 125 | −3745 | 857 | −3624 | 398 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 317 | −2657 | −4074 | −2526 | 316 | −4372 | −3639 | 1386 | −4106 | −615 | 184 | 2373 | 1396 | −3732 | −408 | 2214 | 57 | −990 | −682 | −4271 | −371 | 399 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 318 | 846 | −2929 | −4142 | −3561 | −501 | −4246 | 1724 | −55 | −1217 | −649 | −2121 | −3497 | −4309 | −1174 | 2985 | 72 | −1212 | −1159 | −3360 | 226 | 400 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 319 | −136 | −4123 | 1683 | 457 | −4444 | −3624 | −189 | −1466 | 948 | −4139 | 866 | −806 | −3717 | 1775 | 1378 | −1365 | 880 | −1443 | −4307 | −3624 | 401 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 320 | −1458 | −3381 | −3130 | 362 | 789 | −537 | 966 | −934 | −659 | 27 | −459 | −2775 | −3996 | 1034 | 970 | −476 | 178 | 511 | −3737 | 2110 | 402 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 321 | −1461 | 509 | −6861 | −6252 | 2466 | −6213 | −5074 | 28 | −5908 | 2527 | 1086 | −5873 | −6007 | −5305 | −5643 | −5355 | −4402 | −71 | −4536 | −4388 | 403 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 322 | 13 | 390 | −966 | −4188 | −45 | −4386 | 267 | −762 | 98 | −1429 | −1995 | −3879 | −4441 | −3577 | 1962 | −3450 | 1328 | 1479 | −3245 | 1899 | 404 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 323 | 1001 | −4124 | 1595 | 1028 | −4445 | −338 | −2283 | −4195 | 824 | −966 | −3213 | 680 | −1098 | 653 | −1347 | 347 | −420 | −1561 | −4307 | −3624 | 405 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 324 | 924 | −4107 | −2506 | 1170 | −4420 | 1120 | 1644 | −298 | 458 | −288 | −310 | −37 | −3722 | −336 | −181 | 203 | −1224 | −1482 | −4295 | −3616 | 406 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −38 | −10521 | −5290 | −894 | −1115 | −701 | −1378 | * | * | | | | | | | | | | | | |
| 325 | −5848 | 1551 | −8236 | −7640 | 872 | −7959 | −6633 | −350 | −7422 | 2934 | 1279 | −7672 | −7069 | −6236 | −6924 | −7289 | −5695 | −314 | −5248 | −5446 | 407 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −382 | −10484 | −2109 | −894 | −1115 | −1470 | −646 | * | * | | | | | | | | | | | | |
| 326 | 446 | −3766 | 1021 | 1036 | −4087 | −189 | −1925 | −3838 | 489 | −3782 | −2855 | 939 | −3360 | 1458 | 627 | −107 | 625 | −355 | −3949 | −3267 | 408 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10104 | −11146 | −894 | −1115 | −528 | −1706 | * | * | | | | | | | | | | | | |
| 327 | 1427 | −4027 | 353 | 1514 | −4348 | −1097 | 278 | −4099 | 1607 | −4043 | −3116 | −553 | −3621 | 188 | 359 | 56 | −906 | −2008 | 819 | −3527 | 409 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −39 | −10410 | −5263 | −894 | −1115 | −2317 | −323 | * | * | | | | | | | | | | | | |
| 328 | 1262 | 604 | −724 | 125 | −3126 | −3881 | −2619 | 1666 | 56 | 843 | −409 | −2836 | −123 | −2439 | −225 | −1129 | −205 | −143 | −3474 | −3027 | 410 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −860 | −10372 | −1158 | −894 | −1115 | −2600 | −260 | * | * | | | | | | | | | | | | |
| 329 | −1824 | −3212 | 1186 | 901 | 269 | −2811 | 820 | −374 | 1402 | 182 | −2310 | −1460 | 1252 | −1025 | 851 | −1720 | −1763 | −2816 | −3416 | −15 | 411 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −558 | −9515 | −1647 | −894 | −1115 | −4608 | −60 | * | * | | | | | | | | | | | | |
| 330 | −1529 | 1792 | −2385 | −1817 | −1817 | 2213 | −1590 | −1385 | 713 | −1684 | 1306 | −1892 | 523 | −1511 | −1922 | 153 | −1471 | −1255 | 1915 | 844 | 412 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −359 | −8962 | −2196 | −894 | −1115 | −4982 | −46 | * | * | | | | | | | | | | | | |
| 331 | 714 | −1238 | −3224 | −2621 | −1212 | −2804 | −1678 | −749 | −2309 | 883 | 1704 | −2311 | 378 | −2015 | −2268 | 1178 | 1374 | 627 | −1700 | −1346 | 413 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −130 | −8608 | −3581 | −894 | −1115 | −5127 | −42 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 332 | 212 | -2612 | 693 | 1233 | -2931 | -120 | -762 | -2683 | -353 | -2627 | -1704 | 686 | 1855 | -305 | 954 | 183 | -1076 | -2233 | -2796 | -2109 | 414 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -142 | -8484 | -3458 | -894 | -1115 | -4230 | -79 | * | * | | | | | | | | | | | | |
| 333 | -1108 | -2570 | -959 | 668 | -2893 | 999 | 1407 | -2639 | 678 | -603 | -1660 | -715 | -2171 | 1707 | 1337 | 575 | -1045 | -2193 | -2749 | -2074 | 415 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -6 | -8474 | -9516 | -894 | -1115 | -25 | -5847 | * | * | | | | | | | | | | | | |
| 334 | -2743 | -4214 | 1845 | -611 | -4529 | 2795 | -2370 | -4280 | -1966 | -4228 | -3308 | -72 | -1013 | -1914 | -103 | -682 | -1222 | -1318 | -4400 | -277 | 416 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -1 | -10521 | -11563 | -894 | -1115 | -701 | -1378 | * | * | | | | | | | | | | | | |
| 335 | -1199 | -2738 | -5244 | -1350 | 2445 | -4456 | -3327 | 1468 | -1365 | 1440 | -1940 | -4098 | -4506 | -828 | -4010 | -3540 | -959 | -86 | 3195 | -230 | 417 |
| — | -149 | -500 | 233 | 43 | -381 | 399 | 106 | -626 | 210 | -466 | -720 | 275 | 394 | 45 | 96 | 359 | 117 | -369 | -294 | -249 | |
| C | -1 | -10521 | -11563 | -894 | -1115 | -701 | -1378 | * | * | | | | | | | | | | | | |
| 336 | 158 | -4123 | 263 | 197 | -4444 | -509 | -2283 | 245 | 919 | -4139 | -3212 | 954 | 989 | 776 | -722 | 732 | 116 | -520 | -4307 | -558 | 418 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -10521 | -11563 | -894 | -1115 | -701 | -1378 | * | * | | | | | | | | | | | | |
| 337 | -708 | 3195 | -5243 | -1395 | 397 | -4456 | 2303 | -95 | -4205 | -679 | 1118 | -952 | -88 | -3830 | -856 | -3540 | -899 | 1792 | 1151 | 558 | 419 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -10521 | -11563 | -894 | -1115 | -701 | -1378 | * | * | | | | | | | | | | | | |
| 338 | -516 | -2755 | -5093 | -1255 | 270 | -677 | -3297 | 1471 | -1258 | 1022 | 909 | -4028 | -1357 | -453 | -1340 | -1342 | 1076 | 740 | 951 | 643 | 420 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -1 | -10521 | -11563 | -894 | -1115 | -701 | -1378 | * | * | | | | | | | | | | | | |
| 339 | -61 | -4119 | 912 | 531 | -4438 | 906 | -2284 | 785 | 600 | -1249 | 17 | -1113 | 1432 | -218 | -722 | -995 | 247 | -1614 | -4303 | -3622 | 421 |
| — | -149 | -500 | 233 | 43 | -381 | 399 | 106 | -626 | 210 | -466 | -720 | 275 | 394 | 45 | 96 | 359 | 117 | -369 | -294 | -249 | |
| C | -30 | -10521 | -5641 | -894 | -1115 | -701 | -1378 | * | * | | | | | | | | | | | | |
| 340 | -564 | -4098 | -299 | -403 | -4418 | -105 | -2258 | -4169 | 574 | -1910 | -3187 | 658 | 1979 | 397 | -2346 | 1950 | -2565 | -1261 | -4281 | -533 | 422 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -79 | -10492 | -4241 | -894 | -1115 | -1333 | -730 | * | * | | | | | | | | | | | | |
| 341 | -1062 | 444 | 860 | 1198 | -4353 | -3532 | -311 | -4104 | 484 | -4048 | -3121 | 1538 | 367 | 2876 | -629 | -1003 | -2498 | -3654 | -4215 | -3532 | 423 |
| — | -149 | -500 | 235 | 43 | -381 | 398 | 105 | -626 | 210 | -466 | -721 | 275 | 394 | 45 | 96 | 359 | 117 | -366 | -295 | -250 | |
| S | -85 | -4136 | -11456 | -82 | -4183 | -199 | -2957 | * | * | | | | | | | | | | | | |
| 342 | 1434 | -4053 | -2553 | -919 | -4346 | 1470 | 1011 | 653 | -1921 | -4062 | -3160 | -204 | -3752 | -1878 | -172 | 1272 | 1051 | -3662 | -4266 | -3606 | 425 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -1 | -10521 | -11563 | -894 | -1115 | -701 | -1378 | * | * | | | | | | | | | | | | |
| 343 | 1716 | 528 | -6159 | -6171 | -6581 | 2297 | 1324 | -6366 | -6024 | -6599 | -5665 | 2048 | 3 | -5654 | -5968 | -3743 | 545 | -5219 | -6786 | -6630 | 426 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -1 | -10521 | -11563 | -894 | -1115 | -701 | -1378 | * | * | | | | | | | | | | | | |
| 344 | -5173 | -4752 | -7542 | -6949 | 2714 | -7026 | -5753 | 1424 | -6650 | 430 | 3469 | -6685 | -6578 | -5819 | -6301 | -6224 | -5066 | 668 | -4881 | 1281 | 427 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -1 | -10521 | -11563 | -894 | -1115 | -701 | -1378 | * | * | | | | | | | | | | | | |
| 345 | -4194 | -3909 | -6463 | -5921 | 3113 | -5800 | -4242 | 1088 | -5550 | -76 | -2551 | -5354 | -5725 | -762 | -5306 | -4925 | -4126 | 1769 | -3768 | 2376 | 428 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -10521 | -11563 | -894 | -1115 | -701 | -1378 | * | * | | | | | | | | | | | | |
| 346 | -648 | 2280 | -5230 | -4596 | -625 | -4454 | 262 | -2231 | -4196 | 1004 | 264 | -4092 | 1511 | -647 | -4005 | 1220 | -183 | 1104 | -3196 | 502 | 429 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -10521 | -11563 | -894 | -1115 | -701 | -1378 | * | * | | | | | | | | | | | | |
| 347 | -1234 | -2760 | -5281 | -4645 | 1951 | -4484 | -3355 | 385 | -4240 | 1036 | 1543 | -4130 | -4532 | -3861 | -4040 | -3569 | -1038 | 1049 | 3559 | 2057 | 430 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -30 | -10521 | -5641 | -894 | -1115 | -701 | -1378 | * | * | | | | | | | | | | | | |
| 348 | -1101 | -3686 | -797 | -797 | -3848 | -1304 | 104 | 264 | -2097 | -43 | 2212 | -2465 | 332 | 418 | 445 | 421 | 1282 | 936 | -3973 | -3403 | 431 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -10492 | -11534 | -894 | -1115 | -412 | -2010 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 349 | −2697 | −3732 | 1671 | −46 | 190 | 1523 | 948 | −351 | −2107 | 309 | −2864 | −611 | −1215 | −2050 | 801 | −1375 | −2637 | 635 | −4015 | −3439 | 432 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 350 | −2910 | 1110 | −5250 | −4614 | 850 | 1282 | 297 | 483 | −298 | 1719 | 482 | −1011 | −216 | −3834 | −4012 | −3541 | −818 | −199 | 622 | −237 | 433 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 351 | 226 | 430 | 1788 | −112 | −4445 | −596 | −2283 | −4196 | −219 | −4140 | −3213 | 675 | 600 | −1823 | 1410 | 1275 | −64 | −3746 | −4307 | −3625 | 434 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −42 | −10521 | −5148 | −894 | −1115 | −701 | −1378 | * | * | | | | | | | | | | | | |
| 352 | 987 | −4088 | −720 | 90 | −4409 | 121 | 1297 | −4159 | 651 | −1776 | 52 | 739 | 2059 | −795 | 254 | −120 | −2554 | −1391 | −4271 | −3588 | 435 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10480 | −11522 | −894 | −1115 | −1531 | −613 | * | * | | | | | | | | | | | | |
| 353 | 716 | −4070 | −862 | 1829 | −4383 | −3593 | 206 | −1186 | 297 | 617 | −3162 | −617 | −1072 | −440 | −2342 | 483 | −44 | 23 | −4258 | −244 | 436 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1775 | −10480 | −500 | −894 | −1115 | −1531 | −613 | * | * | | | | | | | | | | | | |
| 354 | 797 | −1752 | −2024 | 297 | −1781 | −2601 | −1332 | 275 | 596 | 1768 | 1063 | −1581 | −2673 | −1172 | 724 | −1584 | −1298 | −1209 | −2138 | −1703 | 437 |
| — | −151 | −503 | 232 | 42 | −379 | 400 | 102 | −626 | 211 | −469 | −724 | 272 | 398 | 42 | 101 | 357 | 120 | −371 | −298 | −236 | |
| . | −846 | −1176 | −9752 | −2218 | −349 | −3408 | −143 | * | * | | | | | | | | | | | | |
| 355 | −1390 | 1804 | 564 | 151 | −3184 | −210 | 1471 | −2934 | 1894 | −2879 | −1952 | −999 | 365 | 869 | 626 | 591 | −1329 | −2485 | −3046 | −2363 | 445 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −4 | −8938 | −9980 | −894 | −1115 | −4993 | −46 | * | * | | | | | | | | | | | | |
| 356 | −1391 | −2856 | −84 | 1856 | 448 | 429 | −1024 | −2922 | 1413 | −2871 | −1946 | −1001 | −2458 | −565 | −16 | 347 | 368 | −2476 | −3041 | 842 | 446 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −4 | −8938 | −9980 | −894 | −1115 | −4993 | −46 | * | * | | | | | | | | | | | | |
| 357 | 124 | −2863 | 12 | 568 | −3184 | −2363 | −1022 | −2934 | 990 | −2879 | −1952 | 138 | 1432 | 1474 | 1039 | 553 | 266 | −2485 | −3046 | −2363 | 447 |
| — | −151 | −502 | 233 | 44 | −382 | 400 | 104 | −624 | 210 | −465 | −722 | 274 | 392 | 43 | 96 | 361 | 121 | −369 | −296 | −251 | |
| S | −4102 | −88 | −9980 | −15 | −6619 | −2825 | −219 | * | * | | | | | | | | | | | | |
| 358 | −3023 | −2728 | −5382 | −4807 | 3371 | −4741 | −3558 | 1472 | −4463 | 644 | −1251 | 1813 | −4630 | −3971 | −4250 | −3877 | −2958 | −223 | −3139 | −2764 | 449 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | −9237 | −10279 | −894 | −1115 | −4825 | −52 | * | * | | | | | | | | | | | | |
| 359 | 272 | −3135 | 1692 | 2341 | −3444 | −2627 | −1308 | 62 | 761 | −3146 | −2229 | 556 | −2735 | −854 | −1414 | −1559 | −1620 | −388 | −3324 | −2642 | 450 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | −9237 | −10279 | −894 | −1115 | −1496 | −631 | * | * | | | | | | | | | | | | |
| 360 | 871 | −3516 | −4 | −173 | −3834 | −1290 | −1683 | −3582 | 975 | −604 | −2605 | 43 | −3117 | −1224 | 327 | 982 | 1309 | 651 | −3701 | −3020 | 451 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −61 | −9808 | −4624 | −894 | −1115 | −2680 | −245 | * | * | | | | | | | | | | | | |
| 361 | 1880 | 576 | 1621 | 1344 | −3760 | −714 | −1753 | −3484 | −1350 | −3478 | 1603 | −211 | −3181 | −1306 | −1851 | −477 | −358 | −846 | −3685 | −3027 | 452 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9855 | −10897 | −894 | −1115 | −2066 | −394 | * | * | | | | | | | | | | | | |
| 362 | −834 | −3673 | 365 | 152 | −3985 | −3199 | 1572 | −1548 | 1568 | 416 | 2184 | 54 | −512 | 94 | −1948 | −566 | 20 | −25 | −3862 | −3184 | 453 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10016 | −11059 | −894 | −1115 | −2830 | −219 | * | * | | | | | | | | | | | | |
| 363 | 1544 | −3736 | 683 | 2044 | −4057 | −3237 | −1895 | −3808 | 585 | −3752 | −2825 | −1872 | −3330 | 1575 | −533 | −17 | −2202 | −3358 | 804 | −169 | 454 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10066 | −11108 | −894 | −1115 | −3796 | −108 | * | * | | | | | | | | | | | | |
| 364 | −267 | −2515 | −5043 | −4411 | 2835 | −4264 | −3139 | −581 | −862 | 2234 | −1612 | −3909 | −4297 | −3625 | −3813 | −3353 | −526 | −431 | −2980 | −2650 | 455 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10066 | −11108 | −894 | −1115 | −3796 | −108 | * | * | | | | | | | | | | | | |
| 365 | 1469 | 602 | −4372 | −3765 | 1597 | −3978 | −2823 | −1899 | −3453 | −2247 | −1594 | −3464 | −4033 | 838 | −520 | 1199 | −527 | −667 | 3664 | 862 | 456 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −10066 | −11108 | −894 | −1115 | −66 | −4473 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 366 | −87 | −4123 | 277 | 622 | −4443 | −3624 | −493 | 245 | 1459 | −1935 | −3212 | −2260 | −3718 | 2356 | 1643 | −583 | −989 | −3745 | −4306 | −558 | 457 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 367 | 1090 | −3985 | −834 | −265 | −4245 | −3664 | −2330 | −881 | 1658 | −2521 | 68 | −2326 | −3756 | 770 | −739 | −6 | −2604 | 1925 | −4205 | 394 | 458 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1544 | −10521 | −607 | −894 | −1115 | −701 | −1378 | * | * | | | | | | | | | | | | |
| 368 | 749 | −2868 | 1707 | 1319 | −3177 | −2399 | 1517 | −2920 | −644 | −958 | 1012 | −1039 | −2492 | −603 | 18 | 658 | 368 | −2483 | −3058 | −2382 | 459 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | −8981 | −10023 | −894 | −1115 | −4972 | −47 | * | * | | | | | | | | | | | | |
| 369 | −1522 | −2230 | −1826 | 343 | −2317 | −2654 | −1349 | 717 | −1097 | 249 | −1386 | 261 | −2735 | 945 | 2531 | −1607 | −1459 | −1725 | 2204 | 514 | 460 |
| — | −150 | −503 | 232 | 52 | −374 | 395 | 109 | −621 | 212 | −467 | −724 | 275 | 393 | 46 | 92 | 357 | 116 | −370 | −298 | −247 | |
| H | −123 | −3628 | −10023 | −4287 | −76 | −29 | −5649 | * | * | | | | | | | | | | | | |
| 370 | −1527 | 462 | −7738 | −7191 | −3627 | −7335 | −6262 | 1089 | −6955 | 2936 | 1768 | −7019 | −6808 | −6119 | −6635 | −6591 | −5190 | −1505 | −5250 | −5279 | 483 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 371 | 177 | −2748 | −5163 | −4533 | −2703 | −4445 | −3311 | 1760 | −1647 | 1572 | −1950 | −4061 | −4496 | 821 | 1408 | −3526 | 257 | −41 | 912 | −383 | 484 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 372 | −1182 | −4131 | 1646 | 2309 | −1464 | −3629 | −2289 | −4203 | 371 | −4147 | −3220 | 1734 | −3723 | 917 | −2378 | −1379 | 560 | −3753 | −4314 | −1045 | 485 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 373 | −535 | −4124 | −553 | 2740 | −4445 | −3624 | 290 | −4196 | −139 | −4140 | −121 | −620 | −3717 | 1563 | 1345 | −1340 | −1145 | −3746 | −4307 | −280 | 486 |
| — | −149 | −500 | 233 | 43 | −381 | 398 | 111 | −627 | 210 | −464 | −721 | 275 | 393 | 45 | 96 | 360 | 117 | −370 | −295 | −250 | |
| T | −594 | −3790 | −1914 | −61 | −4593 | −701 | −1378 | * | * | | | | | | | | | | | | |
| 374 | −98 | 1044 | −3007 | 990 | 1158 | −197 | 2389 | −2436 | 550 | −1066 | −1998 | −2589 | −3704 | −111 | −2648 | −1093 | −2336 | 1070 | 823 | 1408 | 488 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10076 | −11118 | −894 | −1115 | −68 | −4448 | * | * | | | | | | | | | | | | |
| 375 | −237 | −4068 | −2529 | −645 | −889 | 2403 | 2359 | −1209 | 1104 | −4073 | −3164 | 702 | −3733 | −1851 | −701 | −560 | −2596 | −588 | −4267 | −3600 | 489 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10521 | −11563 | −894 | −1115 | −701 | −1378 | * | * | | | | | | | | | | | | |
| 376 | −1326 | 475 | −6986 | −6546 | −4455 | −6567 | −5936 | 2316 | −6349 | 131 | −3328 | −6217 | −6440 | −6139 | −6332 | −5799 | −4386 | 2930 | −5615 | 573 | 490 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 377 | 585 | −2741 | −5221 | −4587 | −558 | −4453 | 1147 | 777 | −4189 | −133 | −1943 | 1122 | −4503 | −690 | −1064 | −3536 | −2850 | 923 | 866 | 3209 | 491 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 378 | −238 | 1450 | −5484 | −4862 | −2921 | −4711 | −3607 | 1281 | −4469 | 127 | 1854 | −4358 | −4750 | −4101 | 338 | −3804 | −973 | 2741 | −3464 | −3118 | 492 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 379 | −2889 | −2803 | −1137 | −4142 | 161 | −1471 | −3221 | 747 | −3836 | 382 | 451 | −3853 | −235 | 437 | 1122 | 503 | 1747 | 879 | −3252 | −2896 | 493 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 380 | 867 | 352 | 11 | −1953 | −4433 | −570 | 1417 | −4181 | −333 | −4130 | −3206 | −2263 | 2696 | −297 | 988 | −163 | −760 | −1284 | −4301 | −1099 | 494 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −355 | −10521 | −2199 | −894 | −1115 | −701 | −1378 | * | * | | | | | | | | | | | | |
| 381 | −915 | 898 | −4897 | −4264 | 584 | 2496 | −3004 | 1474 | −3868 | −1073 | −1626 | 992 | −620 | −3498 | −538 | −3218 | −2532 | −487 | 1097 | −2538 | 495 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10167 | −11209 | −894 | −1115 | −3522 | −131 | * | * | | | | | | | | | | | | |
| 382 | −850 | −3815 | −2196 | 241 | −557 | −160 | −1980 | −3883 | 368 | −3830 | −2905 | 1703 | −3415 | −1521 | 1425 | 1426 | 1339 | −3436 | −3999 | 116 | 496 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10167 | −11209 | −894 | −1115 | −3522 | −131 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 383 | 140 | 801 | −3346 | 457 | −143 | −339 | 200 | 767 | −2614 | −2652 | −1959 | −2858 | 1142 | 556 | −2897 | 1112 | −419 | 84 | −3183 | 1637 | 497 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10167 | −11209 | −894 | −1115 | −3522 | −131 | * | * | | | | | | | | | | | | |
| 384 | −2638 | 1104 | −662 | −1144 | 3027 | −4163 | −2998 | −1979 | −3831 | −375 | −1687 | −3751 | 2766 | −3478 | −3684 | −3244 | −2579 | −435 | −2890 | 274 | 498 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10167 | −11209 | −894 | −1115 | −3522 | −131 | * | * | | | | | | | | | | | | |
| 385 | −853 | −3638 | −2297 | −124 | −3882 | 1790 | 2038 | −3581 | −1656 | −305 | −2748 | −930 | −670 | −1610 | 516 | −805 | 1610 | −1006 | −3870 | 950 | 499 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −49 | −10167 | −4939 | −894 | −1115 | −3522 | −131 | * | * | | | | | | | | | | | | |
| 386 | 395 | 3253 | −4872 | −764 | −123 | −4095 | −2965 | 323 | −733 | 682 | −1583 | −3734 | −4146 | −3465 | −3646 | −916 | 181 | 1862 | −2838 | 88 | 500 |
| — | −150 | −501 | 232 | 49 | −382 | 397 | 111 | −627 | 211 | −465 | −722 | 274 | 393 | 48 | 95 | 358 | 119 | −370 | −296 | −251 | |
| C | −1638 | −3816 | −719 | −1947 | −433 | −3659 | −119 | * | * | | | | | | | | | | | | |
| 387 | −3067 | −4023 | −1957 | −2132 | −5207 | −3353 | −2585 | −4985 | 727 | −4795 | −4126 | 924 | 3864 | −2249 | −1995 | −2979 | −3189 | −4414 | −4698 | −4275 | 505 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8771 | −9814 | −894 | −1115 | −2013 | −411 | * | * | | | | | | | | | | | | |
| 388 | 938 | −3179 | −1581 | 328 | −3492 | −2703 | −1362 | 682 | 1325 | −848 | −2270 | 435 | −2796 | 30 | 1412 | −128 | 904 | −2797 | −3367 | −2690 | 506 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −3 | −9395 | −10437 | −894 | −1115 | −4711 | −56 | * | * | | | | | | | | | | | | |
| 389 | −205 | −3065 | −1711 | 1719 | −3309 | 2444 | −1526 | −195 | −35 | −3056 | −2200 | 322 | −2934 | −1107 | −1647 | −1770 | −1786 | −198 | −3323 | −2700 | 507 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −3 | −9395 | −10437 | −894 | −1115 | −847 | −1172 | * | * | | | | | | | | | | | | |
| 390 | −921 | −3780 | −537 | 949 | −4101 | −1294 | −1939 | −3851 | 370 | −3796 | −2869 | −1916 | 2629 | 634 | −197 | 663 | 955 | −1761 | −3963 | −3280 | 508 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10120 | −11162 | −894 | −1115 | −3659 | −119 | * | * | | | | | | | | | | | | |
| 391 | 289 | −3824 | −532 | 1134 | −4146 | 1930 | −1979 | −3898 | −1566 | −3842 | −2917 | 585 | −80 | −1520 | −319 | 1298 | 307 | −3447 | −4009 | −3324 | 509 |
| — | −149 | −500 | 233 | 43 | −381 | 399 | 106 | −626 | 210 | −464 | −720 | 275 | 394 | 45 | 96 | 359 | 117 | −369 | −294 | −249 | |
| T | −94 | −5215 | −4785 | −187 | −3038 | −73 | −4336 | * | * | | | | | | | | | | | | |
| 392 | −1273 | 1985 | 668 | −2747 | 1261 | −3963 | 283 | −2830 | −2610 | −827 | −2381 | −208 | −4039 | −2504 | 1729 | 916 | −983 | −2673 | 3899 | −620 | 511 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10481 | −11523 | −894 | −1115 | −357 | −2191 | * | * | | | | | | | | | | | | |
| 393 | −3952 | −3675 | −6361 | −5774 | 1770 | 1593 | −4627 | 1125 | −5427 | 2056 | −2443 | −5334 | −5615 | −4997 | −5234 | −4807 | −1098 | 458 | −4321 | −4038 | 512 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 394 | −6082 | −6362 | −7082 | −5444 | −7458 | −6270 | −4294 | −6846 | −758 | −6407 | −5805 | −5217 | −6264 | −3903 | 4202 | −5986 | −5716 | −6645 | −6045 | −6162 | 513 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 395 | −1700 | −3843 | −6672 | −6146 | 327 | −6103 | −5199 | 3038 | −5859 | 900 | −20 | −5753 | −6010 | −5509 | −5732 | −5271 | −1170 | 1750 | −4885 | −4559 | 514 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 396 | −543 | 3374 | −5409 | −5086 | −5816 | −1159 | −4905 | −5516 | −4926 | −5740 | −4889 | 1416 | −4992 | −715 | −5122 | 1865 | 2348 | −1315 | −6041 | −5716 | 515 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10521 | −11563 | −894 | −1115 | −701 | −1378 | * | * | | | | | | | | | | | | |
| 397 | 97 | 1559 | −5258 | −4622 | 1468 | −4460 | −3332 | 740 | −4217 | 371 | 2479 | −4106 | 114 | −3840 | −4017 | −3545 | −935 | 1793 | −3197 | 1134 | 516 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2023 | −10521 | −409 | −894 | −1115 | −701 | −1378 | * | * | | | | | | | | | | | | |
| 398 | −1262 | −2167 | −1436 | −946 | −2477 | −2286 | 1802 | −2128 | −851 | −2284 | 1693 | 1116 | −2457 | −796 | −1285 | 1228 | 2490 | −1836 | −2631 | −2084 | 517 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8504 | −9546 | −894 | −1115 | −1192 | −830 | * | * | | | | | | | | | | | | |
| 399 | 3393 | 932 | −6112 | −6454 | −6054 | −3618 | −5399 | −5875 | −6077 | −6140 | −5165 | −4463 | 1016 | −5503 | −5672 | −570 | −3206 | −4549 | −6278 | −6267 | 518 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9710 | −10752 | −894 | −1115 | −820 | −1206 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 400 | 1486 | 780 | −632 | −2018 | −3633 | 1992 | 198 | −3279 | −1919 | −1728 | −2612 | 1425 | −3621 | −1858 | −2379 | 145 | 608 | −865 | −3767 | −3203 | 519 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10220 | −11262 | −894 | −1115 | −92 | −4022 | * | * | | | | | | | | | | | | |
| 401 | −2905 | 769 | −5117 | −4490 | −2708 | 1344 | 2391 | −579 | −1139 | 889 | 2699 | −4039 | −843 | −3762 | −1022 | −1270 | 111 | 770 | −3208 | −2862 | 520 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10521 | −11563 | −894 | −1115 | −701 | −1378 | * | * | | | | | | | | | | | | |
| 402 | −3891 | −5535 | 1714 | −936 | −5807 | −4327 | −3361 | −5621 | −244 | −5536 | −4695 | 643 | 619 | −2961 | −3854 | 1436 | 2699 | −5141 | −5713 | −4900 | 521 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10521 | −11563 | −894 | −1115 | −701 | −1378 | * | * | | | | | | | | | | | | |
| 403 | 216 | −4123 | 1423 | 1349 | −4444 | −3624 | 83 | −1271 | 21 | −1219 | −21 | −149 | 1055 | 319 | 140 | 19 | 413 | −1318 | −4306 | −3624 | 522 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 404 | 1349 | −4124 | 434 | 2190 | −4445 | −559 | −2283 | −4195 | 581 | −4140 | −773 | −171 | −1231 | 618 | −903 | −27 | −864 | −1318 | −4307 | −3624 | 523 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 405 | −1698 | −4121 | 776 | 1633 | −4441 | −1193 | −2283 | −4191 | 393 | −711 | 802 | 1455 | −3718 | 1528 | −903 | −2531 | 1007 | −457 | −4305 | −338 | 524 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 406 | −1413 | 1192 | −990 | −4600 | −2693 | −4455 | −3325 | 1409 | −4199 | 1654 | 1663 | 959 | −4505 | −3826 | −1378 | −1346 | −899 | 1362 | −3196 | −271 | 525 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 407 | −331 | −4124 | 1878 | 1907 | −4445 | −1714 | −493 | −4196 | 925 | −1812 | −3213 | −650 | −794 | 634 | 1148 | −2531 | 251 | −3746 | −4307 | −3624 | 526 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 408 | −1150 | −4064 | −2530 | 1624 | −4358 | −3641 | 1604 | −74 | 36 | −2337 | −18 | 689 | −1392 | 140 | 1588 | −2550 | −990 | 173 | −4264 | 1925 | 527 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 409 | 2097 | −3319 | −5933 | −5328 | 869 | −401 | −4116 | −53 | −4954 | 1897 | −2309 | −4846 | −5189 | −4557 | −4761 | −4297 | −3493 | 834 | −3903 | −3586 | 528 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 410 | 1555 | 2824 | −5774 | −5168 | −3176 | −5034 | −3961 | 1316 | −4793 | 1324 | −362 | −4682 | −5053 | −4429 | −1102 | −4139 | −3334 | 1668 | −3795 | −3451 | 529 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 411 | 86 | −4124 | 1445 | 1964 | −4445 | −437 | 525 | −4196 | 297 | −4140 | −3213 | 91 | −3717 | 889 | 667 | 32 | −263 | −1346 | −4307 | −3624 | 530 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 412 | 1879 | −3267 | −3304 | −2744 | −772 | −1177 | 1066 | −925 | 568 | −3160 | −2438 | −2909 | −4061 | −2508 | 2240 | 237 | −1025 | 189 | −3644 | −476 | 531 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10521 | −11563 | −894 | −1115 | −701 | −1378 | * | * | | | | | | | | | | | | |
| 413 | −5582 | −5000 | −8123 | −7659 | 1086 | −7986 | −7088 | 2908 | −7547 | 1985 | −2573 | −7680 | −7211 | −6595 | −7231 | −7390 | −5493 | 652 | −5672 | −5775 | 532 |
| — | * | * | * | * | * | * | * | * | * | * | * | * | * | * | * | * | * | * | * | * | |
| H | * | * | * | * | * | * | * | * | 0 | | | | | | | | | | | | |
| // | | | | | | | | | | | | | | | | | | | | | |

HMMER2.0 [2.3.2]
NAME AUX_IAA
ACC PF02309.8
DESC AUX/IAA family
LENG 269
ALPH Amino
RF no
CS no
MAP yes
COM hmmbuild -F HMM_ls.ann SEED.ann
COM hmmcalibrate --seed 0 HMM_ls.ann
NSEQ 11
DATE Wed Apr 23 14:47:59 2008
CKSUM 3890
GA −83.0000 −83.0000;
TC −82.0000 −82.0000;
NC −83.5000 −83.5000;
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −177.830048 0.164010

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −193 | * | −2999 | | | | | | | | | | | | | | | | | | |
| 1 | −2947 | −2479 | -5371 | −4809 | −1241 | −4959 | −3843 | 1102 | −4560 | 2441 | 2742 | −4635 | −4433 | −3718 | −4232 | −4203 | −2848 | 1143 | −2848 | −2878 | 1 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | −193 | * | | | | | | | | | | | | |
| 2 | 417 | −2549 | −606 | 566 | −3186 | 1483 | −1040 | −2950 | −792 | −2932 | −2059 | 2744 | −2275 | −632 | −1334 | 446 | −1292 | −2444 | −3128 | −2430 | 2 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 3 | −3689 | −3084 | -5627 | -5279 | 3024 | -5347 | −3004 | −873 | −4994 | 2547 | −182 | −4768 | −4717 | −3849 | −4490 | −4714 | −3550 | −1650 | −2024 | −1289 | 3 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 4 | −2445 | −3644 | −1150 | 2315 | −4213 | −2718 | −1438 | −3857 | 3073 | −3629 | −2926 | −1388 | −3002 | −1052 | −739 | −2235 | −2351 | −3491 | −3568 | −3147 | 4 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 5 | 2358 | −1704 | −1682 | 1176 | −2046 | −2379 | −1605 | 1871 | −1564 | −1682 | −1132 | −1583 | −2665 | −1431 | −1882 | −1578 | −1368 | −704 | −2517 | −2066 | 5 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 6 | −2430 | −2823 | −4179 | −4462 | −4591 | −3027 | −4037 | −4454 | −4406 | −4707 | −4191 | −3664 | −3724 | −4237 | −4215 | −2689 | 4010 | −3747 | −4431 | −4588 | 6 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 7 | −4205 | −4417 | −2343 | 3901 | -5349 | −3698 | −3534 | -5837 | −3838 | -5561 | -5237 | −3039 | −4218 | −3453 | −4201 | −4072 | −4352 | -5409 | −4640 | −4860 | 7 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 8 | −4119 | −3542 | -5389 | -5357 | −2027 | −4767 | −4358 | −1609 | -5118 | 3293 | −979 | -5230 | −4771 | −4474 | −4724 | -5069 | −4106 | −2331 | −3412 | −3400 | 8 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | -2287 | -2851 | -3422 | -2614 | -4158 | -2930 | -1828 | -3733 | -569 | -3593 | -2947 | -2354 | -3266 | -1472 | 3856 | -2379 | 707 | -3293 | -3486 | -3366 | 9 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 10 | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 10 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 11 | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 11 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 12 | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 12 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 13 | -1438 | -2041 | -3094 | -3394 | -4272 | -2225 | -3357 | -4272 | -3665 | -4461 | -3622 | -2656 | 4004 | -3348 | -3624 | 347 | -1887 | -3152 | -4374 | -4203 | 13 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 14 | -1779 | 1829 | 872 | 872 | -3722 | 2990 | -1505 | -3506 | -1522 | -3523 | -2747 | -958 | -2627 | -1159 | -2163 | -1639 | -1878 | -3004 | -3752 | -2990 | 14 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -318 | -7942 | -2366 | -894 | -1115 | -701 | -1378 | * | * | | | | | | | | | | | | |
| 15 | 312 | -1985 | 918 | -51 | -2317 | 10 | -393 | 17 | -25 | -2052 | -1172 | 1153 | -1779 | 38 | -525 | 1698 | -651 | -1634 | -2283 | -1637 | 15 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7634 | -8676 | -894 | -1115 | -327 | -2302 | * | * | | | | | | | | | | | | |
| 16 | -1056 | -2539 | -499 | 1713 | -2854 | 231 | -652 | -2612 | -299 | -2560 | -1660 | 1017 | -2048 | 1889 | -824 | -916 | 1728 | -2164 | -2736 | -2032 | 16 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -388 | -7942 | -2111 | -894 | -1115 | -701 | -1378 | * | * | | | | | | | | | | | | |
| 17 | -1019 | -2549 | 885 | 1428 | -2845 | 545 | 1683 | -2618 | -299 | -2560 | -1678 | -332 | -1941 | -150 | -859 | 1883 | -984 | -2164 | -2740 | -2002 | 17 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -949 | -7566 | -1068 | -894 | -1115 | -1752 | -508 | * | * | | | | | | | | | | | | |
| 18 | -2023 | -2135 | -2499 | -2712 | -3306 | -2200 | -2597 | -3526 | -2816 | -3517 | -3138 | -2542 | 4110 | -2770 | -2769 | -2249 | -2350 | -3059 | -2925 | -3167 | 18 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -2619 | -256 | * | * | | | | | | | | | | | | |
| 19 | 1293 | -1757 | 179 | 2502 | -2356 | -1247 | -455 | -1970 | -255 | -2120 | -1358 | -115 | -1628 | -97 | -744 | -577 | -716 | -1574 | -2401 | -1757 | 19 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -2619 | -256 | * | * | | | | | | | | | | | | |
| 20 | -2117 | -2369 | -2441 | -1861 | -2996 | -2357 | -1217 | -2987 | -119 | -2797 | -2289 | -1786 | -2615 | -943 | 3869 | -2167 | -2072 | -2743 | -2456 | -2397 | 20 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -2619 | -256 | * | * | | | | | | | | | | | | |
| 21 | -616 | -1918 | 1769 | 1643 | -2150 | -1259 | -206 | -1725 | -9 | -1893 | -1099 | 81 | -1533 | 179 | -565 | -488 | -594 | 1193 | -2199 | -1505 | 21 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -1813 | -483 | * | * | | | | | | | | | | | | |
| 22 | -931 | -1946 | 1908 | -181 | -2770 | -1445 | -935 | -2431 | -925 | -2618 | -1886 | -446 | -1932 | -619 | -1471 | -892 | 2936 | -1973 | -2871 | -2223 | 22 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 23 | -1109 | -2751 | 1847 | 2355 | -3025 | -1428 | -555 | -2848 | -504 | -2775 | -1972 | -43 | -1824 | -175 | -1168 | 1222 | -1122 | -2371 | -2966 | -2126 | 23 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 24 | -448 | -1042 | -826 | 1132 | 1300 | -1594 | -271 | -654 | -29 | 507 | -154 | -459 | -1672 | -23 | 1307 | -572 | -383 | -504 | -1315 | -803 | 24 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 25 | -384 | -637 | -1341 | -852 | 1602 | 695 | -561 | -249 | -709 | -593 | 78 | 1327 | -1787 | -551 | -953 | -696 | -373 | 1258 | -1072 | -602 | 25 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −2638 | −2256 | −3993 | −3845 | −871 | −3609 | −2933 | −361 | −3459 | 3083 | 119 | −3676 | −3610 | −3057 | −3241 | −3452 | −2638 | −926 | −2214 | −2009 | 26 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 27 | 1035 | −942 | −3214 | −2668 | −636 | −2808 | −1823 | 1870 | −2366 | 1824 | 375 | −2384 | −2777 | −2026 | −2306 | −1946 | −1115 | 583 | −1616 | −1337 | 27 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 28 | -565 | −1222 | −1020 | −456 | −1437 | −1607 | −393 | −1050 | 104 | 633 | -520 | -588 | −1765 | −99 | 1537 | 1708 | -544 | −842 | −1634 | −1166 | 28 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 29 | −803 | −2043 | −242 | 10 | −2501 | −1531 | −330 | −2205 | 1608 | −2166 | −1338 | 1738 | 2164 | 79 | −99 | −696 | −771 | −1801 | −2312 | −1726 | 29 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 30 | 919 | −2142 | −1273 | -525 | −2689 | −1937 | −284 | −2237 | 1880 | −2117 | −1340 | −654 | −1992 | 138 | 2561 | −1045 | −992 | −1917 | −2163 | −1799 | 30 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 31 | −366 | −1456 | −476 | −12 | −2084 | 876 | −286 | −1779 | 1381 | −1835 | −973 | −238 | −1542 | 122 | −331 | 1116 | 1225 | −1346 | −2076 | −1486 | 31 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −1644 | -556 | * | * | | | | | | | | | | | | |
| 32 | −616 | -598 | −2131 | −1561 | 1597 | −2030 | −698 | −121 | −1304 | 690 | 208 | −1366 | 910 | −1052 | −1369 | 770 | -558 | −34 | −716 | 1837 | 32 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −15 | −7203 | −8245 | −894 | −1115 | −2223 | −348 | * | * | | | | | | | | | | | | |
| 33 | -587 | 2893 | 2226 | −686 | −2527 | −1419 | −1067 | −2221 | −930 | −2390 | −1574 | −783 | −1896 | −750 | −1363 | 1941 | −787 | −1690 | −2671 | −2133 | 33 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −15 | −7203 | −8245 | −894 | −1115 | −909 | −1097 | * | * | | | | | | | | | | | | |
| 34 | −1769 | −3376 | −15 | 3144 | −3738 | −1959 | −1197 | −3591 | −1201 | −3509 | −2755 | 1022 | 1141 | −841 | −1859 | −1521 | −1816 | −3092 | −3681 | −2824 | 34 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7611 | −8653 | −894 | −1115 | −1670 | -544 | * | * | | | | | | | | | | | | |
| 35 | −707 | −1363 | −1040 | 507 | −1470 | −1854 | -562 | 737 | 1856 | −1257 | -532 | −695 | −1936 | −273 | −702 | −816 | 841 | 1198 | −1743 | −1250 | 35 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −685 | −7611 | −1424 | −894 | −1115 | −1670 | -544 | * | * | | | | | | | | | | | | |
| 36 | −351 | −902 | −1246 | −861 | −1435 | −1376 | −824 | −1034 | −720 | 692 | −600 | −839 | 1365 | −636 | −1011 | 2008 | −486 | −771 | −1783 | −1328 | 36 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −18 | −6944 | −7986 | −894 | −1115 | −2437 | −294 | * | * | | | | | | | | | | | | |
| 37 | -554 | −439 | −2503 | −1915 | 1628 | 780 | −925 | 333 | −1599 | 993 | 487 | −1587 | −2112 | −1286 | −1541 | −1146 | -505 | 1464 | −866 | −471 | 37 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −745 | −6944 | −1339 | −894 | −1115 | −2437 | −294 | * | * | | | | | | | | | | | | |
| 38 | −1880 | −1567 | −2771 | −2762 | 3903 | −2519 | -522 | −754 | −2533 | −412 | −445 | −2106 | −2712 | −2041 | −2341 | −2150 | −1931 | −970 | 96 | 1156 | 38 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −29 | −6227 | −7270 | −894 | −1115 | −2788 | −226 | * | * | | | | | | | | | | | | |
| 39 | −1254 | −1492 | −1693 | −1828 | −2523 | −1576 | −1802 | −2566 | −1884 | −2643 | −2219 | −1711 | 3905 | −1860 | −1931 | −1458 | −1551 | −2160 | −2316 | −2366 | 39 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −29 | −6227 | −7270 | −894 | −1115 | −2788 | −226 | * | * | | | | | | | | | | | | |
| 40 | −1607 | −1392 | −2838 | −2606 | −248 | −2686 | −1862 | 347 | −2180 | 2738 | 655 | −2465 | −2749 | −1988 | −2111 | −2272 | −1618 | -55 | −1452 | −1102 | 40 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −29 | −6227 | −7270 | −894 | −1115 | −1971 | −425 | * | * | | | | | | | | | | | | |
| 41 | 1416 | −840 | −2250 | −1886 | −675 | −1916 | −1395 | 196 | −1593 | 2041 | 265 | −1641 | −2202 | −1428 | −1663 | −1149 | −801 | 108 | −1557 | −1218 | 41 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |
| 42 | −937 | −1813 | −707 | −420 | −2466 | −1606 | −497 | −2144 | 2028 | −2141 | −1409 | -580 | 2717 | −133 | 93 | −914 | −946 | −1785 | −2217 | −1814 | 42 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 43 | −496 | −1315 | −922 | −493 | −2173 | −1340 | −471 | −1891 | 234 | −1946 | −1171 | -555 | −1680 | −118 | 2004 | 2188 | -596 | −1454 | −2086 | −1634 | 43 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |
| 44 | −757 | −1328 | −1147 | −608 | −1619 | −1731 | −448 | -588 | 2459 | −1191 | −629 | −706 | −1886 | −129 | 135 | −886 | −722 | 1520 | −1788 | −1360 | 44 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |
| 45 | −1149 | −1830 | 2790 | −354 | 2343 | −1718 | -545 | −1517 | −927 | −1541 | −1107 | -587 | −2046 | −629 | −1388 | −1123 | −1174 | −1389 | −1059 | −88 | 45 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |
| 46 | −625 | −2038 | 381 | 1681 | −2408 | −1223 | −215 | −2171 | 16 | −2152 | −1310 | 1874 | −1524 | 185 | -532 | 1326 | −623 | −1731 | −2354 | −1628 | 46 |
| — | −149 | -500 | 234 | 43 | −381 | 399 | 105 | −626 | 210 | −466 | −721 | 275 | 394 | 45 | 96 | 359 | 117 | −369 | −295 | −249 | |
| — | −965 | −1050 | −7680 | −125 | −3585 | −2619 | −256 | * | * | | | | | | | | | | | | |
| 47 | 1445 | -516 | −1546 | −1108 | −1011 | −1296 | −832 | 1607 | −932 | −804 | −164 | −941 | −1667 | −777 | −1141 | 1301 | −293 | −46 | −1449 | −1056 | 48 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −2619 | −256 | * | * | | | | | | | | | | | | |
| 48 | 1248 | 3000 | −2529 | −2038 | −722 | −1816 | −1262 | 1978 | −1745 | −334 | 149 | −1624 | −2076 | −1490 | −1737 | −998 | −497 | 738 | −1349 | −989 | 49 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6638 | −7680 | −894 | −1115 | −925 | −1079 | * | * | | | | | | | | | | | | |
| 49 | -568 | 1551 | −467 | 1864 | −2191 | −1532 | −300 | −1900 | 74 | −1930 | −1052 | 1275 | −1674 | 129 | −419 | 691 | 870 | −1503 | −2166 | −1528 | 50 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −13 | −7426 | −8468 | −894 | −1115 | −1344 | −723 | * | * | | | | | | | | | | | | |
| 50 | −621 | −2045 | 1463 | 762 | −2344 | −1578 | −258 | −2080 | 863 | −2053 | −1144 | −222 | −1684 | 191 | −365 | 594 | 1478 | 18 | −2243 | −1570 | 51 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7566 | −8608 | −894 | −1115 | −1752 | -508 | * | * | | | | | | | | | | | | |
| 51 | 971 | −1910 | −636 | −195 | −2510 | 1277 | -534 | −2238 | 800 | −2245 | −1353 | 879 | −1824 | −106 | −643 | 1406 | −703 | −1770 | −2451 | −1814 | 52 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7566 | −8608 | −894 | −1115 | −1752 | -508 | * | * | | | | | | | | | | | | |
| 52 | −634 | −1816 | −603 | -52 | −2038 | −1647 | 2651 | 77 | 809 | −1783 | −935 | 1665 | −1736 | 1347 | −357 | -574 | -570 | 120 | −2055 | −1452 | 53 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −152 | −7566 | −3398 | −894 | −1115 | −1190 | −832 | * | * | | | | | | | | | | | | |
| 53 | −803 | −1895 | −775 | 1759 | −2103 | −1793 | −418 | 197 | 2158 | −321 | −999 | −492 | −1881 | −14 | −286 | −757 | −730 | −1385 | −2123 | −1564 | 54 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −1779 | −497 | * | * | | | | | | | | | | | | |
| 54 | −628 | −2083 | 967 | 775 | −2394 | −1576 | 1463 | −2140 | 165 | −2093 | −1177 | 1793 | −1682 | 204 | 1269 | -507 | -568 | −1701 | 2428 | −1587 | 55 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −1779 | −497 | * | * | | | | | | | | | | | | |
| 55 | −696 | −1704 | −609 | 995 | −1943 | 11 | −474 | −1580 | −181 | −1728 | −921 | 1119 | −1828 | −102 | −650 | −682 | 1164 | 1676 | −2068 | −1492 | 56 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −1779 | −497 | * | * | | | | | | | | | | | | |
| 56 | 609 | −756 | −1923 | −1358 | 1262 | −2001 | 1446 | −324 | −1147 | −655 | 15 | −1288 | −2101 | −956 | −1311 | 1484 | −606 | 1375 | −1200 | −798 | 57 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −1779 | −497 | * | * | | | | | | | | | | | | |
| 57 | 1700 | 2274 | −3519 | −3524 | −3438 | −1557 | −2861 | −3124 | −3256 | −3435 | −2569 | −2204 | −2324 | −2877 | −3126 | 2877 | −1082 | −2181 | −3715 | −3541 | 58 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −290 | −2456 | * | * | | | | | | | | | | | | |
| 58 | 365 | 3467 | −3137 | −2741 | −2076 | 1278 | −2108 | −1633 | −2492 | −1977 | −1273 | −2151 | 1592 | −2221 | −2527 | −1277 | 882 | 1044 | −2499 | −2168 | 59 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 59 | −830 | −1788 | −935 | −398 | −1974 | 1291 | −602 | −1609 | 597 | -504 | −960 | 2220 | −1989 | −234 | −726 | −834 | 651 | −26 | −2114 | −1559 | 60 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −159 | −7942 | −3315 | −894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 60 | −1457 | −2680 | −1373 | −748 | −3182 | −2285 | −720 | −2800 | 2797 | −2653 | −1825 | 653 | −2357 | −282 | 977 | 1300 | −1342 | −2421 | −2699 | −2240 | 61 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −10 | −7792 | −8834 | −894 | −1115 | −1247 | −789 | * | * | | | | | | | | | | | | |
| 61 | −940 | −2108 | −951 | −485 | −2748 | −1850 | −743 | −2456 | −250 | −2453 | −1579 | 2580 | −2064 | −320 | 1673 | 1082 | 826 | −1999 | −2637 | −2046 | 62 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −307 | −7792 | −2417 | −894 | −1115 | −1247 | −789 | * | * | | | | | | | | | | | | |
| 62 | −865 | −1649 | −1230 | −1297 | −3345 | 2183 | −1762 | −3108 | −1718 | −3246 | −2402 | 2789 | −2246 | −1485 | −2088 | −987 | 1280 | −2321 | −3455 | −2971 | 63 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −453 | −7497 | −1921 | −894 | −1115 | −1241 | −793 | * | * | | | | | | | | | | | | |
| 63 | 817 | −1591 | −392 | 1509 | 2013 | −1555 | −357 | −1427 | −101 | −1575 | −787 | 1020 | −1718 | -5 | -570 | -595 | -572 | −1153 | −1893 | −1294 | 64 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −14 | −7237 | −8280 | −894 | −1115 | −213 | −2866 | * | * | | | | | | | | | | | | |
| 64 | 395 | −1831 | −1143 | −606 | −2276 | −1891 | −801 | −1908 | 2597 | −2054 | −1235 | −819 | −2082 | −424 | −873 | 425 | 724 | 375 | −2376 | −1825 | 65 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 65 | −1358 | −2769 | 2069 | −465 | −3152 | 300 | −793 | −2861 | 1851 | −2759 | −1894 | −755 | −2279 | −357 | 2039 | −1213 | −1288 | −2436 | −2871 | −2260 | 66 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −116 | −7942 | −3775 | −894 | −1115 | −701 | −1378 | * | * | | | | | | | | | | | | |
| 66 | −724 | −2079 | 789 | −66 | −2353 | −1713 | −379 | −2071 | 948 | −258 | −1181 | 736 | −1807 | 1547 | −476 | −627 | 1284 | 490 | −2291 | −1638 | 67 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7835 | −8877 | −894 | −1115 | −1115 | −894 | * | * | | | | | | | | | | | | |
| 67 | −972 | −838 | −3017 | −2395 | −701 | −2493 | −1336 | −209 | 1107 | 1103 | 2709 | −2032 | −2527 | −1709 | −1913 | −1569 | −910 | 1385 | 2423 | −935 | 68 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7835 | −8877 | −894 | −1115 | −492 | −1792 | * | * | | | | | | | | | | | | |
| 68 | −833 | −2203 | 1367 | −153 | −2506 | 159 | −487 | −2231 | −87 | −303 | −1327 | −456 | 807 | −44 | 2001 | 129 | −778 | −1822 | −2429 | −1771 | 69 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 69 | −780 | −2099 | −685 | 1492 | −2360 | −1776 | −444 | −2069 | -51 | −2090 | 1057 | 945 | −1869 | 1649 | -547 | 462 | 268 | 770 | −2321 | −1676 | 70 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 70 | 83 | −1009 | −33 | −1448 | 2429 | 159 | −1046 | -573 | −1267 | 860 | −221 | −1427 | −2297 | −1086 | −1465 | −1240 | 992 | −459 | −1455 | −1062 | 71 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 71 | 700 | −1635 | −3702 | −3780 | −4060 | −1911 | −3273 | −3808 | −3626 | −4078 | −3163 | −2541 | −2690 | −3246 | −3522 | 3166 | 1266 | −2700 | −4285 | −4138 | 72 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 72 | −1589 | −3213 | 1112 | 2538 | −3486 | 1213 | −1073 | −3292 | −915 | −3214 | −2366 | −674 | −2390 | 893 | −1533 | 483 | −1577 | −2819 | −3392 | −2592 | 73 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 73 | 319 | −1877 | 337 | 502 | −2062 | −1828 | -507 | 744 | 1573 | −1833 | 1455 | -538 | 475 | −110 | −638 | −752 | −725 | 197 | −2148 | −1560 | 74 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 74 | −792 | −2258 | 1081 | 1527 | −2577 | −1759 | −420 | −2325 | 1424 | −2272 | 1385 | −395 | −1855 | 38 | 824 | 709 | −731 | −1879 | −2441 | −1761 | 75 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 75 | 423 | −1307 | 229 | −882 | −1394 | 733 | −835 | 866 | −748 | −1242 | -524 | −1025 | −2142 | −641 | −1102 | 319 | 1388 | 843 | −1733 | −1282 | 76 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 76 | 516 | −1915 | −1159 | 983 | −2630 | −10 | −1024 | −2310 | −729 | −2419 | −1574 | −935 | −2169 | −643 | −1188 | 2442 | −1008 | 40 | −2704 | −2133 | 77 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | −990 | −1014 | −2924 | −2384 | −1172 | −128 | −1568 | 1234 | −2102 | −1007 | −378 | −2035 | −2568 | −1829 | −2101 | 1310 | 751 | 2189 | −1674 | −1318 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 78 | 349 | −2115 | 439 | 611 | −2383 | −1770 | −435 | −2097 | −39 | −2108 | −1219 | −428 | −1862 | 5 | 725 | 1069 | 1096 | 192 | −2331 | 899 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 79 | 370 | −2190 | −641 | 1109 | −2490 | −333 | −418 | −2225 | 1644 | −370 | −1287 | −401 | 359 | 34 | −510 | 140 | 558 | −1801 | −2389 | −1721 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −103 | −7942 | −3949 | −894 | −1115 | −701 | −1378 | * | * | | | | | | | | | | | | |
| 80 | 883 | −2220 | 1487 | 849 | −2532 | 97 | −391 | −2279 | 16 | −2233 | −1314 | 1370 | −1819 | 64 | 494 | −641 | −702 | −210 | −2409 | −1727 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −233 | −7848 | −2787 | −894 | −1115 | −1072 | −932 | * | * | | | | | | | | | | | | |
| 81 | 728 | −1717 | −993 | −499 | −2509 | 1340 | −756 | −2215 | 977 | −2279 | −1404 | −690 | −1915 | −352 | −859 | 1088 | 1497 | −1735 | −2521 | −1937 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1953 | −7626 | −441 | −894 | −1115 | −1641 | −558 | * | * | | | | | | | | | | | | |
| 82 | −310 | −1040 | 256 | 155 | −1405 | −812 | −283 | −1507 | −119 | −1688 | −1080 | 3006 | −1284 | −79 | −430 | −338 | −471 | −1137 | −1571 | −972 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −41 | −5714 | −6756 | −894 | −1115 | −2926 | −204 | * | * | | | | | | | | | | | | |
| 83 | −1301 | −1085 | −1863 | −1724 | 634 | −1658 | −307 | −942 | −1231 | −752 | −570 | −1433 | −1941 | −1221 | −1190 | −1529 | −1347 | −976 | 5274 | 987 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −41 | −5714 | −6756 | −894 | −1115 | −2926 | −204 | * | * | | | | | | | | | | | | |
| 84 | −659 | −720 | −1743 | −1420 | −70 | −1758 | −955 | 616 | −988 | 780 | 3648 | −1323 | −1949 | −969 | −1066 | −1111 | −708 | 404 | −1038 | −617 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −41 | −5714 | −6756 | −894 | −1115 | −2926 | −204 | * | * | | | | | | | | | | | | |
| 85 | −1138 | −969 | −2053 | −1919 | 3350 | −1960 | −173 | −37 | −1692 | 196 | 209 | −1478 | −2145 | −1337 | −1629 | −1456 | −1178 | −220 | 344 | 1362 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −41 | −5714 | −6756 | −894 | −1115 | −2926 | −204 | * | * | | | | | | | | | | | | |
| 86 | −416 | −776 | −795 | −835 | −1626 | −887 | −883 | −1494 | −839 | −1647 | −1181 | −784 | 3363 | −834 | −975 | −597 | −668 | −1156 | −1599 | −1452 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −41 | −5714 | −6756 | −894 | −1115 | −2166 | −364 | * | * | | | | | | | | | | | | |
| 87 | −632 | −1793 | 524 | 2103 | −2359 | 1684 | −317 | −2122 | −183 | −2170 | −1413 | 104 | −1482 | 25 | −696 | −517 | −700 | −1691 | −2331 | −1695 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −29 | −6227 | −7270 | −894 | −1115 | −2788 | −226 | * | * | | | | | | | | | | | | |
| 88 | 1494 | −488 | −1992 | −1597 | −767 | −1724 | −1213 | 2195 | −1363 | −138 | 179 | −1389 | −2001 | −1224 | −1493 | −932 | −488 | 955 | −1526 | −1133 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −29 | −6227 | −7270 | −894 | −1115 | −1480 | −640 | * | * | | | | | | | | | | | | |
| 89 | 1804 | −2047 | 138 | 1534 | −2480 | −1379 | −402 | −2212 | −170 | −2233 | −1400 | 1699 | −1685 | −9 | −702 | −617 | −750 | −1785 | −2460 | −1765 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6939 | −7981 | −894 | −1115 | −2441 | −294 | * | * | | | | | | | | | | | | |
| 90 | 1831 | −944 | −988 | −575 | −1338 | −1418 | −609 | −871 | −463 | −1159 | 2326 | 1571 | −1705 | −384 | −797 | −534 | −436 | −640 | −1656 | −1192 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6939 | −7981 | −894 | −1115 | −2441 | −294 | * | * | | | | | | | | | | | | |
| 91 | −449 | −1732 | 1354 | 1343 | −1975 | −1350 | −101 | −1667 | 235 | −1716 | 1970 | −19 | −1497 | 317 | −270 | −357 | 1097 | −1307 | −1975 | −1328 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −18 | −6939 | −7981 | −894 | −1115 | −2441 | −294 | * | * | | | | | | | | | | | | |
| 92 | −451 | −1530 | −321 | 128 | −1733 | −1416 | −138 | −1406 | 245 | 282 | −692 | 1470 | 1076 | 1675 | −185 | −411 | −398 | −1107 | −1804 | −1218 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −339 | −6939 | −2312 | −894 | −1115 | −2441 | −294 | * | * | | | | | | | | | | | | |
| 93 | −374 | −965 | −1587 | −1709 | −2488 | −1139 | −1726 | −2483 | −1808 | −2720 | −2020 | −1300 | −1825 | −1663 | −1914 | 3241 | −760 | −1740 | −2677 | −2294 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −22 | −6621 | −7664 | −894 | −1115 | −2627 | −255 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | −494 | −744 | −1993 | −1741 | −1272 | −1602 | −1425 | 164 | −1535 | −814 | −411 | −1455 | 1760 | −1424 | −1652 | −894 | −672 | 2601 | −1889 | −1490 | 95 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −22 | −6621 | −7664 | −894 | −1115 | −1620 | -568 | * | * | | | | | | | | | | | | |
| 95 | −407 | −1534 | −393 | 148 | −1747 | −1423 | 1700 | −1412 | 1281 | −1501 | −666 | 1042 | −1517 | 312 | −142 | −361 | 1018 | 686 | −1790 | −1201 | 96 |
| — | −149 | -500 | 233 | 43 | −381 | 398 | 106 | −626 | 212 | −466 | −721 | 275 | 394 | 45 | 96 | 359 | 117 | −368 | −295 | −249 | |
| — | −2199 | −1515 | −1209 | −131 | −3529 | −1042 | −959 | * | * | | | | | | | | | | | | |
| 96 | −1011 | −1893 | −1118 | −631 | −2608 | −1785 | -525 | −2141 | 2913 | −2169 | −1430 | −740 | −2004 | −137 | 242 | −1000 | 1456 | −1796 | −2298 | −1908 | 98 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 97 | −1180 | −2471 | 3198 | 68 | −3219 | −1438 | −919 | −3116 | −1056 | −3116 | −2386 | −264 | −1969 | -599 | −1749 | 1359 | −1326 | −2545 | −3268 | −2449 | 99 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 98 | -549 | −989 | −1228 | −699 | −1237 | −1698 | -593 | −334 | 1357 | −957 | −316 | −789 | −1862 | −371 | -521 | −770 | 1329 | 1926 | −1576 | −1144 | 100 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 99 | −350 | −1320 | -528 | −72 | −1826 | −1324 | 2363 | −1504 | 8 | −1623 | −799 | −284 | 1117 | 59 | −430 | 1017 | 1316 | −1140 | −1924 | −1359 | 101 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 100 | −761 | −1736 | −768 | −206 | 1511 | −1695 | −210 | −1591 | 2213 | −1611 | −868 | −415 | −1778 | 1781 | 183 | −722 | −672 | −1333 | −1712 | −1102 | 102 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 101 | −343 | −1168 | −830 | −601 | −2357 | −1216 | −885 | −2056 | −671 | −2202 | −1368 | 1734 | −1692 | -559 | −1063 | 1277 | 2406 | −1494 | −2474 | −1962 | 103 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 102 | −946 | −917 | −2322 | −1718 | −715 | −2404 | −1169 | 2289 | 1239 | 1111 | 234 | −1645 | −2404 | −1167 | −1189 | −1491 | −881 | 360 | −1451 | −1109 | 104 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 103 | −1184 | −2001 | −720 | −712 | −2693 | −1747 | −1058 | −2597 | -592 | −2590 | −1920 | −886 | 3285 | 2091 | −839 | −1191 | −1305 | −2181 | −2653 | −2177 | 105 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 104 | 966 | −1977 | −198 | 1347 | −2337 | −1464 | −181 | −2032 | 2145 | −2001 | −1143 | −133 | −1625 | 247 | -54 | -528 | -590 | −1632 | −2172 | −1554 | 106 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 105 | −603 | −1557 | −222 | 2106 | −1944 | 887 | −459 | −1435 | −230 | −1716 | −956 | −296 | −1703 | −112 | −693 | -599 | −625 | 1108 | −2097 | −1516 | 107 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −1424 | −673 | * | * | | | | | | | | | | | | |
| 106 | -518 | −1972 | 739 | 192 | −2300 | −1476 | 1590 | −2040 | 1283 | −1980 | −1063 | −113 | 825 | 1516 | 1111 | −398 | −454 | −1599 | −2141 | −1475 | 108 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −14 | −7290 | −8332 | −894 | −1115 | −1510 | −624 | * | * | | | | | | | | | | | | |
| 107 | -569 | −1727 | -515 | 783 | −1969 | −1572 | −283 | −1641 | 75 | −1726 | −882 | −284 | −1683 | 1155 | −401 | 1638 | 908 | 545 | −2014 | −1408 | 109 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −12 | −7443 | −8485 | −894 | −1115 | −1155 | −860 | * | * | | | | | | | | | | | | |
| 108 | −774 | −2032 | −694 | −138 | −2305 | −1747 | 2453 | −1995 | 1156 | −70 | −1146 | −416 | −1835 | 1102 | −262 | 1587 | −703 | −1634 | −2219 | −1618 | 110 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7626 | −8668 | −894 | −1115 | −1018 | −982 | * | * | | | | | | | | | | | | |
| 109 | 431 | −1605 | −826 | 833 | −1742 | 626 | 1329 | 117 | −171 | −31 | −748 | -529 | −1859 | −108 | −623 | 496 | 681 | −1126 | −1912 | −1364 | 111 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −10 | −7748 | −8790 | −894 | −1115 | −1366 | −708 | * | * | | | | | | | | | | | | |
| 110 | −765 | −1611 | −1047 | -520 | −1923 | 762 | −675 | −1534 | 1570 | −1721 | −935 | −728 | 689 | −333 | −772 | −814 | 741 | 1485 | −2093 | −1569 | 112 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −10 | −7748 | −8790 | −894 | −1115 | −401 | −2044 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 111 | 372 | −2322 | -588 | 1575 | −2645 | 710 | −478 | −2396 | 1636 | −2343 | −1424 | 918 | −1901 | −24 | -583 | 216 | −797 | −1948 | −2514 | −1827 | 113 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 112 | −1262 | −2623 | 1722 | −408 | −3186 | 1427 | −991 | −2957 | −742 | −2924 | −2047 | 1032 | −2257 | -577 | −1295 | 1069 | 1482 | −2458 | −3113 | −2398 | 114 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 113 | −830 | −2185 | 1103 | 1522 | −2459 | −1793 | −482 | −2176 | −97 | −378 | −1294 | −449 | 477 | −43 | −600 | 1384 | −772 | −212 | −2403 | −1746 | 115 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 114 | 1154 | −2023 | −992 | −473 | −2633 | −1826 | −751 | −2346 | −360 | −2376 | −1490 | 919 | −2032 | −327 | 1213 | 1758 | 950 | −1894 | −2597 | −1984 | 116 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 115 | 1014 | −2054 | −741 | −195 | −2327 | −1797 | −484 | −2024 | 1675 | −305 | −1193 | 877 | −1898 | -55 | -579 | 844 | 651 | −1657 | −2312 | −1683 | 117 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −116 | −7942 | −3775 | −894 | −1115 | −701 | −1378 | * | * | | | | | | | | | | | | |
| 116 | 1975 | −1562 | −3311 | −3391 | −3933 | −1821 | −3064 | −3701 | −3357 | −3947 | −3038 | −2363 | 3098 | −3001 | −3323 | 1196 | −1377 | −2611 | −4148 | −3966 | 118 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7835 | −8877 | −894 | −1115 | −492 | −1792 | * | * | | | | | | | | | | | | |
| 117 | −1580 | −1656 | −3672 | −3323 | −1788 | −2859 | −2611 | −448 | −2954 | −1042 | 1585 | −2834 | 3410 | −2753 | −2923 | −2119 | −1717 | 1487 | −2652 | −2316 | 119 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −159 | −7942 | −3315 | −894 | −1115 | −701 | −1378 | * | * | | | | | | | | | | | | |
| 118 | 1492 | −2086 | 550 | 698 | −2365 | −1706 | −389 | −2082 | 2 | −2088 | −1198 | −364 | 1396 | 51 | 513 | −637 | −676 | 234 | −2306 | −1652 | 120 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | -569 | −7792 | −1638 | −894 | −1115 | −441 | −1924 | * | * | | | | | | | | | | | | |
| 119 | 2169 | −1825 | −655 | −261 | −2466 | −1595 | -584 | −2174 | 910 | −2211 | −1344 | 1021 | −1842 | −173 | −643 | 850 | −729 | −1724 | −2435 | −1830 | 121 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −12 | −7452 | −8494 | −894 | −1115 | −259 | −2607 | * | * | | | | | | | | | | | | |
| 120 | −4125 | −4091 | −4017 | −3615 | -5101 | −3960 | −2958 | -5182 | 3972 | −4825 | −4345 | −3552 | −4249 | −2709 | −1809 | −4154 | −4044 | −4895 | −4132 | −4389 | 122 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 121 | 2764 | −1712 | −2512 | −2299 | −3574 | −1909 | −2350 | −3303 | −2295 | −3485 | −2607 | 1592 | −2555 | −2104 | −2563 | 678 | 923 | −2474 | −3731 | −3360 | 123 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 122 | −2740 | −3536 | −2261 | −1808 | −4262 | −3114 | −1408 | −3815 | 1496 | −3500 | −2847 | −1861 | −3239 | 4039 | −202 | −2600 | −2538 | −3537 | −3332 | −3130 | 124 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 123 | 268 | −1861 | −4935 | −4578 | −2490 | −4579 | −4364 | 2671 | −4464 | −1384 | −1256 | −4297 | −4452 | −4346 | −4547 | −3891 | −2305 | 2774 | −3952 | −3477 | 125 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 124 | −2838 | −2616 | −4834 | −4880 | −3213 | −3955 | −4416 | −610 | −4757 | −2310 | −2253 | −4383 | −4345 | −4643 | −4642 | −3732 | −3007 | 3763 | −4157 | −3886 | 126 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 125 | −4088 | −3924 | −4774 | -5139 | -5615 | 3825 | −4753 | −6303 | -5453 | −6014 | -5662 | −4812 | −4539 | -5232 | -5106 | −4370 | −4472 | -5527 | −4696 | -5561 | 127 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 126 | -5598 | −4432 | -5385 | -5722 | −3380 | −4524 | −4140 | -5941 | -5643 | -5318 | -5354 | -5427 | −4938 | -5474 | -5178 | -5909 | -5751 | -5890 | 6275 | −2993 | 128 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 127 | −4497 | −4117 | −4899 | -5251 | -5560 | −4139 | −4798 | −6328 | -5454 | -5976 | -5741 | -5026 | 4302 | -5328 | -5104 | −4798 | −4844 | -5739 | −4665 | -5484 | 129 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128 | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 130 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 129 | -2454 | -1957 | -5123 | -4806 | -2583 | -4915 | -4898 | 2605 | -4752 | -1355 | -1296 | -4602 | -4686 | -4684 | -4897 | -4287 | -2450 | 3067 | -4290 | -3786 | 131 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 130 | -2748 | 3830 | -4416 | -3730 | -4308 | -3282 | -2795 | -4179 | -1740 | -4165 | -3597 | -3273 | -3742 | -2579 | 3677 | -2940 | -2956 | -3724 | -3878 | -3874 | 132 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 131 | -1944 | -2458 | -3696 | -4011 | -4410 | -2644 | -3753 | -4675 | -4191 | -4807 | -4070 | -3198 | -3384 | -3886 | -4051 | 3656 | -2393 | -3615 | -4374 | -4307 | 133 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 132 | -4609 | -3570 | -5024 | -5362 | 2535 | -4897 | -1137 | -3495 | -4925 | -2817 | -2908 | -3545 | -4766 | -3679 | -4306 | -4162 | -4471 | -3659 | -385 | 4425 | 134 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 133 | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 135 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 134 | -3026 | -3582 | -3851 | -2340 | -4536 | -3447 | -1304 | -3819 | 3629 | -3424 | -2785 | -2164 | -3384 | -889 | 1433 | -2903 | -2669 | -3611 | -3211 | -3177 | 136 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 135 | -2488 | -3492 | -1364 | -1377 | -4198 | -2771 | -1608 | -3981 | 2043 | -3763 | -3089 | 3669 | -3109 | -1245 | -834 | -2340 | -2461 | -3576 | -3621 | -3223 | 137 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 136 | -835 | -2058 | -786 | -253 | -2348 | -1828 | -533 | -2038 | 875 | -2087 | 1498 | 2028 | -1940 | -110 | -604 | 1286 | 1264 | -1677 | -2339 | -1722 | 138 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -116 | -7942 | -3775 | -894 | -1115 | -701 | -1378 | * | * | | | | | | | | | | | | |
| 137 | -865 | -722 | -2990 | -2372 | -674 | -2397 | -1261 | 710 | -2017 | 1327 | 2685 | 722 | -2445 | -1682 | -1897 | 13 | -807 | 1180 | -1191 | -845 | 139 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7835 | -8877 | -894 | -1115 | -492 | -1792 | * | * | | | | | | | | | | | | |
| 138 | 1772 | -1752 | -919 | -371 | -1902 | -1877 | 1230 | -1539 | -260 | -1695 | 1161 | 877 | -1967 | 1830 | -710 | -814 | -748 | 36 | -2055 | -1501 | 140 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -683 | -7942 | -1423 | -894 | -1115 | -701 | -1378 | * | * | | | | | | | | | | | | |
| 139 | -473 | -977 | -2303 | -1976 | -2092 | -1477 | -1693 | -1408 | -1798 | -1932 | -1229 | -1537 | -2050 | -1613 | -1958 | 2301 | 1959 | 1227 | -2468 | -2114 | 141 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -242 | -7273 | -2754 | -894 | -1115 | -2151 | -368 | * | * | | | | | | | | | | | | |
| 140 | -772 | -2032 | -518 | -54 | -2456 | -1615 | -239 | -2134 | 1785 | -2069 | -1222 | -306 | -1746 | 1835 | 140 | 1704 | -703 | -1742 | -2196 | -1642 | 142 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -772 | -7047 | -1298 | -894 | -1115 | -2360 | -312 | * | * | | | | | | | | | | | | |
| 141 | -825 | -1899 | -527 | -44 | -2343 | -1532 | 22 | -1960 | 2201 | -1837 | -1078 | -222 | -1641 | 2407 | 830 | -716 | -701 | -1642 | -1885 | -1469 | 143 |
| — | -149 | -500 | 232 | 42 | -381 | 399 | 105 | -627 | 211 | -467 | -721 | 278 | 395 | 47 | 95 | 360 | 117 | -370 | -295 | -250 | |
| — | -580 | -1621 | -7345 | -2597 | -261 | -1507 | -626 | * | * | | | | | | | | | | | | |
| 142 | -221 | -857 | -1942 | -1852 | -2688 | -1112 | -1767 | -2352 | -1792 | -2638 | -1820 | -1322 | -1799 | -1612 | -1941 | 2384 | 2544 | -1588 | -2922 | -2589 | 151 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 143 | -343 | 2506 | -993 | 1154 | -1049 | -1495 | -457 | -539 | -360 | -883 | -171 | -599 | -1675 | -257 | -706 | 921 | -345 | 1151 | -1388 | -937 | 152 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 144 | -564 | -1588 | -617 | -202 | -2278 | 990 | -398 | -1937 | 2192 | -1982 | -1153 | -396 | -1694 | -2 | -161 | -552 | 1391 | -1517 | -2188 | -1658 | 153 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145 | −1331 | −2901 | 433 | 2491 | −3202 | −1508 | −731 | −3074 | −704 | −3007 | −2270 | 2727 | −1963 | −381 | −1324 | −1083 | −1372 | −2602 | −3148 | −2317 | 154 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 146 | -554 | −1745 | −104 | 2163 | −2295 | −1342 | −362 | −2003 | −69 | −2051 | −1203 | −170 | −1621 | 37 | -564 | 1056 | 1254 | −1570 | −2290 | −1643 | 155 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −2432 | −296 | * | * | | | | | | | | | | | | |
| 147 | 1227 | −1744 | 2425 | −36 | −2635 | −1306 | −660 | −2377 | -517 | −2433 | −1597 | −290 | −1726 | −292 | −1056 | 1267 | −761 | −1841 | −2665 | −2000 | 156 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −17 | −6952 | −7994 | −894 | −1115 | −1466 | −648 | * | * | | | | | | | | | | | | |
| 148 | −1547 | −2909 | −263 | 2972 | −3324 | −1927 | −794 | −3041 | 1733 | −2912 | −2153 | -580 | −2235 | −405 | -501 | −1347 | −1501 | −2639 | −2968 | −2385 | 157 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −14 | −7273 | −8315 | −894 | −1115 | −663 | −1441 | * | * | | | | | | | | | | | | |
| 149 | 498 | −2059 | -549 | 918 | −2343 | −1672 | −348 | −2063 | 1021 | −2062 | −1168 | 1810 | −1773 | 94 | −446 | 241 | −638 | 994 | −2274 | −1619 | 158 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −10 | −7736 | −8778 | −894 | −1115 | −391 | −2075 | * | * | | | | | | | | | | | | |
| 150 | −1976 | −3729 | 1863 | 2823 | −3957 | −2181 | −1353 | −3809 | 805 | −3704 | −2924 | 1223 | −2611 | −982 | −2058 | −1705 | −1995 | −3315 | −3885 | −2995 | 159 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 151 | 1763 | −1650 | −3642 | −3798 | −4181 | 2220 | −3341 | −3977 | −3752 | −4222 | −3282 | −2551 | −2699 | −3320 | −3626 | 2212 | −1485 | −2778 | −4391 | −4266 | 160 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −325 | −7942 | −2338 | −894 | −1115 | −701 | −1378 | * | * | | | | | | | | | | | | |
| 152 | −784 | −2199 | -572 | 700 | −2542 | 366 | −357 | −2267 | 1096 | −2208 | −1307 | −356 | −1817 | 93 | 1007 | 1909 | −718 | −1838 | −2364 | −1721 | 161 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7627 | −8670 | −894 | −1115 | −1638 | -559 | * | * | | | | | | | | | | | | |
| 153 | −1755 | −2780 | −1424 | −982 | −3243 | −2409 | 1655 | −2950 | 2264 | −2799 | −2046 | −1140 | 2883 | −483 | −24 | −1650 | −1642 | −2615 | −2769 | −2356 | 162 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | -521 | −7627 | −1745 | −894 | −1115 | −324 | −2315 | * | * | | | | | | | | | | | | |
| 154 | −1786 | −3580 | 1253 | 2500 | −3798 | 1582 | −1138 | −3672 | −1233 | −3563 | −2815 | 1553 | −2365 | −780 | −1990 | −1494 | −1823 | −3167 | −3753 | −2821 | 163 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −213 | −7550 | −2923 | −894 | −1115 | −1779 | −497 | * | * | | | | | | | | | | | | |
| 155 | -528 | −1123 | −977 | −444 | −1256 | 1292 | −482 | −841 | −310 | 280 | −356 | −618 | −1796 | 1459 | −688 | 672 | −493 | 499 | −1551 | −1076 | 164 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −13 | −7350 | −8392 | −894 | −1115 | −2063 | −394 | * | * | | | | | | | | | | | | |
| 156 | −1097 | −2577 | 1176 | 37 | −2950 | 1967 | −665 | −2731 | −477 | −2688 | −1844 | −304 | 1179 | 1967 | −1058 | −927 | −1100 | −2269 | −2882 | −2127 | 165 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −13 | −7350 | −8392 | −894 | −1115 | −756 | −1294 | * | * | | | | | | | | | | | | |
| 157 | 2145 | 2685 | −3556 | −3388 | −2668 | 2048 | −2602 | −2092 | −3096 | −2568 | −1842 | −2293 | −2472 | −2736 | −2983 | −1106 | −1164 | 807 | −3074 | −2808 | 166 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −10 | −7720 | −8763 | −894 | −1115 | −379 | −2113 | * | * | | | | | | | | | | | | |
| 158 | −976 | −841 | −3052 | −2440 | −767 | −2501 | −1367 | 2038 | −2090 | 1386 | 2282 | 169 | −2548 | −1764 | −1986 | 270 | −918 | −168 | −1305 | −962 | 167 |
| — | −149 | -500 | 233 | 43 | −381 | 400 | 106 | −626 | 210 | −466 | −720 | 275 | 394 | 45 | 96 | 359 | 117 | −369 | −294 | −249 | |
| — | −155 | −3326 | −8984 | −220 | −2824 | −701 | −1378 | * | * | | | | | | | | | | | | |
| 159 | −4612 | −3570 | -5027 | -5365 | 3420 | −4900 | −1135 | −3495 | −4928 | −2817 | −2907 | −3544 | −4767 | −3678 | −4307 | −4162 | −4473 | −3659 | −383 | 3928 | 169 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 160 | −2380 | −2010 | −4897 | −4562 | −2123 | −4360 | −4085 | 361 | −4323 | −966 | 1564 | −4214 | −4328 | −4090 | −4298 | −3698 | −2405 | 3499 | −3572 | −3202 | 170 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 161 | −4125 | −4091 | −4017 | −3615 | -5101 | −3960 | −2958 | -5182 | 3972 | −4825 | −4345 | −3552 | −4249 | −2709 | −1809 | −4154 | −4044 | −4895 | −4132 | −4389 | 171 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 162 | -2838 | -2616 | -4834 | -4880 | -3213 | -3955 | -4416 | -610 | -4757 | -2310 | -2253 | -4383 | -4345 | -4643 | -4642 | -3732 | -3007 | 3763 | -4157 | -3886 | 172 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 163 | -1944 | -2458 | -3696 | -4011 | -4410 | -2644 | -3753 | -4675 | -4191 | -4807 | -4070 | -3198 | -3384 | -3886 | -4051 | 3656 | -2393 | -3615 | -4374 | -4307 | 173 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 164 | -3870 | -3616 | -4923 | -5074 | -3041 | -4123 | -4208 | -2775 | -4736 | -2183 | 5292 | -4720 | -4529 | -4612 | -4478 | -4340 | -4085 | -3170 | -3793 | -3651 | 174 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 165 | -2689 | -4635 | 3805 | 1052 | -4824 | -2408 | -1881 | -4857 | -2312 | -4685 | -4144 | -1016 | -3001 | -1583 | -3307 | -2298 | -2797 | -4296 | -4798 | -3747 | 175 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 166 | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 176 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 167 | 3317 | -1708 | -3973 | -4078 | -3410 | -2176 | -3406 | -1858 | -3832 | -2969 | -2503 | -2804 | -2913 | -3485 | -3656 | -1541 | -1635 | 761 | -3989 | -3742 | 177 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 168 | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 178 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 169 | -4592 | -3568 | -5012 | -5345 | 1524 | -4882 | -1148 | -3485 | -4912 | -2812 | -2901 | -3549 | -4761 | -3681 | -4301 | -4158 | -4461 | -3650 | -397 | 4655 | 179 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 170 | -3651 | -3064 | -5938 | -5374 | -1120 | -5684 | -4336 | -611 | -5088 | 3059 | 2168 | -5433 | -4786 | -3927 | -4594 | -5078 | -3497 | -1435 | -2917 | -3080 | 180 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 171 | -4488 | -4181 | -4789 | -4318 | -5193 | -4148 | -3436 | -5568 | -2393 | -5152 | -4748 | -4156 | -4479 | -3286 | 4202 | -4614 | -4467 | -5273 | -4267 | -4649 | 181 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 172 | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 182 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 173 | -2423 | -1940 | -5055 | -4683 | -2333 | -4803 | -4471 | 2975 | -4578 | -1136 | 1518 | -4459 | -4558 | -4389 | -4636 | -4122 | -2404 | 2527 | -3893 | -3493 | 183 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 174 | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 184 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 175 | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 185 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 176 | -916 | 1441 | -897 | -330 | -2556 | 783 | -569 | -2253 | 1853 | -2252 | -1375 | -602 | -2001 | -133 | 1844 | 107 | 262 | -1858 | -2453 | -1845 | 186 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 177 | -901 | 1542 | -3045 | -2429 | -736 | -2420 | -1308 | -223 | -2071 | 180 | 2852 | -2011 | -2482 | -1734 | -1947 | 986 | 1407 | 1129 | -1240 | -893 | 187 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 178 | -3284 | -3117 | -3428 | -3438 | 103 | -3920 | 2626 | -3141 | -3196 | -2745 | -2589 | -2856 | -4060 | -2837 | -3158 | 385 | -3295 | -3118 | -600 | 4289 | 188 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 179 | −1202 | −2443 | −944 | -570 | −3032 | 664 | −871 | −2740 | 2635 | −2697 | −1830 | 1016 | −2245 | −445 | −702 | −1120 | 1395 | −2286 | −2850 | −2253 | 189 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 180 | −1363 | −2463 | −834 | −820 | −3504 | 2059 | −1426 | −3279 | −1227 | −3289 | −2438 | 1058 | −2465 | 783 | −1723 | 2215 | −1505 | −2677 | −3478 | −2822 | 190 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 181 | −4791 | −3935 | −4914 | -5231 | −815 | −4530 | −2178 | −4357 | -5024 | −3745 | −3807 | −4206 | −4772 | −4328 | −4584 | −4677 | −4837 | −4435 | −1477 | 4857 | 191 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 182 | −808 | −1661 | −991 | −437 | −1786 | 30 | -599 | 401 | −316 | 453 | −810 | −681 | 795 | 1083 | 743 | 1088 | −748 | −1175 | −1979 | −1446 | 192 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 183 | −2149 | −3976 | 1001 | 3147 | −4176 | −2223 | −1477 | −4059 | −1589 | −3941 | −3204 | 1212 | −2702 | 1224 | −2356 | −1845 | −2188 | −3550 | −4129 | −3181 | 193 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 184 | −4119 | −3542 | -5389 | -5357 | −2027 | −4767 | −4358 | −1609 | -5118 | 3293 | −979 | -5230 | −4771 | −4474 | −4724 | -5069 | −4106 | −2331 | −3412 | −3400 | 194 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 185 | 791 | −889 | −2857 | −2265 | −870 | −2427 | −1358 | −300 | −1960 | 984 | 1413 | −1958 | −2514 | −1671 | −1930 | 1912 | −920 | 849 | −1389 | −1038 | 195 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 186 | −789 | −2013 | 700 | −193 | 230 | −1801 | −476 | −1930 | 1736 | -575 | −1131 | −483 | −1894 | -54 | -588 | 1468 | 605 | −1586 | −2257 | −1636 | 196 |
| — | −149 | -500 | 233 | 43 | −381 | 399 | 106 | −626 | 210 | −466 | −720 | 275 | 394 | 45 | 96 | 359 | 117 | −369 | −294 | −24 | |
| — | −9 | −7942 | −8984 | −894 | −1115 | −701 | −1378 | * | * | | | | | | | | | | | | |
| 187 | 3008 | −1583 | −3739 | −3722 | −3526 | −1951 | −3105 | −2929 | −3498 | −3444 | −2663 | −2536 | −2695 | −3138 | −3395 | 1299 | −1440 | 641 | −3866 | −3649 | 197 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 188 | −4119 | −3542 | -5389 | -5357 | −2027 | −4767 | −4358 | −1609 | -5118 | 3293 | −979 | -5230 | −4771 | −4474 | −4724 | -5069 | −4106 | −2331 | −3412 | −3400 | 198 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 189 | −2820 | −3926 | −976 | 3619 | −4850 | 618 | −2397 | −4922 | −2645 | −4795 | −4203 | −1674 | −3343 | −2134 | −3305 | −2623 | −2989 | −4311 | −4566 | −4055 | 199 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 190 | −1125 | −2274 | −1087 | -569 | −2694 | −2052 | −751 | −2327 | 2735 | −2370 | −1533 | 1515 | −2191 | −333 | -505 | −1066 | 991 | −176 | −2579 | −2023 | 200 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 191 | −3526 | −2989 | -5762 | -5228 | −1135 | -5444 | −4167 | −610 | −4881 | 1755 | 4584 | -5201 | −4703 | −3865 | −4450 | −4828 | −3396 | −1382 | −2878 | −2962 | 201 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 192 | −4720 | −3927 | -5139 | -5454 | 4513 | −4504 | −2520 | −3938 | -5326 | −3307 | −3429 | −4469 | −4782 | −4575 | −4818 | −4787 | −4810 | −4172 | −1812 | −736 | 202 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 193 | −928 | −2343 | 546 | −198 | −2730 | 807 | -590 | −2478 | 1803 | −2438 | −1530 | -505 | −1979 | −145 | −715 | 1580 | 582 | −2025 | −2617 | −1936 | 203 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 194 | −925 | 4101 | −3103 | −2511 | 1370 | −2384 | −1395 | −360 | −2154 | 630 | −81 | −2056 | −2508 | −1816 | −2031 | 323 | 657 | −275 | −1335 | −975 | 204 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 195 | 127 | 1680 | -3023 | -2402 | 2687 | -2398 | -1264 | -237 | -2041 | 380 | 57 | -1982 | -2454 | -1701 | -1912 | 526 | 363 | -156 | -1191 | 957 | 205 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 196 | -1245 | -1254 | -3361 | -2883 | -1574 | 1462 | -2090 | 1383 | -2604 | -1233 | -710 | -2452 | -2897 | -2336 | -2586 | -1814 | 2421 | 1246 | -2175 | -1817 | 206 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 197 | -1433 | -1223 | -3728 | -3105 | 1174 | 1476 | -1882 | 2040 | -2729 | 1166 | 1660 | -2654 | -2998 | -2293 | -2529 | -2122 | -1367 | -384 | -1633 | -1344 | 207 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 198 | -1653 | -2638 | -826 | 2292 | -3549 | 2605 | -1710 | -3115 | -1664 | -3357 | -2623 | -1225 | -2688 | -1395 | -2173 | -1631 | -1817 | 104 | -3654 | -3020 | 208 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -155 | -7942 | -3356 | -894 | -1115 | -701 | -1378 | * | * | | | | | | | | | | | | |
| 199 | -1220 | -2659 | -405 | 1324 | -2791 | -1922 | -742 | -2684 | -410 | -2643 | -1789 | 1187 | -2142 | 2572 | -904 | -1068 | -1177 | -2270 | -2754 | 2625 | 209 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -10 | -7797 | -8839 | -894 | -1115 | -446 | -1911 | * | * | | | | | | | | | | | | |
| 200 | 879 | 3595 | -3205 | -2658 | 2120 | -2294 | -1572 | -547 | -2308 | -945 | -298 | -2123 | -2530 | -1968 | -2185 | 724 | -967 | 819 | -1552 | -1205 | 210 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 201 | 421 | -2123 | -848 | 2201 | -2537 | 1650 | -1017 | -2172 | -778 | 338 | -1534 | -872 | -2260 | -661 | -1248 | -1132 | -1165 | -1846 | -2670 | -2087 | 211 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 202 | -1738 | -2787 | -1885 | -1114 | -3269 | -2574 | -891 | -2832 | 2005 | -206 | -1929 | -1257 | -2607 | -467 | 2218 | 1703 | -1593 | -2517 | -2769 | -2389 | 212 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 203 | -1535 | -3151 | 1411 | 2066 | -3424 | -2046 | 2755 | -3226 | -841 | -3146 | -2290 | 1704 | -2354 | 1290 | -1445 | -1332 | -1516 | -2754 | -3322 | -2532 | 213 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 204 | 443 | -1647 | -3721 | -3895 | -3879 | 3366 | -3333 | -3254 | -3783 | -3812 | -3012 | -2607 | -2739 | -3372 | -3612 | -1325 | -1510 | 267 | -4191 | -4025 | 214 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -1326 | -7942 | -744 | -894 | -1115 | -701 | -1378 | * | * | | | | | | | | | | | | |
| 205 | 2566 | -652 | -1714 | -1730 | -2586 | 1821 | -1677 | -2245 | -1804 | -2543 | -1726 | -1160 | -1601 | -1555 | -1923 | -252 | -423 | -1441 | -2794 | -2521 | 215 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -2619 | -256 | * | * | | | | | | | | | | | | |
| 206 | 1348 | 3110 | -1091 | -639 | -1328 | -1184 | -589 | -875 | -410 | -1165 | -443 | -624 | -1546 | 1947 | -698 | -335 | -275 | -590 | -1624 | -1188 | 216 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -22 | -6638 | -7680 | -894 | -1115 | -1813 | -483 | * | * | | | | | | | | | | | | |
| 207 | -723 | -1173 | -1950 | -1826 | -1873 | 2846 | -1634 | -1445 | -1656 | -1624 | 2885 | -1544 | -2151 | -1589 | -1780 | -977 | -982 | -1203 | -2301 | -1916 | 217 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 208 | -1907 | -2634 | -2420 | -1227 | -3433 | -2464 | -430 | -2800 | 2677 | -2483 | -1804 | -1156 | -2426 | -12 | 2828 | -1792 | -1619 | -2560 | -2342 | -2212 | 218 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 209 | -1619 | -3464 | 3298 | 1766 | -3659 | -1517 | -890 | -3594 | -1152 | -3477 | -2831 | -122 | -2058 | -566 | -2007 | -1279 | -1693 | -3079 | -3640 | -2654 | 219 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 210 | -410 | -645 | -1350 | -781 | 1518 | 712 | -465 | -210 | -507 | -476 | 2215 | -818 | -1782 | -427 | 1142 | -719 | -358 | -97 | -1007 | -558 | 220 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 211 | -2334 | -1918 | -4419 | -3864 | -356 | -4133 | -2891 | 223 | -3494 | 2288 | 3708 | -3749 | -3630 | -2761 | -3223 | -3384 | -2226 | -419 | -1952 | -1940 | 221 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 212 | -578 | -1426 | -521 | -599 | -2737 | -1278 | -1129 | -2633 | -1025 | -2740 | -1930 | 2854 | -1845 | -840 | -1420 | 2151 | -840 | -1944 | -2858 | -2267 | 222 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 213 | -2358 | -3091 | -658 | 3674 | -3700 | -2238 | -1776 | -3777 | -1820 | -3720 | -3233 | -1275 | -2731 | -1557 | -2256 | -2198 | -2459 | -3405 | -3352 | -3111 | 223 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 214 | -343 | -723 | -1685 | -1246 | -1235 | -1464 | -999 | 1409 | -1062 | -1029 | -385 | -1095 | -1839 | -923 | -1281 | 1998 | 1407 | -287 | -1662 | -1264 | 224 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 215 | -1879 | -2620 | -2344 | -1198 | -3405 | -2442 | -431 | -2787 | 3092 | -2477 | -1795 | -1139 | -2412 | -13 | 2198 | -1765 | -1600 | -2542 | -2341 | -2201 | 225 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 216 | -2638 | -2256 | -3993 | -3845 | -871 | -3609 | -2933 | -361 | -3459 | 3083 | 119 | -3676 | -3610 | -3057 | -3241 | -3452 | -2638 | -926 | -2214 | -2009 | 226 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 217 | -664 | -1880 | -400 | 14 | -2321 | -1509 | -224 | -1997 | 2156 | -1978 | -1136 | 1625 | -1673 | 197 | 45 | -577 | 1291 | -1607 | -2143 | -1574 | 227 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 218 | -2520 | -3231 | 3969 | -951 | -3894 | -2249 | -1948 | -4204 | -2341 | -4098 | -3667 | -1302 | -2795 | -1775 | -2959 | -2329 | -2670 | -3755 | -3517 | -3297 | 228 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -2432 | -296 | * | * | | | | | | | | | | | | |
| 219 | -2638 | -2256 | -3993 | -3845 | -871 | -3609 | -2933 | -361 | -3459 | 3083 | 119 | -3676 | -3610 | -3057 | -3241 | -3452 | -2638 | -926 | -2214 | -2009 | 229 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -17 | -6952 | -7994 | -894 | -1115 | -864 | -1150 | * | * | | | | | | | | | | | | |
| 220 | -3034 | -2551 | -4364 | -4205 | 143 | -4149 | -1404 | -1231 | -3732 | 2392 | -681 | -3302 | -4000 | -3048 | -3424 | -3428 | -2952 | -1682 | -694 | 3371 | 230 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -11 | -7550 | -8592 | -894 | -1115 | -290 | -2456 | * | * | | | | | | | | | | | | |
| 221 | -1206 | -2579 | -1034 | 1115 | -2976 | -2098 | 1703 | -2665 | 2281 | -2556 | -1677 | 1718 | -2181 | -190 | 1057 | -1081 | -1116 | -2248 | -2655 | -2083 | 231 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 222 | -1402 | -2552 | -831 | -762 | -3458 | 2676 | -1296 | -3209 | 821 | -3189 | -2343 | 1554 | -2453 | -908 | -1386 | 541 | -1498 | -2656 | -3357 | -2721 | 232 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 223 | -1026 | 3123 | -2460 | -2125 | -3296 | 200 | -2099 | -2987 | 668 | -3168 | -2328 | -1859 | -2532 | -1838 | -2112 | 2794 | -1328 | -2309 | -3441 | -3059 | 233 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 224 | -2625 | -4591 | 2620 | 3097 | -4761 | -2375 | -1826 | -4772 | -2227 | -4605 | -4039 | -975 | -2959 | -1521 | -3203 | -2239 | -2725 | -4216 | -4745 | -3684 | 234 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 225 | -4600 | -3560 | -5009 | -5334 | 2635 | -4899 | 2666 | -3516 | -4891 | -2849 | -2927 | -3524 | -4760 | -3655 | -4282 | -4144 | -4455 | -3662 | -365 | 4072 | 235 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 226 | 684 | -1829 | -4834 | -4471 | -2433 | -4365 | -4146 | 1495 | -4328 | -1374 | -1228 | -4141 | -4317 | -4181 | -4382 | -3662 | -2242 | 3236 | -3803 | -3348 | 236 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 227 | -1996 | -1699 | -4301 | -3760 | -1423 | -3788 | -2832 | 1247 | -3457 | 1150 | -374 | -3420 | 2969 | -3065 | -3336 | -2948 | -1952 | 1152 | -2495 | -2229 | 237 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 228 | -1767 | -1840 | -4035 | -3868 | -2376 | -3028 | -3292 | 2122 | -3538 | -1538 | -1371 | -3226 | -3484 | -3384 | -3494 | -2373 | 3280 | -219 | -3364 | -2990 | 238 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 229 | -4791 | -3935 | -4914 | -5231 | -815 | -4530 | -2178 | -4357 | -5024 | -3745 | -3807 | -4206 | -4772 | -4328 | -4584 | -4677 | -4837 | -4435 | -1477 | 4857 | 239 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 230 | -4205 | -4417 | -2343 | 3901 | -5349 | -3698 | -3534 | -5837 | -3838 | -5561 | -5237 | -3039 | -4218 | -3453 | -4201 | -4072 | -4352 | -5409 | -4640 | -4860 | 240 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 231 | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 241 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 232 | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 242 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 233 | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 243 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 234 | -1274 | -1955 | -2502 | -2453 | -3965 | 3211 | -2433 | -3734 | -1975 | -3840 | -2994 | -2099 | -2750 | -2185 | 939 | 699 | -1633 | -2829 | -3940 | -3648 | 244 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 235 | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 245 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 236 | -5598 | -4432 | -5385 | -5722 | -3380 | -4524 | -4140 | -5941 | -5643 | -5318 | -5354 | -5427 | -4938 | -5474 | -5178 | -5909 | -5751 | -5890 | 6275 | -2993 | 246 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 237 | -3870 | -3616 | -4923 | -5074 | -3041 | -4123 | -4208 | -2775 | -4736 | -2183 | 5292 | -4720 | -4529 | -4612 | -4478 | -4340 | -4085 | -3170 | -3793 | -3651 | 247 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 238 | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 248 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 239 | -2440 | -1969 | -5081 | -4773 | -2525 | -4790 | -4760 | 1259 | -4687 | -1315 | -1266 | -4532 | -4623 | -4595 | -4801 | -4162 | -2445 | 3533 | -4180 | -3689 | 249 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 240 | -4088 | -3924 | -4774 | -5139 | -5615 | 3825 | -4753 | -6303 | -5453 | -6014 | -5662 | -4812 | -4539 | -5232 | -5106 | -4370 | -4472 | -5527 | -4696 | -5561 | 250 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 241 | -4232 | -4465 | 4158 | -2649 | -5412 | -3676 | -3575 | -6036 | -4125 | -5722 | -5419 | -2993 | -4216 | -3512 | -4617 | -4077 | -4401 | -5553 | -4696 | -4914 | 251 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 242 | -2838 | -2616 | -4834 | -4880 | -3213 | -3955 | -4416 | -610 | -4757 | -2310 | -2253 | -4383 | -4345 | -4643 | -4642 | -3732 | -3007 | 3763 | -4157 | -3886 | 252 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 243 | -4497 | -4117 | -4899 | -5251 | -5560 | -4139 | -4798 | -6328 | -5454 | -5976 | -5741 | -5026 | 4302 | -5328 | -5104 | -4798 | -4844 | -5739 | -4665 | -5484 | 253 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 244 | -5598 | -4432 | -5385 | -5722 | -3380 | -4524 | -4140 | -5941 | -5643 | -5318 | -5354 | -5427 | -4938 | -5474 | -5178 | -5909 | -5751 | -5890 | 6275 | -2993 | 254 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 245 | -2352 | -4269 | 1605 | 3243 | -4435 | -2274 | -1615 | -4361 | -1844 | -4223 | -3552 | -861 | -2805 | 1284 | -2686 | -2008 | -2415 | -3834 | -4412 | -3395 | 255 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 246 | -2968 | -2568 | -5237 | -4809 | -1360 | -4764 | -3887 | 1099 | -4419 | -34 | 4847 | -4576 | -4450 | -3793 | -4171 | -4117 | -2930 | -671 | -2954 | -2840 | 256 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 247 | -4720 | -3927 | -5139 | -5454 | 4513 | -4504 | -2520 | -3938 | -5326 | -3307 | -3429 | -4469 | -4782 | -4575 | -4818 | -4787 | -4810 | -4172 | -1812 | -736 | 257 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 248 | -1307 | -1108 | -3455 | -2868 | -1188 | -2949 | -1880 | 2331 | 358 | -846 | 1520 | -2507 | -2970 | -2242 | -2451 | -2047 | 597 | 2097 | -1808 | -1449 | 258 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 249 | -996 | 2634 | 795 | 2343 | -2711 | -1863 | -676 | -2442 | -336 | -2441 | -1558 | -559 | -2042 | -247 | -853 | 114 | 971 | -2019 | -2654 | -1982 | 259 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 250 | -1030 | -1592 | -3503 | -3413 | -3404 | -1964 | -2934 | -2769 | -3206 | -3298 | -2538 | -2445 | -2684 | -2918 | -3188 | 3064 | 1489 | 582 | -3746 | -3489 | 260 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 251 | -4036 | 5830 | -5292 | -5636 | -5234 | -3985 | -4807 | -5543 | -5599 | -5572 | -5320 | -5040 | -4554 | -5432 | -5141 | -4361 | -4425 | -5051 | -4590 | -5211 | 261 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 252 | -2841 | -3548 | -2782 | -2003 | -4369 | -3246 | -1330 | -3793 | 3622 | -3439 | -2789 | -1967 | -3285 | 1301 | 3 | -2706 | -2569 | -3547 | -3256 | -3128 | 262 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 253 | -3040 | -3587 | -3993 | -2356 | -4556 | -3464 | -1277 | -3807 | 2376 | -3405 | -2766 | -2163 | -3383 | -860 | 3455 | -2914 | -2666 | -3606 | -3193 | -3167 | 263 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 254 | -4119 | -3542 | -5389 | -5357 | -2027 | -4767 | -4358 | -1609 | -5118 | 3293 | -979 | -5230 | -4771 | -4474 | -4724 | -5069 | -4106 | -2331 | -3412 | -3400 | 264 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 255 | -3051 | -3591 | -3985 | -2369 | -4560 | -3468 | -1291 | -3819 | 1907 | -3417 | -2780 | -2175 | -3392 | -876 | 3661 | -2926 | -2679 | -3617 | -3203 | -3178 | 265 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 256 | -3202 | -2787 | -5004 | -4996 | -2836 | -4384 | -4440 | 3937 | -4838 | -1815 | -1871 | -4704 | -4600 | -4683 | -4704 | -4353 | -3280 | -603 | -3938 | -3661 | 266 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 257 | -2529 | -2315 | -4845 | -4518 | -1580 | -4064 | -3663 | -283 | -4108 | -355 | 4839 | -4078 | -4123 | -3684 | -3934 | -3416 | -2594 | 956 | -3026 | -2805 | 267 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |
| 258 | -4125 | -4091 | -4017 | -3615 | -5101 | -3960 | -2958 | -5182 | 3972 | -4825 | -4345 | -3552 | -4249 | -2709 | -1809 | -4154 | -4044 | -4895 | -4132 | -4389 | 268 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -9 | -7942 | -8984 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 259 | −1329 | −2035 | −2429 | −2244 | −3895 | 2854 | −2166 | −3627 | −1525 | −3684 | −2851 | −1989 | −2743 | −1869 | 2143 | 670 | −1640 | −2809 | −3768 | −3462 | 269 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 260 | 333 | 2173 | −1976 | −1501 | −2712 | −1910 | −1559 | −2364 | 756 | −2555 | −1742 | −1465 | −2354 | −1261 | −1690 | 2683 | 445 | −1889 | −2895 | −2438 | 270 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 261 | −2629 | −4603 | 2982 | 2824 | −4769 | −2374 | −1827 | −4781 | −2233 | −4613 | −4050 | −973 | −2960 | −1523 | −3215 | −2241 | −2729 | −4224 | −4756 | −3689 | 271 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 262 | 3227 | −1598 | −3808 | −3853 | −3675 | −1943 | −3208 | −3121 | −3627 | −3612 | −2811 | −2572 | −2704 | −3246 | −3487 | 659 | −1456 | 120 | −3999 | −3805 | 272 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 263 | −1678 | −2306 | −2163 | −1368 | −2580 | −2636 | −1002 | 2355 | 2343 | −2186 | −1484 | −1443 | −2669 | −654 | 876 | −1735 | 641 | −1817 | −2475 | −2127 | 273 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 264 | −4088 | −3924 | −4774 | -5139 | -5615 | 3825 | −4753 | −6303 | -5453 | −6014 | -5662 | −4812 | −4539 | -5232 | -5106 | −4370 | −4472 | -5527 | −4696 | -5561 | 274 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 265 | −3686 | −3083 | -5691 | -5304 | 2479 | -5415 | −3206 | −817 | -5030 | 2801 | −119 | −4892 | −4733 | −3869 | −4522 | −4791 | −3543 | −1610 | −2174 | −1529 | 275 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 266 | 1903 | −2297 | 702 | −1544 | −4168 | 2837 | −2339 | −3984 | −2585 | −4104 | −3288 | −1618 | −2762 | −2091 | −3086 | −1567 | −1822 | −3080 | −4284 | −3742 | 276 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −403 | −7942 | −2060 | −894 | −1115 | −701 | −1378 | * | * | | | | | | | | | | | | |
| 267 | 834 | 3930 | −2831 | −2402 | −1432 | −1861 | −1668 | −863 | −2105 | 526 | −631 | −1870 | 1986 | −1849 | −2106 | −1085 | −873 | −679 | −1916 | −1576 | 277 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −11 | −7550 | −8592 | −894 | −1115 | −290 | −2456 | * | * | | | | | | | | | | | | |
| 268 | 1108 | −1096 | −2107 | −1546 | −1182 | 1531 | −1149 | −706 | −1287 | 1092 | −370 | −1499 | −2344 | −1160 | 691 | −1261 | −890 | 408 | −1610 | −1222 | 278 |
| — | −149 | -500 | 233 | 43 | −381 | 399 | 106 | −626 | 210 | −466 | −720 | 275 | 394 | 45 | 96 | 359 | 117 | −369 | −294 | −249 | |
| — | −9 | −7942 | −8984 | −894 | −1115 | −701 | −1378 | * | * | | | | | | | | | | | | |
| 269 | 447 | −1594 | −1489 | −1022 | −2056 | −171 | −1111 | −1648 | −921 | −1888 | −1129 | −1139 | 1521 | 2213 | −1300 | −1044 | −979 | 1814 | −2309 | −1831 | 279 |
| — | * | * | * | * | * | * | * | * | * | * | * | * | * | * | * | * | * | * | * | * | |
| — | * | * | * | * | * | * | * | * | 0 | | | | | | | | | | | | |
| // | | | | | | | | | | | | | | | | | | | | | |

| | |
|---|---|
| HMMER2.0 | [2.3.2] |
| NAME | Auxin_resp |
| ACC | PF06507.5 |
| DESC | Auxin response factor |
| LENG | 84 |
| ALPH | Amino |
| RF | no |
| CS | no |
| MAP | yes |
| COM | hmmbuild -F HMM_ls.ann SEED.ann |
| COM | hmmcalibrate --seed 0 HMM_ls.ann |
| NSEQ | 17 |
| DATE | Tue Apr 22 21:04:11 2008 |
| CKSUM | 5386 |
| GA | 25.0000 25.0000; |
| TC | 26.0000 25.7000; |
| NC | 22.6000 22.6000; |
| XT | −8455 −4 −1000 −1000 −8455 −4 −8455 −4 |
| NULT | −4 −8455 |
| NULE | 595 −1558 85 338 −294 453 −1158 197 249 902 −1085 −141 −21 −313 45 531 201 384 −1998 −644 |
| EVD | −75.925690 0.233690 |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −126 | * | −3584 | | | | | | | | | | | | | | | | | | |
| 1 | 3158 | −2363 | −4879 | −5046 | −4109 | −2910 | −4298 | −2021 | −4794 | −3510 | −3120 | −3604 | −3648 | −4394 | −4552 | −2284 | −2337 | 1877 | −4810 | −4582 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | −126 | * | | | | | | | | | | | | |
| 2 | 2404 | −1457 | −2392 | −1812 | −1455 | −2644 | −1427 | 389 | −180 | −1328 | −649 | −1813 | −2713 | −1438 | −25 | −223 | −1240 | 50 | 3011 | −1486 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 3 | −1601 | −2389 | −1668 | −1348 | −2708 | −2543 | 4340 | −2420 | −1284 | −169 | −1835 | 1780 | −2798 | −1256 | −1658 | −276 | −53 | −2135 | −2918 | −2372 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 4 | 2915 | −2554 | 707 | −1372 | −2968 | −2600 | −1658 | −2581 | −1354 | −64 | −2011 | −1576 | −2882 | −1337 | 414 | −1767 | −1763 | −2295 | −3143 | −2616 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 5 | 1682 | −1177 | −3545 | −2918 | 345 | −2865 | −1732 | 1439 | −2543 | −239 | −380 | −154 | −2916 | −2192 | −2391 | −379 | 692 | 1423 | −1637 | −1292 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 6 | 1460 | −2603 | 76 | −485 | −2909 | −2150 | −811 | −532 | 339 | −2613 | −1698 | −792 | −2243 | 677 | 303 | 1897 | 76 | −2217 | −2797 | −2125 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 7 | −1401 | −2399 | −1584 | −1137 | −2996 | −2361 | −1401 | −2671 | −1077 | −2779 | −1940 | 1426 | −2613 | 803 | −1526 | 1478 | 2614 | −128 | −3069 | −2498 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 8 | 241 | −2662 | −1052 | −502 | −2986 | 1687 | 1227 | −2730 | 1693 | −2675 | −1753 | 974 | −2264 | 612 | 165 | −1083 | 119 | −2286 | −2840 | −2166 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | −1285 | 2015 | −1615 | −1058 | −2188 | −2393 | −1153 | −1798 | −880 | −428 | −1241 | −1264 | −2506 | 1518 | 69 | 1848 | 1819 | −1576 | −2414 | −1913 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 10 | −1452 | 1402 | −3760 | −3145 | −1285 | −2998 | −1931 | 1785 | −2762 | −1120 | 2902 | −2654 | 2375 | −2402 | −2590 | −443 | −1406 | 478 | −1814 | −1469 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 11 | −5765 | −4802 | −5973 | −6324 | 4566 | −5247 | −3479 | −5215 | −6252 | −4532 | −4649 | −5413 | −5556 | −5531 | −5699 | −5820 | −5855 | −5401 | −2775 | −1729 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 12 | −1184 | −2349 | −1170 | 1209 | −2557 | −2212 | 2089 | 403 | −525 | −948 | −1470 | 267 | −2302 | −474 | 673 | 569 | 1440 | −280 | −2605 | −1999 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 13 | −3033 | −2524 | −5724 | −5423 | −3214 | −5548 | −5661 | 2319 | −5397 | −1959 | −1903 | −5236 | −5303 | −5366 | −5577 | −4943 | −3030 | 3306 | −5003 | −4468 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 14 | −246 | −1216 | −3577 | −2962 | 2607 | −2872 | −1758 | −716 | −2587 | −1078 | −434 | −2496 | −2942 | −2233 | −2434 | −200 | 583 | 1556 | −1654 | 2395 | 14 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 15 | −5286 | −4226 | −5668 | −6022 | 1003 | −5533 | −1778 | −4182 | −5588 | −3489 | −3587 | −4191 | −5409 | −4330 | −4959 | −4817 | −5149 | −4346 | −1026 | 4765 | 15 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 16 | −1301 | 1855 | −1228 | −680 | −2768 | −2288 | 1051 | −2516 | 2062 | −2542 | −1679 | 2145 | −2382 | −512 | −934 | 70 | −1238 | −2156 | −2744 | 1860 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 17 | −5672 | −5016 | −5908 | −6280 | −6507 | −5021 | −5699 | −7438 | −6489 | −6950 | −6782 | −6096 | 4323 | −6350 | −6037 | −6019 | −5995 | −6875 | −5439 | −6461 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 18 | −2727 | −3554 | −3162 | −2163 | −4157 | −3465 | −1607 | −3633 | 705 | −3463 | −2737 | −2184 | −3465 | −1194 | 3552 | −511 | 202 | −3369 | 2570 | −3202 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 19 | 2153 | −1573 | −2221 | −1661 | −1630 | −2573 | −1421 | 176 | −1488 | −289 | −803 | −1712 | −2681 | 940 | −1758 | 313 | 1560 | −1048 | −2030 | −1618 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −324 | −8606 | −2330 | −894 | −1115 | −701 | −1378 | * | * | | | | | | | | | | | | |
| 20 | 143 | 1765 | −4338 | −4388 | −4343 | 1503 | −3673 | −4106 | −4108 | −4368 | −3452 | −2932 | −3014 | −3687 | −3938 | 2844 | 719 | −3003 | −4586 | −4460 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8289 | −9331 | −894 | −1115 | −2001 | −415 | * | * | | | | | | | | | | | | |
| 21 | −1173 | −2357 | −1154 | −580 | −2602 | −2164 | 1564 | −2283 | −268 | −2323 | −1478 | −848 | 1740 | 1593 | 537 | −1106 | 1579 | −1948 | 3058 | −1972 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −7 | −8289 | −9331 | −894 | −1115 | −245 | −2679 | * | * | | | | | | | | | | | | |
| 22 | 1767 | −2279 | −4528 | −4787 | −4908 | −2548 | −4144 | −4721 | −4673 | −4976 | −4021 | −3277 | 20 | −4180 | −4427 | 3129 | −2134 | −3455 | −5124 | −5050 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 23 | −2603 | −4389 | 1294 | 2902 | −4604 | −2756 | −1964 | −4471 | −2021 | −4361 | −3595 | 640 | −44 | 2208 | −2756 | −2318 | −2630 | −3969 | −4546 | −3630 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 24 | −5765 | −4802 | −5973 | −6324 | 4566 | −5247 | −3479 | −5215 | −6252 | −4532 | −4649 | −5413 | −5556 | −5531 | −5699 | −5820 | −5855 | −5401 | −2775 | −1729 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 25 | −2983 | 1350 | −5676 | −5358 | −3204 | −5464 | −5493 | 2754 | −5317 | −1987 | −1903 | −5149 | −5241 | −5276 | −5479 | −4833 | −2980 | 2948 | −4915 | −4383 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −3034 | −2523 | −5726 | −5424 | −3216 | −5558 | −5670 | 2911 | −5401 | −1960 | −1903 | −5240 | −5307 | −5371 | −5582 | −4952 | −3030 | 2939 | −5010 | −4474 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 27 | −1551 | −2924 | −1428 | −851 | −3317 | −389 | −1043 | −3016 | 1430 | −2926 | −2039 | −1121 | 2513 | 658 | 847 | 1213 | −1471 | −2594 | −3045 | −2454 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 28 | 1326 | −1201 | −3604 | −2977 | 475 | −2898 | −1749 | −677 | −2591 | 989 | −390 | −2508 | −2947 | −2232 | 482 | −1979 | −1302 | 1261 | −1631 | 2428 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 29 | 1034 | −2632 | 1184 | 1570 | −2942 | −2154 | −820 | −2685 | −408 | −1035 | −1726 | 1515 | 21 | −365 | −915 | −92 | −1124 | −2248 | 1726 | −2145 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 30 | −1366 | −2829 | 955 | 674 | −3163 | −2282 | −944 | −2904 | 2774 | −2835 | −1923 | −915 | −2394 | 685 | 906 | −198 | −1302 | −2460 | −2987 | −2321 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 31 | −573 | −2764 | −4904 | −4634 | 2430 | −4358 | −1850 | −2102 | −4237 | −2323 | −1974 | −3629 | −4367 | −3558 | −3920 | −3513 | −3056 | 1569 | −1225 | 3804 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 32 | −1255 | −1621 | −1953 | 1029 | −1645 | −2511 | −1259 | 878 | −1237 | 926 | 2458 | 129 | −2584 | 338 | 651 | −1493 | −31 | −56 | −2015 | −1582 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 33 | 865 | −2660 | 708 | 1533 | −2981 | 65 | −816 | −2731 | 1814 | −2676 | −1750 | −787 | −2250 | −358 | 381 | −1066 | 273 | −2282 | −2843 | −2160 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 34 | 2828 | −2243 | −4729 | −4922 | −4653 | −2554 | −4101 | −4218 | −4649 | −4651 | −3779 | −3304 | −3349 | −4174 | −4381 | 2220 | −2112 | −2 | −4935 | −4824 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −135 | −8606 | −3522 | −894 | −1115 | −701 | −1378 | * | * | | | | | | | | | | | | |
| 35 | −1408 | −1222 | −3717 | −3095 | 696 | −2986 | −1873 | 1608 | −233 | −980 | 3641 | −2615 | −3024 | −2347 | −2535 | −2076 | 93 | 1469 | −1741 | −1398 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8477 | −9519 | −894 | −1115 | −1410 | −681 | * | * | | | | | | | | | | | | |
| 36 | 102 | 1006 | 380 | −411 | 10 | −2070 | −732 | −2514 | 1033 | −2494 | −1587 | 1007 | −2163 | −281 | 1431 | 649 | 159 | −2097 | −2691 | 1181 | 36 |
| — | −149 | −500 | 233 | 43 | −381 | 399 | 109 | −626 | 210 | −466 | −720 | 275 | 394 | 45 | 96 | 359 | 117 | −369 | −294 | −249 | |
| — | −167 | −3215 | −9519 | −152 | −3318 | −387 | −2087 | * | * | | | | | | | | | | | | |
| 37 | −264 | −2169 | −1297 | −745 | −2320 | −2266 | 1108 | 1075 | −643 | −2111 | 829 | 1746 | 438 | 1339 | −1102 | 543 | 62 | −1698 | −2465 | 609 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 38 | −1263 | −2695 | −1119 | −566 | 270 | −407 | −865 | −2754 | 1286 | −2701 | −1789 | 999 | 2184 | 1942 | 281 | −1147 | −1198 | −2321 | −2865 | −2209 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 39 | −1466 | −1285 | −3789 | −3165 | 2448 | −3007 | −1797 | 332 | −2762 | 960 | −442 | −2636 | −226 | −2369 | −2558 | −2095 | −1406 | 914 | 3293 | 1447 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 40 | 454 | 3590 | −4308 | −4068 | −3051 | −2608 | −3173 | 711 | −3750 | −2951 | −2248 | −3040 | −3239 | −3383 | −3618 | 2601 | 393 | −2151 | −3486 | −3199 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 41 | −1871 | −1643 | −4219 | −3641 | −1738 | −3543 | −2538 | 1710 | −3294 | 308 | −873 | −3191 | 1329 | −2961 | −3153 | 237 | −1829 | 2506 | −2393 | −2038 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 42 | −5249 | −4846 | −5805 | −6182 | −6521 | 3848 | −5650 | −7348 | −6455 | −6931 | −6666 | −5891 | −5413 | −6249 | −6011 | −5566 | −5614 | −6629 | −5452 | −6497 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −1676 | −2204 | −4295 | −4313 | −3842 | −2610 | −3630 | −3414 | −3990 | −3691 | 4490 | −3163 | −3338 | −3713 | −3859 | 545 | 2236 | −2819 | −4249 | −3995 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 44 | −5677 | −5058 | −5817 | −5522 | −6223 | −5022 | −4626 | −6808 | −3755 | −6307 | −5975 | −5374 | −5388 | −4598 | 4244 | −5871 | −5687 | −6494 | −5162 | −5792 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 45 | −3849 | −3458 | −5602 | −5638 | 4188 | −4959 | −2644 | −1797 | −5340 | −2003 | −2115 | −4492 | −5045 | −4488 | −4945 | −4379 | −3914 | 1287 | −1909 | −813 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 46 | −452 | −3393 | −2564 | −1776 | −4088 | −601 | −1504 | −3633 | 2769 | −3449 | −2660 | −1888 | −3210 | −1074 | 2654 | −2258 | −187 | −3269 | −3443 | −3096 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 47 | −313 | −3137 | −5778 | −5307 | −1776 | −4999 | −4282 | −1158 | −4931 | 1098 | 4789 | −4957 | −4805 | −4165 | −4607 | −4292 | −3407 | −1758 | −3365 | −3386 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 48 | 933 | −1482 | −2775 | −2167 | −1424 | −2820 | −1593 | 121 | −1766 | 586 | 1828 | −2079 | −2872 | 195 | 2706 | −1860 | −1364 | −887 | −1901 | −1536 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 49 | −3620 | −3153 | −5277 | −5067 | 3926 | −4844 | −2036 | −2178 | −4669 | −1773 | 2622 | −3982 | −4721 | −3836 | −4280 | −4014 | −3532 | 42 | −1344 | 1353 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 50 | −3327 | −5016 | −989 | 3683 | −5391 | −3101 | −2592 | −5490 | −2924 | −5315 | −4768 | 1054 | −3690 | −2301 | −3760 | −2981 | −3450 | −4913 | −5309 | −4385 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 51 | −1579 | −2188 | −3546 | −3267 | −3804 | 2080 | −3055 | −3476 | −3125 | −3725 | 1432 | −2722 | 776 | −2913 | −3295 | 869 | 2548 | −2812 | −4071 | −3748 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 52 | −3136 | −5164 | 2005 | 3364 | −5294 | −2912 | −2331 | −5270 | −211 | −5101 | −4513 | −1495 | −3488 | −2017 | −3605 | −2749 | −3226 | −4718 | −5291 | −4195 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 53 | −3331 | −5323 | 3517 | 2295 | −5495 | −3020 | −2505 | −5542 | −2968 | −5354 | −4832 | −1623 | −3620 | −2209 | −4000 | −2928 | −3443 | −4971 | −5469 | −4396 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 54 | 2071 | 1447 | −4593 | −4549 | 1139 | −2572 | −3620 | −3400 | −4226 | −3727 | −2962 | −3194 | −3299 | −3802 | −4024 | 2692 | −2016 | −2769 | −4084 | −3785 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 55 | −1734 | −2436 | −3189 | −3067 | −4553 | 478 | −3071 | −4316 | −2778 | −4439 | −3546 | −2669 | 2412 | −2815 | 751 | 2669 | −2103 | −3345 | −4583 | −4272 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 56 | −2424 | −3531 | −2382 | 2744 | −4085 | −3177 | −1466 | −3622 | 1040 | −3435 | −2653 | −1829 | −3217 | −1035 | 2208 | −2301 | −2261 | 397 | −3431 | −3069 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2104 | −8606 | −387 | −894 | −1115 | −701 | −1378 | * | * | | | | | | | | | | | | |
| 57 | −1459 | −1175 | −3249 | −3035 | −1029 | −2949 | −2488 | 3389 | −2728 | −54 | −62 | −2796 | −3066 | −2610 | −2714 | −2453 | −1501 | 936 | −2199 | −1781 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −23 | −6526 | −7568 | −894 | −1115 | −86 | −4112 | * | * | | | | | | | | | | | | |
| 58 | −2606 | −3632 | −2809 | −1920 | −4277 | −3345 | −1519 | −3767 | 1117 | −3527 | −2764 | −2006 | −3348 | 639 | 3424 | 340 | 202 | −3449 | −3475 | −3184 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 59 | −2336 | −2643 | −3496 | −2604 | −2448 | −3337 | −1801 | 4 | −946 | −2595 | −1970 | −2455 | −3448 | −1637 | 3429 | 241 | −2269 | −2298 | 3457 | −2140 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 60 | −1706 | 1723 | −3011 | −2447 | 2711 | −3057 | −1572 | −1297 | −2126 | −1576 | −946 | −2292 | −3116 | 934 | 165 | −182 | −1647 | −1201 | −1578 | 3104 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 61 | 23 | −2178 | −21 | −746 | −73 | −2267 | −957 | −1978 | −646 | −2125 | 2814 | −1009 | 1121 | 814 | −1106 | 467 | 1568 | −1711 | −2477 | −1914 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 62 | −3434 | −3779 | −4840 | −5207 | −5953 | 3677 | −4997 | −6231 | −5599 | −6197 | −5534 | −4559 | 890 | −5230 | −5366 | −3681 | −3876 | −5136 | −5373 | −5949 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 63 | −2791 | −2402 | −5433 | −5090 | −3009 | −4898 | −4792 | 1931 | −4946 | −1920 | −1793 | −4731 | −4881 | −4800 | −4995 | −4211 | 3152 | 1607 | −4423 | −3972 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 64 | −2899 | −2434 | −5494 | −5124 | −2757 | −5193 | −4582 | 3125 | −4986 | −1836 | −1726 | −4827 | −5006 | −4806 | −5024 | −4489 | −2883 | 2404 | −4077 | 1257 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 65 | −1381 | −1235 | −3615 | −2999 | 693 | 77 | −1823 | 1697 | −2627 | −1093 | −458 | −2538 | −2977 | −2277 | −2476 | 862 | 1302 | 1818 | −1730 | −1384 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 66 | −142 | −2219 | −3922 | −3850 | −4111 | 3247 | −3489 | −3829 | −3755 | −4094 | −3260 | −2980 | −3266 | −3443 | −3782 | −181 | 723 | −3027 | −4398 | 996 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 67 | −2416 | −2139 | −4955 | −4522 | −2616 | −4236 | −3775 | 2429 | −4277 | −1855 | −1561 | −4064 | −4324 | −4030 | −4223 | 528 | 203 | 2736 | −3591 | −3191 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 68 | −1170 | 1424 | −1019 | 331 | −2953 | −412 | −802 | −2701 | 402 | −2649 | −1724 | 1365 | −2237 | 1255 | 1256 | 1452 | −1108 | −2255 | −2819 | 648 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 69 | −2806 | −4638 | 3415 | 1491 | −4825 | −2822 | −2115 | −4703 | −2278 | −4602 | −3895 | −1414 | −3323 | 808 | −3073 | −2491 | −2856 | 412 | −4803 | −3836 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −104 | −8606 | −3898 | −894 | −1115 | −701 | −1378 | * | * | | | | | | | | | | | | |
| 70 | 581 | 1447 | −3544 | −2911 | 423 | −2794 | −1663 | −580 | −2519 | 1651 | 1200 | 81 | −2845 | −2152 | −2338 | 389 | −1193 | 769 | −1544 | 667 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8508 | −9550 | −894 | −1115 | −432 | −1951 | * | * | | | | | | | | | | | | |
| 71 | −2326 | −4006 | 3154 | 502 | −4259 | −2668 | 1821 | −4084 | 79 | −3992 | −3175 | −1269 | −3045 | −1366 | −2311 | 1350 | −2326 | −3603 | −4170 | −3332 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 72 | −1642 | 2346 | −4813 | −5021 | −4767 | −2542 | −4146 | −4541 | −4699 | −4816 | −3888 | −3316 | 3597 | −4217 | −4410 | 1250 | 418 | −3368 | −5013 | −4933 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −616 | −8606 | −1535 | −894 | −1115 | −701 | −1378 | * | * | | | | | | | | | | | | |
| 73 | −907 | −784 | −2948 | −2331 | −743 | 146 | −1274 | 1385 | −1991 | 144 | 1577 | 314 | −2472 | −1670 | −1898 | 64 | 508 | 1186 | −1236 | 1326 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −7998 | −9041 | −894 | −1115 | −489 | −1798 | * | * | | | | | | | | | | | | |
| 74 | −1534 | −2489 | −1675 | −1047 | −2713 | −2535 | 2456 | −2330 | −436 | −2415 | 1231 | −1262 | 285 | 766 | 2938 | −1516 | −1445 | −205 | −2684 | −2192 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8477 | −9519 | −894 | −1115 | −1410 | −681 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 75 | −6425 | −5097 | −6048 | −6410 | −4432 | −5141 | −5003 | −6948 | −6438 | −6277 | −6316 | −6204 | −5561 | −6262 | −5919 | −6797 | −6574 | −6838 | 6295 | −4062 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8477 | −9519 | −894 | −1115 | −1410 | −681 | * | * | | | | | | | | | | | | |
| 76 | −3091 | −3857 | −3522 | −2373 | −4664 | −3649 | 2349 | −4023 | 1940 | −3689 | −3003 | −2317 | 3196 | −1184 | 1030 | −2963 | −2799 | −3775 | −3544 | −3406 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8477 | −9519 | −894 | −1115 | −387 | −2087 | * | * | | | | | | | | | | | | |
| 77 | −127 | 967 | 1232 | −506 | −2991 | 1303 | −849 | −2737 | 402 | −2690 | −1771 | 2327 | −2277 | −393 | 701 | −1098 | −1157 | −2294 | −2863 | −2185 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 78 | −2873 | −3334 | −4781 | −5130 | −5373 | −3522 | −4723 | −5714 | −5297 | −5786 | −5056 | −4198 | −4255 | −4941 | −5056 | 3723 | −3329 | −4590 | −5178 | −5309 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 79 | −1800 | −3196 | −1381 | 1717 | −3585 | −2608 | 1114 | −3282 | 2656 | −3170 | −2302 | −1240 | 1388 | 525 | −887 | −1660 | −1718 | −2862 | −3271 | −2682 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 80 | −6613 | −5251 | −6201 | −6567 | −4682 | −5286 | −5202 | −7171 | −6615 | −6493 | −6531 | −6381 | −5707 | −6440 | −6087 | −7000 | −6761 | −7049 | 6298 | −4318 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 81 | −3576 | −4162 | −4201 | −2830 | −5136 | −3986 | −1828 | −4377 | 751 | −3973 | −3333 | 545 | −3925 | −1411 | 3869 | −3440 | −3212 | −4170 | −3770 | −3729 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 82 | −1403 | 3478 | −3083 | −2545 | −1621 | −2718 | −1874 | −1162 | −2277 | 174 | 1752 | 1360 | −2928 | −2052 | −2344 | 2075 | −1427 | −1041 | −2091 | −1724 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 83 | −4196 | −3597 | −6531 | −5970 | 817 | −6277 | −4734 | −1153 | −5752 | 3096 | −503 | −5959 | −5364 | −4517 | −5228 | −5635 | −4041 | −59 | −3378 | −3348 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8606 | −9649 | −894 | −1115 | −701 | −1378 | * | * | | | | | | | | | | | | |
| 84 | −1444 | −2812 | −1345 | 1389 | −3158 | −2393 | −972 | −2859 | 1653 | 130 | −1909 | −1037 | −2472 | 2515 | 574 | −1332 | −1365 | −261 | −2944 | −2339 | 85 |
| — | * | * | * | * | * | * | * | * | * | * | * | * | * | * | * | * | * | * | * | * | |
| — | * | * | * | * | * | * | * | * | 0 | | | | | | | | | | | | |
| // | | | | | | | | | | | | | | | | | | | | | |

HMMER2.0 [2.3.2]
NAME B3
ACC PF02362.13
DESC B3 DNA binding domain
LENG 104
ALPH Amino
RF no
CS yes
MAP yes
COM hmmbuild -F HMM__ls.ann SEED.ann
COM hmmcalibrate --seed 0 HMM__ls.ann
NSEQ 160
DATE Wed Apr 23 15:07:36 2008
CKSUM 643
GA 26.5000 26.5000;
TC 26.9000 26.7000;
NC 26.3000 26.3000;
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −43.962971 0.265053

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −14 | * | −6727 | | | | | | | | | | | | | | | | | | |
| 1 | −2155 | 2065 | −1645 | −916 | 2112 | −2620 | 960 | −224 | −282 | 151 | 277 | −2530 | −602 | 131 | −839 | 625 | −355 | −1870 | 391 | 1591 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | −14 | * | | | | | | | | | | | | |
| 2 | −1692 | 369 | −6521 | −5885 | 3718 | −2463 | −4603 | −694 | −2672 | 684 | −888 | −961 | −1404 | −2004 | −2662 | −941 | −2575 | 14 | −4471 | −543 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 3 | −1038 | 622 | −562 | 450 | 1832 | −4926 | −652 | −2103 | −189 | −735 | −656 | −2042 | −5017 | 779 | −459 | −465 | 1499 | 1474 | −5423 | −4791 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −36 | −11881 | −5350 | −894 | −1115 | −701 | −1378 | * | * | | | | | | | | | | | | |
| 4 | 629 | −4402 | −4705 | −2860 | −738 | −818 | −453 | −709 | 2645 | 421 | −623 | −4267 | −5350 | 852 | −230 | −563 | −2301 | −226 | −4795 | −2004 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11845 | −12887 | −894 | −1115 | −1473 | −645 | * | * | | | | | | | | | | | | |
| 5 | −897 | 102 | −1215 | 14 | −2296 | −1948 | 584 | 722 | −190 | −1636 | 786 | −214 | 349 | −91 | −403 | −145 | 1791 | 1031 | −5497 | −4826 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11853 | −12895 | −894 | −1115 | −1028 | −972 | * | * | | | | | | | | | | | | |
| 6 | −2460 | −3997 | −1924 | −5879 | 1158 | −2743 | −4589 | 1184 | −2512 | 1994 | 1897 | −5364 | −2486 | −5097 | −5274 | −1675 | −1066 | 1534 | −4454 | −1036 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −11864 | −7604 | −894 | −1115 | −1568 | −593 | * | * | | | | | | | | | | | | |
| 7 | −1681 | −1513 | −6322 | −5698 | −689 | −5683 | −4545 | −70 | 789 | 455 | −65 | 219 | −2859 | −2569 | 99 | 641 | 2569 | −391 | −979 | −4119 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11857 | −12899 | −894 | −1115 | −1825 | −479 | * | * | | | | | | | | | | | | |
| 8 | 777 | 388 | −1216 | −1603 | −586 | −1180 | 1192 | −2993 | −5 | −3211 | −4431 | −372 | 2645 | 138 | 2 | 287 | −793 | −382 | −5526 | −2042 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −39 | −11857 | −5257 | −894 | −1115 | −1825 | −479 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | −2008 | −1444 | 6 | 241 | −2587 | 215 | −176 | −5169 | −3117 | −2550 | −1268 | 440 | −4940 | −1539 | −2362 | 2775 | −1126 | −813 | −863 | 779 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −47 | −11819 | −4970 | −894 | −1115 | −1787 | −494 | * | * | | | | | | | | | | | | |
| 10 | −2568 | −231 | 2498 | −1439 | 959 | −2468 | 1609 | −5313 | −3028 | −5270 | −127 | 1378 | −2391 | −904 | −659 | 1262 | −1363 | −686 | −5447 | 298 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11784 | −12826 | −894 | −1115 | −982 | −1019 | * | * | | | | | | | | | | | | |
| 11 | 72 | −943 | −1952 | −1154 | 824 | −1822 | 725 | 115 | 0 | 1494 | −487 | −5164 | −5686 | −1580 | −1916 | −4702 | −82 | 1876 | −4459 | −1287 | 11 |
| — | −146 | −500 | 232 | 43 | −381 | 401 | 105 | −627 | 210 | −466 | −721 | 277 | 393 | 45 | 95 | 359 | 117 | −370 | −295 | −250 | |
| H | −39 | −6925 | −5779 | −2168 | −363 | −2467 | −288 | * | * | | | | | | | | | | | | |
| 12 | −2666 | −5297 | −17 | −515 | −5617 | 1046 | 81 | −749 | 542 | −824 | 609 | 287 | −1821 | 72 | 730 | 1417 | 206 | −1562 | −5480 | 216 | 17 |
| — | −149 | −500 | 233 | 45 | −381 | 399 | 106 | −626 | 210 | −466 | −720 | 275 | 394 | 45 | 96 | 359 | 117 | −369 | −294 | −249 | |
| H | −47 | −6791 | −5447 | −176 | −3122 | −2919 | −205 | * | * | | | | | | | | | | | | |
| 13 | −1526 | −771 | −688 | −1746 | −519 | −1346 | 1256 | −549 | 1379 | −2366 | −4354 | 1081 | −1462 | 364 | 1111 | 1042 | 744 | −2878 | −5448 | 886 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −81 | −11772 | −4195 | −894 | −1115 | −2461 | −289 | * | * | | | | | | | | | | | | |
| 14 | −2430 | 2241 | 1611 | −320 | −1647 | 1099 | 525 | −699 | −138 | 1226 | 83 | −411 | −2606 | −1709 | −366 | −694 | −3671 | −4780 | −5360 | −532 | 20 |
| — | −149 | −500 | 233 | 43 | −381 | 398 | 105 | −626 | 210 | −466 | −721 | 275 | 394 | 48 | 96 | 360 | 117 | −369 | −295 | −250 | |
| T | −14 | −6688 | −12745 | −984 | −1016 | −2589 | −262 | * | * | | | | | | | | | | | | |
| 15 | −511 | 547 | −573 | −1265 | 859 | 814 | −851 | −258 | 335 | −1264 | 1464 | 1304 | −4822 | 251 | 1664 | −1562 | 226 | −2947 | −5386 | −4711 | 23 |
| — | −149 | −500 | 233 | 43 | −381 | 399 | 106 | −626 | 210 | −466 | −720 | 275 | 394 | 45 | 96 | 359 | 117 | −369 | −294 | −245 | |
| — | −38 | −6964 | −5811 | −203 | −2929 | −3011 | −191 | * | * | | | | | | | | | | | | |
| 16 | −2342 | −3850 | −6340 | −1896 | −1124 | −330 | −4434 | 1319 | −5306 | 1921 | 1943 | −3166 | −2382 | −1049 | 1789 | −4648 | −1829 | −480 | 894 | −3964 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −233 | −11708 | −2749 | −894 | −1115 | −693 | −1390 | * | * | | | | | | | | | | | | |
| 17 | −3904 | 187 | −1761 | −2511 | 1381 | −1814 | −351 | 893 | −2307 | 687 | 1860 | −4928 | −541 | −2516 | 787 | −338 | −316 | −389 | −4245 | 2377 | 26 |
| — | −149 | −500 | 233 | 43 | −381 | 398 | 105 | −624 | 210 | −466 | −714 | 275 | 394 | 45 | 96 | 360 | 117 | −370 | −295 | −250 | |
| E | −63 | −6932 | −4849 | −1479 | −641 | −3542 | −130 | * | * | | | | | | | | | | | | |
| 18 | −1556 | −3712 | −6231 | −5595 | −501 | −1028 | −1334 | 1369 | −5190 | 2082 | −254 | −5079 | −2101 | −4812 | −829 | −151 | −2189 | 1469 | 688 | −1281 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11566 | −12609 | −894 | −1115 | −2962 | −198 | * | * | | | | | | | | | | | | |
| 19 | −1322 | −3745 | −2677 | −5608 | −383 | −2432 | −4332 | 1336 | −2824 | 182 | −618 | −5101 | 3031 | −4833 | −1471 | 145 | −2345 | 817 | −804 | −3860 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11599 | −12641 | −894 | −1115 | −3028 | −189 | * | * | | | | | | | | | | | | |
| 20 | −836 | −1069 | −2535 | −5034 | −215 | −2606 | −4213 | −227 | 764 | −103 | −625 | −4803 | 2922 | −2160 | 1065 | −233 | −1251 | −448 | −4301 | −1332 | 32 |
| — | −149 | −500 | 233 | 43 | −377 | 400 | 105 | −626 | 210 | −466 | −721 | 275 | 394 | 45 | 96 | 359 | 117 | −369 | −295 | −249 | |
| H | −14 | −6676 | −12667 | −984 | −1016 | −4362 | −72 | * | * | | | | | | | | | | | | |
| 21 | −1201 | −5128 | 60 | −591 | −5449 | −811 | 523 | −2380 | 2060 | −1867 | 37 | −411 | 481 | 657 | 1026 | 900 | −474 | −2848 | −5311 | −7 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −24 | −11625 | −5933 | −894 | −1115 | −4362 | −72 | * | * | | | | | | | | | | | | |
| 22 | −1324 | −5089 | −714 | −2318 | 3372 | −792 | 472 | −2325 | 701 | −2573 | −213 | −469 | −1445 | 1215 | 667 | −2258 | −2324 | −4707 | −194 | −585 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11601 | −12643 | −894 | −1115 | −4468 | −67 | * | * | | | | | | | | | | | | |
| 23 | 889 | 2045 | −344 | −1322 | 1687 | −5147 | 1768 | −683 | −2437 | −1517 | 1296 | −1943 | −5216 | −1701 | −654 | −658 | 816 | 1001 | −4455 | 317 | 37 |
| — | −149 | −502 | 233 | 41 | −372 | 397 | 107 | −623 | 209 | −466 | −714 | 274 | 392 | 49 | 94 | 357 | 119 | −369 | −296 | −241 | |
| H | −341 | −2983 | −3572 | −287 | −2469 | −408 | −2021 | * | * | | | | | | | | | | | | |
| 24 | 1882 | 1400 | −1606 | −1393 | −5465 | −4723 | −982 | −1414 | 989 | −1497 | −724 | −2300 | 922 | −1580 | 1803 | 24 | −1686 | −877 | −5360 | −1605 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11712 | −12754 | −894 | −1115 | −2656 | −249 | * | * | | | | | | | | | | | | |
| 25 | −39 | −5224 | 671 | 2363 | −5543 | −2629 | −997 | −781 | −115 | −1549 | −284 | −71 | −2175 | −2927 | 111 | 1013 | −853 | −133 | −5408 | −4726 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11730 | −12772 | −894 | −1115 | −813 | −1214 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | 99 | −5308 | 587 | 333 | −1100 | −1233 | −11 | −510 | 1327 | −2377 | −4397 | 2690 | −4903 | −858 | 344 | −1370 | −737 | −1276 | −5491 | −1774 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11817 | −12859 | −894 | −1115 | −2742 | −233 | * | * | | | | | | | | | | | | |
| 27 | −2477 | 875 | −1647 | −1871 | 1782 | 1954 | 2319 | −1335 | −930 | −2397 | 222 | −178 | −488 | −2431 | −2730 | −774 | −3877 | −135 | −4986 | 1760 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −14 | −11817 | −6757 | −894 | −1115 | −1989 | −419 | * | * | | | | | | | | | | | | |
| 28 | −2471 | −3948 | −6460 | −1025 | 2384 | −3139 | −4538 | 1570 | −2564 | 2143 | 1367 | −2731 | −5717 | −5044 | −2577 | −2245 | −4061 | −1078 | −423 | −4063 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11812 | −12854 | −894 | −1115 | −1801 | −488 | * | * | | | | | | | | | | | | |
| 29 | −2400 | −5291 | 796 | −225 | −5600 | −2948 | −51 | −667 | −868 | −2416 | −132 | 1555 | 3005 | −3029 | −2064 | 210 | −1356 | −679 | −1031 | −4806 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −30 | −11825 | −5615 | −894 | −1115 | −2586 | −263 | * | * | | | | | | | | | | | | |
| 30 | −858 | −5289 | −2103 | 1325 | −106 | −1540 | 483 | −2560 | 2266 | −543 | −4378 | 420 | 175 | 1107 | 568 | −2226 | −1072 | −4911 | −5472 | −1830 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −466 | −11796 | −1858 | −894 | −1115 | −3049 | −186 | * | * | | | | | | | | | | | | |
| 31 | −86 | −4642 | −3357 | 577 | −1091 | −2295 | 2060 | 126 | −1007 | 1469 | −1127 | −1606 | 1471 | −845 | −415 | −905 | −1304 | −4215 | −4882 | 964 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11331 | −12373 | −894 | −1115 | −523 | −1717 | * | * | | | | | | | | | | | | |
| 32 | −2984 | −5231 | 768 | 538 | −131 | 1690 | −766 | 327 | 140 | −732 | −4320 | −173 | −2338 | −1032 | 1016 | 383 | −348 | −1274 | −5415 | −4732 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −377 | −11736 | −2123 | −894 | −1115 | −3670 | −118 | * | * | | | | | | | | | | | | |
| 33 | −351 | 1657 | 349 | 882 | −1541 | 245 | −81 | −2245 | −491 | −1149 | 1257 | −131 | 299 | 467 | −319 | 408 | 136 | −660 | −5058 | 102 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −229 | −11360 | −2775 | −894 | −1115 | −5205 | −40 | * | * | | | | | | | | | | | | |
| 34 | 23 | 1529 | −1087 | −620 | −847 | 1543 | 843 | −1962 | 949 | −4688 | −3761 | 677 | −4266 | −270 | 630 | 1040 | 131 | −2828 | −4855 | −4172 | 50 |
| — | −149 | −505 | 234 | 52 | −386 | 393 | 103 | −627 | 221 | −468 | −709 | 274 | 392 | 54 | 96 | 355 | 114 | −372 | −300 | −255 | |
| S | −6297 | −768 | −1322 | −5 | −8116 | −5607 | −30 | * | * | | | | | | | | | | | | |
| 35 | −106 | −4004 | 772 | −1207 | −4319 | 1648 | 1320 | 74 | −1761 | −4017 | −3094 | 1690 | 236 | −308 | −2268 | 451 | −8 | −2166 | −4190 | 63 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −66 | −10396 | −4503 | −894 | −1115 | −6257 | −19 | * | * | | | | | | | | | | | | |
| 36 | −1724 | −3696 | −2494 | 698 | −3908 | 83 | −65 | 1223 | −1850 | −563 | −2815 | −489 | 1418 | 195 | 73 | −713 | −26 | 1477 | −3948 | −3338 | 53 |
| — | −152 | −503 | 233 | 42 | −384 | 402 | 102 | −627 | 211 | −468 | −724 | 274 | 402 | 48 | 93 | 359 | 117 | −366 | −298 | −253 | |
| . | −5496 | −636 | −1580 | −8 | −7452 | −6291 | −19 | * | * | | | | | | | | | | | | |
| 37 | 299 | 8 | −1862 | 757 | −3744 | −337 | −1641 | −3484 | 1403 | −3447 | −2531 | −10 | −3073 | −1186 | −751 | 1444 | 1155 | 417 | 190 | −2957 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −9745 | −10787 | −894 | −1115 | −4814 | −52 | * | * | | | | | | | | | | | | |
| 38 | 636 | −3610 | −2012 | −1458 | −3936 | 554 | −1772 | −3678 | 1321 | −2237 | −2702 | 696 | −3217 | 2547 | −352 | −2038 | 1610 | −3236 | −3786 | −3117 | 56 |
| — | −144 | −505 | 234 | 44 | −386 | 402 | 101 | −628 | 212 | −469 | −700 | 270 | 391 | 40 | 93 | 359 | 119 | −361 | −299 | −254 | |
| . | −681 | −1412 | −10905 | −1845 | −471 | −47 | −4953 | * | * | | | | | | | | | | | | |
| 39 | −1011 | −5333 | 322 | 1621 | −5649 | −2604 | −3505 | 9 | 1083 | −226 | 1105 | −2263 | −98 | −202 | −2367 | −552 | 1443 | 14 | −5519 | −4839 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11852 | −12895 | −894 | −1115 | −1958 | −429 | * | * | | | | | | | | | | | | |
| 40 | −185 | −3987 | −2308 | −1313 | 247 | −5705 | −4575 | 2511 | −709 | 1058 | 1653 | −2164 | −5755 | −5079 | −5258 | −4789 | −1048 | 1331 | −4445 | −2586 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11852 | −12895 | −894 | −1115 | −1958 | −429 | * | * | | | | | | | | | | | | |
| 41 | −1353 | 224 | −198 | −860 | −1555 | −5062 | −3760 | 675 | 749 | 453 | −1173 | −70 | −3250 | −1052 | −328 | −889 | 1727 | 1121 | −5094 | 391 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11852 | −12895 | −894 | −1115 | −1958 | −429 | * | * | | | | | | | | | | | | |
| 42 | −1303 | −4020 | −6543 | −5907 | 677 | −5747 | −4619 | 623 | −1076 | 2402 | 1511 | −5393 | −5794 | −5124 | −266 | −4832 | −613 | 1031 | −4480 | −4140 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11852 | −12895 | −894 | −1115 | −1958 | −429 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −2118 | −792 | −2587 | 908 | −5375 | −3251 | 47 | −1409 | 1011 | 879 | 2175 | −3583 | −4998 | 362 | 1036 | −374 | −95 | 583 | −5379 | −414 | 71 |
| — | −150 | −501 | 234 | 42 | −382 | 399 | 105 | −624 | 209 | −467 | −713 | 274 | 393 | 47 | 95 | 359 | 122 | −370 | −295 | −250 | |
| E | −13 | −6816 | −12895 | −2988 | −194 | −875 | −1137 | * | * | | | | | | | | | | | | |
| 44 | −1278 | −5338 | 2972 | −3200 | −5647 | 1062 | 160 | −5390 | −3117 | −3362 | −4431 | 1653 | −2557 | −363 | −3622 | 173 | −174 | −1219 | −5529 | −1499 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11867 | −12909 | −894 | −1115 | −1468 | −647 | * | * | | | | | | | | | | | | |
| 45 | −80 | −5324 | −2555 | 1424 | −1726 | −1044 | −3526 | −664 | 901 | 78 | −422 | −2152 | 1725 | 455 | 497 | −886 | −339 | −575 | −5516 | −1840 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11867 | −12909 | −894 | −1115 | −1468 | −647 | * | * | | | | | | | | | | | | |
| 46 | −821 | −5355 | 1373 | 583 | −1137 | 545 | 2215 | −2643 | 15 | −2308 | −1636 | 829 | −4950 | −273 | −546 | 1330 | −2253 | −3447 | 1762 | −1220 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11867 | −12909 | −894 | −1115 | −1468 | −647 | * | * | | | | | | | | | | | | |
| 47 | −1768 | −5363 | 242 | −285 | −2796 | 3350 | −3522 | −5435 | −867 | −5379 | −635 | −2574 | −4956 | −1549 | −624 | −1906 | −1093 | −4985 | −5547 | −4864 | 84 |
| — | −152 | −503 | 229 | 42 | −381 | 398 | 102 | −630 | 215 | −468 | −717 | 272 | 390 | 42 | 96 | 373 | 119 | −368 | −298 | −253 | |
| S | −185 | −3056 | −12909 | −1030 | −971 | −370 | −2145 | * | * | | | | | | | | | | | | |
| 48 | −1398 | −239 | −1571 | 124 | −1701 | −1603 | −470 | −1486 | 2189 | −1381 | −164 | 576 | −4967 | −241 | 2134 | −835 | −405 | −411 | −5543 | −2032 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11881 | −12923 | −894 | −1115 | −701 | −1378 | * | * | | | | | | | | | | | | |
| 49 | −1393 | −1244 | −3845 | 679 | −1459 | −4922 | −1896 | −1053 | 1441 | −2358 | −2336 | −935 | −561 | 256 | −742 | 1644 | 1259 | 811 | −430 | −4795 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 50 | −4213 | −1089 | −6555 | −5921 | −437 | −5759 | −4613 | −1038 | −5516 | −3074 | −87 | −5402 | −5808 | −1438 | −1356 | −3032 | −4154 | −1543 | 5926 | 887 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 51 | −1546 | −1054 | 648 | 1209 | −1309 | −4870 | −619 | −2930 | 1079 | −669 | −1784 | 648 | 478 | 572 | 951 | −67 | 994 | −1650 | −5552 | −4869 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 52 | −308 | −4032 | −6554 | −5919 | 2287 | −3274 | −4631 | 121 | −5515 | 375 | 1444 | −5404 | −5807 | −5139 | −5316 | −527 | −143 | 2509 | −4496 | −4154 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 53 | −1263 | −5366 | −249 | −113 | −2060 | 114 | −1277 | −1652 | 1874 | −1253 | −1588 | 531 | −4964 | 201 | 1748 | −502 | −332 | −312 | −5550 | 724 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 54 | −4187 | 1014 | −6532 | −5896 | 273 | −2864 | 1491 | 429 | −5491 | 1830 | 1482 | −5380 | −5784 | −2303 | −5291 | −4819 | −1633 | 1018 | −477 | 2556 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11881 | −12923 | −894 | −1115 | −701 | −1378 | * | * | | | | | | | | | | | | |
| 55 | −1065 | 634 | −4 | −299 | −5644 | −2306 | −3539 | 360 | 1372 | 298 | −1820 | −557 | −4972 | −534 | 1695 | 733 | 173 | −485 | −620 | −4856 | 100 |
| — | −149 | −483 | 235 | 41 | −379 | 397 | 103 | −622 | 211 | −465 | −723 | 275 | 391 | 43 | 95 | 358 | 120 | −368 | −285 | −252 | |
| E | −1003 | −4172 | −1166 | −1582 | −586 | −701 | −1378 | * | * | | | | | | | | | | | | |
| 56 | −1330 | −4079 | −866 | −2762 | 2008 | 1322 | 1447 | −3845 | 77 | −2584 | −537 | −3015 | −4342 | −794 | −112 | −382 | −1510 | −1167 | 1529 | 2755 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11030 | −12072 | −894 | −1115 | −3248 | −160 | * | * | | | | | | | | | | | | |
| 57 | −1250 | −449 | 434 | −93 | −1417 | −1613 | −203 | −4740 | 141 | −3038 | −822 | 1042 | −1739 | −181 | 2206 | −645 | −3135 | −4290 | 3884 | 726 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11130 | −12172 | −894 | −1115 | −694 | −1389 | * | * | | | | | | | | | | | | |
| 58 | −1495 | −5140 | −77 | −821 | −5461 | 446 | −3300 | −1866 | 1848 | −2033 | 93 | 1549 | 876 | −1627 | 2136 | −2409 | −1161 | −4762 | −5323 | −2026 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −135 | −11638 | −3492 | −894 | −1115 | −47 | −4974 | * | * | | | | | | | | | | | | |
| 59 | −1198 | −5263 | 768 | 251 | −5584 | −459 | 500 | −734 | 658 | −5279 | −4352 | 1714 | −4857 | 49 | −916 | 1805 | −166 | −1048 | −5446 | 13 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11768 | −12810 | −894 | −1115 | −3373 | −146 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −360 | −395 | 191 | −1422 | −5584 | 1113 | −347 | −5335 | 877 | −3447 | −1591 | 1041 | 887 | −172 | 370 | 1463 | 91 | −4885 | −5446 | −4763 | 111 |
| — | −153 | −489 | 242 | 44 | −390 | 398 | 96 | −633 | 215 | −469 | −723 | 276 | 384 | 62 | 113 | 358 | 118 | −377 | −304 | −252 | |
| — | −2215 | −490 | −3780 | −3 | −9024 | −2760 | −230 | * | * | | | | | | | | | | | | |
| 61 | −2385 | 556 | 26 | 146 | −247 | 2105 | −3331 | −2524 | 335 | −3629 | −1225 | −305 | −4765 | −1657 | 1400 | 1188 | −1435 | −1727 | −5341 | −1708 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −37 | −11667 | −5303 | −894 | −1115 | −1944 | −434 | * | * | | | | | | | | | | | | |
| 62 | −874 | −5115 | −2060 | −508 | −47 | −4702 | 2073 | −1107 | 517 | −3542 | −1146 | −1741 | −4795 | 331 | 2111 | −1951 | 1519 | −1139 | 195 | 1887 | 114 |
| — | −149 | −490 | 233 | 43 | −381 | 399 | 106 | −626 | 210 | −466 | −720 | 275 | 394 | 45 | 96 | 359 | 117 | −369 | −294 | −249 | |
| — | −14 | −6686 | −12724 | −178 | −3108 | −2954 | −199 | * | * | | | | | | | | | | | | |
| 63 | −212 | −1043 | −6356 | −5720 | 1916 | −2527 | −4430 | 137 | −921 | 601 | 3091 | −5204 | −1370 | −1138 | −5115 | −1197 | −133 | 1398 | −4296 | −392 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −403 | −11698 | −2037 | −894 | −1115 | −3950 | −97 | * | * | | | | | | | | | | | | |
| 64 | −715 | −991 | −5973 | −5337 | 1643 | −5176 | −4047 | −125 | −1123 | −1317 | 1631 | −4822 | −5226 | −4555 | −271 | 678 | −1395 | 964 | 1018 | 3153 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11296 | −12338 | −894 | −1115 | −60 | −4626 | * | * | | | | | | | | | | | | |
| 65 | −4175 | −4001 | −6520 | −718 | 1864 | −2901 | −1130 | 813 | −5479 | 2367 | 1729 | −5368 | −5772 | −5102 | −5279 | −1977 | −1988 | 270 | −4459 | −1779 | 118 |
| — | −149 | −500 | 233 | 43 | −381 | 398 | 105 | −626 | 211 | −466 | −721 | 275 | 394 | 45 | 96 | 360 | 118 | −369 | −295 | −249 | |
| E | −24 | −5939 | −12910 | −102 | −3876 | −390 | −2076 | * | * | | | | | | | | | | | | |
| 66 | −72 | −1242 | −1118 | −2341 | −5683 | 1209 | −213 | −3043 | −401 | −824 | −4454 | −2005 | −1828 | 555 | 814 | 928 | 2077 | −913 | −5549 | −1666 | 120 |
| — | −149 | −500 | 236 | 42 | −381 | 399 | 105 | −627 | 210 | −465 | −721 | 279 | 393 | 45 | 95 | 358 | 117 | −368 | −295 | −250 | |
| — | −12 | −6974 | −12923 | −2625 | −255 | −701 | −1378 | * | * | | | | | | | | | | | | |
| 67 | −640 | −407 | −264 | 647 | −1781 | 1097 | −769 | −2593 | 1377 | −2565 | −4458 | 19 | −1867 | −611 | 1248 | 698 | 761 | −1767 | −5552 | −4870 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11881 | −12923 | −894 | −1115 | −701 | −1378 | * | * | | | | | | | | | | | | |
| 68 | −4966 | −793 | −2630 | −7146 | −8246 | 3698 | −7197 | −8082 | −7758 | −8309 | −7365 | −615 | −6599 | −7167 | −2976 | −919 | −5434 | −2361 | −8448 | −8304 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11881 | −12923 | −894 | −1115 | −701 | −1378 | * | * | | | | | | | | | | | | |
| 69 | −5321 | −1084 | −8066 | −7961 | −4574 | −6344 | −5694 | −5868 | −7522 | −3396 | −5570 | −6606 | −6895 | −6938 | −7191 | −2262 | −317 | −2140 | 6150 | −1774 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11881 | −12923 | −894 | −1115 | −701 | −1378 | * | * | | | | | | | | | | | | |
| 70 | −926 | −974 | −650 | 592 | −5689 | −255 | −3529 | −1502 | 2062 | −2291 | −605 | −509 | −983 | −288 | 1452 | 1037 | −379 | −1324 | −5552 | −1705 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11881 | −12923 | −894 | −1115 | −701 | −1378 | * | * | | | | | | | | | | | | |
| 71 | −786 | −309 | 834 | 1602 | −5691 | 305 | −1246 | −5441 | 1095 | −2734 | −4458 | 311 | −1429 | 477 | 1381 | 754 | −1602 | −2583 | −5553 | −4870 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11881 | −12923 | −894 | −1115 | −701 | −1378 | * | * | | | | | | | | | | | | |
| 72 | −7134 | −1300 | −9178 | −3355 | 4401 | −8818 | −6481 | −1336 | −8455 | −462 | −707 | −8190 | −8256 | −7384 | −7982 | −8061 | −6995 | −5291 | −5575 | −1043 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −6 | −11881 | −8092 | −894 | −1115 | −701 | −1378 | * | * | | | | | | | | | | | | |
| 73 | 1416 | 3659 | −6535 | −5900 | −1257 | −5737 | −4611 | −298 | −5495 | −1940 | −3220 | −2798 | −5788 | −5118 | −1983 | −956 | −844 | 2598 | −4476 | −4134 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11876 | −12918 | −894 | −1115 | −1027 | −974 | * | * | | | | | | | | | | | | |
| 74 | −386 | −459 | 874 | 946 | −2870 | −3343 | −532 | −840 | 1608 | −1612 | −1116 | 816 | −4959 | 1178 | 952 | −5 | −424 | −705 | −5547 | −4864 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11876 | −12918 | −894 | −1115 | −1027 | −974 | * | * | | | | | | | | | | | | |
| 75 | 2192 | −5362 | 2206 | 1267 | −2255 | −1412 | −1681 | −3102 | −1999 | −3014 | −4452 | −1403 | −4959 | −1005 | −2058 | 76 | −1209 | −1186 | −5546 | −4864 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11876 | −12918 | −894 | −1115 | −1027 | −974 | * | * | | | | | | | | | | | | |
| 76 | −1991 | −5094 | −3912 | −1610 | −2280 | −4954 | 3004 | −1817 | 1237 | −2029 | 66 | 3337 | −5044 | −277 | −3749 | −3023 | −1419 | −4654 | −5349 | 26 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11876 | −12918 | −894 | −1115 | −1027 | −974 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | −667 | −245 | 1082 | −259 | −5686 | 2388 | 500 | −5436 | 524 | −5381 | −1645 | 448 | −1598 | 49 | 766 | −310 | −2345 | −3200 | −5548 | −4865 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11876 | −12918 | −894 | −1115 | −1027 | −974 | * | * | | | | | | | | | | | | |
| 78 | −3194 | −5215 | −7850 | −7228 | 355 | −7151 | −6005 | 547 | −989 | 2877 | −380 | −6807 | −7019 | −2580 | −6612 | −6273 | −5411 | 730 | −5578 | −5382 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11876 | −12918 | −894 | −1115 | −1027 | −974 | * | * | | | | | | | | | | | | |
| 79 | −1936 | −538 | −297 | 980 | −3251 | 39 | −1936 | −573 | 1988 | −943 | −731 | 103 | −4959 | 1259 | 1337 | −1124 | −2042 | −174 | −5544 | −4863 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11876 | −12918 | −894 | −1115 | −1027 | −974 | * | * | | | | | | | | | | | | |
| 80 | 1179 | −5328 | 813 | 1175 | −2243 | −1706 | −3536 | 318 | −1592 | −1237 | 672 | −541 | −344 | −379 | −1116 | −596 | 849 | 822 | −5521 | −4849 | 141 |
| — | −149 | −500 | 233 | 43 | −381 | 398 | 105 | −626 | 210 | −466 | −721 | 275 | 394 | 45 | 96 | 359 | 119 | −367 | −295 | −249 | |
| T | −65 | −5935 | −5169 | −101 | −3886 | −1027 | −974 | * | * | | | | | | | | | | | | |
| 81 | −4071 | −5557 | −589 | −1171 | −5873 | 3428 | −419 | −5628 | −2195 | −3151 | −4653 | 657 | −5103 | −3229 | −1142 | −1348 | −2138 | −5178 | −5738 | −1932 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11835 | −12877 | −894 | −1115 | −2391 | −305 | * | * | | | | | | | | | | | | |
| 82 | −5015 | −6636 | 3682 | 1447 | −6909 | −2265 | −1198 | −6712 | −1877 | −6632 | −5775 | −1291 | −5834 | −342 | −4932 | −1384 | −4997 | −6239 | −413 | −1805 | 144 |
| — | −150 | −464 | 231 | 42 | −373 | 397 | 104 | −626 | 213 | −467 | −722 | 274 | 392 | 44 | 94 | 359 | 116 | −365 | −296 | −251 | |
| — | −115 | −3963 | −6285 | −699 | −1381 | −769 | −1275 | * | * | | | | | | | | | | | | |
| 83 | −487 | 401 | −6492 | −5856 | 2294 | −3242 | −4568 | 876 | −2726 | 47 | −980 | −1201 | −2532 | −2373 | −5253 | 1320 | 944 | 1003 | −4435 | −12 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11843 | −12886 | −894 | −1115 | −1372 | −704 | * | * | | | | | | | | | | | | |
| 84 | −2787 | 3229 | −6529 | −5894 | 2267 | −5733 | −4606 | 630 | −5490 | 1287 | −471 | −5379 | −5782 | −5113 | −5290 | −3079 | −2562 | 1850 | −4470 | 181 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11853 | −12895 | −894 | −1115 | −1935 | −437 | * | * | | | | | | | | | | | | |
| 85 | −1838 | −4599 | −2321 | −1048 | −2221 | −2873 | −955 | 646 | −414 | 157 | −986 | −2526 | −5236 | −1842 | −749 | −763 | 2213 | 2147 | −4958 | −2067 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11853 | −12895 | −894 | −1115 | −1935 | −437 | * | * | | | | | | | | | | | | |
| 86 | −7606 | −6912 | −9559 | −9201 | 4203 | −9393 | −6724 | −1985 | −8948 | 925 | −902 | −8665 | −8548 | −7620 | −8354 | −8735 | −7427 | −2725 | −1717 | −162 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11853 | −12895 | −894 | −1115 | −1208 | −818 | * | * | | | | | | | | | | | | |
| 87 | −2603 | −5245 | −3786 | 1769 | −5519 | −3551 | −95 | −1312 | 1847 | −1816 | 1209 | −3539 | −4976 | 102 | 1562 | 99 | 164 | −916 | 175 | −56 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11862 | −12904 | −894 | −1115 | −1664 | −547 | * | * | | | | | | | | | | | | |
| 88 | −2485 | −4186 | −1474 | −1023 | 793 | −5493 | 2097 | −2547 | −2959 | 1798 | −332 | −4736 | −1620 | −1854 | 1519 | −1953 | −1104 | −441 | −1201 | 2031 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11862 | −12904 | −894 | −1115 | −1664 | −547 | * | * | | | | | | | | | | | | |
| 89 | −2427 | −494 | 1065 | −65 | −1440 | −634 | 410 | 1544 | −440 | −276 | −1424 | −920 | −1603 | −1949 | −102 | 279 | −864 | 1597 | −5438 | −4793 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11862 | −12904 | −894 | −1115 | −937 | −1066 | * | * | | | | | | | | | | | | |
| 90 | −702 | −1361 | 289 | 504 | −5680 | 2020 | −952 | −5430 | 831 | −2554 | −1618 | −583 | −2090 | −107 | 1025 | 68 | −2274 | −2537 | 2640 | −1574 | 154 |
| — | −145 | −500 | 244 | 44 | −382 | 406 | 100 | −632 | 207 | −471 | −717 | 273 | 392 | 41 | 93 | 360 | 119 | −373 | −300 | −255 | |
| S | −867 | −3043 | −1598 | −1614 | −571 | −1330 | −732 | * | * | | | | | | | | | | | | |
| 91 | −813 | −1495 | 1593 | 965 | −5139 | 133 | 330 | −2281 | 491 | −4834 | −3907 | 1863 | 843 | −1437 | −673 | 480 | −1651 | −1249 | −5001 | −1034 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11292 | −12334 | −894 | −1115 | −215 | −2854 | * | * | | | | | | | | | | | | |
| 92 | −942 | −5309 | −1480 | 1049 | −124 | 850 | 177 | −5380 | 588 | −633 | 1842 | 688 | −4903 | −759 | 353 | 1141 | −70 | −2850 | −5492 | −4810 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11817 | −12860 | −894 | −1115 | −2728 | −236 | * | * | | | | | | | | | | | | |
| 93 | −813 | 307 | 109 | 1332 | −999 | 869 | −304 | −1054 | 230 | −2827 | −4030 | −276 | −998 | −19 | 774 | −102 | 649 | 322 | 134 | −4449 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11817 | −12860 | −894 | −1115 | −1802 | −488 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | −219 | −774 | −1009 | 334 | 2838 | −743 | −3525 | −2301 | 47 | 971 | −170 | −1569 | −1561 | −888 | −844 | −3044 | 329 | −4783 | −5411 | 383 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11829 | −12871 | −894 | −1115 | −2517 | −277 | * | * | | | | | | | | | | | | |
| 95 | −1170 | −709 | −884 | −94 | −705 | −2112 | 2240 | −3390 | 638 | −720 | −514 | 425 | −1745 | −979 | 868 | 203 | 1794 | −1287 | 453 | 80 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11829 | −12871 | −894 | −1115 | −1378 | −701 | * | * | | | | | | | | | | | | |
| 96 | −2559 | −576 | −1390 | −1498 | −154 | −5694 | −637 | 769 | −5430 | −645 | −278 | −2670 | 2196 | −5059 | −1547 | −2992 | −1263 | 2610 | −4439 | −774 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −11 | −11844 | −7067 | −894 | −1115 | −2177 | −361 | * | * | | | | | | | | | | | | |
| 97 | −1474 | −1086 | −857 | −2043 | −5257 | 384 | 828 | −16 | 86 | 348 | 2090 | −488 | −5005 | −1063 | −341 | −139 | 444 | 1465 | −5306 | 40 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11834 | −12876 | −894 | −1115 | −2421 | −298 | * | * | | | | | | | | | | | | |
| 98 | 55 | −1717 | −6487 | −5851 | 677 | −749 | −2129 | 2244 | −3000 | 1465 | −571 | −2540 | −1952 | −5068 | −5245 | −3135 | −618 | 1261 | 934 | −4083 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11834 | −12876 | −894 | −1115 | −2421 | −298 | * | * | | | | | | | | | | | | |
| 99 | −4097 | −880 | −5619 | −3136 | 2448 | −5533 | 253 | −347 | 514 | 397 | −3292 | −2473 | −2815 | 24 | 1735 | 875 | −4038 | −323 | −867 | 628 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11834 | −12876 | −894 | −1115 | −1547 | −604 | * | * | | | | | | | | | | | | |
| 100 | −2524 | −5302 | 1112 | −598 | 1148 | 710 | −3505 | −868 | 201 | 917 | −1837 | 156 | −4938 | −1026 | 2152 | −1428 | −3805 | −2768 | −5495 | −4821 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11844 | −12887 | −894 | −1115 | −1664 | −547 | * | * | | | | | | | | | | | | |
| 101 | 25 | 3255 | −4103 | −1296 | −967 | −375 | 619 | −92 | 374 | −653 | −3967 | −790 | 814 | −816 | 1352 | −661 | −1692 | 466 | −1724 | −2054 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11850 | −12892 | −894 | −1115 | −719 | −1349 | * | * | | | | | | | | | | | | |
| 102 | −1514 | −1023 | −46 | −1011 | −1703 | −643 | −987 | −1471 | −850 | −2863 | −2333 | 927 | 1366 | −132 | 373 | 2008 | −21 | −344 | −610 | −669 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11869 | −12911 | −894 | −1115 | −396 | −2060 | * | * | | | | | | | | | | | | |
| 103 | −111 | 1629 | −228 | 206 | −641 | 1104 | 1393 | −3223 | 1048 | −1365 | −707 | −614 | −2168 | −468 | 626 | −264 | 891 | −1460 | −5550 | −2101 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11881 | −12923 | −894 | −1115 | −701 | −1378 | * | * | | | | | | | | | | | | |
| 104 | −759 | 3024 | −293 | 935 | −5674 | −1145 | −2048 | −144 | 597 | −1133 | −955 | 337 | 441 | 152 | −1149 | −2 | 266 | −522 | −1791 | 212 | 174 |
| — | * | * | * | * | * | * | * | * | * | * | * | * | * | * | * | * | * | * | * | * | |
| — | * | * | * | * | * | * | * | * | 0 | | | | | | | | | | | | |
| // | | | | | | | | | | | | | | | | | | | | | |

HMMER2.0 [2.3.2]
NAME Cu-oxidase
ACC PF00394.14
DESC Multicopper oxidase
LENG 189
ALPH Amino
RF no
CS yes
MAP yes
COM hmmbuild -F HMM_ls.ann SEED.ann
COM hmmcalibrate --seed 0 HMM_ls.ann
NSEQ 72
DATE Thu Apr 24 19:20:05 2008
CKSUM 4184
GA −18.9000 −18.9000;
TC −18.6000 −18.6000;
NC −19.1000 −19.1000;
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −98.859215 0.169857

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −44 | * | −5045 | | | | | | | | | | | | | | | | | | |
| 1 | −720 | −3824 | 1695 | 2320 | 154 | 815 | −547 | −3896 | 780 | −3840 | −2914 | 22 | −3416 | −1522 | 102 | −2230 | −1286 | −3446 | −4007 | −3324 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −354 | −10161 | −2205 | −894 | −1115 | −701 | −1378 | −44 | * | | | | | | | | | | | | |
| 2 | −167 | −3422 | 1897 | 1450 | 276 | −3051 | −1714 | −389 | −1313 | −853 | −2523 | 226 | −3143 | −582 | −234 | 970 | −239 | −430 | −3632 | −2977 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9809 | −10851 | −894 | −1115 | −403 | −2036 | * | * | | | | | | | | | | | | |
| 3 | −1663 | −2460 | −4151 | −3555 | 1059 | −690 | 667 | −280 | −1027 | −1072 | −1657 | 1036 | −4012 | −985 | −312 | −3004 | 1789 | 1044 | 887 | 2233 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10093 | −11135 | −894 | −1115 | −307 | −2384 | * | * | | | | | | | | | | | | |
| 4 | −2588 | −2415 | −4933 | −4296 | 72 | −4135 | −3006 | 981 | −3891 | −17 | 142 | −1579 | 1315 | −3515 | −3692 | −1719 | 1824 | 2047 | 6 | 373 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 5 | −3759 | −3472 | −137 | −5559 | 814 | −5480 | −4370 | 2747 | −5211 | 1583 | −2050 | −5127 | −5382 | −4735 | −4999 | −4611 | −3695 | 1308 | 685 | −3707 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −148 | −10161 | −3368 | −894 | −1115 | −701 | −1378 | * | * | | | | | | | | | | | | |
| 6 | −2456 | −2298 | −4699 | −256 | 27 | −50 | 163 | 728 | −3687 | 1186 | 1259 | −3604 | −583 | −3330 | −3524 | −755 | 2225 | −72 | −2754 | −2409 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10015 | −11057 | −894 | −1115 | −191 | −3009 | * | * | | | | | | | | | | | | |
| 7 | −1690 | −2417 | −4928 | −80 | 505 | −1374 | −3007 | 853 | −3889 | 2504 | 73 | −812 | −4186 | −3513 | −3691 | −3221 | −2530 | 317 | 803 | −2532 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 8 | 1038 | −3822 | −755 | −594 | −273 | 1632 | −1984 | −3892 | −514 | −3838 | −2912 | −134 | −3417 | −140 | −2074 | 1675 | 1158 | −3444 | −4006 | −3324 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | −4713 | −6794 | 3776 | 1480 | −6944 | −4410 | −3898 | −6968 | −4379 | −6785 | −6261 | −2999 | −5018 | −3598 | −5450 | −57 | −4831 | −6380 | −6987 | −5814 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 10 | −6394 | −302 | −7091 | −7330 | 212 | −6901 | 1630 | −5357 | −6892 | −1320 | −762 | −5609 | −6776 | −5715 | −6311 | −6127 | −6266 | −5474 | 5870 | 1249 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −22 | −10161 | −6152 | −894 | −1115 | −701 | −1378 | * | * | | | | | | | | | | | | |
| 11 | −6765 | −5695 | −7158 | −7506 | 966 | −7038 | 309 | −5663 | −7061 | −4981 | −5069 | −1071 | −6894 | −5791 | −6429 | −6284 | 17 | −5813 | 3916 | 4259 | 11 |
| — | −149 | −500 | 232 | 43 | −381 | 398 | 105 | −624 | 210 | −465 | −721 | 275 | 393 | 45 | 95 | 360 | 117 | −366 | −295 | −250 | |
| T | −199 | −2960 | −11184 | −45 | −5013 | −1076 | −928 | * | * | | | | | | | | | | | | |
| 12 | −2326 | −3796 | 675 | 18 | −4116 | −3300 | 3975 | −2019 | 1065 | −2079 | −2885 | 840 | 679 | −1500 | −1062 | −2207 | −450 | −3417 | −3980 | 529 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −53 | −10142 | −4826 | −894 | −1115 | −1076 | −928 | * | * | | | | | | | | | | | | |
| 13 | 786 | −3751 | 230 | 384 | −4070 | −1301 | −274 | −1011 | 1586 | −3766 | −50 | −1892 | −3349 | 688 | 472 | −994 | 1486 | 160 | −3935 | −1172 | 14 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −10090 | −11133 | −894 | −1115 | −1164 | −853 | * | * | | | | | | | | | | | | |
| 14 | 370 | −3726 | 1722 | −1621 | −4026 | −215 | −1946 | −1219 | −477 | −1032 | −2821 | 1797 | 1081 | −291 | −2038 | 322 | 483 | −1322 | −3922 | −884 | 15 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10111 | −11153 | −894 | −1115 | −1506 | −626 | * | * | | | | | | | | | | | | |
| 15 | 1564 | −3189 | −871 | 5 | −941 | −1352 | 2653 | 77 | −1913 | −3113 | 608 | −505 | 189 | −1843 | −2350 | 336 | −202 | 612 | −3512 | −753 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10111 | −11153 | −894 | −1115 | −359 | −2183 | * | * | | | | | | | | | | | | |
| 16 | −2341 | −3813 | 635 | 532 | −1039 | −1745 | 1498 | −3884 | 1568 | −1138 | 297 | 177 | 802 | 319 | −912 | 219 | 728 | −484 | −3997 | −1235 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 17 | 595 | −3802 | 1396 | 1283 | −4117 | −168 | −1977 | −848 | −991 | −77 | −2893 | −513 | −3411 | −307 | −1026 | 319 | 905 | 157 | −3989 | −3309 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −260 | −10161 | −2607 | −894 | −1115 | −701 | −1378 | * | * | | | | | | | | | | | | |
| 18 | −1268 | −2238 | −4325 | −3713 | −2198 | −3852 | −320 | 267 | −369 | 2029 | 568 | −586 | 351 | 902 | −3314 | −2920 | −1136 | 1213 | −2689 | 26 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9903 | −10946 | −894 | −1115 | −2890 | −209 | * | * | | | | | | | | | | | | |
| 19 | −293 | 716 | −2595 | 1308 | −1122 | −1596 | −2097 | −114 | 780 | −572 | −2010 | −577 | −3462 | 827 | 386 | −2336 | 110 | 996 | 823 | 1181 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −9903 | −10946 | −894 | −1115 | −2890 | −209 | * | * | | | | | | | | | | | | |
| 20 | 426 | −3598 | 149 | 171 | −3918 | −3101 | −1759 | −3668 | 1624 | −1094 | −442 | 1095 | −297 | 1122 | 275 | −20 | −1062 | 470 | 763 | −3099 | 21 |
| — | −148 | −502 | 234 | 47 | −379 | 396 | 107 | −619 | 209 | −467 | −723 | 273 | 391 | 55 | 98 | 358 | 115 | −372 | −297 | −249 | |
| C | −1500 | −693 | −5173 | −12 | −6974 | −2890 | −209 | * | * | | | | | | | | | | | | |
| 21 | 970 | −3422 | −68 | 256 | −1242 | 266 | −1773 | −3389 | −444 | 1346 | −2528 | −1770 | −669 | −356 | −1877 | 127 | −351 | −1312 | −3644 | 1437 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9864 | −10906 | −894 | −1115 | −3039 | −187 | * | * | | | | | | | | | | | | |
| 22 | 14 | −2288 | 1652 | 390 | 1499 | −3729 | −2550 | 64 | −2981 | 1145 | 1324 | −3078 | −1635 | −135 | −3060 | −1516 | −424 | −426 | −2728 | −53 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −9864 | −10906 | −894 | −1115 | −3039 | −187 | * | * | | | | | | | | | | | | |
| 23 | 1493 | −3564 | −415 | −583 | 239 | 265 | −1727 | −3634 | 1072 | −1192 | 511 | 110 | −3161 | 850 | 219 | 936 | −1156 | −3186 | −3748 | −3066 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −31 | −9864 | −5628 | −894 | −1115 | −3039 | −187 | * | * | | | | | | | | | | | | |
| 24 | −2074 | −3527 | −570 | −392 | −3839 | 1481 | 10 | −3584 | −1295 | −1550 | −2619 | −606 | −69 | −1253 | −674 | 1780 | 1821 | −969 | −3716 | −3038 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −160 | −9835 | −3269 | −894 | −1115 | −3135 | −174 | * | * | | | | | | | | | | | | |
| 25 | 520 | −3392 | −285 | −1255 | −3702 | 1941 | 62 | −3445 | 103 | −353 | −2484 | −1564 | −1179 | 45 | 1521 | −6 | −813 | −1329 | 853 | −2906 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −67 | −9678 | −4511 | −894 | −1115 | −3548 | −129 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | 883 | −3341 | −242 | 446 | −907 | 429 | −1533 | −3392 | 1652 | −312 | −2433 | 78 | −2967 | −1077 | −162 | −1065 | 572 | −334 | −3531 | 408 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −147 | −9614 | −3390 | −894 | −1115 | −1582 | −587 | * | * | | | | | | | | | | | | |
| 27 | 1082 | −3393 | −279 | −478 | −3705 | 450 | −1578 | −226 | 596 | 815 | −2484 | 1584 | 644 | −1121 | −871 | −554 | −1880 | −3010 | −3582 | −2904 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −922 | −9671 | −1086 | −894 | −1115 | −599 | −1558 | * | * | | | | | | | | | | | | |
| 28 | 163 | −1991 | −2927 | −2352 | −1984 | 1092 | −1973 | −106 | −2160 | −749 | 549 | 379 | 2246 | −235 | −2375 | −345 | −582 | −1428 | 1604 | 1303 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −3 | −9348 | −10390 | −894 | −1115 | −4076 | −88 | * | * | | | | | | | | | | | | |
| 29 | 781 | −2252 | −2358 | 525 | 211 | −820 | −1746 | −239 | −1660 | −439 | 1587 | −1953 | 1391 | 558 | −2014 | 105 | 1346 | −1716 | −2633 | −2181 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −28 | −9348 | −5823 | −894 | −1115 | −4076 | −88 | * | * | | | | | | | | | | | | |
| 30 | 842 | −3132 | 1611 | −975 | −3447 | 1515 | −1306 | −3194 | 523 | −1050 | −2222 | −1285 | −1258 | 679 | 1246 | −1555 | −605 | −1474 | −3318 | −2639 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −3 | −9324 | −10366 | −894 | −1115 | −3658 | −119 | * | * | | | | | | | | | | | | |
| 31 | 832 | −1725 | −4229 | −3593 | 1753 | −333 | 373 | −270 | −3191 | −458 | 1542 | −3084 | −3493 | −2817 | −2996 | −682 | 830 | 585 | 3488 | 64 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1563 | −9350 | −599 | −894 | −1115 | −4074 | −88 | * | * | | | | | | | | | | | | |
| 32 | −904 | −1969 | 709 | 560 | −2123 | −1840 | −600 | −1785 | −316 | −1915 | −1110 | −547 | −1985 | 1473 | −798 | −863 | −852 | 2251 | −2241 | 963 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −10 | −7796 | −8838 | −894 | −1115 | −4043 | −90 | * | * | | | | | | | | | | | | |
| 33 | 527 | −2376 | 884 | 1350 | −2691 | −1803 | −505 | −2447 | 604 | −2389 | −1470 | 2000 | 574 | 796 | −629 | −760 | −832 | −1995 | −2558 | −1864 | 35 |
| — | −149 | −500 | 232 | 42 | −379 | 398 | 105 | −627 | 210 | −465 | −717 | 275 | 395 | 45 | 95 | 360 | 117 | −365 | −295 | −247 | |
| H | −3125 | −349 | −3321 | −34 | −5420 | −4873 | −50 | * | * | | | | | | | | | | | | |
| 34 | −872 | −991 | −2003 | −1442 | −784 | −2222 | 1526 | −535 | −1218 | −843 | 3209 | 1888 | −2288 | −1053 | −1402 | −1248 | −813 | 862 | −1255 | 1170 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −10 | −7811 | −8853 | −894 | −1115 | −4909 | −49 | * | * | | | | | | | | | | | | |
| 35 | −1537 | −2718 | 361 | −833 | −3161 | −2368 | −740 | −2788 | 2124 | −2645 | −1832 | −1021 | −2417 | −307 | 2693 | −1423 | −1404 | −2436 | 2723 | −2237 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −10 | −7811 | −8853 | −894 | −1115 | −92 | −4010 | * | * | | | | | | | | | | | | |
| 36 | −163 | −2909 | −2940 | 544 | −473 | 44 | −2354 | 570 | −1284 | −2801 | 262 | −2546 | 3000 | −2145 | −401 | −1489 | −26 | −793 | −3285 | −2826 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −146 | −10110 | −3395 | −894 | −1115 | −1519 | −619 | * | * | | | | | | | | | | | | |
| 37 | −1667 | −2367 | −3971 | −3378 | −1099 | 842 | −2657 | −1171 | −3117 | 855 | 423 | 1756 | 2521 | −2875 | −407 | −2877 | 256 | −1791 | −2809 | −2443 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −256 | −9966 | −2629 | −894 | −1115 | −873 | −1140 | * | * | | | | | | | | | | | | |
| 38 | −499 | −2912 | −2396 | 1160 | −3013 | −378 | −333 | 1115 | −1729 | −1405 | 925 | −113 | 479 | −696 | −1367 | −1347 | 1234 | 1382 | −3245 | −2730 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −9837 | −10879 | −894 | −1115 | −469 | −1850 | * | * | | | | | | | | | | | | |
| 39 | 442 | −2859 | −3850 | −3314 | −1478 | −874 | −2963 | −2617 | −3128 | −1104 | −2240 | −3241 | 3218 | 481 | −3341 | 1420 | −2630 | −964 | −3468 | −3077 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10086 | −11128 | −894 | −1115 | −1776 | −498 | * | * | | | | | | | | | | | | |
| 40 | −818 | −3748 | 3225 | −1593 | −4063 | −1792 | −1927 | −3809 | −1512 | −1889 | −2841 | 504 | −3360 | 1700 | −650 | −10 | −1259 | −1404 | −3937 | −3258 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10086 | −11128 | −894 | −1115 | −1776 | −498 | * | * | | | | | | | | | | | | |
| 41 | 1659 | −3496 | −2326 | −1779 | −273 | 829 | 1482 | −3420 | −927 | −3499 | −2648 | 1026 | −3450 | −1635 | −2167 | 1461 | 1077 | −1814 | −3781 | −3173 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10086 | −11128 | −894 | −1115 | −291 | −2453 | * | * | | | | | | | | | | | | |
| 42 | −854 | −2415 | −4929 | −4293 | 609 | −28 | 1566 | 1209 | −3889 | 210 | −1618 | −3780 | −4185 | −3513 | −3691 | −1824 | 1690 | 1591 | −2872 | 1399 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −2588 | −2420 | −4901 | −4267 | −2375 | −1476 | −3003 | −87 | −3869 | 2447 | 862 | −1291 | −4183 | −3499 | −1425 | −1254 | 1476 | 500 | −2878 | −2535 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 44 | −4347 | −3942 | −687 | −6315 | 2125 | −6349 | −5420 | 3262 | −6061 | −184 | 977 | −6007 | −6094 | −5542 | −5880 | −5556 | −4289 | 521 | −4813 | −4626 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 45 | −1716 | −4402 | −3121 | −2876 | −4966 | −4198 | −3074 | −4585 | −1213 | −2446 | −3863 | 4158 | −1029 | −307 | −2659 | −3422 | −3451 | −1741 | −4848 | −4365 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 46 | −1915 | −6358 | −808 | 138 | −6644 | 3527 | −3761 | −6597 | −4082 | −6452 | −5820 | −263 | −4905 | −3441 | −1500 | −2007 | −4567 | −6028 | −6649 | −5587 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −239 | −10161 | −2718 | −894 | −1115 | −701 | −1378 | * | * | | | | | | | | | | | | |
| 47 | −1442 | −3610 | −824 | −666 | −3928 | −1163 | 1662 | −3676 | 1827 | 576 | −811 | −1756 | −3213 | 1169 | 1568 | −2026 | 1140 | −1884 | −3795 | −3114 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −9924 | −10966 | −894 | −1115 | −2805 | −223 | * | * | | | | | | | | | | | | |
| 48 | −1075 | −3617 | −823 | −461 | −3937 | 2534 | −136 | −3687 | −577 | −3633 | 593 | 97 | 1534 | −1318 | −342 | 373 | −1098 | −3238 | −3800 | −3118 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −9924 | −10966 | −894 | −1115 | −2805 | −223 | * | * | | | | | | | | | | | | |
| 49 | −1331 | −3532 | −2036 | −1487 | −3816 | 1794 | −1803 | −448 | −7 | −2089 | −2631 | 811 | −330 | 1028 | 2161 | −996 | −96 | −1614 | 39 | −3079 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −124 | −9924 | −3625 | −894 | −1115 | −2177 | −360 | * | * | | | | | | | | | | | | |
| 50 | −391 | −365 | −545 | −2292 | 2191 | 345 | −2185 | −2188 | −189 | −1417 | −1761 | 625 | 868 | −2030 | −2477 | −124 | −2134 | −688 | 1254 | 2380 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −9831 | −10873 | −894 | −1115 | −3147 | −173 | * | * | | | | | | | | | | | | |
| 51 | 688 | −3337 | 403 | −1480 | −1171 | −341 | −299 | −966 | −176 | 862 | −2449 | 1800 | 166 | −496 | −972 | −1390 | −630 | 612 | −3574 | −2947 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −260 | −9831 | −2607 | −894 | −1115 | −3147 | −173 | * | * | | | | | | | | | | | | |
| 52 | 72 | 3043 | −1051 | −679 | −815 | 1731 | −1506 | −3338 | −368 | −3305 | −2390 | −600 | −1124 | −92 | −757 | 172 | −1119 | −2909 | −3490 | 2259 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9573 | −10616 | −894 | −1115 | −3751 | −111 | * | * | | | | | | | | | | | | |
| 53 | −413 | −3340 | 622 | −1164 | −3660 | 1324 | 1240 | −3411 | −423 | −3356 | −2429 | 2123 | −944 | −1040 | −628 | 743 | 1180 | −2962 | −3523 | −2841 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −458 | −9573 | −1885 | −894 | −1115 | −3751 | −111 | * | * | | | | | | | | | | | | |
| 54 | −1605 | 3854 | −768 | −138 | −2201 | 711 | −1523 | −732 | −1388 | 731 | −1314 | −337 | 352 | −1292 | −1766 | −296 | −397 | −445 | −2516 | −2048 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −4 | −9119 | −10161 | −894 | −1115 | −4309 | −75 | * | * | | | | | | | | | | | | |
| 55 | 1679 | 78 | −1666 | −1118 | −2875 | 104 | −1354 | −2535 | 46 | −419 | −1825 | −211 | −974 | −963 | −1488 | 1650 | 898 | −2228 | −2971 | −2391 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −51 | −9119 | −4927 | −894 | −1115 | −1531 | −613 | * | * | | | | | | | | | | | | |
| 56 | 586 | −3267 | 1099 | −1117 | −3581 | −453 | −1448 | −3327 | 321 | −486 | −2359 | −1426 | 1818 | −42 | −577 | 1126 | 444 | −1479 | −3455 | −2777 | 59 |
| — | −149 | −502 | 231 | 42 | −382 | 398 | 104 | −628 | 212 | −468 | −690 | 275 | 394 | 46 | 98 | 357 | 119 | −371 | −281 | −251 | |
| — | −4672 | −3798 | −170 | −3119 | −176 | −3859 | −103 | * | * | | | | | | | | | | | | |
| 57 | −1554 | −2445 | 3678 | −97 | −2948 | −1480 | −1047 | −3051 | −1301 | −3063 | −2548 | −442 | −2000 | −825 | −1912 | −1378 | −1677 | −2649 | −2758 | −2345 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −261 | −6346 | −2705 | −894 | −1115 | −1818 | −481 | * | * | | | | | | | | | | | | |
| 58 | −244 | −2470 | 187 | −412 | −2756 | 523 | −730 | −2483 | 1866 | −104 | −1568 | −717 | −2160 | 1402 | 46 | −977 | −10 | −75 | −2674 | −103 | 73 |
| — | −148 | −500 | 233 | 43 | −381 | 398 | 106 | −626 | 210 | −466 | −721 | 275 | 394 | 45 | 96 | 360 | 117 | −369 | −294 | −249 | |
| . | −177 | −3133 | −9508 | −146 | −3376 | −3787 | −109 | * | * | | | | | | | | | | | | |
| 59 | −1156 | −2527 | 2282 | −494 | 789 | −87 | −810 | −2529 | −408 | −2526 | −1628 | −798 | −409 | 410 | 195 | 129 | 597 | −2127 | −2736 | 1243 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1636 | −8579 | −566 | −894 | −1115 | −4071 | −88 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −361 | −873 | −1860 | −1527 | −1816 | 1259 | −1343 | −1365 | −1420 | −1698 | −962 | −1248 | 961 | −1237 | −1635 | 611 | −599 | 2279 | −2163 | −1787 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −15 | −7136 | −8178 | −894 | −1115 | −3893 | −101 | * | * | | | | | | | | | | | | |
| 61 | −635 | −1664 | −736 | −302 | −2205 | 1157 | −589 | −1888 | −274 | −294 | −1148 | 1956 | 434 | −201 | −738 | 1102 | −668 | −1499 | −2276 | −1693 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −12 | −7487 | −8529 | −894 | −1115 | −4097 | −87 | * | * | | | | | | | | | | | | |
| 62 | 347 | −2242 | 1454 | 8 | −2568 | 759 | −393 | −2322 | 1095 | −2270 | −1357 | 1221 | −1804 | 56 | −530 | 767 | −720 | −1872 | −2444 | −1751 | 78 |
| — | −148 | −500 | 232 | 42 | −381 | 398 | 105 | −624 | 210 | −466 | −721 | 276 | 394 | 45 | 95 | 360 | 119 | −370 | −295 | −250 | |
| . | −2855 | −219 | −8733 | −37 | −5287 | −4936 | −48 | * | * | | | | | | | | | | | | |
| 63 | 716 | −1685 | −934 | −402 | −2187 | −279 | −634 | −1860 | −308 | −1970 | −1130 | 1205 | 80 | −245 | −768 | 1202 | 1366 | 89 | −2270 | −1698 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7690 | −8733 | −894 | −1115 | −4936 | −48 | * | * | | | | | | | | | | | | |
| 64 | −1567 | −1526 | −2997 | −2595 | −156 | −2819 | −1143 | −1042 | −2269 | 1578 | −686 | −2199 | −2944 | −1984 | −2255 | 1380 | −1557 | −1018 | −818 | 3115 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7690 | −8733 | −894 | −1115 | −4936 | −48 | * | * | | | | | | | | | | | | |
| 65 | −846 | −2225 | −467 | 1095 | −2571 | 691 | −487 | −2302 | 590 | −2284 | −1396 | −395 | 1992 | −52 | −600 | −735 | 1310 | −1879 | −2481 | −1813 | 82 |
| — | −149 | −500 | 232 | 43 | −381 | 398 | 107 | −627 | 210 | −466 | −717 | 275 | 394 | 47 | 95 | 359 | 118 | −368 | −295 | −246 | |
| . | −1605 | −580 | −8733 | −48 | −4946 | −4936 | −48 | * | * | | | | | | | | | | | | |
| 66 | −2749 | 4930 | −4320 | −4375 | −397 | −3436 | −1691 | −2778 | −3914 | −2689 | −2491 | −3287 | −3820 | −3424 | −3628 | −2950 | −2951 | −2691 | −1076 | 3414 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7690 | −8733 | −894 | −1115 | −4143 | −84 | * | * | | | | | | | | | | | | |
| 67 | −817 | −2256 | 823 | 569 | −2556 | −1746 | −441 | −2297 | 1352 | 938 | −1355 | 1666 | −1864 | 8 | −554 | −697 | 145 | −1867 | −2448 | −1769 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −9 | −7847 | −8889 | −894 | −1115 | −4901 | −49 | * | * | | | | | | | | | | | | |
| 68 | −830 | −660 | −3147 | −2513 | 1167 | −2376 | −1245 | 1099 | −2115 | 1259 | 1728 | −2012 | 545 | −1742 | −1925 | −69 | −771 | 683 | 1767 | −775 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −9 | −7847 | −8889 | −894 | −1115 | −4901 | −49 | * | * | | | | | | | | | | | | |
| 69 | 406 | −2279 | −743 | −199 | −2643 | −1831 | −472 | −2364 | 1904 | −2308 | −1407 | 2122 | −1931 | −22 | 509 | 763 | −822 | −1935 | −2465 | −1829 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −100 | −7847 | −3997 | −894 | −1115 | −3746 | −112 | * | * | | | | | | | | | | | | |
| 70 | −862 | 1829 | −914 | 743 | −2308 | 1971 | −666 | −1985 | −323 | −2076 | −1232 | 558 | 580 | −263 | −798 | 121 | −839 | −295 | −2367 | −1771 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −8 | −8000 | −9043 | −894 | −1115 | −2407 | −301 | * | * | | | | | | | | | | | | |
| 71 | 1036 | −2650 | −1048 | −499 | −2964 | 202 | −830 | −2709 | 624 | −2663 | −1741 | 21 | −593 | 654 | 465 | 448 | 1106 | −2268 | −2837 | 1682 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −5 | −8649 | −9691 | −894 | −1115 | −2910 | −206 | * | * | | | | | | | | | | | | |
| 72 | −397 | −2439 | 1630 | 889 | −2607 | 1212 | −1223 | −107 | −924 | −2393 | −1593 | −1250 | −2610 | −854 | −1388 | −1460 | 741 | 1406 | −2753 | −2188 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −106 | −8891 | −3860 | −894 | −1115 | −1367 | −708 | * | * | | | | | | | | | | | | |
| 73 | 791 | −3219 | 165 | 258 | −184 | 1386 | −1385 | −3287 | −66 | −1023 | −2309 | 743 | 572 | 699 | −1474 | −319 | 426 | −1595 | −3404 | −2723 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9432 | −10474 | −894 | −1115 | −2342 | −317 | * | * | | | | | | | | | | | | |
| 74 | 1182 | 3018 | −3288 | −2707 | −175 | 485 | −2213 | −255 | −1247 | −1048 | −1302 | −665 | −3477 | −245 | −372 | 552 | 368 | 622 | −2540 | −548 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9566 | −10609 | −894 | −1115 | −3763 | −110 | * | * | | | | | | | | | | | | |
| 75 | 905 | −3326 | 1565 | 76 | −3645 | −1193 | −1489 | −3395 | 74 | −138 | 69 | 586 | 798 | 481 | −1578 | 797 | −885 | −1378 | −3510 | −2828 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9566 | −10609 | −894 | −1115 | −955 | −1046 | * | * | | | | | | | | | | | | |
| 76 | −559 | −2286 | −3997 | −988 | 392 | −680 | −2618 | −1799 | −3127 | 1589 | 96 | −164 | 586 | −2870 | −510 | −2838 | 1706 | −289 | −2730 | 1166 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −9896 | −10938 | −894 | −1115 | −606 | −1544 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | 1262 | −2653 | −3388 | −1667 | 1676 | −103 | −2528 | −1200 | −1329 | −1157 | −1838 | −1374 | 1087 | −75 | −2895 | −673 | 825 | −672 | 1398 | 1753 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10079 | −11121 | −894 | −1115 | −276 | −2524 | * | * | | | | | | | | | | | | |
| 78 | −1124 | −3788 | −1219 | 33 | −4097 | −457 | −1982 | 526 | 511 | −1307 | −2880 | −871 | −1577 | −353 | −89 | −244 | 1874 | 1710 | −3978 | −3303 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10161 | −11203 | −894 | −1115 | −701 | −1378 | * | * | | | | | | | | | | | | |
| 79 | −2589 | −2415 | −4932 | −4296 | 1892 | −554 | −3007 | 1909 | −1913 | 1623 | −392 | −341 | −4186 | −3515 | −3692 | −3220 | −302 | 699 | 1265 | −2531 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −2 | −10161 | −11203 | −894 | −1115 | −701 | −1378 | * | * | | | | | | | | | | | | |
| 80 | 292 | −3814 | −232 | −226 | −4135 | −1986 | 1315 | −1174 | 699 | −1392 | −1041 | 1575 | −227 | −455 | −61 | 207 | 1894 | −3436 | −3997 | −3315 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 81 | −1210 | −2494 | −5023 | −4390 | 1142 | −575 | −3109 | 174 | −3989 | 311 | 1788 | −3879 | −4277 | −1330 | −3790 | −3320 | −2615 | 2957 | −2967 | −2627 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 82 | −2343 | 1382 | 223 | 1718 | −1542 | −3320 | −507 | −1852 | 1159 | −2316 | −866 | −961 | −3413 | 1222 | 331 | −2228 | 1654 | 44 | −3983 | −3306 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 83 | 430 | −3877 | −2280 | −1724 | −4207 | −3391 | 1216 | −3948 | 731 | −3888 | −2969 | −1119 | 2990 | 1606 | 182 | −70 | −2359 | −1901 | −4048 | −3382 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 84 | −1392 | −5570 | −1007 | −807 | −5845 | 3314 | −3258 | −5665 | −170 | −5552 | −4761 | 1170 | −4557 | −2877 | −190 | −3636 | −3893 | −5184 | −5709 | −4884 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 85 | −2470 | −3911 | −706 | 669 | −4238 | −3429 | −2070 | −3974 | 3353 | −1437 | −3004 | −2067 | −3522 | −277 | −1289 | −2352 | −440 | −110 | −4079 | −3420 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 86 | −3186 | −4048 | −3540 | −2863 | −4477 | −131 | −2753 | −484 | 881 | −4133 | −3357 | −3006 | −4262 | −2374 | 2376 | −1211 | 2868 | −2162 | −4365 | −3935 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10161 | −11203 | −894 | −1115 | −701 | −1378 | * | * | | | | | | | | | | | | |
| 87 | −2903 | −2796 | −1823 | −367 | −2405 | −4343 | 993 | −327 | −3853 | −1603 | −1996 | −3767 | −4409 | −3530 | −3810 | −3442 | −2844 | 439 | −2951 | 4375 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 88 | −2588 | −3235 | −2959 | −2376 | −1174 | −3725 | −2391 | −2920 | 532 | 799 | 2 | −527 | −3798 | −914 | 3346 | −1756 | −1506 | −2730 | −3563 | −300 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 89 | −4002 | −3720 | −6341 | −5719 | 2446 | −5651 | −4424 | 1263 | −5352 | 2099 | 977 | −5298 | −5483 | −4754 | −5079 | −4775 | −3918 | 551 | 1957 | −299 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 90 | −1758 | −5263 | −6151 | −4677 | −3746 | −5579 | 1082 | −5258 | −2199 | −531 | −4485 | −4367 | −5528 | −3185 | 3953 | −4968 | −4723 | −5154 | −4031 | −190 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 91 | −5262 | −4694 | −7764 | −7261 | 1552 | −7562 | −6545 | 2578 | −7109 | 1756 | −356 | −7259 | −6795 | −6118 | −6751 | −6927 | −5160 | 1578 | −5190 | −5318 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 92 | −97 | 1070 | −4938 | −4302 | −425 | −2068 | −749 | 2814 | −3898 | −702 | −1624 | −3788 | −4192 | −3522 | −3699 | 766 | −2535 | 1640 | −2881 | −2539 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2839 | −10161 | −219 | −894 | −1115 | −701 | −1378 | * | * | | | | | | | | | | | | |
| 93 | −1873 | −2460 | −1604 | −1767 | −2864 | 2423 | 4327 | −3662 | −1985 | −3637 | −3006 | −1843 | −2869 | −1979 | −2202 | −1952 | −2121 | −3092 | −3013 | −2426 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −13 | −7336 | −8378 | −894 | −1115 | −28 | −5677 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | −1619 | 385 | −5411 | −5204 | −5129 | −1378 | −4739 | −4788 | −5020 | −5076 | 1107 | 3570 | −4706 | −4732 | −5057 | 2052 | −3433 | −4189 | −5468 | −1313 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 95 | 1184 | −2425 | −4868 | −4237 | −2381 | 212 | −2998 | 847 | −3847 | 318 | −499 | −3754 | −4180 | 581 | −3671 | −829 | 1537 | 1650 | −2883 | −2539 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 96 | 1668 | −3756 | −5768 | −5688 | −6085 | 2006 | −5244 | −1711 | −5502 | −6085 | −5170 | −752 | −1668 | −5166 | −5489 | 1874 | 1355 | −4784 | −6300 | −6114 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10161 | −11203 | −894 | −1115 | −701 | −1378 | * | * | | | | | | | | | | | | |
| 97 | 955 | 3255 | −4885 | −1292 | −1167 | −386 | −2998 | 327 | −3858 | 958 | 966 | 798 | −4179 | −3489 | −3674 | −816 | 168 | 382 | −2877 | −2533 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10161 | −11203 | −894 | −1115 | −701 | −1378 | * | * | | | | | | | | | | | | |
| 98 | −1126 | −3767 | 1820 | −459 | 564 | −3328 | −254 | −1741 | −585 | 422 | 454 | 1659 | −915 | 665 | 822 | −686 | −2285 | −1231 | 592 | −3294 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10161 | −11203 | −894 | −1115 | −701 | −1378 | * | * | | | | | | | | | | | | |
| 99 | −242 | −3801 | 1453 | 411 | −4115 | −530 | −335 | −1698 | −1561 | −1951 | −353 | 661 | 1449 | −110 | −2067 | 714 | 1198 | −458 | −3988 | −3309 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10161 | −11203 | −894 | −1115 | −701 | −1378 | * | * | | | | | | | | | | | | |
| 100 | 177 | −3696 | −2254 | 991 | −382 | −1465 | 1138 | −3679 | −1616 | −1817 | −2799 | 1580 | −1605 | −560 | −2113 | 1844 | 334 | −390 | −3911 | 460 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −10161 | −11203 | −894 | −1115 | −701 | −1378 | * | * | | | | | | | | | | | | |
| 101 | −2589 | −2416 | −4927 | −4291 | 2303 | −4135 | 2164 | −344 | −3888 | 1711 | −65 | −3779 | −4185 | 220 | 232 | −3220 | −1148 | −374 | 751 | 1281 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 102 | −1055 | −3713 | 96 | −1695 | 1719 | −3343 | −2007 | −3708 | −1607 | −3709 | −2814 | 2208 | 253 | 1163 | −698 | 314 | 1049 | −99 | −3924 | 486 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 103 | −1243 | −2904 | −5466 | −4837 | 3755 | −4702 | 1425 | 1082 | −4447 | 214 | 230 | −4349 | −4697 | −4022 | −4234 | −3799 | −3049 | −59 | −3342 | −3037 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 104 | 575 | −3069 | −2812 | −1307 | 249 | −499 | −2315 | −1307 | 285 | −480 | −119 | −2458 | −3680 | −244 | 1622 | 1647 | −57 | −1145 | 1898 | −2938 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 105 | −5036 | −4486 | −7597 | −7147 | 1021 | −7409 | −6623 | 3507 | −7027 | 283 | −235 | −7092 | −6773 | −6229 | −6788 | −6777 | −4964 | 901 | −5372 | −5408 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 106 | 1225 | −3829 | 1962 | 1462 | −4147 | 239 | 747 | −3897 | −1574 | −2327 | −2919 | −1963 | −549 | 1850 | −2082 | −1536 | −2298 | −1025 | −4013 | −3330 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 107 | −4650 | −6623 | 1027 | −2603 | −6910 | 3066 | −3895 | −6921 | −4361 | −6750 | −6207 | 2387 | −5002 | 47 | −5405 | −2412 | −4779 | −6315 | −6956 | −5800 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 108 | −5611 | −5798 | −5027 | −5012 | −3537 | −5801 | 5339 | −5998 | −3838 | −1363 | −5249 | −4902 | −6091 | −573 | −3843 | −5530 | −5606 | −6031 | −4109 | −3075 | 126 |
| — | −149 | −500 | 233 | 43 | −381 | 399 | 106 | −626 | 210 | −466 | −720 | 275 | 394 | 48 | 96 | 359 | 117 | −369 | −294 | −249 | |
| C | −216 | −5403 | −3117 | −203 | −2928 | −701 | −1378 | * | * | | | | | | | | | | | | |
| 109 | −2194 | −3667 | −581 | 783 | −3988 | −3168 | −1826 | −1935 | 1452 | −3683 | −768 | 1842 | −790 | 698 | 501 | 1009 | 1254 | −3289 | −3850 | −3168 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −9985 | −11027 | −894 | −1115 | −2508 | −279 | * | * | | | | | | | | | | | | |
| 110 | −5717 | −5049 | −8079 | −7472 | 1395 | −7951 | −6461 | 45 | −7290 | 2012 | 4229 | −7693 | −6778 | −5887 | −6681 | −7384 | −5527 | −3386 | −4833 | −5099 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9985 | −11027 | −894 | −1115 | −2508 | −279 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111 | −2237 | −3463 | −2193 | −1058 | −3694 | −3251 | −1916 | −1824 | 914 | −1145 | −2578 | −1099 | −3340 | 112 | −848 | −207 | 3202 | −232 | −3701 | −3083 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9985 | −11027 | −894 | −1115 | −2508 | −279 | * | * | | | | | | | | | | | | |
| 112 | −4505 | −3973 | −7160 | −6805 | −1044 | −7019 | −6754 | 2180 | −6756 | 862 | −2664 | −6680 | −6600 | −6390 | −6773 | −6405 | −4476 | 3033 | −5753 | −5523 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9985 | −11027 | −894 | −1115 | −2508 | −279 | * | * | | | | | | | | | | | | |
| 113 | −2178 | −3733 | −6932 | −6614 | −4474 | −6753 | −6782 | 2737 | −6579 | −3253 | −261 | −6418 | −6510 | −6552 | −6752 | −6124 | −1040 | 3034 | −6199 | −5657 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9985 | −11027 | −894 | −1115 | −2508 | −279 | * | * | | | | | | | | | | | | |
| 114 | 383 | −5402 | −2092 | 3552 | −5842 | −889 | 290 | −5693 | −3279 | −5599 | −4826 | −2670 | −4472 | −435 | −3960 | −1673 | −3847 | −5163 | −5780 | −4908 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9985 | −11027 | −894 | −1115 | −2508 | −279 | * | * | | | | | | | | | | | | |
| 115 | 2087 | −2519 | −5081 | −4468 | −2543 | −4316 | −3241 | −159 | −4085 | −1543 | 1121 | −3970 | −4360 | −3723 | −3904 | −488 | 390 | 2526 | −3101 | −2753 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5149 | −9985 | −43 | −894 | −1115 | −1039 | −962 | * | * | | | | | | | | | | | | |
| 116 | −1423 | −1686 | −2052 | −2290 | −3178 | 3569 | −2293 | −3362 | −2572 | −3429 | −2897 | −2066 | −2362 | −2411 | −2558 | −1639 | −1785 | −2703 | −2768 | −3024 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −25 | −6448 | −7490 | −894 | −1115 | −4521 | −64 | * | * | | | | | | | | | | | | |
| 117 | −1278 | −2546 | 3281 | 127 | −3255 | 1131 | −899 | −3188 | −1093 | −3157 | −2472 | −220 | −1937 | −596 | −1807 | −1089 | −1412 | −2640 | −3189 | −2473 | 136 |
| — | −149 | −500 | 234 | 43 | −381 | 398 | 105 | −627 | 210 | −465 | −721 | 275 | 393 | 45 | 96 | 359 | 117 | −370 | −284 | −245 | |
| E | −1855 | −476 | −7733 | −337 | −2262 | −5079 | −43 | * | * | | | | | | | | | | | | |
| 118 | −1313 | −1184 | −3200 | −3080 | −1531 | −2616 | −2626 | 763 | −2836 | −685 | −588 | −2690 | −2948 | −2749 | −2831 | −2115 | −1448 | 3353 | −2550 | −2123 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −21 | −6691 | −7733 | −894 | −1115 | −5079 | −43 | * | * | | | | | | | | | | | | |
| 119 | −3270 | −2624 | −3539 | −3684 | −917 | −2942 | −1919 | −3105 | −3277 | −2706 | −2658 | −3264 | −3308 | −3199 | −3032 | −3496 | −3381 | −3147 | 6087 | −529 | 140 |
| — | −148 | −500 | 233 | 46 | −381 | 398 | 105 | −626 | 210 | −466 | −721 | 275 | 394 | 45 | 96 | 359 | 118 | −370 | −295 | −250 | |
| E | −1855 | −476 | −7733 | −85 | −4126 | −67 | −4470 | * | * | | | | | | | | | | | | |
| 120 | −4653 | −6702 | 3689 | 1449 | −6894 | −1455 | −3856 | −6911 | −4333 | −6733 | −6202 | −2960 | −4973 | −3556 | −5397 | −4255 | 666 | −6318 | −6939 | −5770 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10124 | −11166 | −894 | −1115 | −1336 | −727 | * | * | | | | | | | | | | | | |
| 121 | 1019 | −3367 | −5886 | −5693 | 1039 | 3266 | −4565 | −3889 | −5335 | −2195 | −434 | −4533 | −4688 | −4909 | −5105 | −986 | −3324 | −3558 | −4706 | −4354 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10124 | −11166 | −894 | −1115 | −1336 | −727 | * | * | | | | | | | | | | | | |
| 122 | −1049 | −761 | −2314 | 209 | −1208 | −1373 | 846 | −532 | 322 | −1619 | −2640 | 837 | −3451 | 610 | −1367 | 307 | 968 | 1901 | −3773 | −420 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10124 | −11166 | −894 | −1115 | −411 | −2014 | * | * | | | | | | | | | | | | |
| 123 | −1098 | −2604 | −3874 | −643 | 1144 | −3945 | 2283 | −2136 | −3069 | −1784 | −1797 | 1611 | 1212 | −2866 | −3212 | −2974 | −1239 | −770 | 695 | 3251 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 124 | −835 | −2433 | −4773 | −4147 | −2389 | −2123 | 1852 | 318 | −3776 | −795 | −1635 | −1573 | −4164 | −3428 | −953 | −1685 | 2287 | 2333 | 801 | −2543 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 125 | −1004 | −3810 | 327 | 1243 | −4128 | −3316 | 411 | −459 | 1423 | −827 | −2899 | 1156 | −3409 | 1713 | −2063 | −1499 | 343 | 569 | −3994 | −3313 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2443 | −10161 | −295 | −894 | −1115 | −701 | −1378 | * | * | | | | | | | | | | | | |
| 126 | 1314 | −2160 | −577 | −86 | −2483 | −1724 | 2041 | −2208 | 1107 | −2184 | −1290 | 1280 | 1313 | 33 | −439 | −679 | −729 | −1793 | −2374 | −1723 | 148 |
| — | −149 | −500 | 232 | 43 | −381 | 398 | 105 | −627 | 212 | −466 | −721 | 275 | 398 | 45 | 95 | 359 | 117 | −370 | −295 | −246 | |
| . | −1957 | −730 | −2840 | −51 | −4841 | −30 | −5605 | * | * | | | | | | | | | | | | |
| 127 | −1302 | −5099 | −1106 | −662 | −5372 | −3934 | −2942 | −5179 | −597 | −5095 | −4248 | −499 | 3621 | 2130 | −3386 | −1698 | −3455 | −4704 | −5269 | −4469 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10124 | −11166 | −894 | −1115 | −1336 | −727 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128 | 6 | −2537 | −3948 | −1281 | 2304 | −3932 | 2 | −592 | −3124 | 670 | −1731 | 1163 | −3993 | 238 | −854 | −1711 | 133 | 396 | −2973 | 1782 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10124 | −11166 | −894 | −1115 | −411 | −2014 | * | * | | | | | | | | | | | | |
| 129 | −1626 | −3805 | 445 | 798 | −1292 | −1918 | −1977 | −668 | −178 | −2659 | 213 | 856 | −1480 | 376 | 509 | 435 | 1802 | 363 | −3991 | −1303 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 130 | −932 | −2418 | −1362 | −4282 | −198 | −4135 | −3005 | −601 | −3881 | −794 | 194 | −3775 | −4185 | −89 | −3687 | −3219 | 1977 | 2506 | −2875 | 1834 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 131 | −1145 | −4182 | 3149 | 971 | −4493 | −3526 | −2274 | −4255 | −92 | −4194 | −3283 | 698 | −3680 | −169 | −2441 | 91 | 553 | −3800 | −4363 | −3656 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10161 | −11203 | −894 | −1115 | −701 | −1378 | * | * | | | | | | | | | | | | |
| 132 | −593 | −3799 | 582 | −136 | −4113 | −2190 | −1978 | −1461 | −638 | −2209 | −494 | 418 | −3412 | −754 | 135 | 2204 | 1237 | −107 | −3986 | −876 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −10161 | −11203 | −894 | −1115 | −701 | −1378 | * | * | | | | | | | | | | | | |
| 133 | −5292 | −4775 | −7677 | −7080 | 214 | −7299 | −6020 | 2681 | −6830 | 2143 | −429 | −6993 | −6586 | −5781 | −6392 | −6569 | −5158 | 351 | 2302 | −4944 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 134 | −2361 | −3620 | 2006 | −315 | 1694 | −3371 | −34 | −3554 | −1659 | −222 | 926 | 147 | −2131 | 1982 | 191 | −2286 | −1523 | −352 | −3855 | 492 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 135 | −4625 | −4091 | −7303 | −6971 | −4267 | −7185 | −7093 | 3366 | −6945 | 1134 | −2969 | −6846 | −6795 | −6682 | −7026 | −6587 | −4604 | 1524 | −6123 | −5826 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 136 | 776 | −2773 | −3358 | −2790 | 1912 | 852 | 2622 | −2351 | −2625 | −2652 | −1959 | −2866 | −969 | −2486 | −337 | 203 | 285 | −1134 | −3183 | 2060 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10161 | −11203 | −894 | −1115 | −701 | −1378 | * | * | | | | | | | | | | | | |
| 137 | 1314 | −2444 | −4873 | −4247 | −2408 | −176 | −3019 | −286 | −3860 | −1646 | 983 | −3764 | 2004 | −3498 | −3688 | 651 | −557 | 1862 | −2910 | −2566 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 138 | 1500 | −3853 | −6388 | −6736 | −6494 | 3429 | −5851 | −1140 | −6501 | −6548 | −5635 | −4943 | −4946 | −5951 | −6135 | −3510 | −3730 | −4982 | −6715 | −6691 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 139 | −2046 | −4957 | −2649 | 1314 | −6176 | −4188 | −3771 | −6013 | −3767 | −5971 | −5181 | −3158 | −4734 | 4085 | −4339 | −410 | −125 | −5303 | −6135 | −5381 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 140 | −110 | 1087 | −4668 | −4136 | −537 | −4033 | −3385 | −2677 | −3825 | −1417 | −2344 | −3776 | −4318 | −3592 | 2914 | 1008 | 2074 | −2528 | −3582 | −3229 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 141 | −1726 | −2424 | −4942 | −4306 | 1317 | −449 | −3017 | −951 | −3902 | −794 | 1802 | −3791 | −4195 | −3524 | −3702 | −3231 | 831 | −625 | −2881 | 3900 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 142 | −191 | −5347 | 2048 | −997 | −5781 | −1180 | −3280 | −5617 | −3244 | −5533 | −4722 | 1274 | −4509 | −2901 | −3916 | 2641 | 163 | −5094 | −5715 | −4870 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 143 | 1102 | −3655 | −6649 | −6209 | 1956 | −6223 | −5602 | 943 | −6013 | −2145 | −2990 | −5878 | −6100 | −5802 | −5996 | −5457 | −1993 | 2994 | −5279 | −4857 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 144 | −2868 | −2679 | −5216 | −4582 | −1090 | −4433 | −3302 | 1331 | −4183 | 2421 | 775 | −4081 | −4456 | −640 | −3976 | −3523 | −673 | 1338 | −3121 | −219 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145 | −3348 | −3112 | −5720 | −5104 | −117 | −4987 | −3877 | 1319 | −4728 | 1750 | 336 | −4636 | −4954 | −4293 | −4519 | −4094 | −971 | 2435 | −3613 | 956 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 146 | −2343 | −3807 | 192 | 455 | −1344 | −3318 | 947 | −3873 | 1372 | −1732 | −2897 | 957 | −3411 | −1518 | −1271 | −1701 | 2798 | −1243 | −3993 | −3312 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 147 | 2920 | −2592 | −5031 | −4443 | 657 | −2068 | −3226 | −2172 | −4058 | −656 | 1189 | −3893 | −556 | −3690 | −3882 | −3253 | 1248 | −2078 | −3135 | −2795 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2116 | −10161 | −380 | −894 | −1115 | −701 | −1378 | * | * | | | | | | | | | | | | |
| 148 | −1297 | −2825 | 2043 | −308 | −3129 | −2020 | 971 | −2898 | 2217 | −2830 | −1941 | 1749 | −2232 | −414 | −1052 | −121 | −1255 | −2442 | −2998 | −2274 | 171 |
| — | −149 | −500 | 233 | 45 | −381 | 398 | 105 | −626 | 210 | −466 | −721 | 275 | 394 | 45 | 96 | 359 | 119 | −369 | −295 | −249 | |
| . | −158 | −3296 | −9096 | −982 | −1018 | −32 | −5524 | * | * | | | | | | | | | | | | |
| 149 | −1123 | −3814 | 1792 | −678 | −4135 | −3315 | −1974 | −3885 | 1252 | −2347 | 607 | 2492 | −350 | 1611 | −2062 | −748 | −602 | −2352 | −3997 | −3315 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −152 | −10161 | −3331 | −894 | −1115 | −701 | −1378 | * | * | | | | | | | | | | | | |
| 150 | 265 | −3689 | 75 | −552 | −4010 | −608 | −551 | −2107 | −1 | −3705 | −2778 | 886 | −1722 | 3536 | −1170 | −1180 | −2155 | −3311 | −3872 | −508 | 175 |
| — | −149 | −500 | 234 | 42 | −381 | 398 | 105 | −627 | 210 | −464 | −716 | 277 | 393 | 45 | 95 | 360 | 117 | −370 | −295 | −245 | |
| S | −711 | −2344 | −2381 | −33 | −5472 | −188 | −3034 | * | * | | | | | | | | | | | | |
| 151 | 1248 | −3588 | 1142 | −87 | −3908 | −1823 | −1748 | −3659 | −729 | −3604 | −2677 | −214 | 2025 | −1289 | −359 | 123 | 1472 | −1497 | −3772 | −3089 | 177 |
| — | −150 | −501 | 232 | 44 | −382 | 399 | 105 | −627 | 209 | −467 | −721 | 274 | 399 | 47 | 97 | 359 | 119 | −370 | −295 | −250 | |
| S | −270 | −2555 | −10930 | −705 | −1372 | −447 | −1908 | * | * | | | | | | | | | | | | |
| 152 | 119 | −3632 | 945 | −1662 | −3895 | −996 | −1967 | 197 | −990 | −1643 | −2737 | −263 | 1709 | −471 | −209 | 99 | 326 | 1589 | −3851 | −3205 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10102 | −11144 | −894 | −1115 | −330 | −2291 | * | * | | | | | | | | | | | | |
| 153 | −286 | −3817 | 1474 | −506 | −4138 | 1930 | −603 | −3889 | 1071 | −3833 | −2906 | −525 | −3410 | 958 | 1111 | −101 | −1170 | −3439 | −4000 | −3317 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 154 | −782 | −3811 | 1290 | −598 | −4130 | −3316 | −1975 | −1119 | −217 | −3826 | −2900 | 3184 | −3409 | −177 | −20 | −629 | 202 | −458 | −3995 | −878 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 155 | −6831 | −5737 | −7191 | −7554 | 1905 | −7076 | −757 | −5713 | −7109 | −5014 | −5113 | −5680 | −6929 | −5822 | −6467 | −6325 | −6678 | −5870 | 1123 | 4634 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 156 | 830 | −2420 | −1878 | −4255 | 681 | −4129 | −2998 | −1912 | −3860 | −543 | 772 | −3761 | −1073 | −3491 | −3675 | −988 | −510 | −1006 | 4671 | 2544 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 157 | −2049 | −3183 | −5807 | −5196 | 263 | −5086 | −3982 | 2982 | −4826 | 264 | 2826 | −4735 | −5042 | −4387 | −4618 | −4198 | −3366 | 766 | −3702 | 955 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 158 | 463 | −2542 | −4104 | −3512 | 745 | −3992 | −66 | −2061 | −3258 | −993 | 1089 | −4 | −4052 | −689 | 1918 | 598 | 110 | 1674 | 701 | −2615 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 159 | 2648 | 1499 | −1327 | −3913 | −560 | −4073 | −2923 | −17 | −3590 | −2319 | −13 | 207 | −4127 | −277 | −3528 | −1223 | −748 | 1200 | −2918 | −2565 | 188 |
| — | −149 | −500 | 232 | 43 | −381 | 400 | 105 | −625 | 211 | −465 | −721 | 275 | 393 | 45 | 95 | 360 | 117 | −370 | −295 | −247 | |
| E | −2515 | −3001 | −514 | −46 | −4993 | −701 | −1378 | * | * | | | | | | | | | | | | |
| 160 | −293 | −1268 | −41 | −1779 | 387 | −2534 | −1328 | −86 | −1574 | −517 | 2644 | 2236 | −2598 | 49 | −1757 | −382 | −1099 | 227 | 2018 | −1308 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −6 | −8426 | −9468 | −894 | −1115 | −3642 | −120 | * | * | | | | | | | | | | | | |
| 161 | −2818 | −4486 | 2377 | −1101 | −4984 | −2814 | −2243 | −4906 | −2487 | −4796 | −4121 | −1479 | 3341 | 738 | −3308 | −541 | −2929 | −4326 | −4986 | −4003 | 191 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −6 | −8570 | −9612 | −894 | −1115 | −4659 | −58 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 162 | −1151 | −2487 | 102 | 870 | −894 | −982 | −812 | −2467 | −417 | −2480 | 1556 | 2306 | −2239 | −372 | −914 | 751 | 783 | −191 | −2704 | −2056 | 192 |
| — | −149 | −500 | 232 | 42 | −381 | 399 | 105 | −626 | 210 | −467 | −721 | 276 | 393 | 45 | 96 | 360 | 123 | −370 | −295 | −250 | |
| C | −912 | −1097 | −9612 | −37 | −5287 | −4659 | −58 | * | * | | | | | | | | | | | | |
| 163 | 642 | −1167 | −3334 | −2717 | 1252 | 290 | −1658 | 21 | −703 | 234 | 2848 | −549 | −2856 | −2055 | −2283 | −691 | 311 | 701 | −1619 | −1270 | 194 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −6 | −8570 | −9612 | −894 | −1115 | −4659 | −58 | * | * | | | | | | | | | | | | |
| 164 | −239 | 1631 | −3598 | −2965 | 583 | 2268 | −1712 | 30 | −2571 | 715 | 1460 | −644 | −2893 | −2203 | −2388 | −1926 | −1241 | 130 | −1591 | −1248 | 195 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2842 | −8570 | −221 | −894 | −1115 | −1635 | −561 | * | * | | | | | | | | | | | | |
| 165 | −216 | −1994 | −971 | −422 | 559 | 304 | 1245 | −1865 | −320 | −1978 | −1150 | −693 | −2060 | −268 | 1478 | 1209 | 1312 | −1563 | −2294 | −1709 | 196 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −8 | −8157 | −9200 | −894 | −1115 | −2128 | −375 | * | * | | | | | | | | | | | | |
| 166 | 185 | −2461 | −4597 | −4663 | 2000 | −2801 | −3982 | −4215 | −4501 | −4484 | −3664 | −3412 | 2646 | −4086 | −4357 | 2405 | −2318 | −3352 | −4643 | −4282 | 197 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | −8851 | −9893 | −894 | −1115 | −4506 | −65 | * | * | | | | | | | | | | | | |
| 167 | −47 | −1805 | −3296 | −2786 | 1548 | 601 | −2166 | −1612 | −2559 | −1937 | −1263 | −2522 | −3154 | −2326 | −2656 | 1111 | 1334 | −1456 | −2427 | 3021 | 198 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | −8851 | −9893 | −894 | −1115 | −1279 | −766 | * | * | | | | | | | | | | | | |
| 168 | −499 | −3290 | −782 | −307 | 104 | 311 | 575 | −3361 | −355 | −3306 | 1054 | 731 | −1188 | 645 | 1967 | 365 | 1081 | −2912 | −3473 | −2791 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −3 | −9517 | −10559 | −894 | −1115 | −1106 | −901 | * | * | | | | | | | | | | | | |
| 169 | −1197 | −2853 | 293 | −1913 | 1906 | 800 | 1684 | −1342 | −1796 | −2764 | −516 | 658 | −92 | −1717 | −2211 | 895 | 1103 | −624 | −3198 | −274 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −9840 | −10882 | −894 | −1115 | −529 | −1704 | * | * | | | | | | | | | | | | |
| 170 | 408 | 216 | 849 | −612 | −4024 | 1467 | 351 | −961 | −773 | −804 | −2808 | 950 | −3343 | −109 | −695 | −851 | 686 | 663 | −3906 | −3231 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −445 | −10076 | −1918 | −894 | −1115 | −1875 | −459 | * | * | | | | | | | | | | | | |
| 171 | 57 | −3225 | −460 | −1291 | −937 | −2924 | −1591 | −692 | 940 | 292 | −2332 | 957 | −997 | −251 | 1426 | −250 | 1040 | 281 | −3450 | −2810 | 202 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −3 | −9633 | −10675 | −894 | −1115 | −947 | −1055 | * | * | | | | | | | | | | | | |
| 172 | −382 | 1460 | −2092 | −44 | −3679 | 114 | −1835 | 1322 | 202 | −498 | −792 | 1372 | 506 | 825 | −536 | −60 | −1215 | −286 | −3666 | −3033 | 203 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9923 | −10965 | −894 | −1115 | −2808 | −222 | * | * | | | | | | | | | | | | |
| 173 | 792 | −3609 | −27 | 805 | −3927 | 591 | −1777 | −293 | −682 | −3624 | −2699 | −249 | 1377 | −1318 | 1062 | −290 | −646 | 721 | −3794 | −3113 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9923 | −10965 | −894 | −1115 | −2808 | −222 | * | * | | | | | | | | | | | | |
| 174 | 1266 | −3601 | 340 | 304 | −3915 | −3120 | 1582 | −1064 | 739 | 218 | −215 | −46 | 659 | −1322 | −511 | 18 | −80 | −1008 | −3788 | −3110 | 205 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −285 | −9923 | −2487 | −894 | −1115 | −135 | −3485 | * | * | | | | | | | | | | | | |
| 175 | −809 | −2859 | 113 | −989 | 2835 | −14 | −2121 | −1541 | −1945 | −414 | −439 | −664 | 940 | −148 | −1097 | −268 | −1384 | 355 | 998 | −2732 | 206 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −2 | −9925 | −10968 | −894 | −1115 | −2799 | −224 | * | * | | | | | | | | | | | | |
| 176 | 290 | −3616 | 1775 | 666 | −805 | −1127 | 996 | −1224 | 658 | −415 | −2705 | 742 | −1227 | 168 | 194 | −1330 | 136 | −1955 | −3800 | −511 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −9925 | −10968 | −894 | −1115 | −2799 | −224 | * | * | | | | | | | | | | | | |
| 177 | −856 | −3585 | −487 | −1460 | −3892 | 618 | −1787 | −1507 | −704 | −733 | −2678 | 2842 | −289 | 658 | −473 | −1509 | 1288 | −1162 | −3777 | −3104 | 208 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −9925 | −10968 | −894 | −1115 | −2799 | −224 | * | * | | | | | | | | | | | | |
| 178 | −440 | −63 | −3181 | −2613 | −2559 | 2105 | −179 | −2123 | −2445 | −889 | −1736 | −701 | 1494 | −1021 | −2717 | −528 | 1302 | 512 | −2961 | −177 | 209 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −9925 | −10968 | −894 | −1115 | −136 | −3476 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 179 | −128 | −2600 | −3858 | −3275 | −2581 | −3935 | −400 | 577 | −3054 | 224 | 738 | 1559 | −21 | 150 | −504 | −618 | 1929 | −222 | −3032 | 960 | 210 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10161 | −11203 | −894 | −1115 | −701 | −1378 | * | * | | | | | | | | | | | | |
| 180 | 1331 | −3746 | −2226 | −614 | −4036 | 419 | −1996 | −244 | −672 | −3749 | −2844 | 1728 | −170 | 303 | −2092 | −1441 | 1864 | −3 | −3948 | −3285 | 211 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 181 | 1182 | −2422 | −4868 | −4237 | −925 | −2263 | −2995 | −102 | −3846 | 187 | −1624 | −3752 | −4177 | −3480 | 376 | 1321 | 2044 | 445 | −2878 | −319 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 182 | 2583 | −2717 | −3482 | −2911 | −521 | 1468 | 1137 | −1109 | −2733 | −1837 | −1904 | −1190 | −3902 | −1248 | −2981 | −611 | 50 | −2159 | −3133 | −243 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 183 | −1721 | −2415 | −4931 | −4295 | 697 | −4135 | −3006 | 2763 | −3891 | −41 | −1617 | −1233 | −4185 | −1122 | −3691 | −2042 | 579 | 1505 | 1592 | 84 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 184 | −2827 | −2644 | −5159 | −4524 | 1035 | −4385 | −3251 | 1198 | 30 | 2613 | 651 | −4027 | −4411 | −637 | −3921 | −2086 | −2765 | −1299 | −3079 | −2759 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 185 | −797 | −3864 | −2262 | −778 | −4189 | −3378 | 2716 | −3931 | −980 | −3874 | −2955 | 894 | −3470 | 900 | 2592 | −253 | −2346 | 1271 | −4038 | −3370 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 186 | −4233 | −5697 | −578 | −90 | −5621 | −4306 | −3592 | −5615 | −3796 | −5655 | −4991 | −2933 | −4804 | −496 | −4530 | −3978 | −589 | −912 | −5820 | 4590 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −10161 | −11203 | −894 | −1115 | −701 | −1378 | * | * | | | | | | | | | | | | |
| 187 | −490 | −3814 | 660 | 399 | −4134 | 668 | −219 | −390 | 521 | −1352 | −2903 | 817 | −3408 | 1118 | −318 | 1096 | −543 | −568 | −3997 | −245 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10161 | −11203 | −894 | −1115 | −701 | −1378 | * | * | | | | | | | | | | | | |
| 188 | −1123 | 1381 | −2189 | 1074 | −4135 | 2271 | 709 | −3886 | 320 | −3830 | −2904 | 1339 | 465 | −747 | −1303 | −451 | −995 | −3436 | −3998 | −3315 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −2 | −10161 | −11203 | −894 | −1115 | −701 | −1378 | * | * | | | | | | | | | | | | |
| 189 | 2118 | −3734 | −944 | −1708 | −4028 | 170 | −694 | −3751 | −1623 | −2494 | −2847 | 1159 | 368 | −1579 | −2124 | 1377 | −365 | −3345 | 2139 | −3297 | 220 |
| — | * | * | * | * | * | * | * | * | * | * | * | * | * | * | * | * | * | * | * | * | |
| T | * | * | * | * | * | * | * | * | 0 | | | | | | | | | | | | |
| // | | | | | | | | | | | | | | | | | | | | | |

```
HMMER2.0  [2.3.2]
NAME      Cu-oxidase_2
ACC       PF07731.6
DESC      Multicopper oxidase
LENG      154
ALPH      Amino
RF        no
CS        yes
MAP       yes
COM       hmmbuild -F HMM_ls.ann SEED.ann
COM       hmmcalibrate --seed 0 HMM_ls.ann
NSEQ      127
DATE      Wed Apr 23 01:56:48 2008
CKSUM     810
GA        -5.8000 -5.8000;
TC        -5.2000 -5.2000;
NC        -6.0000 -6.0000;
XT        -8455  -4  -1000  -1000  -8455  -4  -8455  -4
NULT      -4  -8455
NULE      595  -1558  85  338  -294  453  -1158  197  249  902  -1085  -142  -21  -313  45  531  201  384  -1998  -644
EVD       -72.886528  0.222053
HMM       A      C      D      E      F      G      H      I      K      L      M      N      P      Q      R      S      T      V      W      Y
          m->m   m->i   m->d   i->m   i->i   d->m   d->d   b->m   m->e
          -18    *      -6340
1         -2561  -5000  1601   540    818    -1256  431    -5071  -1583  -1368  -4089  380    845    -32    699    -448   -46    -4622  184    2209   1
—         -149   -500   233    43     -381   399    106    -626   210    -466   -720   275    394    45     96     359    117    -369   -294   -249
B         -1     -11488 -12530 -894   -1115  -701   -1378  -18    *
2         -905   -4564  -1340  -1173  1454   -2493  -805   882    -604   -549   341    -1068  753    -1635  786    -2062  1574   981    -4858  -1575  2
—         -149   -500   233    43     -381   399    106    -626   210    -466   -720   275    394    45     96     359    117    -369   -294   -249
—         -1     -11488 -12530 -894   -1115  -701   -1378  *      *
3         201    -4999  1078   -381   -2135  -751   -738   -5070  -2740  -1641  -4088  1169   2526   -271   -1129  879    54     -2703  -5182  -4500  3
—         -149   -500   233    43     -381   399    106    -626   210    -466   -720   275    394    45     96     359    117    -369   -294   -249
S         -1     -11488 -12530 -894   -1115  -701   -1378  *      *
4         -525   -506   -480   -1047  -419   -2494  -1073  -1521  -1976  779    1226   -1377  2601   -925   -896   -1817  -684   -724   2750   -854   4
—         -149   -500   233    43     -381   399    106    -626   210    -466   -720   275    394    45     96     359    117    -369   -294   -249
—         -1     -11488 -12530 -894   -1115  -701   -1378  *      *
5         -818   -4999  837    -1009  -2301  -1456  -3159  -2465  1834   -2966  -1092  880    1026   290    706    455    557    -2099  -5183  59     5
—         -149   -500   233    43     -381   399    106    -626   210    -466   -720   275    394    45     96     359    117    -369   -294   -249
S         -12    -11488 -7014  -894   -1115  -701   -1378  *      *
6         -317   -4974  -117   -742   -5288  109    -172   -781   -360   370    644    -122   1426   -802   273    -396   -124   1098   -5162  -1290  6
—         -149   -500   233    43     -381   399    106    -626   210    -466   -720   275    394    45     96     359    117    -369   -294   -249
C         -1     -11477 -12519 -894   -1115  -1199  -825   *      *
7         608    -4822  -738   253    -5070  -4542  -880   -1046  -2823  -1973  278    -1583  3228   -678   -1225  -514   -1694  27     -5051  -1280  7
—         -149   -500   233    43     -381   399    106    -626   210    -466   -720   275    394    45     96     359    117    -369   -294   -249
G         -1     -11477 -12519 -894   -1115  -1199  -825   *      *
8         -1361  -546   730    -1205  -1150  -926   -1619  668    -613   428    -3929  -1126  502    -375   -2136  -476   1687   1226   -5049  -4414  8
—         -149   -500   233    43     -381   399    106    -626   210    -466   -720   275    394    45     96     359    117    -369   -294   -249
H         -1     -11477 -12519 -894   -1115  -1199  -825   *      *
```

-continued

| | | | | | | | | | | | | | | | | | | | | | |
|---|---|---|---|---|---|---|---|---|---|---|---|---|---|---|---|---|---|---|---|---|---|
| 9 | −1717 | −4638 | −1863 | −261 | −1321 | −2682 | 260 | −423 | 72 | 1905 | 304 | −1132 | 385 | −113 | 134 | −1260 | −2197 | 625 | −771 | 378 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11477 | −12519 | −894 | −1115 | −1199 | −825 | * | * | | | | | | | | | | | | |
| 10 | −778 | −4631 | −958 | −822 | 2072 | −795 | 635 | −82 | −1370 | 1134 | 957 | −628 | 371 | 76 | −2020 | −1132 | −1106 | −933 | −4907 | 1251 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11477 | −12519 | −894 | −1115 | −1199 | −825 | * | * | | | | | | | | | | | | |
| 11 | −1544 | −4989 | 1169 | −326 | −5310 | −954 | 1078 | −2513 | 622 | −1207 | 187 | 1004 | −4584 | 2233 | −433 | −941 | 1082 | −1713 | −5173 | 688 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11477 | −12519 | −894 | −1115 | −1199 | −825 | * | * | | | | | | | | | | | | |
| 12 | 84 | −3630 | −6117 | −2659 | 335 | −1667 | −1020 | 1769 | −1924 | 954 | 1169 | −4981 | −2499 | −4712 | −279 | −1255 | 12 | 1075 | −4087 | 1619 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1508 | −11477 | −626 | −894 | −1115 | −1199 | −825 | * | * | | | | | | | | | | | | |
| 13 | −2188 | −3600 | −299 | −1510 | −625 | 135 | 1286 | 714 | 225 | −3606 | −9 | −473 | −512 | −1380 | 1147 | −265 | 2371 | −3209 | −3799 | −3131 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9971 | −11013 | −894 | −1115 | −5890 | −25 | * | * | | | | | | | | | | | | |
| 14 | −886 | −3495 | 782 | −1571 | −3747 | 2012 | −1869 | −3451 | −1481 | −632 | 1460 | 959 | −902 | 640 | −1975 | −240 | 1060 | −1022 | −3722 | −3083 | 14 |
| — | −149 | −492 | 235 | 39 | −372 | 396 | 114 | −630 | 207 | −466 | −724 | 281 | 390 | 46 | 94 | 360 | 122 | −371 | −298 | −245 | |
| E | −5135 | −42 | −11013 | −7 | −7683 | −5890 | −25 | * | * | | | | | | | | | | | | |
| 15 | −116 | −3604 | −705 | −590 | −3901 | −372 | 1033 | 743 | −1421 | −3610 | 3227 | 480 | 153 | 776 | −443 | −912 | −32 | 339 | −3801 | −3133 | 16 |
| — | −147 | −504 | 243 | 45 | −380 | 399 | 102 | −630 | 207 | −464 | −711 | 272 | 391 | 41 | 101 | 359 | 115 | −371 | −298 | −253 | |
| E | −5135 | −42 | −11013 | −7 | −7683 | −5890 | −25 | * | * | | | | | | | | | | | | |
| 16 | −309 | −3647 | 96 | −1485 | −3964 | −1113 | 159 | −3712 | 237 | −1345 | −2737 | −369 | 1885 | −226 | 1967 | −728 | −64 | 257 | 2030 | −3152 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9971 | −11013 | −894 | −1115 | −5890 | −25 | * | * | | | | | | | | | | | | |
| 17 | −1203 | −2640 | −576 | −827 | 788 | −235 | 80 | 82 | −2381 | −185 | 1690 | −2637 | −3675 | 1041 | 314 | −1209 | 1074 | −65 | −3041 | 2093 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9971 | −11013 | −894 | −1115 | −5890 | −25 | * | * | | | | | | | | | | | | |
| 18 | −908 | −3607 | 1092 | −454 | 1394 | −3169 | 218 | 393 | 834 | −3613 | 685 | 926 | 287 | 768 | 123 | −2077 | −933 | −908 | 2032 | −211 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9971 | −11013 | −894 | −1115 | −5890 | −25 | * | * | | | | | | | | | | | | |
| 19 | −176 | −2624 | −3141 | −2574 | 1425 | −1397 | 142 | 309 | −962 | −591 | −1805 | 1228 | −3686 | −2279 | −151 | 306 | 958 | −2072 | 3975 | −2607 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2 | −9971 | −11013 | −894 | −1115 | −5890 | −25 | * | * | | | | | | | | | | | | |
| 20 | 63 | 2678 | −4235 | −1046 | 1173 | −1434 | −2727 | −1827 | −3328 | −292 | 764 | −3352 | 174 | −3044 | 536 | 1450 | 664 | −614 | −2768 | 568 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −93 | −9971 | −4030 | −894 | −1115 | −5890 | −25 | * | * | | | | | | | | | | | | |
| 21 | −1027 | −3522 | 1171 | 549 | 1033 | 1159 | −1767 | 1643 | −1360 | −3526 | −2620 | 981 | −910 | −1317 | 116 | −2014 | 382 | −3129 | −3724 | −3059 | 23 |
| — | −147 | −491 | 237 | 41 | −384 | 395 | 102 | −620 | 210 | −469 | −716 | 280 | 392 | 45 | 105 | 357 | 116 | −370 | −298 | −253 | |
| E | −5045 | −92 | −5001 | −8 | −7545 | −5935 | −24 | * | * | | | | | | | | | | | | |
| 22 | −784 | −2908 | −2398 | −595 | −605 | 1885 | 1581 | −2621 | −1731 | −593 | −2061 | −2073 | −641 | −121 | −2158 | 1457 | 772 | −580 | −3242 | −181 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −269 | −9836 | −2565 | −894 | −1115 | −5956 | −23 | * | * | | | | | | | | | | | | |
| 23 | −132 | −3163 | 413 | 794 | 819 | 571 | −1545 | −3115 | −1158 | −546 | 590 | 1397 | −2969 | 277 | −1652 | 554 | −283 | −446 | −3391 | 382 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −195 | −9570 | −3001 | −894 | −1115 | −6063 | −22 | * | * | | | | | | | | | | | | |
| 24 | −272 | −3044 | −184 | 682 | 537 | 427 | −1387 | −501 | 26 | −197 | 1789 | 333 | 441 | 431 | −1490 | −330 | −17 | −498 | −3264 | −2620 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −86 | −9378 | −4156 | −894 | −1115 | −3979 | −95 | * | * | | | | | | | | | | | | |
| 25 | 906 | −3249 | 1379 | −271 | 765 | 585 | 573 | −3281 | −1066 | −1133 | −2344 | 72 | −2908 | 118 | −1569 | 792 | 77 | −2858 | 1550 | 39 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −3 | −9531 | −10573 | −894 | −1115 | −1989 | −419 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −99 | −3120 | 331 | 109 | 12 | 538 | 737 | −2766 | −2337 | 293 | 1166 | 776 | −3833 | −2243 | −2718 | −1519 | 1661 | 112 | 1951 | −3017 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −32 | −10296 | −5581 | −894 | −1115 | −5686 | −28 | * | * | | | | | | | | | | | | |
| 27 | 193 | −3901 | 466 | −688 | −993 | 915 | −2064 | −3970 | 326 | −892 | 1527 | −136 | −3498 | 544 | 458 | 1015 | 797 | −3522 | −4085 | −585 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −296 | −10266 | −2436 | −894 | −1115 | −2260 | −338 | * | * | | | | | | | | | | | | |
| 28 | 507 | 270 | 518 | −763 | 1233 | 383 | −2295 | 1018 | 51 | −3573 | −32 | 315 | 1008 | −1906 | −2432 | 361 | −557 | −409 | −3900 | −3319 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10372 | −11414 | −894 | −1115 | −4334 | −73 | * | * | | | | | | | | | | | | |
| 29 | −1258 | −4024 | 123 | −278 | 488 | 1923 | −2202 | −4084 | −737 | 51 | −3115 | 1887 | −1562 | −341 | −227 | −1135 | −1185 | −266 | −4211 | −413 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −192 | −10423 | −3014 | −894 | −1115 | −4154 | −83 | * | * | | | | | | | | | | | | |
| 30 | −38 | −3869 | −896 | −279 | −4162 | 345 | −2108 | 1801 | −433 | −650 | −2965 | 1221 | 333 | 285 | −665 | −2356 | −1068 | 1195 | −4069 | −3403 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −77 | −10297 | −4293 | −894 | −1115 | −4881 | −50 | * | * | | | | | | | | | | | | |
| 31 | −414 | 1371 | 1040 | −930 | 770 | −516 | −326 | 60 | −2458 | −287 | −2147 | 1997 | −3856 | −328 | −2801 | −533 | −2488 | −101 | −3359 | 1949 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −32 | −10251 | −5553 | −894 | −1115 | −5719 | −28 | * | * | | | | | | | | | | | | |
| 32 | −61 | −3859 | 943 | −649 | 303 | 1418 | −2025 | −1445 | 687 | −1070 | −2949 | 938 | −218 | −152 | 425 | −255 | −515 | −1730 | −4044 | −333 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −80 | −10220 | −4231 | −894 | −1115 | −3975 | −95 | * | * | | | | | | | | | | | | |
| 33 | −399 | −3163 | −2842 | −2286 | 1414 | −477 | −2364 | −833 | 692 | 146 | −520 | 604 | −594 | 1733 | 621 | −674 | −116 | −891 | 2219 | −3020 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −73 | −10238 | −4363 | −894 | −1115 | −4916 | −49 | * | * | | | | | | | | | | | | |
| 34 | 470 | 508 | 1149 | −521 | −1025 | 39 | 136 | 20 | −768 | 179 | 736 | 808 | 69 | −210 | 104 | −651 | 464 | −3435 | −4010 | −3334 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −120 | −10197 | −3664 | −894 | −1115 | −4976 | −47 | * | * | | | | | | | | | | | | |
| 35 | −231 | −3433 | 757 | −477 | 1408 | −567 | −2054 | −84 | −162 | −1805 | 978 | 1406 | −3464 | 275 | −2184 | 549 | −75 | −521 | 1694 | −182 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −2 | −10110 | −11152 | −894 | −1115 | −3612 | −123 | * | * | | | | | | | | | | | | |
| 36 | −1323 | −2792 | 2210 | −3009 | 1138 | −368 | 307 | 611 | −2829 | −858 | 389 | 1280 | −3988 | −2673 | 345 | −714 | −139 | 261 | −3208 | −2804 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10254 | −11296 | −894 | −1115 | −1938 | −436 | * | * | | | | | | | | | | | | |
| 37 | −64 | −3778 | −526 | −148 | −1251 | −781 | −2614 | −139 | −359 | 170 | 2379 | −328 | 1256 | 643 | −2770 | −175 | −328 | −127 | 1260 | −522 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10674 | −11716 | −894 | −1115 | −2244 | −342 | * | * | | | | | | | | | | | | |
| 38 | −80 | −4435 | 901 | 1 | −319 | −2036 | 1052 | −4506 | −171 | −4451 | −372 | 2086 | 15 | 467 | −1227 | 931 | 197 | −1472 | 484 | −223 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −10872 | −11914 | −894 | −1115 | −2267 | −336 | * | * | | | | | | | | | | | | |
| 39 | 606 | −4557 | 583 | −522 | −2038 | 1011 | 562 | −4627 | −125 | −1050 | 492 | −899 | −463 | 53 | 1841 | −1191 | 218 | −884 | −4741 | −425 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11008 | −12050 | −894 | −1115 | −1892 | −453 | * | * | | | | | | | | | | | | |
| 40 | 1429 | −3948 | −1406 | −1336 | 491 | −1377 | −624 | 302 | −1266 | −903 | 67 | 376 | 2088 | −2926 | −1416 | −744 | −816 | 410 | 969 | −3817 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11142 | −12184 | −894 | −1115 | −3460 | −137 | * | * | | | | | | | | | | | | |
| 41 | −41 | −4689 | 1362 | 199 | −2219 | −2613 | −1225 | −93 | −454 | 163 | 640 | 1143 | 274 | −154 | 24 | −22 | 774 | −1486 | −4874 | −2063 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11160 | −12202 | −894 | −1115 | −4296 | −75 | * | * | | | | | | | | | | | | |
| 42 | −174 | −4662 | −855 | 133 | 885 | 1176 | −1228 | 180 | −1767 | −2943 | −652 | 2171 | −2293 | −25 | −1382 | −667 | 996 | −635 | −4855 | −1902 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11160 | −12202 | −894 | −1115 | −4296 | −75 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | 495 | −345 | 155 | 1039 | −5000 | 321 | −2860 | −4747 | −1526 | −251 | −153 | 1844 | 991 | −2402 | −290 | −426 | 206 | −494 | −4871 | −4192 | 46 |
| — | −149 | −505 | 231 | 44 | −375 | 394 | 107 | −630 | 208 | −460 | −703 | 271 | 391 | 52 | 93 | 361 | 122 | −371 | −280 | −255 | |
| C | −1359 | −713 | −12202 | −5 | −8197 | −265 | −2574 | * | * | | | | | | | | | | | | |
| 44 | 205 | −4944 | 298 | −273 | −89 | −633 | −1315 | 223 | −135 | −611 | −864 | −10 | 1341 | 974 | 54 | −152 | −29 | 131 | −5131 | −1332 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −11444 | −12486 | −894 | −1115 | −2104 | −382 | * | * | | | | | | | | | | | | |
| 45 | −932 | −4587 | −1107 | −1399 | 1080 | −1743 | −99 | −1412 | 256 | 42 | −1698 | −358 | 1380 | 792 | −3403 | −990 | 978 | 269 | 1009 | 1587 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11444 | −12486 | −894 | −1115 | −2104 | −382 | * | * | | | | | | | | | | | | |
| 46 | −606 | 1564 | −1864 | −369 | 1135 | 330 | 359 | −2865 | −1109 | 291 | −1843 | −666 | 899 | 185 | 239 | −386 | 300 | −151 | −278 | 749 | 50 |
| — | −155 | −511 | 235 | 40 | −386 | 410 | 107 | −626 | 205 | −470 | −708 | 277 | 408 | 45 | 93 | 355 | 115 | −371 | −305 | −245 | |
| T | −6608 | −15 | −12486 | −2 | −9174 | −2104 | −382 | * | * | | | | | | | | | | | | |
| 47 | 395 | 1247 | 1022 | −487 | −5279 | 821 | −3118 | −5029 | −414 | −2235 | −1204 | 1183 | −70 | 1090 | −2051 | 525 | 843 | −1659 | −5141 | −64 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11444 | −12486 | −894 | −1115 | −613 | −1530 | * | * | | | | | | | | | | | | |
| 48 | 497 | −4872 | −1398 | −235 | −2316 | 240 | −3186 | −600 | −1318 | −1885 | −3975 | −1706 | −153 | −1308 | −126 | 3 | 2310 | 359 | 1483 | 368 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11474 | −12516 | −894 | −1115 | −1315 | −741 | * | * | | | | | | | | | | | | |
| 49 | −1766 | −4987 | −1078 | 1243 | −1856 | −3033 | 1694 | −5059 | 465 | −1750 | −4076 | 2176 | 350 | 26 | 107 | 1231 | −2115 | −423 | −5170 | −4487 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11474 | −12516 | −894 | −1115 | −1315 | −741 | * | * | | | | | | | | | | | | |
| 50 | −56 | −4188 | −4102 | −1296 | −4245 | −756 | −3553 | 1166 | −839 | −44 | −507 | −1608 | 1188 | −1545 | −512 | −723 | −66 | 2228 | −4557 | −4087 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11474 | −12516 | −894 | −1115 | −1315 | −741 | * | * | | | | | | | | | | | | |
| 51 | −1126 | −3625 | −2356 | −5494 | 1566 | −2552 | −1757 | 1825 | −146 | 479 | 1098 | −4985 | −5393 | −2085 | −2379 | −3020 | −3737 | 786 | 3451 | 1513 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11474 | −12516 | −894 | −1115 | −418 | −1992 | * | * | | | | | | | | | | | | |
| 52 | −575 | −4996 | 187 | 758 | −2676 | −984 | 243 | 61 | −1231 | −1780 | −1482 | 680 | −428 | 1022 | 168 | −371 | 1381 | 1070 | −5180 | −4499 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 53 | 32 | −3637 | −2080 | −2431 | 552 | −1523 | −4229 | 1957 | −5114 | 1652 | 118 | −5003 | −5408 | −4737 | −4914 | −1969 | −515 | 1544 | −4095 | −1244 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 54 | −798 | −5000 | 141 | 942 | −1943 | −1369 | −516 | −1083 | 953 | −5016 | −1619 | 607 | 1851 | 11 | 720 | −363 | 660 | −1001 | −5183 | −788 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 55 | −537 | −4981 | −3384 | −35 | 1020 | −463 | 1365 | −2548 | 516 | −345 | −4072 | 1661 | −563 | 271 | −274 | −546 | −285 | −1393 | −5170 | 2036 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11488 | −12530 | −894 | −1115 | −701 | −1378 | * | * | | | | | | | | | | | | |
| 56 | −321 | −5000 | 784 | −525 | −5321 | 1856 | 302 | −2274 | 30 | −3238 | −4089 | 2355 | −2201 | −591 | 430 | −796 | −1525 | −1025 | −5183 | −1559 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11488 | −12530 | −894 | −1115 | −701 | −1378 | * | * | | | | | | | | | | | | |
| 57 | 39 | −5000 | 1660 | 1164 | −5321 | −452 | −3159 | −5072 | 584 | −5016 | −1273 | 709 | −2116 | 1220 | −968 | 750 | 1027 | −2741 | −5183 | −4500 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −27 | −11488 | −5785 | −894 | −1115 | −701 | −1378 | * | * | | | | | | | | | | | | |
| 58 | −1528 | −1033 | −800 | −1172 | 1308 | −1150 | 810 | −159 | −276 | −2021 | −1047 | −752 | −1276 | 444 | 1495 | −641 | 1180 | 1092 | 1194 | −1761 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −35 | −11462 | −5419 | −894 | −1115 | −1686 | −537 | * | * | | | | | | | | | | | | |
| 59 | −2441 | −3580 | −1457 | −1816 | −163 | −995 | −4172 | 1585 | −5057 | 456 | 1298 | −2284 | −2140 | −4680 | −4857 | −4385 | −3694 | 2569 | 2359 | 20 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −117 | −11428 | −3692 | −894 | −1115 | −2389 | −306 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −2137 | −4816 | 625 | 2555 | −1486 | −2486 | −949 | −1306 | −1792 | −4827 | −312 | −2982 | −4436 | 1456 | 1541 | −1197 | −491 | −1324 | 1541 | −380 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −87 | −11312 | −4107 | −894 | −1115 | −3562 | −128 | * | * | | | | | | | | | | | | |
| 61 | −2263 | −3441 | −5964 | −1698 | 1372 | −5168 | −4039 | 2314 | −4924 | 1008 | 966 | −4815 | −5214 | −4544 | −4723 | −4254 | −3557 | 1641 | 2360 | 634 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11226 | −12268 | −894 | −1115 | −4031 | −91 | * | * | | | | | | | | | | | | |
| 62 | −3560 | −3398 | −5824 | −2261 | −1598 | −5098 | −611 | 1283 | −4807 | −1526 | 192 | −12 | −1907 | −1818 | −987 | −285 | 106 | 2699 | 2474 | 201 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11226 | −12268 | −894 | −1115 | −4031 | −91 | * | * | | | | | | | | | | | | |
| 63 | −3928 | −3735 | −6275 | −5642 | 2647 | −5495 | −1058 | 1414 | −5244 | 1904 | 1199 | −5142 | −5510 | −4832 | −5033 | −4587 | −1903 | 866 | −4158 | −492 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11226 | −12268 | −894 | −1115 | −4031 | −91 | * | * | | | | | | | | | | | | |
| 64 | −1997 | −4743 | −495 | −149 | −1263 | −1344 | 495 | 869 | −427 | −310 | −693 | 1107 | 549 | 2498 | −845 | −1235 | −430 | 107 | −4930 | −4252 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −75 | −11226 | −4306 | −894 | −1115 | −4031 | −91 | * | * | | | | | | | | | | | | |
| 65 | −3217 | −4676 | 252 | −472 | −4991 | 675 | −2853 | −2885 | −2435 | −1959 | −1683 | 3551 | −1805 | 185 | −1643 | −421 | −861 | −2163 | −4863 | −1550 | 70 |
| — | −151 | −505 | 228 | 38 | −383 | 398 | 104 | −612 | 205 | −464 | −705 | 274 | 391 | 40 | 94 | 359 | 138 | −370 | −299 | −254 | |
| E | −289 | −2615 | −5775 | −1755 | −507 | −3811 | −107 | * | * | | | | | | | | | | | | |
| 66 | −612 | −4524 | 514 | −588 | −1526 | −1608 | 1538 | −474 | −974 | 661 | 1357 | 1892 | −488 | −363 | −1047 | −1673 | 87 | 72 | 307 | −450 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −11134 | −12176 | −894 | −1115 | −4386 | −71 | * | * | | | | | | | | | | | | |
| 67 | 459 | −4650 | 1606 | 752 | −4961 | 757 | −774 | −441 | −1556 | −1209 | −3742 | −34 | −500 | −2383 | −2930 | 511 | 1426 | −1237 | −4840 | −1211 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −38 | −11134 | −5280 | −894 | −1115 | −1910 | −446 | * | * | | | | | | | | | | | | |
| 68 | −211 | −4722 | −419 | −227 | −186 | 281 | −2886 | −1893 | −300 | −4737 | 2366 | 570 | 919 | 651 | −1797 | 675 | 1238 | −774 | −4906 | −4224 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11191 | −12233 | −894 | −1115 | −4179 | −82 | * | * | | | | | | | | | | | | |
| 69 | −1060 | −4072 | −130 | 1202 | −1352 | 1238 | −3186 | 195 | −645 | −628 | 1986 | 108 | −636 | −2885 | −3382 | −293 | 876 | −1147 | −182 | 158 | 81 |
| — | −150 | −514 | 243 | 34 | −367 | 400 | 96 | −611 | 201 | −468 | −718 | 271 | 406 | 41 | 90 | 353 | 127 | −365 | −286 | −264 | |
| S | −3611 | −1789 | −669 | −2404 | −302 | −4179 | −82 | * | * | | | | | | | | | | | | |
| 70 | 1211 | −2178 | 389 | −3403 | −2156 | 607 | −2561 | 1162 | −3118 | 1080 | −1388 | −3151 | 776 | −2846 | −3122 | 367 | −2180 | 135 | −2637 | −2278 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −9762 | −10804 | −894 | −1115 | −14 | −6666 | * | * | | | | | | | | | | | | |
| 71 | 617 | −4914 | −102 | −874 | −2326 | −2647 | −909 | −24 | −678 | −671 | −223 | 637 | 2054 | −1296 | −123 | −219 | 735 | −145 | −691 | 45 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11488 | −12530 | −894 | −1115 | −701 | −1378 | * | * | | | | | | | | | | | | |
| 72 | −2448 | −6991 | −2289 | −2341 | −7351 | −5646 | 5180 | −7090 | −2581 | −6918 | −6175 | −2075 | −6021 | 1232 | −2563 | −5171 | −5399 | −1806 | −6997 | −6314 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 73 | −4493 | −5104 | −7645 | −7985 | −7786 | −5384 | −7107 | −7589 | −7745 | −4070 | −6903 | −1990 | 3943 | −7195 | −7387 | 741 | 538 | −2317 | −8014 | −7979 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 74 | −2359 | −4256 | −6809 | −6184 | 3041 | −6049 | −4866 | 2091 | −5792 | −586 | 3013 | −5690 | −6032 | −5345 | −5570 | −5147 | −4402 | −471 | 1877 | 533 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 75 | −9985 | −8342 | −9234 | −9620 | −9476 | −8295 | 5478 | −10922 | −9812 | −10192 | −10212 | −9658 | −8728 | −9706 | −9237 | −10555 | −10115 | −10647 | −8385 | −9365 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 76 | −6658 | −6135 | −9021 | −8407 | 289 | −8638 | −7314 | 1663 | −1619 | 2852 | 415 | −8338 | −7888 | −7056 | −7684 | −7908 | −6512 | −1167 | −265 | −6235 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | −6023 | −8155 | 765 | −1518 | −8243 | −5706 | 5258 | −8269 | −5667 | −8083 | −7563 | −2274 | −6313 | −4885 | −6742 | −2475 | −6136 | −7690 | −8290 | −7104 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11488 | −12530 | −894 | −1115 | −701 | −1378 | * | * | | | | | | | | | | | | |
| 78 | −1822 | −5251 | −2049 | −6320 | −7623 | 3622 | −6592 | −7399 | −7179 | −660 | −6769 | −1963 | −6199 | −6543 | −7226 | −1722 | −5057 | −1429 | −7869 | −7635 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11488 | −12530 | −894 | −1115 | −701 | −1378 | * | * | | | | | | | | | | | | |
| 79 | −952 | −3649 | −6056 | −5427 | 1073 | −5344 | 4190 | −3143 | −5043 | −2315 | 53 | 400 | −5395 | −1663 | −4877 | −1617 | −317 | 229 | −4104 | 2548 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11488 | −12530 | −894 | −1115 | −701 | −1378 | * | * | | | | | | | | | | | | |
| 80 | −190 | −4999 | 1865 | −1222 | −651 | −4501 | −671 | −5070 | −1136 | −5015 | −372 | 1285 | −66 | 1011 | −579 | 1231 | 756 | −694 | 1622 | −4500 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11488 | −12530 | −894 | −1115 | −701 | −1378 | * | * | | | | | | | | | | | | |
| 81 | −2671 | −3795 | −6282 | −5668 | 4305 | −2660 | −4287 | −3304 | −5266 | −3649 | −357 | −1741 | −2105 | −4878 | −5065 | −1519 | −3910 | −1386 | 1243 | −529 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 82 | 221 | −4941 | 737 | −676 | 1364 | −4518 | −1354 | −2360 | 12 | −1256 | −1346 | −1561 | −4610 | 2168 | 745 | −643 | −1972 | −1312 | 1933 | 1995 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 83 | −807 | −3650 | −2122 | −5536 | −1428 | −5374 | −4247 | 1536 | −5131 | 903 | −23 | −5020 | −5424 | −4755 | −4932 | −2222 | −1440 | 2942 | −4112 | −1245 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 84 | −2632 | −3673 | −5854 | −1023 | −3631 | −5312 | −4168 | 1388 | −1524 | 1814 | −2874 | −1801 | −2194 | −4570 | −733 | −2207 | −747 | 2328 | −4125 | −1532 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 85 | 485 | −298 | 379 | 2 | −1652 | 2220 | −408 | −5071 | −824 | −2760 | −4088 | 31 | −4594 | 147 | 1092 | 392 | −1265 | −1773 | −5183 | −2010 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 86 | −1550 | −4595 | −3653 | −622 | −564 | −913 | −145 | −843 | −912 | −2022 | 1820 | −3369 | −1793 | 1470 | 1967 | 1104 | 342 | −225 | −4882 | 862 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 87 | 46 | −5000 | 1448 | −480 | −5321 | 2245 | 448 | −5072 | −1625 | −2068 | −4089 | 858 | −4594 | −259 | −1131 | 849 | −274 | −2703 | −5183 | −4500 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 88 | −1538 | −4909 | 107 | −340 | 1091 | 1893 | −959 | −758 | −1383 | −1695 | −1233 | 387 | 1295 | −2745 | 531 | −481 | −47 | −825 | −5117 | −1301 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 89 | 35 | −4998 | −149 | −65 | −678 | 2341 | −738 | −2246 | −396 | −850 | −4088 | 296 | −935 | −223 | −393 | 301 | −915 | −2160 | −5182 | −197 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −11488 | −12530 | −894 | −1115 | −701 | −1378 | * | * | | | | | | | | | | | | |
| 90 | −956 | −4990 | 579 | −676 | −183 | −672 | −3162 | −1280 | 494 | −1870 | −363 | 1635 | 1424 | 352 | 183 | −141 | 592 | −1980 | 122 | 461 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −279 | −11488 | −2512 | −894 | −1115 | −701 | −1378 | * | * | | | | | | | | | | | | |
| 91 | −161 | −4321 | 211 | −567 | 1606 | −101 | −908 | −768 | −1549 | −1718 | −3456 | −837 | 1164 | −2697 | −1611 | −1992 | 470 | −933 | 3668 | 1544 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −223 | −11210 | −2811 | −894 | −1115 | −4100 | −87 | * | * | | | | | | | | | | | | |
| 92 | −629 | −4532 | 1741 | −733 | −2215 | 561 | −2703 | −4596 | −2285 | −2460 | −3622 | 1456 | −903 | 581 | −1249 | 465 | 1241 | −1591 | 125 | 1410 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −216 | −10989 | −2849 | −894 | −1115 | −4785 | −53 | * | * | | | | | | | | | | | | |
| 93 | 169 | −4336 | 616 | 525 | −1689 | 59 | −2510 | −570 | −36 | −2410 | −3427 | 827 | 2453 | −422 | −213 | −2757 | −400 | −2124 | 242 | −142 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −68 | −10773 | −4465 | −894 | −1115 | −5180 | −40 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | 480 | −4269 | 1038 | 396 | 341 | −789 | 41 | −998 | 71 | −1283 | −3360 | 826 | −3887 | −811 | −822 | 256 | 790 | −248 | 1484 | 469 | 132 |
| — | −147 | −521 | 245 | 55 | −382 | 390 | 98 | −619 | 206 | −470 | −732 | 276 | 403 | 36 | 101 | 354 | 122 | −371 | −314 | −245 | |
| H | −2109 | −543 | −3612 | −2770 | −229 | −5274 | −38 | * | * | | | | | | | | | | | | |
| 95 | −418 | 459 | 2280 | −327 | −4500 | −450 | −415 | −4250 | 558 | −2101 | 374 | −849 | 356 | −93 | −2426 | 1062 | 888 | −3801 | −4362 | −3680 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10584 | −11626 | −894 | −1115 | −3336 | −150 | * | * | | | | | | | | | | | | |
| 96 | −508 | −4256 | −685 | −743 | −4573 | −2020 | −2426 | −4321 | −219 | −1538 | 1332 | 149 | 2260 | −1967 | 2055 | 308 | 32 | −1773 | −4441 | −179 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10680 | −11722 | −894 | −1115 | −3174 | −169 | * | * | | | | | | | | | | | | |
| 97 | 1082 | −4345 | −180 | −266 | −1531 | −336 | 1213 | −1689 | 665 | −399 | −3434 | −781 | 267 | −423 | 201 | 613 | 362 | 152 | −4529 | −3846 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10773 | −11815 | −894 | −1115 | −4416 | −69 | * | * | | | | | | | | | | | | |
| 98 | −325 | −4347 | −2747 | −808 | −4660 | −969 | 973 | −1080 | 1345 | −739 | −225 | 300 | 380 | −898 | 852 | 751 | 1244 | −6 | −4535 | −3857 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10792 | −11834 | −894 | −1115 | −3655 | −119 | * | * | | | | | | | | | | | | |
| 99 | −1540 | −3495 | −805 | −1309 | 1690 | −4310 | −763 | −674 | −1352 | 1078 | −2670 | −639 | 173 | −2880 | −80 | −656 | −947 | −1040 | 1339 | 2848 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10839 | −11881 | −894 | −1115 | −884 | −1127 | * | * | | | | | | | | | | | | |
| 100 | −405 | −4746 | −1634 | −909 | 396 | −1163 | −2918 | −1012 | −48 | −4761 | −1187 | 3314 | 426 | 400 | 342 | −3165 | −1564 | −4366 | −152 | −221 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11224 | −12266 | −894 | −1115 | −3114 | −177 | * | * | | | | | | | | | | | | |
| 101 | −328 | −551 | −1650 | −388 | 1088 | −590 | −1087 | −4719 | −378 | 1491 | −3799 | −1020 | 1344 | −991 | −1741 | −1088 | −228 | −1185 | −4904 | 1818 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −11241 | −12283 | −894 | −1115 | −1489 | −635 | * | * | | | | | | | | | | | | |
| 102 | −555 | −4845 | 482 | 1272 | −1512 | −2735 | 1223 | −1311 | 380 | −2428 | −3935 | 395 | −1145 | −493 | −1154 | 211 | −420 | 1670 | 1653 | −848 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11326 | −12368 | −894 | −1115 | −3461 | −137 | * | * | | | | | | | | | | | | |
| 103 | 39 | −4848 | 2431 | 41 | −5169 | −1485 | −3010 | −1627 | −1394 | −2675 | −3938 | 2651 | −1839 | −1193 | −695 | −1340 | −455 | −1111 | −5032 | 182 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11326 | −12368 | −894 | −1115 | −994 | −1006 | * | * | | | | | | | | | | | | |
| 104 | 693 | −4909 | −607 | −2764 | −5222 | −76 | −3094 | −4966 | −1107 | −541 | −4001 | −3073 | 3334 | −46 | 216 | −1170 | −1344 | −4527 | −5098 | −1633 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11406 | −12449 | −894 | −1115 | −1893 | −452 | * | * | | | | | | | | | | | | |
| 105 | −480 | −3595 | −5883 | −971 | −1587 | 928 | −4123 | 385 | −4899 | −1492 | 1739 | −2171 | 2124 | 232 | −1896 | −2494 | −633 | 1628 | 253 | −367 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11419 | −12461 | −894 | −1115 | −2520 | −276 | * | * | | | | | | | | | | | | |
| 106 | −683 | −4027 | −4244 | 322 | −468 | −4851 | 267 | −981 | −1063 | −162 | −645 | −3820 | −503 | −729 | 2525 | 321 | −2244 | −1261 | 3383 | 163 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11419 | −12461 | −894 | −1115 | −167 | −3197 | * | * | | | | | | | | | | | | |
| 107 | −1542 | −1870 | −1672 | −859 | −1708 | −4573 | −1363 | −4731 | 2008 | −1254 | −913 | −3249 | −4663 | −2815 | 3372 | −3490 | −816 | −4380 | −216 | −4417 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 108 | −2246 | 37 | 3641 | −4915 | −7110 | −2364 | 1915 | −6890 | −5356 | −6987 | −6105 | 1347 | −5908 | −5086 | −5787 | −597 | −1491 | −2118 | −7188 | −6675 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11488 | −12530 | −894 | −1115 | −701 | −1378 | * | * | | | | | | | | | | | | |
| 109 | −4555 | −4770 | −7374 | −7198 | −5612 | −5710 | −6164 | −1526 | −6879 | −5283 | −4770 | −2671 | −6277 | −6490 | −6665 | −721 | 3499 | 2005 | −6241 | −2738 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 110 | 223 | −3683 | −6211 | −2759 | 835 | −5418 | −4294 | 1519 | −5175 | −654 | −1154 | −5064 | −5466 | −4800 | −4977 | −4505 | 584 | 2760 | −4158 | 687 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111 | 265 | −4940 | 43 | −234 | −5234 | 306 | −1128 | −888 | −2771 | −376 | 1398 | 621 | −669 | 1886 | −397 | −47 | −36 | −616 | 1634 | 112 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 112 | −739 | −3783 | −6331 | −5704 | −3764 | −5549 | −2119 | 1252 | −5308 | 1366 | 349 | −5196 | −5592 | −4936 | −5114 | −2765 | −290 | 2842 | −4297 | −3953 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −49 | −11488 | −4929 | −894 | −1115 | −701 | −1378 | * | * | | | | | | | | | | | | |
| 113 | −833 | −4946 | −1808 | −68 | −1050 | 821 | −959 | −5010 | −1476 | −1153 | −4036 | 20 | 2863 | −285 | 6 | −2142 | −1429 | −1350 | −548 | 1670 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −89 | −11440 | −4076 | −894 | −1115 | −2177 | −361 | * | * | | | | | | | | | | | | |
| 114 | 742 | −4757 | −996 | −2766 | −5025 | 378 | −794 | −436 | −457 | −3448 | −1676 | −838 | 2965 | −2633 | −484 | −85 | −256 | −104 | −4972 | −4322 | 172 |
| — | −142 | −501 | 233 | 42 | −382 | 400 | 104 | −628 | 209 | −467 | −722 | 275 | 394 | 47 | 94 | 358 | 119 | −370 | −296 | −251 | |
| T | −118 | −3670 | −12394 | −889 | −1121 | −97 | −3939 | * | * | | | | | | | | | | | | |
| 115 | −80 | −4996 | 202 | −1069 | −1214 | 2420 | 30 | −1520 | −527 | −2401 | −103 | 1595 | −743 | −128 | −796 | −891 | −1536 | −4617 | 366 | −762 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11488 | −12530 | −894 | −1115 | −701 | −1378 | * | * | | | | | | | | | | | | |
| 116 | 231 | −5018 | 8 | 710 | −5339 | 2720 | −1006 | −5090 | −1528 | −5034 | −4108 | −1652 | −4608 | 820 | −3266 | 600 | −296 | −2267 | −5202 | −4518 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 117 | −3533 | −4943 | −3406 | −1234 | −385 | −870 | 1175 | −4971 | 1 | −4948 | −67 | 978 | −4610 | −535 | 415 | −934 | 787 | −772 | 4507 | 1746 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 118 | 1007 | −3644 | −6091 | −2295 | −124 | −2416 | −264 | 343 | −5068 | 448 | 1330 | −4974 | −5399 | −721 | −716 | −913 | 1562 | 1840 | −4101 | −3757 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 119 | 1632 | −3921 | −4721 | −455 | −3920 | −5054 | −3830 | 618 | −1262 | −1746 | −3107 | −4182 | −5122 | −2087 | 1303 | −1104 | 1526 | 1718 | −275 | −3935 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11488 | −12530 | −894 | −1115 | −701 | −1378 | * | * | | | | | | | | | | | | |
| 120 | −875 | −4983 | −7806 | −7266 | −229 | −7245 | −6280 | 2971 | −6976 | 1076 | −1805 | −6899 | −7082 | −6522 | −6804 | −6418 | −5287 | 1809 | −5828 | 167 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −18 | −11488 | −6356 | −894 | −1115 | −701 | −1378 | * | * | | | | | | | | | | | | |
| 121 | 1472 | −4178 | −527 | 149 | −4232 | −4831 | −3557 | −2150 | −3423 | 302 | 655 | −3732 | −4910 | −537 | 2958 | −3795 | −1847 | −2141 | −4547 | 139 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11470 | −12512 | −894 | −1115 | −1429 | −670 | * | * | | | | | | | | | | | | |
| 122 | −712 | −3624 | −6144 | −5508 | 3739 | −1948 | −4217 | −16 | −5102 | −390 | 668 | −4992 | −5395 | −4725 | −4902 | −4430 | −1937 | 1115 | 730 | 64 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11470 | −12512 | −894 | −1115 | −1429 | −670 | * | * | | | | | | | | | | | | |
| 123 | −229 | −4948 | 130 | −812 | −1283 | −4494 | 1361 | −321 | 1481 | −1810 | −1405 | −1994 | −4587 | 326 | 1546 | −183 | 392 | 926 | −5142 | 264 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −31 | −11470 | −5574 | −894 | −1115 | −1429 | −670 | * | * | | | | | | | | | | | | |
| 124 | 2494 | −3593 | −6104 | −5468 | 1638 | −5312 | −4183 | −3085 | −5065 | −33 | 440 | −2311 | −224 | −4689 | −4867 | −1014 | 1257 | −807 | −4051 | 443 | 186 |
| — | −152 | −503 | 234 | 42 | −379 | 398 | 117 | −629 | 209 | −467 | −723 | 276 | 396 | 47 | 98 | 358 | 118 | −372 | −297 | −244 | |
| E | −143 | −3409 | −12482 | −1452 | −656 | −678 | −1416 | * | * | | | | | | | | | | | | |
| 125 | 37 | −4983 | 3340 | −531 | −5304 | −701 | −3143 | −5055 | −1907 | −2741 | −4073 | 860 | −500 | −650 | −1177 | −1051 | −1074 | −2461 | −5167 | −493 | 190 |
| — | −149 | −502 | 239 | 42 | −383 | 401 | 103 | −628 | 208 | −468 | −723 | 276 | 401 | 43 | 95 | 357 | 117 | −371 | −287 | −248 | |
| — | −325 | −2311 | −12512 | −12 | −6923 | −381 | −2107 | * | * | | | | | | | | | | | | |
| 126 | −150 | −4830 | −537 | −291 | −1241 | −2274 | 34 | −2199 | −2835 | −4814 | −1082 | 3727 | −1268 | −2788 | −1799 | −1118 | −3486 | −2588 | 272 | 587 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11488 | −12530 | −894 | −1115 | −701 | −1378 | * | * | | | | | | | | | | | | |
| 127 | 433 | −4865 | −2117 | −2079 | −2449 | −4541 | 426 | −4836 | −1363 | −2282 | −3970 | −3203 | 3509 | −547 | −2248 | −196 | −352 | −268 | −5085 | −907 | 193 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11488 | −12530 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128 | -2418 | -1172 | -6422 | -5845 | -975 | 3644 | -230 | -3572 | -5447 | -3897 | -3272 | -5280 | -5735 | -1689 | -5260 | -4752 | -2347 | -2630 | -168 | -1152 | 194 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 129 | 899 | -4472 | -394 | -1181 | -577 | -4695 | -3389 | -337 | -1197 | -2090 | 1898 | -1350 | 1840 | -1498 | 353 | -1002 | -653 | 1678 | -4786 | -630 | 195 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 130 | -7788 | -6881 | -8415 | -8582 | 918 | -8224 | -4560 | -6794 | -2502 | -6221 | -6234 | -6907 | -8099 | -6941 | -2291 | -7464 | -2342 | -2342 | 5908 | 1916 | 196 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 131 | 93 | -3637 | -6156 | -5520 | 2237 | -5358 | -4230 | -592 | -5115 | 1461 | 2903 | 1161 | -2427 | -1669 | -4915 | -4443 | -1976 | 273 | -4095 | -344 | 197 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 132 | -1867 | -951 | -6331 | -5696 | 2919 | -5540 | -4405 | 336 | -5294 | 1586 | 2069 | -5187 | -5575 | -4900 | -5088 | -4628 | -3924 | -373 | 1583 | 1713 | 198 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 133 | -6338 | -7222 | -5000 | -1292 | -6667 | -6420 | 5214 | -7405 | -3621 | -6997 | -6431 | -2147 | -6632 | -4425 | 1062 | -6084 | -6115 | -7162 | -6407 | -1762 | 199 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1 | -11488 | -12530 | -894 | -1115 | -701 | -1378 | * | * | | | | | | | | | | | | |
| 134 | -4486 | 5616 | -7907 | -8248 | -7781 | -5384 | -7165 | -3032 | -7849 | -7834 | -6887 | -6232 | -1378 | -7274 | -7438 | 560 | -1553 | -3150 | -8023 | -8006 | 200 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -7 | -11488 | -7799 | -894 | -1115 | -701 | -1378 | * | * | | | | | | | | | | | | |
| 135 | -2241 | -7737 | -2224 | 30 | -7903 | -5647 | 5212 | -7831 | -2167 | -7670 | -7035 | -2259 | -6193 | -201 | -5989 | -5426 | -5857 | -2370 | -7848 | -6825 | 201 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -1 | -11481 | -12524 | -894 | -1115 | -1006 | -994 | * | * | | | | | | | | | | | | |
| 136 | -2130 | -3632 | -6144 | -5508 | -51 | -5351 | -120 | 2920 | -713 | 665 | 1229 | 929 | -5401 | -1079 | -4906 | -4436 | -2160 | 662 | -4089 | -1004 | 202 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -1 | -11481 | -12524 | -894 | -1115 | -1006 | -994 | * | * | | | | | | | | | | | | |
| 137 | 433 | -4873 | 1834 | 1140 | -5140 | -829 | -3196 | -1447 | -2800 | 1479 | -399 | -1652 | -2429 | -161 | -3297 | -644 | -235 | -4466 | 2127 | -4441 | 203 |
| — | -146 | -493 | 238 | 49 | -382 | 397 | 104 | -628 | 209 | -467 | -722 | 274 | 395 | 44 | 95 | 359 | 116 | -371 | -296 | -251 | |
| H | -6646 | -2974 | -213 | -19 | -6285 | -1006 | -994 | * | * | | | | | | | | | | | | |
| 138 | -1338 | -2767 | -1202 | -639 | -3111 | -2293 | -910 | -2839 | 395 | -2771 | -1862 | 312 | 580 | 832 | 2771 | 404 | 759 | -2404 | -2920 | -2277 | 205 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -5 | -8618 | -9660 | -894 | -1115 | -66 | -4473 | * | * | | | | | | | | | | | | |
| 139 | -896 | -4637 | -934 | 1247 | 526 | -2411 | 28 | -114 | -2050 | -1034 | -3762 | -3266 | -1133 | 823 | -602 | -1602 | -1457 | -426 | 4496 | 995 | 206 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -1 | -11440 | -12482 | -894 | -1115 | -2177 | -361 | * | * | | | | | | | | | | | | |
| 140 | -7991 | -6960 | -8431 | -8701 | -3053 | -8291 | 5188 | -1567 | -7970 | -6234 | -331 | -6915 | -8148 | -6998 | -2520 | -7540 | -7837 | -7056 | 117 | 1823 | 207 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -1 | -11440 | -12482 | -894 | -1115 | -2177 | -361 | * | * | | | | | | | | | | | | |
| 141 | 717 | -3775 | -5009 | 1270 | -3757 | -5101 | -792 | -533 | -2843 | 1713 | 2261 | -2405 | -5164 | -95 | -4359 | -1131 | 159 | 385 | -4207 | -3826 | 208 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -1 | -11440 | -12482 | -894 | -1115 | -2177 | -361 | * | * | | | | | | | | | | | | |
| 142 | -754 | -4954 | 1953 | 1218 | -5274 | 882 | -1071 | -2754 | -1650 | -2696 | -111 | -1170 | -1705 | 654 | -3203 | 1112 | 617 | -372 | -5137 | -4455 | 209 |
| — | -149 | -500 | 233 | 43 | -381 | 399 | 106 | -626 | 210 | -466 | -720 | 275 | 394 | 45 | 96 | 359 | 117 | -369 | -294 | -249 | |
| C | -1 | -11440 | -12482 | -894 | -1115 | -2177 | -361 | * | * | | | | | | | | | | | | |
| 143 | 905 | -4793 | -3426 | 520 | -1777 | -1015 | 86 | -1347 | -1820 | -1396 | 1730 | 652 | -1825 | 2122 | -578 | -250 | 21 | -1512 | 2740 | -718 | 210 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -1 | -11440 | -12482 | -894 | -1115 | -2177 | -361 | * | * | | | | | | | | | | | | |
| 144 | -1720 | -7949 | -408 | -42 | -8077 | 3519 | -1266 | -8059 | -5433 | -7882 | -7313 | -4224 | -6227 | 573 | -1966 | -5499 | -5990 | -7500 | -8075 | -6959 | 211 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -1 | -11440 | -12482 | -894 | -1115 | -2177 | -361 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145 | −4894 | 170 | −7246 | −6616 | 1054 | −6517 | −5364 | −2268 | −6238 | 2074 | 4186 | −6173 | −6417 | −5711 | −5990 | −1891 | −1454 | −2533 | −4981 | −4768 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −11440 | −12482 | −894 | −1115 | −2177 | −361 | * | * | | | | | | | | | | | | |
| 146 | 1875 | −3614 | −5907 | −2268 | −134 | −375 | −4143 | −1892 | −1087 | −1309 | 3231 | −1465 | −5335 | −4581 | −4791 | 477 | −1127 | −130 | −4069 | 1721 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11440 | −12482 | −894 | −1115 | −2177 | −361 | * | * | | | | | | | | | | | | |
| 147 | 598 | −3594 | −6090 | −5455 | −1467 | 831 | −23 | −805 | −5055 | 559 | 2846 | −1454 | −5360 | −4681 | 782 | −1751 | 362 | 1424 | −4051 | −3708 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11440 | −12482 | −894 | −1115 | −2177 | −361 | * | * | | | | | | | | | | | | |
| 148 | 315 | −4926 | −1488 | −343 | −5233 | −1425 | −3124 | −1697 | −1408 | −1851 | −279 | −734 | −157 | 2214 | 579 | 190 | −19 | 1782 | −35 | −1509 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11440 | −12482 | −894 | −1115 | −1709 | −527 | * | * | | | | | | | | | | | | |
| 149 | −2642 | −3711 | −6235 | −5601 | 3416 | −5443 | −4306 | −145 | −5197 | 787 | 976 | −5088 | −5483 | −4809 | −2378 | −4529 | −3830 | 1481 | 356 | 1054 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11446 | −12488 | −894 | −1115 | −2049 | −399 | * | * | | | | | | | | | | | | |
| 150 | 285 | −4367 | −712 | −624 | −4473 | −4688 | −3389 | 1292 | −423 | 889 | −34 | −754 | −1056 | −429 | 106 | −2781 | −44 | 1518 | 799 | 151 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11446 | −12488 | −894 | −1115 | −2049 | −399 | * | * | | | | | | | | | | | | |
| 151 | −2448 | −4263 | −621 | 2043 | −4342 | −2679 | −3462 | 515 | −3266 | −3319 | −3423 | −305 | −2313 | −3183 | −3674 | −1240 | 579 | 2515 | −4613 | −47 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −256 | −11446 | −2623 | −894 | −1115 | −2049 | −399 | * | * | | | | | | | | | | | | |
| 152 | 272 | −4719 | 1271 | −246 | −2112 | 516 | −2887 | −2231 | 520 | −305 | −201 | −713 | 629 | −152 | 1178 | −274 | −492 | −847 | −4904 | −145 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −24 | −11191 | −5944 | −894 | −1115 | −4179 | −82 | * | * | | | | | | | | | | | | |
| 153 | −904 | −4703 | 1159 | 820 | −5024 | −2356 | −2863 | −356 | −127 | −2828 | −3792 | 1093 | 2428 | −678 | −925 | −801 | 70 | 278 | −4887 | −4204 | 220 |
| — | −144 | −509 | 240 | 46 | −384 | 409 | 104 | −631 | 210 | −468 | −722 | 273 | 394 | 53 | 92 | 356 | 113 | −374 | −303 | −256 | |
| H | −6332 | −18 | −12210 | −3 | −8896 | −48 | −4945 | * | * | | | | | | | | | | | | |
| 154 | −366 | −5000 | 1376 | 1087 | −5321 | −114 | −120 | −2368 | 269 | −1638 | −1289 | −66 | 180 | 486 | 97 | 1016 | −919 | 44 | −5183 | −2208 | 222 |
| — | * | * | * | * | * | * | * | * | * | * | * | * | * | * | * | * | * | * | * | * | |
| H | * | * | * | * | * | * | * | * | 0 | | | | | | | | | | | | |
| // | | | | | | | | | | | | | | | | | | | | | |

| | | | | | | | | | | | | | | | | | | | | | |
|---|---|---|---|---|---|---|---|---|---|---|---|---|---|---|---|---|---|---|---|---|---|
| HMMER2.0 | [2.3.2] | | | | | | | | | | | | | | | | | | | | |
| NAME | Cu-oxidase_3 | | | | | | | | | | | | | | | | | | | | |
| ACC | PF07732.7 | | | | | | | | | | | | | | | | | | | | |
| DESC | Multicopper oxidase | | | | | | | | | | | | | | | | | | | | |
| LENG | 124 | | | | | | | | | | | | | | | | | | | | |
| ALPH | Amino | | | | | | | | | | | | | | | | | | | | |
| RF | no | | | | | | | | | | | | | | | | | | | | |
| CS | yes | | | | | | | | | | | | | | | | | | | | |
| MAP | yes | | | | | | | | | | | | | | | | | | | | |
| COM | hmmbuild -F HMM_ls.ann SEED.ann | | | | | | | | | | | | | | | | | | | | |
| COM | hmmcalibrate --seed 0 HMM_ls.ann | | | | | | | | | | | | | | | | | | | | |
| NSEQ | 122 | | | | | | | | | | | | | | | | | | | | |
| DATE | Thu Apr 24 19:18:22 2008 | | | | | | | | | | | | | | | | | | | | |
| CKSUM | 2340 | | | | | | | | | | | | | | | | | | | | |
| GA | 10.0000 10.0000; | | | | | | | | | | | | | | | | | | | | |
| TC | 10.2000 10.2000; | | | | | | | | | | | | | | | | | | | | |
| NC | 9.6000 9.6000; | | | | | | | | | | | | | | | | | | | | |
| XT | −8455 | −4 | −1000 | −1000 | −8455 | −4 | −8455 | −4 | | | | | | | | | | | | | |
| NULT | −4 | −8455 | | | | | | | | | | | | | | | | | | | |
| NULE | 595 | −1558 | 85 | 338 | −294 | 453 | −1158 | 197 | 249 | 902 | −1085 | −142 | −21 | −313 | 45 | 531 | 201 | 384 | −1998 | −644 | |
| EVD | −92.985649 | 0.242445 | | | | | | | | | | | | | | | | | | | |
| HMM | A | C | D | E | F | G | H | I | K | L | M | N | P | Q | R | S | T | V | W | Y | |
| | m->m | m->i | m->d | i->m | i->i | d->m | d->d | b->m | m->e | | | | | | | | | | | | |
| | −27 | * | −5729 | | | | | | | | | | | | | | | | | | |
| 1 | −548 | −4429 | 781 | 864 | −4750 | −2608 | 573 | −2244 | 1037 | −1194 | −3518 | 1151 | −4023 | 470 | 68 | −490 | 1382 | 631 | −4612 | −3929 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −11 | −10865 | −7137 | −894 | −1115 | −701 | −1378 | −27 | * | | | | | | | | | | | | |
| 2 | 678 | 812 | −5539 | −1632 | −2999 | −4761 | −1203 | 1602 | −4504 | −43 | 11 | −898 | −2400 | −4131 | −4312 | −1616 | 457 | 2518 | −3503 | −3160 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10855 | −11897 | −894 | −1115 | −1014 | −986 | * | * | | | | | | | | | | | | |
| 3 | 97 | −4420 | −1986 | 1047 | −769 | 677 | −2579 | −4492 | 301 | −4436 | −3509 | −1548 | −1885 | 1976 | 328 | 460 | 1616 | −1380 | −4603 | −3920 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −14 | −10855 | −6742 | −894 | −1115 | −535 | −1691 | * | * | | | | | | | | | | | | |
| 4 | −700 | −4410 | −143 | 1165 | −1808 | −3920 | −494 | −4476 | 26 | −879 | 880 | −236 | 22 | −391 | 409 | 96 | 370 | −1030 | 2499 | 2042 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10852 | −11894 | −894 | −1115 | −1101 | −906 | * | * | | | | | | | | | | | | |
| 5 | 88 | −4413 | −156 | 147 | −4731 | 1084 | −1010 | 222 | 858 | −2149 | 853 | −1831 | −1306 | −92 | −819 | 413 | 1041 | 441 | −4597 | −3916 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10852 | −11894 | −894 | −1115 | −1101 | −906 | * | * | | | | | | | | | | | | |
| 6 | −1195 | −4410 | 360 | −107 | −2397 | −3920 | 768 | −2025 | −88 | −1610 | −1289 | 1890 | 638 | 1210 | −360 | −803 | 1544 | −465 | −331 | 120 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −15 | −10852 | −6633 | −894 | −1115 | −497 | −1778 | * | * | | | | | | | | | | | | |
| 7 | 792 | 1826 | −1378 | −706 | 28 | −760 | −788 | 1527 | −1596 | −1765 | −2367 | −3947 | −2104 | −3614 | −48 | −923 | −682 | 1628 | 2029 | 448 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 8 | −82 | −4264 | −2878 | −196 | −734 | −3962 | −1103 | −181 | 173 | −488 | −3371 | 1298 | −1348 | −374 | 377 | 1183 | 1579 | −1092 | −885 | 239 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | −1004 | −3175 | −2057 | −4080 | 1557 | −872 | 111 | 642 | −720 | −106 | 59 | −2250 | 2360 | −1960 | 1436 | −3642 | −3110 | 213 | −3614 | −411 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 10 | 469 | −3646 | 1830 | −1215 | −3710 | −926 | −2951 | −1834 | −1825 | 1574 | −113 | −340 | 682 | −2700 | −3180 | −874 | 116 | −674 | 483 | −939 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10851 | −11893 | −894 | −1115 | −1128 | −882 | * | * | | | | | | | | | | | | |
| 11 | −1416 | 3651 | 1620 | −1375 | −4724 | 2307 | −2578 | −4472 | −448 | −2264 | −1199 | −1321 | −575 | −807 | −1735 | −1768 | −1373 | −4027 | −4593 | −1259 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −161 | −10851 | −3254 | −894 | −1115 | −1128 | −882 | * | * | | | | | | | | | | | | |
| 12 | −1295 | −4120 | −2737 | −1714 | −205 | 2076 | 1299 | −1253 | 1114 | −2041 | −3227 | 334 | −3911 | −569 | −464 | 413 | −880 | −454 | −4345 | 1385 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10691 | −11733 | −894 | −1115 | −293 | −2443 | * | * | | | | | | | | | | | | |
| 13 | −470 | −4304 | −1797 | 11 | −1753 | −1078 | −911 | −1641 | 383 | −317 | 772 | −1721 | −40 | −1155 | −362 | 457 | 1924 | 1043 | −4516 | −305 | 13 |
| — | −149 | −500 | 232 | 43 | −379 | 399 | 105 | −625 | 210 | −466 | −721 | 276 | 395 | 45 | 95 | 359 | 117 | −366 | −295 | −250 | |
| E | −1283 | −4009 | −924 | −287 | −2469 | −1321 | −737 | * | * | | | | | | | | | | | | |
| 14 | 386 | −3485 | −693 | 1125 | −3806 | −2987 | 473 | −3557 | 1210 | −1732 | 724 | 421 | 1542 | −527 | −366 | −184 | 981 | −1507 | −3669 | −2986 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −9764 | −10806 | −894 | −1115 | −276 | −2521 | * | * | | | | | | | | | | | | |
| 15 | 324 | −4311 | −1829 | −832 | −4633 | −1377 | 1040 | −4383 | 1419 | −4328 | −3401 | 263 | −3905 | 1551 | 2160 | −468 | 1030 | −981 | −4495 | −3812 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10733 | −11775 | −894 | −1115 | −1254 | −784 | * | * | | | | | | | | | | | | |
| 16 | −584 | −4353 | 532 | 538 | −4674 | −3855 | −134 | −1819 | 974 | −2290 | −109 | 159 | 1342 | 1589 | −52 | 523 | 362 | −1331 | −136 | −812 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10781 | −11823 | −894 | −1115 | −1151 | −863 | * | * | | | | | | | | | | | | |
| 17 | 814 | −99 | −1760 | −4886 | −715 | −204 | −3597 | 1183 | −4481 | −184 | 1938 | −4371 | −4775 | −4104 | −4282 | −658 | 414 | 2229 | −3462 | −3120 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10812 | −11855 | −894 | −1115 | −1876 | −459 | * | * | | | | | | | | | | | | |
| 18 | −774 | −3016 | −5410 | −1912 | −2972 | −4709 | −3574 | 2228 | −1800 | 404 | 2287 | −4319 | −1612 | −653 | −1945 | −2353 | 218 | 897 | 3465 | −3128 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10812 | −11855 | −894 | −1115 | −1876 | −459 | * | * | | | | | | | | | | | | |
| 19 | 727 | −3011 | −5526 | −4891 | −648 | 1737 | −3605 | −1679 | −4487 | 526 | −1018 | −4377 | −4781 | −4111 | −4289 | −939 | 2234 | 937 | −3471 | −3129 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10812 | −11855 | −894 | −1115 | −690 | −1395 | * | * | | | | | | | | | | | | |
| 20 | −1717 | −756 | −5658 | −1965 | 1269 | −4871 | −3753 | 2108 | −4629 | −2957 | −768 | −4517 | −4917 | −4256 | −4433 | −3960 | −1820 | 2537 | −3615 | 2352 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10845 | −11887 | −894 | −1115 | −436 | −1938 | * | * | | | | | | | | | | | | |
| 21 | −2321 | −7037 | −329 | −3347 | −7601 | −929 | −4630 | −7605 | −2395 | −7451 | −6895 | 4277 | −5693 | −4335 | −6111 | −4929 | −5422 | −6947 | −7650 | −6528 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −13 | −10865 | −6869 | −894 | −1115 | −701 | −1378 | * | * | | | | | | | | | | | | |
| 22 | −1892 | −4662 | −3 | −1370 | −4978 | 3255 | −275 | −4734 | −1271 | −4675 | −3757 | 801 | −1905 | −660 | −58 | −2105 | −3115 | −4282 | −4842 | −4146 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10853 | −11895 | −894 | −1115 | −1072 | −931 | * | * | | | | | | | | | | | | |
| 23 | −378 | −4418 | −622 | 153 | −4739 | −632 | −910 | −2482 | 552 | −2631 | 1667 | 225 | −4012 | 2761 | −298 | 667 | 573 | −4040 | −4601 | −1014 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10853 | −11895 | −894 | −1115 | −1072 | −931 | * | * | | | | | | | | | | | | |
| 24 | −2010 | −91 | −5560 | −4924 | 3056 | −2321 | −3633 | 402 | −4519 | 687 | 581 | −4408 | −4812 | −4142 | −4319 | −111 | −3155 | 201 | 1866 | 2139 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10853 | −11895 | −894 | −1115 | −1072 | −931 | * | * | | | | | | | | | | | | |
| 25 | −2227 | −5400 | −8282 | −7686 | −2076 | −7846 | −6617 | −2132 | −7425 | 796 | −590 | −7563 | 3949 | −6406 | −6998 | −7107 | −5767 | −1964 | −5469 | −5579 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10853 | −11895 | −894 | −1115 | −1072 | −931 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −132 | −557 | −5641 | −5096 | −3574 | 3520 | −4042 | −1708 | −4700 | −1909 | −2812 | −1625 | −1215 | −4408 | −2174 | −3894 | −3443 | −2997 | −480 | −3716 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10853 | −11895 | −894 | −1115 | −1072 | −931 | * | * | | | | | | | | | | | | |
| 27 | −2088 | −5019 | −1888 | −4568 | −7184 | −4870 | −5397 | −7017 | −5754 | −7147 | 164 | −4557 | 4187 | −1519 | −6160 | −4377 | −2076 | −5969 | −7339 | −6850 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −14 | −10853 | −6730 | −894 | −1115 | −1072 | −931 | * | * | | | | | | | | | | | | |
| 28 | 692 | −4366 | −588 | −87 | −4669 | −3918 | −1291 | −326 | −666 | −143 | −1741 | −958 | −300 | −1115 | −204 | −1824 | 2781 | −461 | −4561 | −3889 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10839 | −11881 | −894 | −1115 | −1393 | −691 | * | * | | | | | | | | | | | | |
| 29 | −5499 | −5012 | −8000 | −7494 | −602 | −7648 | −6702 | 3195 | −7291 | 1729 | −170 | −7323 | −7156 | −6549 | −7035 | −2824 | −5422 | 620 | −5717 | −5699 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10839 | −11881 | −894 | −1115 | −1393 | −691 | * | * | | | | | | | | | | | | |
| 30 | −2934 | −4401 | −465 | 1353 | −1178 | −3908 | 979 | 449 | 826 | −4416 | −3491 | 1028 | −2043 | −459 | 2050 | −1993 | −382 | 421 | −844 | −152 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10839 | −11881 | −894 | −1115 | −1393 | −691 | * | * | | | | | | | | | | | | |
| 31 | 1934 | 1122 | −2366 | −4911 | −132 | −4750 | −3621 | −629 | −4506 | 775 | 116 | −4396 | −4800 | −1965 | −4306 | −1373 | −3143 | 2136 | 2101 | −3144 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10839 | −11881 | −894 | −1115 | −830 | −1193 | * | * | | | | | | | | | | | | |
| 32 | −2101 | 1532 | 1140 | −872 | −298 | −3924 | 528 | −2151 | 912 | −3074 | −182 | 640 | −482 | 333 | 2131 | −1689 | 487 | −344 | −567 | −1685 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −23 | −10851 | −6021 | −894 | −1115 | −1103 | −904 | * | * | | | | | | | | | | | | |
| 33 | −827 | −4395 | −2773 | 2184 | −4714 | −3899 | −2558 | −4464 | 1284 | −2742 | −3484 | −158 | −3992 | 924 | 232 | 102 | 514 | −1412 | 2814 | 153 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10829 | −11872 | −894 | −1115 | −1208 | −818 | * | * | | | | | | | | | | | | |
| 34 | −5176 | −6763 | −43 | −3398 | −6837 | 3467 | −4621 | −7476 | −5119 | −7323 | −741 | 1680 | −5683 | −4367 | −6094 | −4887 | −5357 | −6819 | −7120 | −1366 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10837 | −11879 | −894 | −1115 | −1438 | −665 | * | * | | | | | | | | | | | | |
| 35 | −2933 | −4406 | 3549 | −78 | −4727 | −3906 | −1400 | −4478 | 186 | −4422 | −3495 | −512 | −4000 | 300 | −504 | −1211 | −1161 | −2512 | 335 | −1364 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10837 | −11879 | −894 | −1115 | −831 | −1192 | * | * | | | | | | | | | | | | |
| 36 | −1670 | −4410 | 386 | 857 | −485 | −3918 | −2577 | −2510 | −913 | −3325 | −1087 | 1537 | −1164 | 11 | 1763 | −414 | 1789 | −2178 | 1675 | −1012 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 37 | −690 | −3778 | −6500 | −5937 | −1526 | −5834 | −4854 | 1496 | −5603 | 1152 | −3032 | −5484 | −5824 | −5276 | −5459 | −2785 | −364 | 2936 | −4667 | −4304 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 38 | −1512 | −4165 | −1476 | 474 | −1430 | −2331 | −546 | 1217 | −115 | −1228 | −3282 | −1120 | −4085 | −230 | 220 | −1691 | 1021 | 2193 | 1029 | −1649 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 39 | −1621 | −4713 | −7850 | −7468 | −1737 | −7629 | −7231 | 2607 | −7375 | 733 | −202 | −7288 | −7283 | −7034 | −7372 | −6967 | −5188 | 2728 | −6421 | −6162 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 40 | −2944 | −4413 | 1274 | −897 | −1696 | −3918 | 1777 | −1637 | 1063 | −1954 | −3502 | 2432 | −4011 | −2117 | 1654 | −710 | 458 | −4034 | −4597 | −851 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 41 | −4393 | −4126 | −6759 | −6145 | 962 | −6057 | −4906 | 314 | −5779 | 487 | −9 | −5707 | −5951 | −833 | −5542 | −5177 | −4322 | 3220 | −4514 | 558 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 42 | −1971 | −4247 | −1688 | −210 | 485 | −3967 | 1689 | 1639 | −63 | −1535 | −3356 | −1394 | −1912 | −492 | −352 | −472 | 1922 | 503 | −4476 | 423 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −8641 | −7558 | −8171 | −8559 | −8966 | −7501 | −8085 | −10112 | −8962 | −9478 | −9402 | 4460 | −7968 | −8777 | −8497 | −9028 | −8880 | −9666 | −7785 | −8900 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 44 | −742 | −4416 | −149 | −920 | −4737 | −1210 | 2771 | −4488 | 1447 | −4432 | −1252 | 2051 | −4010 | 1005 | 1314 | −119 | −1417 | −4038 | −4600 | −861 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10851 | −11893 | −894 | −1115 | −1128 | −882 | * | * | | | | | | | | | | | | |
| 45 | −39 | −3055 | −5576 | −4941 | −946 | −2095 | −3652 | 592 | −4536 | 2587 | 1116 | −4425 | −4828 | −4159 | −4336 | −419 | −1992 | 607 | −3516 | −3174 | 47 |
| — | −148 | −500 | 233 | 43 | −381 | 398 | 105 | −627 | 210 | −466 | −721 | 275 | 393 | 47 | 96 | 360 | 119 | −370 | −295 | −250 | |
| S | −2322 | −4617 | −397 | −606 | −1544 | −486 | −1805 | * | * | | | | | | | | | | | | |
| 46 | 120 | −2800 | −1180 | 310 | −3120 | −681 | 443 | −2869 | 1009 | 105 | 448 | 804 | 995 | 252 | 819 | 417 | −425 | −2421 | −2985 | −2303 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | −8855 | −9897 | −894 | −1115 | −20 | −6166 | * | * | | | | | | | | | | | | |
| 47 | −791 | −4429 | 1769 | −1100 | −4750 | −796 | −163 | −1510 | −129 | −4445 | −700 | 580 | 1831 | 854 | −305 | 187 | 1093 | −4051 | −528 | −992 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10865 | −11907 | −894 | −1115 | −701 | −1378 | * | * | | | | | | | | | | | | |
| 48 | −1433 | −4421 | 677 | 2550 | −77 | −3932 | 527 | −4487 | −2172 | −3006 | −3511 | 1609 | −4025 | 769 | −1490 | −1939 | −874 | −1034 | −4607 | 1652 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10865 | −11907 | −894 | −1115 | −701 | −1378 | * | * | | | | | | | | | | | | |
| 49 | −753 | −4429 | −268 | 225 | −4750 | 1379 | −172 | −4500 | −2169 | −1978 | −3518 | 2284 | 1858 | −971 | −1706 | 113 | 266 | −2700 | −4612 | −3929 | 53 |
| — | −149 | −500 | 234 | 43 | −379 | 398 | 105 | −627 | 210 | −466 | −717 | 279 | 393 | 45 | 96 | 359 | 117 | −370 | −295 | −250 | |
| — | −72 | −4364 | −11907 | −71 | −4383 | −701 | −1378 | * | * | | | | | | | | | | | | |
| 50 | −1841 | −3063 | −5583 | −4947 | 733 | −4787 | −3659 | 594 | −4543 | −162 | 704 | −1400 | −4836 | −4167 | −4344 | −580 | 3061 | 1044 | −3525 | −3182 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10865 | −11907 | −894 | −1115 | −701 | −1378 | * | * | | | | | | | | | | | | |
| 51 | −466 | −3423 | −5778 | −5245 | −3598 | −1826 | −4116 | −1576 | −4883 | 260 | −2838 | −1486 | −5022 | −4527 | −4734 | 2157 | 2799 | −937 | −4088 | −3751 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 52 | −5952 | −5369 | −8479 | −7998 | −29 | −8328 | −7386 | 3042 | −7875 | 1000 | 2210 | −8026 | −7534 | −6889 | −7534 | −7725 | −5855 | 1515 | −5964 | −6099 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 53 | −4082 | −4758 | −5065 | −5434 | −7060 | −4844 | 5204 | −7114 | −6149 | −7277 | −6389 | −1123 | −5619 | −5733 | −6259 | −492 | 562 | −5885 | −7271 | −6884 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 54 | −5337 | −4951 | −7160 | −6860 | 842 | −6633 | −4073 | −841 | −6456 | −849 | −3798 | −5873 | −6567 | −5730 | −6110 | −2530 | −5257 | −946 | 5941 | −1031 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 55 | −2794 | −6705 | −1537 | −3284 | −7229 | −4998 | 5171 | −7156 | −4710 | −7036 | −6368 | 819 | −2948 | −365 | −5555 | −2068 | −2061 | −6559 | −7229 | −6228 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 56 | −8794 | −7589 | −8580 | −8967 | −9149 | 3866 | −8235 | −10213 | −9163 | −9555 | −9501 | −8901 | −8026 | −9034 | −8589 | −9262 | −9036 | −9777 | −7838 | −9165 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −17 | −10865 | −6479 | −894 | −1115 | −701 | −1378 | * | * | | | | | | | | | | | | |
| 57 | −654 | −3147 | −5678 | −5045 | 145 | −4888 | −3763 | 2427 | −4643 | 1763 | 1505 | −4535 | −4929 | −839 | −4443 | −1374 | −3269 | 1068 | −3614 | −3278 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10849 | −11891 | −894 | −1115 | −1174 | −845 | * | * | | | | | | | | | | | | |
| 58 | −1771 | −4399 | −349 | 332 | 886 | −3919 | 2340 | −659 | 203 | −366 | −1396 | −1217 | −592 | 1587 | 2065 | −802 | −2882 | −1683 | −4587 | −884 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10849 | −11891 | −894 | −1115 | −1174 | −845 | * | * | | | | | | | | | | | | |
| 59 | −1076 | −3078 | −5224 | −4608 | −3038 | −4709 | 683 | 446 | −1891 | 423 | 1796 | −1857 | −4762 | 3385 | −4181 | −1053 | −3139 | 993 | −3531 | −3180 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10849 | −11891 | −894 | −1115 | −1174 | −845 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −3019 | −1185 | −1086 | −1850 | 16 | −4125 | 220 | −1687 | 345 | 367 | −890 | 620 | 2350 | −2492 | 2080 | −770 | −1886 | −2028 | −1145 | −873 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10849 | −11891 | −894 | −1115 | −1174 | −845 | * | * | | | | | | | | | | | | |
| 61 | −367 | −4407 | −678 | −688 | −89 | 1553 | −2576 | −2150 | 789 | −1245 | 305 | 955 | −399 | −1484 | 1861 | −330 | −1006 | −4028 | 808 | −3912 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10849 | −11891 | −894 | −1115 | −468 | −1851 | * | * | | | | | | | | | | | | |
| 62 | −654 | −4429 | −1014 | 739 | −4750 | −1694 | 229 | −2722 | −393 | −4445 | −700 | 2226 | −393 | −350 | −2676 | 714 | 2278 | −2884 | −4612 | −3929 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −613 | −10865 | −1533 | −894 | −1115 | −701 | −1378 | * | * | | | | | | | | | | | | |
| 63 | −1085 | 1558 | −4883 | −4256 | −1048 | 1280 | −3065 | −186 | −3879 | −1750 | −1716 | 1695 | 2333 | −3527 | −3725 | 875 | −2607 | −87 | 708 | −2624 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −10253 | −11295 | −894 | −1115 | −4427 | −69 | * | * | | | | | | | | | | | | |
| 64 | −2642 | −2597 | −1939 | −233 | 815 | −4104 | 264 | −392 | −3453 | −1215 | −551 | −3514 | −1868 | −537 | −3482 | −3156 | −77 | −2018 | 5257 | 1677 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −2 | −10253 | −11295 | −894 | −1115 | −1389 | −694 | * | * | | | | | | | | | | | | |
| 65 | 1670 | −3595 | −673 | −2308 | −3725 | −3794 | −931 | −1905 | −2204 | −3527 | 3734 | −798 | −3881 | 1935 | −2652 | 86 | −2646 | −2254 | −3906 | 660 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −10506 | −11548 | −894 | −1115 | −3838 | −105 | * | * | | | | | | | | | | | | |
| 66 | −7080 | −7102 | 4202 | −5675 | −8418 | −1957 | −6529 | −9063 | −7150 | −8642 | −8354 | −5998 | −7014 | −6525 | −7537 | −6994 | −7281 | −8494 | −7442 | −7997 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1 | −10506 | −11548 | −894 | −1115 | −3838 | −105 | * | * | | | | | | | | | | | | |
| 67 | −8283 | −7186 | −8187 | −8573 | −8761 | 3865 | −7853 | −9803 | −8774 | −9168 | −9092 | −8477 | −7638 | −8636 | −8208 | −8726 | −8546 | −9330 | −7470 | −8775 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −26 | −10506 | −5879 | −894 | −1115 | −160 | −3255 | * | * | | | | | | | | | | | | |
| 68 | 366 | −3025 | −5435 | −4806 | −983 | −4721 | −847 | −2518 | −4421 | −697 | 578 | −826 | 1979 | −862 | −4255 | −1369 | −337 | 2703 | −443 | −3136 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10823 | −11866 | −894 | −1115 | −794 | −1241 | * | * | | | | | | | | | | | | |
| 69 | 872 | −4361 | 1598 | 254 | −2053 | −936 | −2588 | −4393 | −2178 | −629 | −1222 | 735 | 2272 | −810 | −1730 | −594 | −1868 | −259 | −4558 | −773 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10846 | −11888 | −894 | −1115 | −1247 | −789 | * | * | | | | | | | | | | | | |
| 70 | −1463 | −3993 | −1412 | −1713 | 600 | 2909 | −37 | −3746 | −2633 | −3922 | 1335 | −2936 | −4276 | −23 | −3084 | −1613 | −3059 | −3507 | −4296 | 2359 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −170 | −10846 | −3173 | −894 | −1115 | −1247 | −789 | * | * | | | | | | | | | | | | |
| 71 | −3054 | −2881 | −5395 | −4760 | −2835 | 1140 | −488 | 2063 | −4355 | 556 | −256 | −383 | −4651 | −3979 | −4157 | −1288 | −2994 | 2214 | 1115 | −2997 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10677 | −11719 | −894 | −1115 | −108 | −3792 | * | * | | | | | | | | | | | | |
| 72 | −962 | −313 | −7130 | −7336 | −6852 | −4756 | −6350 | −6604 | −6973 | −6887 | −5984 | −5546 | 1771 | −1503 | −6647 | 1278 | 3262 | −1077 | −7125 | −7034 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 73 | −1172 | −4432 | −1322 | 718 | 625 | −2444 | 1254 | −4500 | −2179 | −4447 | 1116 | 720 | −4030 | 3584 | −2687 | −761 | −1315 | −4053 | −4617 | −3935 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 74 | −845 | 4887 | 824 | −2742 | −1455 | −2075 | −217 | −1610 | −1025 | −2423 | −1504 | −403 | −107 | −1219 | −92 | −3109 | −1745 | −2518 | 871 | −490 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 75 | 30 | −3101 | −5174 | −2252 | −3062 | 163 | −768 | −626 | −4236 | −1628 | 374 | −4226 | 3544 | −1908 | −4170 | −2184 | −901 | −186 | −3552 | −1136 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 76 | −3891 | −3639 | −3229 | −5712 | −1479 | −5594 | −4556 | 3682 | −5354 | −372 | −520 | −5241 | −5598 | −5004 | −5189 | −2581 | −1066 | 568 | −4379 | −4028 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −1 | −10865 | −11907 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | 733 | −1619 | −2807 | 98 | −4738 | −1969 | −2591 | −4486 | 473 | −2216 | −409 | 505 | 2352 | 2094 | −30 | −1484 | −591 | −1039 | −4606 | −1215 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 78 | −351 | −3765 | −4934 | −4433 | −4160 | −4613 | −4050 | −2347 | −2335 | −4042 | −1526 | −1428 | 3857 | −4050 | −4409 | −406 | 511 | −1916 | −4569 | −4191 | 83 |
| — | −149 | −500 | 233 | 43 | −381 | 398 | 106 | −626 | 211 | −466 | −720 | 276 | 394 | 45 | 97 | 359 | 117 | −369 | −294 | −249 | |
| T | −32 | −5539 | −11907 | −147 | −3369 | −701 | −1378 | * | * | | | | | | | | | | | | |
| 79 | −3225 | −4716 | −1179 | −1636 | −1694 | 3435 | −13 | −4787 | −642 | −4728 | −3813 | 284 | −4247 | −1234 | −2149 | −2185 | −1591 | −4336 | −4896 | −4199 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 80 | 396 | −4429 | −210 | 1600 | −4750 | 1016 | 327 | −4501 | 264 | −4445 | −3518 | −726 | −4023 | 2011 | −1995 | 212 | 495 | −4051 | 1597 | −3930 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 81 | −1640 | −4428 | −386 | −245 | −956 | −2322 | 465 | −4499 | 172 | −4444 | −916 | 1477 | −4023 | −1066 | −570 | 1858 | 1991 | −1225 | −4611 | −229 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 82 | −4286 | −4253 | −5712 | −5004 | 2990 | −5550 | −3713 | −3833 | 882 | −1330 | 215 | −1225 | −5568 | −395 | 654 | −4655 | −4194 | −3750 | 3227 | 2826 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 83 | −1218 | −4355 | 443 | −817 | −4643 | −3951 | 130 | −1072 | −1755 | −501 | −3453 | −1215 | −4043 | −246 | 66 | −73 | 2819 | 848 | −4559 | −1360 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 84 | −6513 | −5839 | −7592 | −7662 | −568 | −7304 | −843 | −1177 | −7215 | −5286 | −5137 | −6164 | 512 | −2389 | −6728 | −6501 | −6411 | −1029 | −3212 | 4671 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 85 | −1574 | −4429 | −171 | 768 | −4750 | −3930 | −1288 | −978 | 1394 | −2991 | −3518 | 1702 | −4023 | 615 | 2131 | −590 | 266 | −1386 | −4612 | −393 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 86 | −5802 | −5327 | −7673 | −7353 | 4116 | −7229 | −4665 | 200 | −6989 | −685 | −1517 | −6483 | −6959 | −6098 | −6582 | −6413 | −5695 | −742 | 1553 | 1262 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 87 | −1152 | −4428 | 444 | −915 | −4749 | −3930 | −1325 | −449 | 699 | −1600 | −3518 | 236 | 919 | 2009 | 792 | −1903 | 2083 | −2693 | −4612 | −3929 | 93 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 88 | 1241 | −3091 | −5617 | −4983 | −409 | −4824 | −3700 | 1271 | −4581 | 341 | −920 | 13 | 402 | −4205 | −4383 | −3910 | −1259 | 2468 | −3564 | −3221 | 94 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 89 | −1344 | −4429 | 1235 | 248 | −4750 | −2174 | 323 | −1990 | 1375 | −2678 | −1205 | 564 | 550 | −372 | 588 | −427 | 1515 | −562 | −4612 | −606 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 90 | −2956 | −4429 | 1633 | −247 | −4750 | 935 | −24 | −2470 | −479 | −2113 | −3518 | 166 | −1945 | 3198 | −343 | −2836 | −914 | −1451 | −4612 | −3929 | 96 |
| — | −148 | −500 | 234 | 44 | −381 | 399 | 105 | −627 | 210 | −466 | −721 | 275 | 393 | 45 | 96 | 359 | 117 | −370 | −295 | −250 | |
| S | −929 | −4471 | −1219 | −76 | −4286 | −701 | −1378 | * | * | | | | | | | | | | | | |
| 91 | −865 | −3728 | −112 | 442 | −1037 | −3230 | −1890 | −3798 | −1471 | −3744 | −2818 | −259 | 1320 | 3399 | −272 | 246 | −2197 | −1521 | −3912 | −3230 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2 | −10055 | −11097 | −894 | −1115 | −66 | −4474 | * | * | | | | | | | | | | | | |
| 92 | 1697 | −4410 | −1772 | 612 | −4728 | −1207 | −1313 | 728 | −819 | −4424 | −3500 | −314 | −741 | −2119 | 917 | 749 | −1402 | −1312 | −4595 | 1959 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −10851 | −11893 | −894 | −1115 | −1128 | −882 | * | * | | | | | | | | | | | | |
| 93 | 540 | −467 | −7106 | −7285 | −7142 | 3540 | −6341 | −6946 | −2214 | −7185 | −6227 | −5536 | −5561 | −6363 | −1018 | −1535 | −2315 | −5666 | −7318 | −7284 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | −3927 | −4529 | −7136 | −7486 | −976 | −4813 | −6368 | −7004 | −7199 | −7205 | −6307 | −5620 | −5624 | −6626 | −6814 | 1436 | 3741 | −5730 | −6908 | −6416 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 95 | −1119 | 1725 | −5550 | −4914 | 1791 | −4759 | 1334 | −1673 | −4511 | 1396 | −2243 | −953 | −4809 | −4135 | −4314 | −114 | −1 | −1704 | −3497 | 3017 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −1128 | −882 | * | * | | | | | | | | | | | | |
| 96 | −4126 | −3894 | −6287 | −5771 | 1941 | −5580 | −3791 | −3402 | −5362 | −636 | −696 | −2739 | −5605 | −4874 | −5117 | −3058 | −2632 | −2461 | 5783 | −548 | 103 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10851 | −11893 | −894 | −1115 | −486 | −1805 | * | * | | | | | | | | | | | | |
| 97 | −7448 | −6392 | −7885 | −8223 | 336 | −7761 | −3965 | −2924 | −7783 | −2646 | −5608 | −6383 | −7606 | −6508 | −7149 | −7008 | −7298 | −1268 | 4244 | 4357 | 104 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 98 | −7417 | −6410 | −7790 | −8084 | 1351 | −7691 | 5260 | −6404 | −7407 | −5713 | −5801 | −6335 | −7574 | −6432 | −2461 | −3593 | −7285 | −6550 | −3208 | −1201 | 105 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 99 | 1920 | −4621 | −150 | −5966 | −7252 | −298 | −6140 | −7094 | −6742 | −7316 | −6374 | −5216 | 2399 | −6095 | −6715 | 2236 | −4437 | −5798 | −7455 | −7285 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 100 | −2397 | −4520 | −1858 | −3763 | −1655 | −4603 | 5135 | −5020 | −4022 | −5206 | −4421 | −1185 | −2794 | −3828 | −4454 | 236 | −1290 | −2520 | −5562 | −5046 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 101 | 362 | −375 | −1273 | −2394 | 1270 | −4740 | −3599 | 709 | −2689 | −125 | 597 | −2145 | 410 | −2194 | −4242 | 1170 | 1116 | 113 | −3532 | 1372 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 102 | −125 | −445 | 122 | −1448 | −4743 | 1137 | 2256 | −2539 | −260 | −676 | 1329 | −237 | −842 | −204 | −464 | 1740 | −2895 | −2539 | −4609 | −3927 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 103 | −88 | −3350 | −1412 | −1926 | 1199 | 1165 | 1107 | −2911 | −3357 | 446 | 1597 | −732 | −356 | −3204 | −3607 | −13 | −220 | −1353 | 3671 | −3359 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −912 | −10865 | −1095 | −894 | −1115 | −701 | −1378 | * | * | | | | | | | | | | | | |
| 104 | −1331 | −3472 | −2111 | −294 | −3721 | −3190 | 1621 | −1670 | 538 | 1755 | 1323 | 754 | −3281 | 248 | −351 | −130 | −14 | −409 | −3701 | −3065 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −100 | −9955 | −3927 | −894 | −1115 | −4836 | −51 | * | * | | | | | | | | | | | | |
| 105 | −944 | −2778 | −2636 | 520 | −2847 | −3377 | −2104 | −987 | −1943 | −2683 | 731 | −2265 | −3460 | −1858 | 2703 | −174 | 2182 | −344 | −3148 | −2673 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −842 | −9857 | −1181 | −894 | −1115 | −4934 | −48 | * | * | | | | | | | | | | | | |
| 106 | 2906 | −2523 | −2573 | −2086 | −3357 | 628 | −2193 | −3007 | −1976 | −3192 | 687 | −2138 | −781 | 141 | −2367 | −500 | 109 | −2597 | −3547 | −3063 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −122 | −9020 | −3663 | −894 | −1115 | −495 | −1783 | * | * | | | | | | | | | | | | |
| 107 | −2694 | −4163 | −1082 | 1335 | −4488 | −3654 | 1950 | −4236 | −47 | −4176 | −3253 | −2289 | −1855 | 3647 | −406 | −2572 | −1256 | −3788 | −4339 | 54 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10490 | −11532 | −894 | −1115 | −3887 | −101 | * | * | | | | | | | | | | | | |
| 108 | −1708 | −4123 | −2513 | 903 | −4447 | −3632 | 279 | −4193 | 160 | −4136 | −526 | 148 | −3724 | 2542 | 1893 | −2542 | −2598 | −1565 | −4302 | 2632 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10490 | −11532 | −894 | −1115 | −3887 | −101 | * | * | | | | | | | | | | | | |
| 109 | 1872 | −2805 | −4550 | −1229 | −506 | 912 | −3149 | −2317 | −3674 | −768 | 213 | −3731 | −34 | 1130 | −3698 | −1129 | 394 | 1330 | 36 | −2888 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1525 | −10490 | −617 | −894 | −1115 | −3887 | −101 | * | * | | | | | | | | | | | | |
| 110 | 589 | −2090 | −3930 | −3394 | 404 | 739 | 917 | −1632 | −3089 | −1904 | −1307 | −2995 | −3663 | −2740 | −3038 | −2692 | −172 | −1554 | 1830 | 3819 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | −8969 | −10011 | −894 | −1115 | −21 | −6128 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111 | 1957 | −4427 | 1420 | −896 | −923 | −2351 | −629 | −4498 | −97 | −2503 | 1953 | 1103 | −4023 | −463 | 831 | −561 | −1151 | −2910 | −4611 | −1765 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 112 | −3902 | −4513 | −7064 | −7422 | −7239 | 3500 | −6537 | −7076 | −7206 | −7332 | −6357 | −5601 | −5604 | −6629 | −6831 | −1885 | 1747 | −5737 | −7445 | −7437 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10865 | −11907 | −894 | −1115 | −701 | −1378 | * | * | | | | | | | | | | | | |
| 113 | −906 | −3054 | −5572 | −4936 | −1644 | 435 | −1236 | 281 | −4531 | 1944 | 1599 | −4421 | −4825 | 244 | −4331 | −3860 | −3168 | 1985 | −3511 | −1473 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 114 | 1346 | −3057 | −5522 | −4889 | 1379 | −1878 | 1897 | −2550 | −4495 | −605 | −541 | −4397 | −4817 | −4127 | 85 | −907 | −1012 | 406 | −3514 | 3175 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 115 | −1018 | −4518 | −7153 | −7509 | −7248 | 3755 | −6558 | −7082 | −7235 | −7339 | −6365 | −5624 | −5612 | −6658 | −6844 | −4168 | −1087 | −5744 | −7448 | −7452 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 116 | 2080 | −3055 | −5563 | −4928 | −128 | 151 | −3645 | −1729 | −4525 | 356 | 1517 | −4416 | 2170 | −4150 | −4328 | −822 | −559 | −695 | −3513 | −3171 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 117 | −5037 | −4706 | −7371 | −6759 | 2079 | −6735 | −5444 | 2386 | −6411 | 1579 | 1412 | −6377 | −6470 | −5721 | −6105 | −5880 | −4942 | 333 | 1874 | 550 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 118 | −3225 | −3054 | −5557 | −4922 | −1637 | −4771 | −28 | 2846 | −2538 | 142 | −919 | −932 | −4821 | −2162 | −242 | −3855 | −798 | 2048 | −3511 | −399 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 119 | −5212 | −4683 | −7904 | −7590 | −407 | −7791 | −7817 | 3282 | −7576 | −1496 | −3835 | −7444 | −7457 | −7450 | −7726 | −7192 | −5199 | 2502 | −6985 | −6549 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 120 | −2957 | −4420 | 1065 | 1407 | −1703 | −3932 | 2008 | −4484 | 49 | −75 | −3510 | 1343 | −4025 | −2132 | 1619 | −1270 | −1198 | −1991 | −1101 | 1426 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10865 | −11907 | −894 | −1115 | −701 | −1378 | * | * | | | | | | | | | | | | |
| 121 | −337 | −4428 | 2106 | −907 | −4749 | 800 | −2588 | −4500 | −988 | −2493 | −974 | −57 | 2532 | −436 | −1532 | 179 | −1429 | −2693 | −4612 | −3929 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1 | −10865 | −11907 | −894 | −1115 | −701 | −1378 | * | * | | | | | | | | | | | | |
| 122 | −30 | −388 | 403 | 207 | −4750 | −1589 | −705 | −2471 | 1571 | −1483 | −1727 | −1870 | 2164 | −894 | 1717 | −680 | −1014 | −4051 | −4612 | −3929 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10865 | −11907 | −894 | −1115 | −701 | −1378 | * | * | | | | | | | | | | | | |
| 123 | 1127 | −4429 | 305 | 968 | −1741 | −1204 | −593 | −4501 | 874 | −987 | −3518 | 1015 | 748 | 21 | −367 | 331 | −369 | −1475 | −4612 | −1273 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10865 | −11907 | −894 | −1115 | −701 | −1378 | * | * | | | | | | | | | | | | |
| 124 | −969 | −4427 | 965 | 588 | −1263 | 1156 | −679 | −637 | −827 | −1222 | −3517 | −34 | 1120 | −279 | −477 | 1266 | −402 | −1402 | −4611 | −3929 | 131 |
| — | * | * | * | * | * | * | * | * | * | * | * | * | * | * | * | * | * | * | * | * | |
| H | * | * | * | * | * | * | * | * | 0 | | | | | | | | | | | | |
| // | | | | | | | | | | | | | | | | | | | | | |

```
HMMER2.0        [2.3.2]
NAME Flavodoxin_1
ACC             PF00258.17
DESC Flavodoxin
LENG            170
ALPH            Amino
RF              no
CS              yes
MAP             yes
COM             hmmbuild -F HMM_ls.ann SEED.ann
COM             hmmcalibrate --seed 0 HMM_ls.ann
NSEQ            93
DATE            Thu Apr 24 21:29:35 2008
CKSUM           2289
GA              6.3000 6.3000;
TC              6.7000 6.7000;
NC              6.2000 6.2000;
XT              -8455  -4  -1000  -1000  -8455  -4  -8455  -4
NULT            -4  -8455
NULE            595  -1558  85  338  -294  453  -1158  197  249  902  -1085  -142  -21  -313  45  531  201  384  -1998  -644
EVD             -68.967041  0.218391
HMM      A       C       D       E       F       G       H       I       K       L       M       N       P       Q       R       S       T       V       W       Y
        m->m    m->i    m->d    i->m    i->i    d->m    d->d    b->m    m->e
         -20      *    -6151
1      -5631   -5102   -8327   -8015   -5580   -8217   -8285    3112   -8005     526   -4262   -7873   -7883   -7887   -8161   -7622   -5618    2474   -7444   -7016     1
—       -149    -500     233      43    -381     399     106    -626     210    -466    -720     275     394      45      96     359     117    -369    -294    -249
E         -1  -11295  -12337    -894   -1115    -701   -1378     -20       *
2      -2071   -3517   -6045   -5412    2586   -2178   -4128    1673   -5009    1531    -909   -4899   -5298   -4631   -4810   -4339   -1781    1672   -3988   -1124     2
—       -149    -500     233      43    -381     399     106    -626     210    -466    -720     275     394      45      96     359     117    -369    -294    -249
E         -1  -11295  -12337    -894   -1115    -701   -1378       *       *
3      -6665   -6122   -8005   -8056    2649   -7560   -4425   -1177   -7638   -5604   -5451   -6585   -7551   -6658   -7162   -1002   -2718   -1547   -3711    4331     3
—       -149    -500     233      43    -381     399     106    -626     210    -466    -720     275     394      45      96     359     117    -369    -294    -249
E         -1  -11295  -12337    -894   -1115    -701   -1378       *       *
4       1566   -4647    1109   -4441   -4656    2591    -832   -4681   -4643   -4933   -4242   -4480   -5518   -4407   -4965    -656   -4277   -1954    1575    1820     4
—       -149    -500     233      43    -381     399     106    -626     210    -466    -720     275     394      45      96     359     117    -369    -294    -249
E         -1  -11295  -12337    -894   -1115    -701   -1378       *       *
5      -4457   -5055   -7645   -8001   -7744   -5329   -7062   -7618   -7737   -7860   -6900   -6160   -6140   -7178   -7348    3219    2463   -6288   -7890   -7929     5
—       -149    -500     233      43    -381     399     106    -626     210    -466    -720     275     394      45      96     359     117    -369    -294    -249
S         -1  -11295  -12337    -894   -1115    -701   -1378       *       *
6      -1138   -4818     595    1081   -5138    -828   -2981   -1340   -1203   -1405    2824      25   -4415    2432    -478    -776     778   -2350   -5002   -4320     6
—       -149    -500     233      43    -381     399     106    -626     210    -466    -720     275     394      45      96     359     117    -369    -294    -249
S         -1  -11295  -12337    -894   -1115    -701   -1378       *       *
7      -3680   -3586   -5562   -4960   -3458    -768      17   -3095   -4632   -1187    -830   -4647   -5220    -592   -4589     367    3196   -3009    1476    2367     7
—       -149    -500     233      43    -381     399     106    -626     210    -466    -720     275     394      45      96     359     117    -369    -294    -249
S         -1  -11295  -12337    -894   -1115    -701   -1378       *       *
8      -5101    -611   -3900   -1856   -7333    3710    -779   -7639   -5724   -7629   -6939    -805   -6082   -5116   -6396   -2522   -5409   -6771   -7561   -1486     8
—       -149    -500     233      43    -381     399     106    -626     210    -466    -720     275     394      45      96     359     117    -369    -294    -249
C         -1  -11295  -12337    -894   -1115    -701   -1378       *       *
```

-continued

| | | | | | | | | | | | | | | | | | | | | | |
|---|---|---|---|---|---|---|---|---|---|---|---|---|---|---|---|---|---|---|---|---|---|
| 9 | −1200 | −4812 | −3200 | −2652 | −125 | −1423 | 2232 | −4877 | 933 | −4826 | −3903 | 2660 | −4418 | −21 | −641 | 17 | 1841 | −2737 | −4998 | −1445 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 10 | 2165 | −343 | −7514 | −7608 | −6513 | −1458 | −6467 | −617 | −7212 | −6456 | −5689 | −5927 | −5949 | −6698 | −6869 | 459 | 2825 | 164 | −6903 | −6710 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 11 | −96 | −4819 | −1986 | 3042 | −5139 | −4322 | −1231 | −4889 | 407 | −1250 | −908 | −2958 | −4416 | 1116 | 753 | −1099 | −3287 | −2611 | −5003 | −1094 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 12 | 576 | −4820 | 868 | −576 | −5141 | 247 | −2980 | −4891 | 1644 | −2030 | 1311 | −27 | −4415 | 507 | 425 | −750 | 978 | −1450 | −579 | −14 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 13 | −651 | −3473 | −5994 | −5358 | 724 | −5197 | −4069 | 1328 | −4954 | 1272 | 2735 | −4843 | −5245 | −4575 | −1903 | −4282 | −919 | 1608 | −3932 | 1598 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 14 | 3618 | −4903 | −7693 | −8036 | −7579 | −5194 | −6972 | −7248 | −7650 | −7606 | 101 | −6039 | −6011 | −7079 | −7244 | −1632 | −4779 | −2063 | −7833 | −7810 | 14 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 15 | −3348 | −4821 | −474 | 2311 | −1653 | −1203 | 571 | −4893 | 1939 | −4837 | −832 | 573 | −4415 | 1146 | 800 | −1336 | −3287 | −4443 | 714 | −1510 | 15 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 16 | 1579 | −444 | −1236 | 768 | −5127 | −4324 | 154 | −1425 | 573 | −98 | −378 | −1478 | −4417 | 1214 | 1203 | 84 | −311 | −1513 | −4997 | −1652 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 17 | −287 | −3639 | −6187 | −629 | −398 | −5407 | −4292 | 2532 | −5163 | 1915 | 271 | −5054 | −5444 | −4785 | −4967 | −2123 | −3772 | 857 | −4141 | −3803 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 18 | 2126 | 1084 | −3242 | 332 | −1672 | 490 | 1044 | −1175 | 694 | −2396 | −3837 | −587 | −4438 | 96 | −207 | −119 | −1565 | −1543 | −249 | −1199 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 19 | 258 | −4831 | 1423 | 2262 | −5152 | −2060 | −2988 | −4902 | 1803 | −4846 | −3920 | −1537 | −4422 | −186 | 1040 | −1113 | −861 | −4453 | −5014 | −4330 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 20 | −355 | −4798 | 8 | 1547 | −5109 | 1942 | −2987 | 460 | −134 | −507 | 42 | −2967 | −4421 | 917 | −454 | −1229 | −697 | −1546 | −4988 | −4312 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 21 | 1715 | −3531 | −6059 | −5425 | 1510 | −668 | −4141 | 1214 | −5023 | 1927 | −435 | −4912 | −5310 | −4642 | −4823 | −2376 | −3650 | −312 | −3998 | −3659 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −58 | −11295 | −4679 | −894 | −1115 | −701 | −1378 | * | * | | | | | | | | | | | | |
| 22 | −132 | −4768 | −321 | 951 | −5089 | 770 | 489 | −2026 | 1194 | −2667 | 1280 | 326 | −1744 | 667 | 796 | 446 | −436 | −1301 | −4951 | −4269 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −237 | −11237 | −2725 | −894 | −1115 | −944 | −1058 | * | * | | | | | | | | | | | | |
| 23 | 1160 | −4581 | −94 | 1963 | −4902 | −1249 | −2740 | −2278 | 339 | −2387 | −3670 | −236 | −4175 | 461 | 745 | 1024 | −924 | −1049 | −4764 | −4082 | 23 |
| — | −149 | −500 | 233 | 43 | −381 | 398 | 106 | −626 | 210 | −466 | −721 | 275 | 394 | 45 | 96 | 361 | 117 | −369 | −294 | −249 | |
| C | −135 | −5579 | −3876 | −136 | −3474 | −307 | −2385 | * | * | | | | | | | | | | | | |
| 24 | 1337 | 854 | −1280 | 609 | −5019 | −310 | 1718 | −1938 | 98 | −876 | −731 | −540 | −1814 | 46 | 1357 | 33 | −1515 | −812 | −4884 | 166 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −14 | −11168 | −6765 | −894 | −1115 | −2086 | −388 | * | * | | | | | | | | | | | | |
| 25 | 435 | −4691 | 688 | −398 | −360 | 2718 | −689 | −2278 | −799 | −1227 | −3783 | −961 | −1558 | −1174 | −1563 | −1656 | −1813 | −1398 | −4880 | 337 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −198 | −11173 | −2970 | −894 | −1115 | −1775 | −498 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −165 | −4348 | −683 | −375 | 2476 | 954 | 1446 | −216 | −603 | 490 | 1726 | −1323 | −1461 | −833 | −1635 | −3038 | −1720 | −3922 | −4588 | −325 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −363 | −11007 | −2172 | −894 | −1115 | −2404 | −302 | * | * | | | | | | | | | | | | |
| 27 | −202 | −4283 | 1293 | 1249 | −4604 | −536 | 499 | −4355 | 755 | −2049 | −3372 | 1215 | −417 | 441 | −192 | 264 | 30 | −256 | −4466 | −3783 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −165 | −10701 | −3220 | −894 | −1115 | −1349 | −719 | * | * | | | | | | | | | | | | |
| 28 | 1807 | −81 | −1952 | −4785 | −1146 | −841 | −3581 | −1117 | −1993 | −259 | −2226 | −4324 | 1029 | −4049 | −4244 | −524 | 399 | 2111 | −3479 | −3135 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10820 | −11862 | −894 | −1115 | −524 | −1715 | * | * | | | | | | | | | | | | |
| 29 | 54 | −4704 | 1543 | 411 | −5025 | −4205 | −2864 | −2691 | 1276 | −1604 | −3793 | −48 | −1871 | 585 | 1321 | −1903 | 792 | 898 | −4888 | −4205 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11168 | −12211 | −894 | −1115 | −116 | −3699 | * | * | | | | | | | | | | | | |
| 30 | −45 | −404 | 335 | 674 | −1451 | −1837 | −3269 | −763 | −710 | 770 | −1367 | −1687 | −747 | −2959 | −788 | −556 | 557 | 1974 | −4526 | −4014 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 31 | −127 | −3535 | −5369 | −1320 | 709 | −5075 | 1250 | 414 | −490 | 180 | 1963 | −1134 | −1821 | −1695 | −1033 | −2289 | −1756 | 2286 | −3981 | 364 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −16 | −11295 | −6544 | −894 | −1115 | −701 | −1378 | * | * | | | | | | | | | | | | |
| 32 | −474 | 2384 | 936 | 331 | −1484 | −2148 | 169 | −4878 | 617 | −4823 | −3896 | 1262 | −1973 | −1046 | 390 | 871 | 511 | 593 | −4990 | −4307 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11279 | −12322 | −894 | −1115 | −427 | −1965 | * | * | | | | | | | | | | | | |
| 33 | 943 | −3459 | −1345 | −5343 | 550 | −1483 | −4054 | 1565 | −4939 | 1120 | 2552 | −4828 | −1873 | −4562 | −4739 | −4267 | −1922 | 1551 | −3919 | −3577 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −11295 | −12337 | −894 | −1115 | −701 | −1378 | * | * | | | | | | | | | | | | |
| 34 | 249 | −4806 | 2083 | −268 | −222 | −1063 | 989 | −1868 | −323 | −1233 | 648 | −6 | 113 | −2527 | −3 | 408 | −745 | −4424 | 55 | 1271 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −11295 | −12337 | −894 | −1115 | −701 | −1378 | * | * | | | | | | | | | | | | |
| 35 | −1706 | −630 | 2301 | 1033 | −969 | −4322 | 1242 | −4891 | −445 | −523 | −262 | 1118 | −858 | 688 | 1100 | −1031 | −1873 | −2254 | −5003 | −4321 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −11295 | −12337 | −894 | −1115 | −701 | −1378 | * | * | | | | | | | | | | | | |
| 36 | 153 | −3920 | −272 | 194 | 683 | −4727 | −930 | −383 | −1774 | 784 | −680 | −849 | −4803 | −1320 | −1916 | −1517 | −533 | 1792 | −4306 | 2063 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11295 | −12337 | −894 | −1115 | −701 | −1378 | * | * | | | | | | | | | | | | |
| 37 | 506 | −719 | 2635 | 1241 | −5142 | −4322 | 73 | −4893 | −255 | −2847 | −3910 | 1021 | 401 | −2520 | −1047 | 202 | −843 | −4443 | −5004 | −4321 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −292 | −11295 | −2450 | −894 | −1115 | −701 | −1378 | * | * | | | | | | | | | | | | |
| 38 | 23 | −4541 | 964 | 1457 | −1216 | −1778 | −2718 | 161 | 707 | −2895 | 590 | −1112 | −163 | −265 | 163 | −951 | −685 | 160 | −4728 | 1536 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −404 | −11003 | −2038 | −894 | −1115 | −2959 | −199 | * | * | | | | | | | | | | | | |
| 39 | 671 | −4136 | 879 | −518 | −1330 | −334 | −2409 | −1435 | −69 | −1964 | −3235 | −890 | −349 | −1963 | −1050 | 1102 | 1707 | −455 | 1278 | 290 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −644 | −10632 | −1477 | −894 | −1115 | −4916 | −49 | * | * | | | | | | | | | | | | |
| 40 | 371 | 475 | 1463 | 294 | −189 | −3895 | −2734 | −34 | −3314 | 1048 | 1152 | −317 | −3951 | −3037 | −3305 | 782 | −284 | −450 | −2791 | 47 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1908 | −9990 | −449 | −894 | −1115 | −5579 | −31 | * | * | | | | | | | | | | | | |
| 41 | 152 | −3922 | 2729 | 1906 | −4193 | −2325 | −1569 | −4057 | −1651 | −3959 | −3204 | −936 | 1867 | −1211 | −2396 | −1906 | −2224 | −3551 | −4152 | −3235 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −344 | −8091 | −2262 | −894 | −1115 | −4051 | −90 | * | * | | | | | | | | | | | | |
| 42 | −2171 | −3243 | 3385 | 500 | 1178 | −2609 | −1661 | −2854 | −1767 | 87 | −2303 | −1281 | −2976 | −1416 | −2365 | −2050 | −2171 | −2684 | −3156 | −2344 | 43 |
| — | −150 | −501 | 236 | 43 | −375 | 397 | 105 | −627 | 209 | −461 | −722 | 274 | 393 | 44 | 95 | 360 | 116 | −370 | −295 | −247 | |
| G | −3496 | −136 | −9374 | −23 | −5981 | −6114 | −21 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −1092 | −2568 | 857 | 2428 | −2882 | −2018 | −713 | −2634 | −316 | −669 | −1663 | 736 | −2136 | 737 | −831 | 150 | 469 | −2187 | −2753 | −2063 | 45 |
| — | −150 | −501 | 233 | 42 | −380 | 397 | 105 | −627 | 209 | −467 | −722 | 278 | 393 | 46 | 97 | 360 | 116 | −370 | −295 | −235 | |
| G | −3496 | −136 | −9374 | −23 | −5981 | −728 | −1335 | * | * | | | | | | | | | | | | |
| 44 | 609 | −3125 | −4114 | −16 | 823 | −2153 | −3135 | 1496 | 102 | 878 | −2314 | −3530 | 1121 | −1526 | −70 | −805 | −1556 | 60 | 575 | −3156 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10683 | −11725 | −894 | −1115 | −1698 | −532 | * | * | | | | | | | | | | | | |
| 45 | −1231 | −4450 | 1071 | 1353 | −4771 | 907 | −2609 | −1640 | 497 | −4466 | −3539 | 1034 | −580 | 1511 | −1038 | 667 | −214 | −1723 | −4633 | −3950 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10888 | −11930 | −894 | −1115 | −107 | −3810 | * | * | | | | | | | | | | | | |
| 46 | −2330 | 218 | 1805 | 1744 | −1257 | −4307 | −899 | −1321 | 447 | 806 | −3894 | 438 | −1655 | 818 | −707 | −431 | −1004 | −4427 | −4989 | −4306 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11279 | −12321 | −894 | −1115 | −1307 | −747 | * | * | | | | | | | | | | | | |
| 47 | −1131 | 407 | −974 | −2279 | 1815 | −2668 | −4026 | 2098 | −978 | 1536 | −154 | −1706 | −1174 | −4525 | −4706 | −4240 | −3552 | 974 | −3899 | −3557 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −18 | −11279 | −6345 | −894 | −1115 | −1307 | −747 | * | * | | | | | | | | | | | | |
| 48 | −168 | −4775 | −166 | 1738 | −5089 | −1832 | −2954 | −1870 | 193 | 682 | 1095 | 155 | 1193 | −794 | −1312 | −1964 | −151 | 48 | −4963 | −562 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −38 | −11261 | −5284 | −894 | −1115 | −819 | −1207 | * | * | | | | | | | | | | | | |
| 49 | −144 | −4772 | 797 | 1558 | −1251 | 624 | 1561 | −4844 | 1261 | −2268 | −3861 | 28 | −4366 | 353 | 178 | −151 | −2 | −2046 | −4956 | −4273 | 52 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −114 | −11242 | −3729 | −894 | −1115 | −1116 | −893 | * | * | | | | | | | | | | | | |
| 50 | −390 | −4686 | 916 | 2226 | −452 | −1894 | −971 | −4756 | 630 | −2372 | 492 | −518 | −1700 | −1322 | −1735 | −579 | −1563 | −2146 | 476 | 2346 | 53 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11151 | −12193 | −894 | −1115 | −104 | −3847 | * | * | | | | | | | | | | | | |
| 51 | −20 | −4818 | 1751 | −405 | −5138 | −339 | −2981 | 826 | 476 | −1384 | 1359 | −130 | −703 | 514 | −96 | −78 | 367 | −782 | −5002 | −4320 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 52 | 334 | −1126 | −682 | −1646 | 420 | −252 | 741 | 317 | −623 | 1470 | −3308 | −398 | 293 | −736 | −1640 | −1730 | −1902 | 410 | −175 | 718 | 55 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 53 | 716 | 583 | 407 | −798 | −363 | −904 | −4025 | 101 | −1120 | 1363 | −2669 | −4769 | −5210 | −4494 | −1787 | −4239 | −3564 | 2136 | 904 | −3578 | 56 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 54 | 270 | −3454 | −5973 | −5337 | −185 | −5175 | −4046 | 1536 | −4932 | 1636 | −692 | −4821 | 124 | −4555 | −1543 | 477 | −1837 | 1179 | 214 | 288 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 55 | −1066 | −3568 | −1832 | −1265 | 2423 | −2435 | −3863 | 1321 | 273 | 547 | −604 | −4412 | 119 | −916 | −1663 | −1855 | −3530 | 1514 | 194 | −3644 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 56 | 262 | 668 | −5970 | −5335 | −116 | 2020 | −4046 | 136 | 447 | −2084 | −1218 | −4820 | −5225 | −4553 | −4731 | −1887 | −1837 | 2301 | −3912 | −504 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 57 | −549 | 3195 | −1088 | −5330 | −1189 | −1501 | −4045 | 1052 | −4926 | −219 | −322 | −1567 | −617 | −4551 | −4729 | −1747 | 2056 | 1527 | −3912 | −3570 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −57 | −11295 | −4708 | −894 | −1115 | −701 | −1378 | * | * | | | | | | | | | | | | |
| 58 | 1206 | −3457 | −1031 | −2629 | −1462 | −5052 | −3899 | −244 | −4548 | −268 | −2657 | −4551 | 1726 | −4250 | −1889 | 2422 | −3496 | −876 | −3907 | −205 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −335 | −11239 | −2272 | −894 | −1115 | −2195 | −355 | * | * | | | | | | | | | | | | |
| 59 | 277 | −4587 | −6184 | −851 | −7250 | −4814 | −6324 | −7080 | −6904 | −7319 | −6362 | −5415 | 222 | −6325 | −6741 | 107 | 3664 | −5778 | −7459 | −7356 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10904 | −11946 | −894 | −1115 | −4323 | −74 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −96 | −3112 | −5422 | −1917 | 1768 | −4784 | 1382 | −2608 | −4432 | −219 | 586 | −4370 | −4836 | −1266 | −4296 | −953 | 1402 | −2527 | 3776 | 2543 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −26 | −10904 | −5869 | −894 | −1115 | −4323 | −74 | * | * | | | | | | | | | | | | |
| 61 | −4544 | −5324 | −1483 | −3594 | −4857 | 3367 | −4038 | −5184 | −3903 | −2397 | −262 | 1211 | −5423 | −3871 | −1085 | −4509 | −4551 | −4960 | −5223 | 1306 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −62 | −10880 | −4585 | −894 | −1115 | −718 | −1351 | * | * | | | | | | | | | | | | |
| 62 | −252 | −4407 | 1836 | 1640 | 45 | −4210 | −2881 | −649 | −1211 | −999 | 447 | 1242 | −4300 | 1171 | −2996 | −1044 | −1519 | 254 | −4652 | −733 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11095 | −12137 | −894 | −1115 | −375 | −2128 | * | * | | | | | | | | | | | | |
| 63 | −5759 | −7820 | 580 | 485 | −7995 | 3394 | −4958 | −1075 | −5433 | −7833 | −7300 | −673 | −6078 | −4658 | −6497 | −584 | −5878 | −7421 | −8042 | −6870 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −98 | −11256 | −3931 | −894 | −1115 | −1874 | −460 | * | * | | | | | | | | | | | | |
| 64 | −1043 | −4640 | 2053 | 2292 | −1613 | −2636 | −726 | −355 | −646 | −2179 | −3736 | −2858 | −4305 | 343 | −2967 | 97 | −218 | 100 | −4839 | −279 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11159 | −12201 | −894 | −1115 | −3105 | −178 | * | * | | | | | | | | | | | | |
| 65 | −554 | 864 | −5841 | −1321 | −474 | −5047 | −3918 | 438 | −4801 | 597 | 258 | −4691 | 3184 | −4425 | −4603 | 502 | −1352 | −1269 | −3785 | −3443 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11159 | −12201 | −894 | −1115 | −326 | −2305 | * | * | | | | | | | | | | | | |
| 66 | −3425 | −4573 | −858 | 868 | −4776 | −4437 | −3128 | −1313 | −2782 | −4540 | −3700 | −3134 | 2976 | 837 | −3264 | −1033 | 1869 | 86 | 398 | −4232 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −107 | −11274 | −3814 | −894 | −1115 | −1455 | −655 | * | * | | | | | | | | | | | | |
| 67 | −48 | −3655 | 2215 | 698 | −3661 | −65 | −3489 | 1131 | −3577 | 848 | 789 | −2029 | −1939 | −1263 | −3844 | −1313 | −3352 | −645 | 510 | −185 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −1 | −11168 | −12210 | −894 | −1115 | −3029 | −189 | * | * | | | | | | | | | | | | |
| 68 | −3231 | −4703 | −213 | 582 | −1706 | −1182 | −510 | −4775 | −419 | −959 | −329 | 3063 | −809 | 668 | −1473 | −232 | 830 | −2330 | −4887 | −1301 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −234 | −11168 | −2743 | −894 | −1115 | −3029 | −189 | * | * | | | | | | | | | | | | |
| 69 | 1861 | −110 | −407 | −515 | −1508 | 1408 | −2690 | −1063 | −896 | −1154 | 1872 | 163 | 558 | −1175 | −1391 | −1142 | −2970 | −3974 | −4593 | 44 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10935 | −11977 | −894 | −1115 | −4230 | −79 | * | * | | | | | | | | | | | | |
| 70 | 843 | −4491 | 538 | 1171 | −1272 | −167 | −106 | −4563 | 1452 | −2439 | −961 | −192 | −1108 | 104 | 356 | −1037 | −2958 | 698 | −4675 | −66 | 73 |
| — | −149 | −490 | 232 | 43 | −372 | 395 | 119 | −620 | 207 | −463 | −698 | 272 | 392 | 44 | 92 | 357 | 114 | −368 | −285 | −248 | |
| H | −1280 | −806 | −5941 | −697 | −1384 | −4230 | −79 | * | * | | | | | | | | | | | | |
| 71 | −37 | −4470 | −491 | 149 | 1511 | −1049 | −257 | −4542 | −544 | 819 | −3560 | −421 | 1910 | 154 | 310 | −423 | −150 | −4092 | −4654 | −3971 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10911 | −11953 | −894 | −1115 | −4302 | −75 | * | * | | | | | | | | | | | | |
| 72 | 243 | −4450 | −970 | 385 | 2687 | −3977 | −2637 | −4506 | 366 | 728 | −3542 | −2616 | −720 | −814 | −595 | 294 | 695 | −4067 | −4639 | −1247 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10911 | −11953 | −894 | −1115 | −133 | −3502 | * | * | | | | | | | | | | | | |
| 73 | −722 | 76 | 1077 | 1403 | −809 | −4511 | 985 | −29 | −1050 | −1866 | 139 | −1929 | −1472 | 761 | −3382 | −176 | −1803 | 747 | 2618 | 1333 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11274 | −12316 | −894 | −1115 | −374 | −2132 | * | * | | | | | | | | | | | | |
| 74 | 458 | −4820 | 1671 | 1245 | −1304 | −268 | −869 | −4891 | 312 | −2472 | −3909 | −2957 | −4415 | 848 | 896 | 720 | −1920 | −1819 | 117 | 762 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 75 | −544 | −420 | 1102 | 740 | 2099 | −878 | −518 | −1865 | −390 | 485 | −948 | −1452 | −4682 | −3030 | −1649 | −1961 | −1572 | −1934 | 3836 | −1563 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 76 | 732 | −3465 | −1690 | 220 | 1918 | −555 | −4027 | 1149 | −4859 | 1504 | 1021 | −4774 | −5212 | −1879 | −2347 | −2476 | −1780 | −165 | −3921 | −293 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | −235 | −588 | 1003 | 825 | 737 | −857 | −76 | −42 | −530 | 719 | −1433 | 264 | −480 | 743 | −1698 | −508 | 327 | −2053 | −4985 | −2014 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −15 | −11295 | −6606 | −894 | −1115 | −701 | −1378 | * | * | | | | | | | | | | | | |
| 78 | −941 | −4574 | 240 | 507 | 858 | −189 | −3053 | −514 | −1608 | 1250 | 1478 | 694 | 164 | −606 | −439 | −1974 | −491 | −898 | −4819 | 156 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −49 | −11280 | −4917 | −894 | −1115 | −1267 | −775 | * | * | | | | | | | | | | | | |
| 79 | −827 | −4736 | −481 | 21 | 2357 | −1554 | −996 | −685 | 817 | −408 | −3829 | −837 | −4364 | 635 | 384 | −389 | −1268 | −2074 | 1115 | 1904 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −740 | −11232 | −1318 | −894 | −1115 | −2303 | −327 | * | * | | | | | | | | | | | | |
| 80 | −2645 | −3927 | 174 | −553 | −4173 | 1781 | −203 | 363 | −924 | 175 | 1187 | 239 | −3742 | −1887 | 721 | 273 | −147 | −699 | −4156 | −118 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −278 | −10493 | −2517 | −894 | −1115 | −4284 | −76 | * | * | | | | | | | | | | | | |
| 81 | −2430 | −3729 | −237 | −213 | 24 | −3433 | 620 | 296 | 845 | 1308 | −2836 | −661 | −338 | −595 | −732 | −246 | 382 | 770 | −3954 | −836 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10247 | −11289 | −894 | −1115 | −5381 | −35 | * | * | | | | | | | | | | | | |
| 82 | 154 | 217 | 973 | 942 | −4188 | 1130 | −2063 | −3932 | −1649 | −3889 | −2969 | −109 | 2525 | −1607 | −19 | −2311 | −2366 | −1430 | −4066 | 347 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −387 | −10247 | −2094 | −894 | −1115 | −4005 | −93 | * | * | | | | | | | | | | | | |
| 83 | −1006 | −2924 | −656 | −1041 | 270 | −3389 | −2100 | 130 | 740 | 883 | −2083 | 860 | −3471 | −1814 | −2306 | 337 | 2118 | −711 | −3271 | −2775 | 90 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −9941 | −10983 | −894 | −1115 | −5610 | −30 | * | * | | | | | | | | | | | | |
| 84 | 423 | 592 | 213 | 896 | −3948 | −654 | −1791 | −3698 | 978 | −1731 | −2718 | −1768 | −3225 | −1331 | 2670 | 90 | −631 | −3250 | −3812 | −3130 | 91 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −453 | −9941 | −1897 | −894 | −1115 | −5610 | −30 | * | * | | | | | | | | | | | | |
| 85 | −1803 | −3220 | −150 | 121 | 2586 | −2785 | 401 | −3252 | −1036 | −1436 | −2315 | 1315 | −83 | 217 | −1540 | 532 | −370 | −2829 | −3417 | 1886 | 92 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1702 | −9490 | −533 | −894 | −1115 | −5833 | −26 | * | * | | | | | | | | | | | | |
| 86 | −765 | −2123 | −575 | 923 | −2399 | 301 | 2336 | −2118 | −6 | −28 | −1229 | −379 | 1388 | 1363 | −499 | −664 | −706 | −1722 | −2332 | −1678 | 93 |
| — | −157 | −489 | 232 | 32 | −373 | 395 | 92 | −617 | 214 | −466 | −707 | 268 | 381 | 44 | 108 | 386 | 117 | −384 | −301 | −259 | |
| . | −2962 | −412 | −3059 | −5165 | −41 | −6177 | −20 | * | * | | | | | | | | | | | | |
| 87 | −787 | −2228 | 2023 | 1072 | −2525 | 448 | −399 | −2266 | −31 | −2236 | −1339 | −299 | −1807 | 42 | 1169 | −661 | −736 | 416 | −2426 | −1740 | 142 |
| — | −149 | −500 | 232 | 43 | −381 | 398 | 105 | −627 | 210 | −466 | −721 | 275 | 393 | 48 | 97 | 360 | 121 | −370 | −295 | −250 | |
| . | −2781 | −442 | −3079 | −46 | −5006 | −4458 | −67 | * | * | | | | | | | | | | | | |
| 88 | −818 | −2136 | 736 | −162 | 357 | −1801 | −479 | −2105 | 741 | −504 | −1245 | 1806 | −1901 | −44 | −590 | 1615 | −759 | −1726 | −2357 | −1710 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −533 | −7959 | −1714 | −894 | −1115 | −1867 | −462 | * | * | | | | | | | | | | | | |
| 89 | −711 | −3347 | 1684 | 1411 | 741 | −822 | 552 | −611 | −129 | −1283 | −2437 | 540 | 585 | −1058 | −1606 | 269 | 119 | −2967 | −3532 | −2852 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −3 | −9600 | −10642 | −894 | −1115 | −5020 | −45 | * | * | | | | | | | | | | | | |
| 90 | 356 | −3391 | 1298 | 1509 | −564 | −203 | −1553 | −3461 | −1134 | −3407 | −2481 | −1528 | −2987 | 682 | −312 | 635 | 1783 | −3012 | −3575 | −2893 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −3 | −9641 | −10683 | −894 | −1115 | −5769 | −27 | * | * | | | | | | | | | | | | |
| 91 | −785 | −2008 | 700 | 1077 | 35 | −3648 | −2504 | 376 | −3227 | 2022 | 1659 | −3194 | −3701 | −2904 | −3130 | −683 | −2074 | −164 | −2462 | −2113 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −3 | −9641 | −10683 | −894 | −1115 | −2059 | −396 | * | * | | | | | | | | | | | | |
| 92 | −1220 | −3861 | 1380 | 1851 | −4182 | 149 | −2021 | −213 | 1139 | −1689 | −2950 | −474 | −3455 | −331 | −507 | 610 | 127 | −1563 | −4044 | −3362 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −2 | −10217 | −11259 | −894 | −1115 | −868 | −1145 | * | * | | | | | | | | | | | | |
| 93 | 1343 | −4459 | 1516 | 989 | 195 | 1221 | −2620 | −733 | −1132 | −1337 | −3549 | 405 | −1697 | −70 | −667 | −639 | −1440 | −4081 | −4643 | −3961 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −218 | −10900 | −2837 | −894 | −1115 | −4336 | −73 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 94 | 303 | −283 | 376 | −1053 | −4156 | 1709 | −2541 | 610 | −465 | −838 | −972 | −848 | 1084 | −92 | −2667 | −1467 | 605 | −81 | −4222 | −870 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10683 | −11725 | −894 | −1115 | −4829 | −52 | * | * | | | | | | | | | | | | |
| 95 | 41 | −4266 | 2251 | −558 | −403 | 418 | −2426 | −4336 | 435 | −1192 | −3355 | −440 | 1126 | 49 | −304 | −306 | −2733 | −3887 | 1790 | 94 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10683 | −11725 | −894 | −1115 | −2332 | −319 | * | * | | | | | | | | | | | | |
| 96 | −518 | −3014 | −5471 | −4837 | 2206 | −4721 | −233 | −1119 | −1282 | 2485 | 486 | −4348 | −4771 | −432 | −76 | −3803 | −3120 | −1350 | −3470 | −3127 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10809 | −11851 | −894 | −1115 | −1597 | −579 | * | * | | | | | | | | | | | | |
| 97 | −2 | 614 | −1207 | 684 | −174 | 223 | −2690 | −1428 | 1052 | −4546 | −3619 | 313 | 395 | 728 | −2778 | 1695 | 262 | −4152 | −4714 | −4031 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −54 | −10978 | −4773 | −894 | −1115 | −606 | −1544 | * | * | | | | | | | | | | | | |
| 98 | −654 | −902 | −166 | −2517 | −4995 | 2294 | −476 | −4743 | 136 | −829 | −599 | 2160 | −4283 | 763 | −1323 | −550 | −715 | −2086 | −4864 | −4184 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11149 | −12191 | −894 | −1115 | −279 | −2507 | * | * | | | | | | | | | | | | |
| 99 | −1913 | 48 | −2262 | −5092 | 398 | −2743 | −3980 | −577 | 1652 | 1018 | 1534 | −294 | −1079 | −4404 | −236 | −1615 | −411 | 1505 | −3919 | 415 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 100 | 46 | −742 | −283 | −907 | −5125 | −717 | −841 | −2230 | 1734 | −1827 | −3893 | −324 | 418 | −414 | 2087 | 116 | 894 | −4426 | −4987 | −4305 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −16 | −11277 | −6526 | −894 | −1115 | −1375 | −702 | * | * | | | | | | | | | | | | |
| 101 | 12 | −291 | −5625 | −5008 | 2183 | −1689 | −3950 | −305 | 307 | −1873 | −2661 | −1311 | −5149 | −1302 | −353 | −737 | −1729 | 1469 | −3912 | 2854 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −58 | −11261 | −4692 | −894 | −1115 | −909 | −1097 | * | * | | | | | | | | | | | | |
| 102 | 2482 | 596 | −5493 | −4882 | −3397 | 967 | −3892 | −1018 | −4558 | −915 | −2636 | −1759 | −904 | 1465 | −4497 | 112 | −1023 | −437 | −3887 | −887 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11221 | −12263 | −894 | −1115 | −493 | −1789 | * | * | | | | | | | | | | | | |
| 103 | 394 | 1696 | −5956 | −5320 | −301 | −941 | −4029 | −461 | −4915 | 818 | 1333 | −4804 | −5208 | −4538 | −4715 | −1864 | −3551 | 2592 | 1369 | 592 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 104 | −591 | −3440 | −5930 | −5295 | 3519 | −2085 | −4024 | −547 | 271 | 913 | −2643 | −4792 | −5205 | −4524 | −250 | −823 | −3550 | −68 | −3897 | −1275 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 105 | 1673 | −4794 | −7480 | −7642 | −6858 | 3113 | −6601 | −2108 | −7283 | −6844 | −6018 | −5927 | −5947 | −1705 | −6952 | −2265 | −81 | 22 | −7196 | −7045 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 106 | −1437 | 2582 | −5958 | −5322 | 2404 | −1000 | −4031 | −1596 | −4917 | 2243 | −2642 | −4806 | −5209 | −4540 | −4717 | 72 | −1002 | −1632 | 220 | −3555 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 107 | −5350 | −5040 | −7255 | −6910 | −602 | 3439 | −4278 | −421 | −6497 | −2611 | −4284 | −5965 | −1531 | −5863 | −6187 | −1138 | −5289 | −4587 | 2423 | 423 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11277 | −12319 | −894 | −1115 | −1375 | −702 | * | * | | | | | | | | | | | | |
| 108 | −2325 | −6477 | 3321 | −1761 | −6786 | −660 | −696 | −6619 | −4228 | −6531 | −5717 | 1169 | −5546 | −3897 | −4897 | 1693 | −1638 | −2291 | −6713 | −5865 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11277 | −12319 | −894 | −1115 | −1375 | −702 | * | * | | | | | | | | | | | | |
| 109 | −2338 | −4652 | −3268 | −2718 | 0 | −1846 | 1392 | −1647 | 457 | −4639 | 604 | −1593 | −4442 | 1705 | 1220 | 2006 | −573 | −4238 | 2045 | 872 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11277 | −12319 | −894 | −1115 | −1375 | −702 | * | * | | | | | | | | | | | | |
| 110 | 724 | −4766 | −133 | 611 | −5069 | 1416 | −2976 | −2560 | −2563 | −910 | 331 | −284 | −4408 | −31 | −1761 | 1003 | 1476 | −598 | −4960 | −4288 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11277 | −12319 | −894 | −1115 | −1375 | −702 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 111 | −4724 | −5226 | −749 | −4400 | −4494 | 1725 | −4575 | −5221 | −5121 | −2291 | −4786 | −131 | −5866 | −4717 | −5521 | −1358 | −1300 | −5004 | 3766 | 3785 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −38 | −11277 | −5281 | −894 | −1115 | −1375 | −702 | * | * | | | | | | | | | | | | |
| 112 | −336 | −4768 | −876 | 1682 | −5088 | 787 | −2929 | −4839 | −411 | −2246 | −1012 | −650 | 1369 | −516 | −1538 | −61 | −128 | −1352 | 1020 | 2053 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1 | −11239 | −12281 | −894 | −1115 | −2186 | −358 | * | * | | | | | | | | | | | | |
| 113 | −716 | −4755 | −3151 | −332 | 465 | 892 | 2352 | −4816 | 320 | 183 | −3846 | 144 | 971 | 133 | −1909 | −102 | −56 | −1765 | −4943 | 1106 | 169 |
| — | −148 | −487 | 233 | 44 | −382 | 399 | 104 | −623 | 213 | −467 | −710 | 274 | 392 | 44 | 97 | 359 | 116 | −371 | −296 | −251 | |
| T | −2844 | −4474 | −294 | −1874 | −460 | −2186 | −358 | * | * | | | | | | | | | | | | |
| 114 | −2174 | −3749 | 2575 | 2167 | −4022 | −2718 | 1575 | −3810 | 177 | 498 | −2886 | −1330 | −3010 | −1256 | −2008 | −1980 | −2149 | −3353 | −3916 | −3151 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −5 | −8801 | −9843 | −894 | −1115 | −3597 | −124 | * | * | | | | | | | | | | | | |
| 115 | −1729 | −3092 | −1558 | 735 | −3344 | −2688 | −1344 | −3100 | 995 | −3085 | −2196 | 2243 | −2788 | −904 | −1369 | −1626 | 2139 | −2700 | 1567 | 1652 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | −9201 | −10243 | −894 | −1115 | −786 | −1251 | * | * | | | | | | | | | | | | |
| 116 | −7339 | −6286 | −7749 | −8107 | 4259 | −1841 | −3824 | −6252 | −7665 | −5553 | 82 | −6244 | −7478 | −6387 | −7027 | −6864 | −7205 | −6413 | −3071 | 2358 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −10733 | −11775 | −894 | −1115 | −2257 | −339 | * | * | | | | | | | | | | | | |
| 117 | −381 | 4555 | −5199 | −4590 | −3068 | −441 | −314 | −895 | −4257 | −651 | −2308 | 2154 | −4769 | 1263 | −4183 | −3780 | −3153 | −433 | −3559 | −3208 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −10854 | −11896 | −894 | −1115 | −41 | −5141 | * | * | | | | | | | | | | | | |
| 118 | 815 | 239 | 378 | 535 | −379 | 1121 | −2983 | −4877 | 240 | −2295 | −466 | 352 | −1476 | −505 | −442 | −956 | −1696 | −2157 | 3342 | 830 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 119 | 2470 | −3511 | −5518 | −4909 | 1247 | −340 | −3950 | 338 | −2528 | −3363 | 847 | −424 | −1189 | 308 | −2577 | −1325 | −1131 | 125 | 1551 | −1249 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 120 | 1225 | −3633 | −4892 | −411 | −1094 | 1260 | −343 | 361 | −1660 | −1384 | 1903 | −4233 | 155 | −620 | −4233 | −279 | −203 | 1264 | −4065 | −3686 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 121 | −2149 | −4818 | 1163 | −1675 | −956 | 1414 | 1140 | −304 | 2075 | −2297 | −3908 | −1361 | −1895 | −5 | 1573 | −2169 | −3287 | −1366 | −5002 | −4320 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 122 | 1057 | −4802 | 122 | −53 | 145 | −2817 | −738 | −192 | 1515 | −650 | 806 | −1358 | −2129 | 592 | 94 | −1654 | 649 | −1373 | −4991 | 681 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 123 | −555 | −4905 | −7602 | −6994 | 1402 | −6955 | −5820 | 1829 | −6652 | 1937 | 640 | −6615 | −6752 | −6054 | −6390 | −6097 | −5141 | 1680 | 1003 | −5134 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 124 | −583 | −4818 | 2583 | 1674 | −893 | −2187 | 1338 | −506 | −47 | −4833 | −3907 | −844 | −4415 | 64 | −1274 | −1244 | −3287 | −832 | 380 | 723 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 125 | 0 | −4821 | 717 | 1817 | −1293 | 815 | −567 | −4893 | 1267 | −2751 | −3910 | 610 | −4415 | 435 | −166 | −494 | 97 | −2139 | −5004 | −4321 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 126 | −751 | −4287 | −2311 | −1113 | −988 | −1448 | −767 | 140 | 2152 | 16 | 1090 | −3289 | −4602 | −168 | 2157 | −3454 | −584 | −1332 | 1615 | −4065 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 127 | −519 | −311 | −5982 | −5347 | 842 | −5185 | −4056 | 822 | −4942 | 2487 | 579 | −4831 | −1159 | −4564 | −4741 | −4270 | −919 | 557 | −3921 | 104 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 128 | 983 | −4820 | −1323 | 1239 | −876 | 18 | −2980 | −2395 | 1098 | −2811 | −3909 | −1375 | −4415 | 1694 | −716 | 1035 | 327 | −1181 | −5003 | −4321 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −18 | −11295 | −6419 | −894 | −1115 | −701 | −1378 | * | * | | | | | | | | | | | | |
| 129 | 694 | −4806 | 850 | 2038 | −1284 | 887 | −1152 | −4877 | 49 | −2614 | −3895 | −4 | −1478 | 625 | −47 | 80 | −1826 | −4428 | −4989 | −869 | 190 |
| — | −149 | −500 | 233 | 43 | −381 | 398 | 105 | −627 | 210 | −466 | −721 | 275 | 393 | 45 | 96 | 361 | 117 | −370 | −295 | −243 | |
| T | −51 | −4852 | −12320 | −74 | −4316 | −1332 | −731 | * | * | | | | | | | | | | | | |
| 130 | 465 | −880 | −5817 | −5190 | −1157 | −1911 | −1277 | −844 | 91 | 2253 | −904 | −4740 | −5190 | 396 | 630 | −1403 | −990 | 243 | −3909 | −1119 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11278 | −12320 | −894 | −1115 | −412 | −2009 | * | * | | | | | | | | | | | | |
| 131 | −2322 | −4951 | −6302 | −6399 | 1425 | 3445 | −6150 | −6753 | −179 | −6985 | −680 | −1547 | −5957 | −6081 | −6182 | −922 | −4761 | −5856 | −7198 | −6929 | 193 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11295 | −12337 | −894 | −1115 | −701 | −1378 | * | * | | | | | | | | | | | | |
| 132 | 2523 | 671 | −5964 | −5328 | 1501 | 1324 | −4045 | −1379 | −824 | −2001 | −453 | −4817 | −2186 | −4550 | −4728 | −1720 | −949 | 188 | −3913 | −1807 | 194 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 133 | −1111 | −828 | 452 | 1395 | −5141 | −4322 | −2980 | −1090 | 1646 | −3167 | −3910 | −5 | −4415 | 837 | 640 | 1053 | 780 | −930 | −5004 | −4321 | 195 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 134 | −840 | −3508 | −5540 | −4930 | 556 | −5107 | −726 | 588 | −2114 | −1125 | 609 | −984 | −5162 | −529 | 2461 | −656 | 1309 | 1391 | −3958 | −3605 | 196 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 135 | −885 | −3454 | −5970 | −2303 | 537 | 594 | −4046 | 1779 | −4929 | 1275 | −751 | −4820 | −1735 | −1386 | −4731 | −1560 | −845 | 1852 | −3912 | −1115 | 197 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 136 | −200 | 1350 | −313 | 32 | 963 | 1547 | −3505 | −1066 | −1482 | 478 | −143 | −1421 | −4831 | −747 | −3804 | 80 | 903 | −197 | −4272 | −1167 | 198 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −949 | −11295 | −1054 | −894 | −1115 | −701 | −1378 | * | * | | | | | | | | | | | | |
| 137 | −499 | −3965 | 1107 | 299 | −213 | −1315 | 1058 | −4030 | −1716 | −936 | −3055 | −169 | 1635 | 1254 | −896 | −96 | 367 | −363 | −4150 | 923 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −725 | −10347 | −1342 | −894 | −1115 | −5285 | −37 | * | * | | | | | | | | | | | | |
| 138 | −1935 | −3291 | −1821 | −262 | −3572 | 505 | −1589 | −3291 | 1114 | −3292 | −2398 | −1579 | 386 | −1146 | −1679 | 740 | 1000 | −2893 | 4315 | 554 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −987 | −9624 | −1017 | −894 | −1115 | −5777 | −27 | * | * | | | | | | | | | | | | |
| 139 | −1644 | 1961 | −4471 | −4401 | −3885 | 694 | −3640 | 234 | −4121 | −3840 | −3054 | −3176 | 3467 | −3740 | −3982 | 815 | −2044 | −2846 | −4240 | −4010 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −399 | −8643 | −2066 | −894 | −1115 | −6063 | −22 | * | * | | | | | | | | | | | | |
| 140 | 286 | −1802 | −1620 | −1088 | −2095 | −2217 | −1137 | 68 | −864 | −1912 | −1161 | 726 | −2400 | −853 | 597 | −1247 | 2947 | −1439 | −2335 | −1858 | 202 |
| — | −146 | −501 | 237 | 49 | −382 | 398 | 105 | −627 | 211 | −467 | −721 | 274 | 393 | 44 | 95 | 358 | 116 | −370 | −295 | −250 | |
| T | −3416 | −144 | −9294 | −24 | −5896 | −6125 | −21 | * | * | | | | | | | | | | | | |
| 141 | −4634 | −4362 | −5271 | −5643 | −6049 | 3838 | −5183 | −6808 | −5939 | −6455 | −6144 | −5328 | −4954 | −5722 | −5542 | −4932 | −5011 | −6052 | −5054 | −6011 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −7 | −8252 | −9294 | −894 | −1115 | −6125 | −21 | * | * | | | | | | | | | | | | |
| 142 | −5251 | −4321 | −5335 | −5670 | −1246 | −4878 | −2603 | −4842 | −5494 | −4203 | −4272 | −4642 | −5130 | −4770 | −5017 | −5137 | −5295 | −4917 | −1898 | 4887 | 205 |
| — | −150 | −501 | 237 | 47 | −382 | 399 | 113 | −627 | 211 | −467 | −721 | 276 | 393 | 44 | 95 | 358 | 116 | −370 | −295 | −250 | |
| — | −3416 | −144 | −9294 | −24 | −5896 | −6125 | −21 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 143 | −4755 | −3874 | −5104 | −5403 | 4356 | −5008 | 1664 | −3856 | −5016 | −3196 | −3270 | −3876 | −4993 | −3998 | −4513 | −4423 | −4684 | −4003 | −845 | 338 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −7 | −8252 | −9294 | −894 | −1115 | −6125 | −21 | * | * | | | | | | | | | | | | |
| 144 | −1644 | −3218 | 616 | 2438 | −3514 | −2233 | −1171 | −3304 | −949 | −3234 | −2365 | 1424 | −2512 | −755 | −1535 | 1447 | 596 | −2836 | −3411 | −2644 | 208 |
| — | −144 | −501 | 235 | 46 | −379 | 399 | 105 | −627 | 209 | −467 | −721 | 274 | 393 | 44 | 95 | 359 | 116 | −370 | −295 | −250 | |
| S | −3416 | −144 | −9294 | −24 | −5896 | −6125 | −21 | * | * | | | | | | | | | | | | |
| 145 | −1611 | −2219 | −3630 | −3929 | −4621 | −2432 | −3739 | −4573 | −4138 | −4776 | −3889 | −2975 | 924 | −3748 | −4032 | 3486 | −2071 | −3374 | −4741 | −4621 | 210 |
| — | −148 | −501 | 232 | 42 | −382 | 398 | 105 | −627 | 220 | −465 | −721 | 274 | 393 | 44 | 95 | 359 | 118 | −370 | −295 | −250 | |
| T | −3416 | −144 | −9294 | −24 | −5896 | −6125 | −21 | * | * | | | | | | | | | | | | |
| 146 | 3294 | −1989 | −3961 | −4221 | −4548 | 214 | −3749 | −4352 | −4243 | −4605 | −3672 | −2915 | 913 | −3769 | −4052 | −1622 | −1840 | −3136 | −4748 | −4663 | 212 |
| — | −149 | −500 | 232 | 43 | −381 | 398 | 105 | −624 | 210 | −462 | −721 | 275 | 393 | 45 | 95 | 359 | 117 | −368 | −295 | −250 | |
| E | −538 | −1692 | −9294 | −409 | −2019 | −6125 | −21 | * | * | | | | | | | | | | | | |
| 147 | 926 | −1394 | −3370 | −126 | −1427 | −3062 | −2047 | −225 | −2589 | 1501 | −564 | −2583 | −3128 | −2321 | −2573 | −2173 | −1485 | 2379 | −2058 | −1705 | 215 |
| — | −150 | −501 | 235 | 48 | −382 | 398 | 105 | −627 | 210 | −467 | −721 | 274 | 393 | 44 | 99 | 358 | 116 | −366 | −295 | −250 | |
| E | −3416 | −144 | −9294 | −24 | −5896 | −6125 | −21 | * | * | | | | | | | | | | | | |
| 148 | −2738 | −4734 | 2467 | 812 | −4882 | 1851 | −1969 | −4844 | −2308 | −4690 | −4070 | 2513 | −3129 | −1649 | −3248 | −2367 | −2823 | −4294 | −4891 | −3805 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −7 | −8252 | −9294 | −894 | −1115 | −6125 | −21 | * | * | | | | | | | | | | | | |
| 149 | −2572 | −4418 | 1672 | −744 | −4666 | 2777 | −1881 | −4585 | −2104 | −4457 | −3776 | 1664 | −3060 | 1210 | −2939 | −2246 | −2644 | −4049 | −4649 | −3646 | 218 |
| — | −150 | −501 | 232 | 45 | −382 | 398 | 108 | −627 | 216 | −465 | −721 | 274 | 393 | 46 | 97 | 358 | 118 | −370 | −295 | −250 | |
| E | −3416 | −144 | −9294 | −24 | −5896 | −4909 | −49 | * | * | | | | | | | | | | | | |
| 150 | −3016 | −3173 | −4871 | −5066 | 4263 | −3788 | −2574 | −3260 | −4824 | −2965 | −2925 | −3880 | −4307 | −4201 | −4502 | −3242 | 1122 | −3238 | −1973 | −877 | 220 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −6 | −8441 | −9483 | −894 | −1115 | −1035 | −966 | * | * | | | | | | | | | | | | |
| 151 | −426 | −4060 | 934 | 1324 | −4381 | −1586 | 1045 | −1828 | 374 | −2138 | −3149 | −37 | 1961 | −564 | −1181 | −580 | −2526 | 1176 | −4243 | −3561 | 221 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −2 | −10448 | −11490 | −894 | −1115 | −2656 | −249 | * | * | | | | | | | | | | | | |
| 152 | −617 | −2808 | −5315 | −4680 | −410 | 1266 | −3397 | −1091 | −1626 | 1302 | 1729 | −4169 | −4577 | −3902 | 1030 | −3611 | 538 | 1229 | −3266 | 174 | 222 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −10598 | −11640 | −894 | −1115 | −29 | −5647 | * | * | | | | | | | | | | | | |
| 153 | −820 | 414 | −5724 | −2346 | −634 | 2372 | 702 | −1428 | −4750 | 1512 | −2684 | −1555 | −1896 | −1681 | −2187 | −4212 | −119 | 579 | −3936 | −3589 | 223 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 154 | 323 | 726 | −522 | 1736 | −5124 | 790 | −610 | −4871 | 1069 | 407 | −258 | −2962 | −2128 | −1327 | −330 | −1885 | −28 | −373 | −4995 | −378 | 224 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 155 | 586 | 970 | −6113 | −5485 | −1599 | 2350 | −4214 | 1774 | −5087 | −387 | 371 | −4975 | −5372 | −4714 | −4892 | −4418 | −1814 | 1285 | −4074 | −3730 | 225 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1 | −11295 | −12337 | −894 | −1115 | −701 | −1378 | * | * | | | | | | | | | | | | |
| 156 | −1345 | −398 | 3271 | −501 | −5142 | −1856 | −271 | −4892 | 685 | −2497 | −3910 | 52 | −4415 | 1166 | −398 | −1644 | −3287 | −1313 | −5004 | −1418 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1 | −11295 | −12337 | −894 | −1115 | −701 | −1378 | * | * | | | | | | | | | | | | |
| 157 | 124 | −4164 | 1739 | 2217 | 215 | 200 | −3285 | −889 | −3063 | −612 | −677 | −698 | −4661 | 136 | −1356 | −3526 | −1683 | −822 | 89 | 125 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −90 | −11295 | −4057 | −894 | −1115 | −701 | −1378 | * | * | | | | | | | | | | | | |
| 158 | 433 | −4738 | 1835 | −618 | −5059 | −501 | −402 | −2555 | 128 | 48 | 453 | 73 | −1387 | 1673 | −680 | −19 | 86 | −878 | −4922 | −4239 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −21 | −11206 | −6172 | −894 | −1115 | −1651 | −553 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 159 | −140 | 1738 | 537 | −66 | −5056 | −828 | 1369 | −4806 | −2479 | −2504 | 156 | 1525 | 1885 | −549 | −404 | −2201 | 1507 | −4358 | −4920 | −482 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −378 | −11206 | −2121 | −894 | −1115 | −1666 | −546 | * | * | | | | | | | | | | | | |
| 160 | 399 | −4417 | −491 | 169 | −4737 | 434 | 482 | −265 | −609 | −1355 | −265 | −1134 | 663 | 1825 | −820 | 813 | 257 | −271 | −4601 | −3919 | 230 |
| — | −150 | −505 | 235 | 49 | −382 | 398 | 107 | −629 | 207 | −463 | −720 | 273 | 397 | 51 | 91 | 360 | 116 | −374 | −291 | −246 | |
| G | −2415 | −592 | −2746 | −6 | −8014 | −3465 | −137 | * | * | | | | | | | | | | | | |
| 161 | −151 | −4220 | 2090 | 1593 | −4532 | −249 | −2403 | −1671 | −1987 | −2223 | −254 | 529 | −587 | −376 | −2493 | 444 | 814 | −1548 | −4408 | −865 | 232 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1 | −10651 | −11693 | −894 | −1115 | −200 | −2951 | * | * | | | | | | | | | | | | |
| 162 | 517 | 358 | 1524 | 1187 | −5065 | 1447 | −781 | −2082 | −1567 | 327 | −30 | 396 | −4362 | −1279 | −3018 | −920 | 296 | −4369 | −4938 | −4259 | 233 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11234 | −12276 | −894 | −1115 | −636 | −1488 | * | * | | | | | | | | | | | | |
| 163 | −947 | −4100 | −271 | 94 | 99 | −4584 | −828 | 937 | −750 | 1028 | 1258 | −1492 | −178 | 1571 | −3506 | −2121 | 927 | −1923 | −84 | 873 | 234 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11274 | −12316 | −894 | −1115 | −377 | −2120 | * | * | | | | | | | | | | | | |
| 164 | −446 | −4818 | 1297 | 2562 | −1646 | −4322 | −2981 | −1112 | 352 | −1938 | −657 | −1755 | −1130 | 405 | 32 | −412 | 207 | −2139 | −5002 | −4320 | 235 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 165 | 469 | −4821 | 1022 | 2038 | −5142 | −89 | −2980 | −4892 | 159 | −1010 | −624 | −1846 | −367 | 1025 | −637 | −310 | 524 | −2350 | −5004 | −1798 | 236 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −39 | −11295 | −5249 | −894 | −1115 | −701 | −1378 | * | * | | | | | | | | | | | | |
| 166 | 1234 | 2147 | 1416 | 122 | −2091 | −2027 | −848 | −711 | −2746 | 89 | 419 | −1082 | −1020 | −645 | 1085 | −532 | −1137 | −312 | −4706 | −1276 | 237 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11256 | −12299 | −894 | −1115 | −873 | −1139 | * | * | | | | | | | | | | | | |
| 167 | 655 | 1793 | −5947 | −1183 | 2523 | −5156 | −4027 | 445 | −2303 | −99 | −418 | −4799 | −5206 | −4532 | 646 | −753 | −1295 | 1118 | −3894 | 1061 | 238 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11275 | −12317 | −894 | −1115 | −1410 | −681 | * | * | | | | | | | | | | | | |
| 168 | 323 | −689 | −1 | 1811 | −5117 | −4305 | 2159 | −134 | 401 | −570 | −151 | −565 | −4398 | −692 | 1431 | −197 | −1609 | −1720 | −4983 | −4301 | 239 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11275 | −12317 | −894 | −1115 | −387 | −2087 | * | * | | | | | | | | | | | | |
| 169 | 1310 | −4819 | −1254 | 926 | −272 | −1204 | 2212 | −640 | 320 | −1086 | −3908 | −1360 | 621 | 456 | −1637 | 312 | 91 | −4440 | 138 | −1285 | 240 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1 | −11295 | −12337 | −894 | −1115 | −701 | −1378 | * | * | | | | | | | | | | | | |
| 170 | −2127 | −4412 | −6961 | −6419 | 983 | 1772 | −4829 | −757 | −6037 | −2221 | −3301 | −5818 | −6192 | −5563 | −5807 | −5294 | −4590 | −1837 | 5535 | −3791 | 241 |
| — | * | * | * | * | * | * | * | * | * | * | * | * | * | * | * | * | * | * | * | * | |
| H | * | * | * | * | * | * | * | * | 0 | | | | | | | | | | | | |
| // | | | | | | | | | | | | | | | | | | | | | |

| HMMER2.0 | [2.3.2] |
|---|---|
| NAME | Glyco__transf__20 |
| ACC | PF00982.13 |
| DESC | Glycosyltransferase family 20 |
| LENG | 514 |
| ALPH | Amino |
| RF | no |
| CS | yes |
| MAP | yes |
| COM | hmmbuild -F HMM__ls.ann SEED.ann |
| COM | hmmcalibrate --seed 0 HMM__ls.ann |
| NSEQ | 23 |
| DATE | Tue Apr 22 16:21:19 2008 |
| CKSUM | 257 |
| GA | −243.6000 −243.6000; |
| TC | −243.2000 −243.2000; |
| NC | −245.0000 −245.0000; |
| XT | −8455 −4 −1000 −1000 −8455 −4 −8455 −4 |
| NULT | −4 −8455 |
| NULE | 595 −1558 85 338 −294 453 −1158 197 249 902 −1085 −142 −21 −313 45 531 201 384 −1998 −644 |
| EVD | −381.697144 0.102587 |

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −100 | * | −3906 | | | | | | | | | | | | | | | | | | |
| 1 | −692 | −2874 | −154 | 374 | −3193 | 703 | 379 | −2942 | 459 | -838 | −1963 | −1015 | 1186 | 846 | −1126 | 1585 | −1344 | −2495 | −3058 | 523 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | −100 | * | | | | | | | | | | | | |
| 2 | −1658 | −3135 | 240 | 287 | −3462 | −2546 | −1239 | −3210 | 1632 | −3142 | −2232 | 1748 | −2674 | −788 | 2524 | 296 | −1598 | −2762 | −3299 | −2620 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 3 | −1489 | −1996 | 55 | −1439 | 1414 | −2692 | −1422 | −347 | 218 | 1289 | −1165 | −1609 | 81 | 552 | −255 | 495 | −1429 | 708 | −2370 | −1909 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 4 | −1921 | −1718 | −4256 | −3645 | −1688 | 33 | 2091 | 1705 | −3262 | 1487 | -876 | −3165 | −3556 | −2901 | −3086 | −2625 | −1866 | 2006 | −2283 | −1939 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 5 | −2001 | −1811 | −4353 | −3770 | −1908 | 771 | −2628 | 2268 | −3411 | -860 | −1081 | −3288 | −3675 | −3070 | −3259 | −455 | 92 | 2429 | −2504 | −2150 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 6 | −2849 | −2511 | −5254 | −4730 | 409 | −4668 | −3452 | 577 | −4418 | −158 | −1325 | −4275 | −4564 | −3982 | −4242 | −3826 | −2797 | 3300 | −3022 | 1229 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 7 | 1227 | −2892 | −2002 | 97 | −3869 | 405 | −2217 | −3596 | −2012 | −3696 | −2854 | −1975 | −3196 | −1861 | −2477 | 2789 | −2100 | −3073 | −3954 | 732 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −4 | -8959 | −10001 | -894 | −1115 | −701 | −1378 | * | * | | | | | | | | | | | | |
| 8 | −1663 | −2284 | −2011 | −1523 | −2330 | −351 | 1216 | −2040 | −1373 | −2266 | 1018 | 3538 | −2904 | −1324 | −1737 | −1783 | 125 | −1840 | 1872 | −2101 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | -80 | -8959 | −4259 | -894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 9 | −1659 | −2996 | −1580 | −988 | −537 | −2612 | −1187 | −3026 | 957 | −2977 | 327 | 994 | −2690 | 1014 | 3048 | −1554 | 146 | −2630 | −3132 | −2537 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8883 | -9925 | -894 | −1115 | −1271 | −772 | * | * | | | | | | | | | | | | |
| 10 | −386 | −1546 | −3183 | −158 | −1549 | 1087 | −1902 | 1844 | −2408 | 1816 | −774 | −2433 | −3085 | −2148 | −2442 | −543 | −1525 | −967 | −2028 | −1666 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8883 | -9925 | -894 | −1115 | −1271 | −772 | * | * | | | | | | | | | | | | |
| 11 | −190 | −2861 | 310 | 350 | −3154 | −2399 | −1092 | −191 | 702 | −2868 | −1967 | −1046 | 3068 | −647 | −1207 | −1344 | 70 | −2470 | −3066 | −2396 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −101 | -8883 | −3935 | -894 | −1115 | −1271 | −772 | * | * | | | | | | | | | | | | |
| 12 | −1559 | −1387 | −3825 | −186 | −1341 | −3115 | −1989 | 1464 | −2819 | 1243 | −570 | −2733 | 917 | −2459 | −2652 | −2199 | −1500 | 1701 | −1870 | 1761 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −5 | -8787 | -9829 | -894 | −1115 | −1745 | −511 | * | * | | | | | | | | | | | | |
| 13 | −20 | −2755 | 1051 | −585 | −3075 | −2260 | −918 | −2825 | 752 | −2771 | −1845 | 77 | −14 | 1189 | 708 | 174 | 1753 | −231 | −2939 | −2257 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1827 | -8787 | −482 | -894 | −1115 | −1745 | −511 | * | * | | | | | | | | | | | | |
| 14 | 1722 | −1083 | −1072 | −545 | −1235 | −1655 | −474 | −696 | 1199 | 806 | −318 | −668 | −1802 | −226 | −368 | −713 | −528 | −545 | −1539 | −1099 | 14 |
| — | −149 | −500 | 233 | 43 | −381 | 398 | 105 | −626 | 210 | −466 | −721 | 275 | 394 | 45 | 98 | 359 | 117 | −369 | −295 | −246 | |
| . | −716 | −1368 | -8020 | −124 | −3604 | −2304 | −327 | * | * | | | | | | | | | | | | |
| 15 | 489 | −1508 | -819 | −264 | −1706 | −1689 | 2122 | −1333 | −61 | −1497 | −709 | −497 | −1798 | −60 | 1894 | 512 | −577 | 786 | −1857 | −1327 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −12 | −7489 | -8531 | -894 | −1115 | −308 | −2379 | * | * | | | | | | | | | | | | |
| 16 | 163 | −1531 | −2635 | −25 | −1518 | −974 | −1598 | 1498 | −1850 | 1034 | −723 | −2020 | −574 | −1664 | 76 | 53 | 253 | 992 | −1959 | −1572 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8803 | -9845 | -894 | −1115 | −1678 | −540 | * | * | | | | | | | | | | | | |
| 17 | −1305 | −2658 | −1201 | 1440 | −2932 | −2298 | 2301 | −2649 | 1515 | −1048 | 1693 | −953 | 86 | −518 | −213 | −412 | −235 | 330 | −2871 | −2218 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8803 | -9845 | -894 | −1115 | -840 | −1180 | * | * | | | | | | | | | | | | |
| 18 | −3467 | −4065 | −4298 | −2935 | 1472 | −4065 | −2011 | −4171 | 1010 | −3923 | −3267 | −2803 | −4024 | −1614 | 3622 | −3399 | −68 | −3963 | −3792 | −3601 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | -9925 | -894 | −1115 | −1271 | −772 | * | * | | | | | | | | | | | | |
| 19 | −1353 | −2797 | 1112 | 718 | 1088 | −2331 | −991 | −2849 | 816 | −350 | −1890 | 1404 | −2424 | −535 | −106 | 946 | −389 | −393 | −2988 | −2312 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −95 | -8883 | −4022 | -894 | −1115 | −1271 | −772 | * | * | | | | | | | | | | | | |
| 20 | −479 | −2743 | 967 | 759 | −3053 | 282 | −932 | −655 | 569 | −712 | −1835 | −910 | 877 | −475 | −1023 | 1672 | −1234 | −2359 | −2933 | −2256 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | -881 | -8793 | −1137 | -894 | −1115 | −1721 | −522 | * | * | | | | | | | | | | | | |
| 21 | 422 | −2134 | 295 | 1006 | 798 | −1761 | −430 | −2126 | −34 | −2130 | −1236 | −415 | −1857 | 1080 | −534 | 1559 | −716 | −1730 | −2345 | 766 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −336 | −7921 | −2296 | -894 | −1115 | −3250 | −160 | * | * | | | | | | | | | | | | |
| 22 | −924 | −2060 | 648 | 2026 | −2266 | −1765 | −598 | 1732 | −339 | −2017 | −1222 | −459 | −1957 | −215 | -847 | -858 | 1037 | −1512 | −2365 | −1739 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −11 | −7596 | -8638 | -894 | −1115 | −2955 | −199 | * | * | | | | | | | | | | | | |
| 23 | 547 | −1837 | −652 | 562 | −2050 | −1692 | −360 | −1724 | 659 | 417 | −957 | 1199 | −1781 | 52 | 1056 | −614 | −607 | 538 | −2087 | −1484 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7694 | -8736 | -894 | −1115 | −230 | −2760 | * | * | | | | | | | | | | | | |
| 24 | −425 | −2517 | 1415 | 1412 | 683 | −1082 | −1066 | −105 | −709 | −2482 | −1638 | 1216 | −2481 | −657 | −1189 | −354 | 637 | −283 | 1671 | −2171 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −5 | -8868 | -9910 | -894 | −1115 | -403 | −2036 | * | * | | | | | | | | | | | | |
| 25 | −150 | −2913 | −227 | 1323 | −3233 | 2027 | −1067 | −2985 | 785 | −2929 | −2004 | 93 | −126 | −608 | −1163 | 437 | −352 | −2535 | −3097 | −2412 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −1408 | −2881 | 138 | 354 | −3202 | −2380 | 1744 | −2953 | 2081 | −2897 | −1970 | 1162 | −9 | −579 | 439 | 608 | 540 | −2503 | −3064 | −2381 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −540 | -8959 | −1690 | -894 | −1115 | −701 | −1378 | * | * | | | | | | | | | | | | |
| 27 | −1060 | −2360 | 633 | 640 | −2613 | −2063 | −729 | −2317 | 653 | 400 | −1467 | −728 | −2154 | −295 | 633 | −219 | 1182 | −45 | 2864 | −1946 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −6 | -8426 | -9468 | -894 | −1115 | −1770 | -501 | * | * | | | | | | | | | | | | |
| 28 | −1125 | 1842 | 508 | 1629 | −2828 | −194 | −770 | −98 | 288 | −2539 | −1630 | −755 | 682 | −319 | 20 | −116 | 373 | −27 | −2733 | −2067 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −6 | -8539 | −9581 | -894 | −1115 | −428 | −1962 | * | * | | | | | | | | | | | | |
| 29 | −1810 | −1968 | −2810 | −2250 | 2058 | −439 | −1675 | −1541 | 57 | −1813 | −1163 | −2227 | −3175 | 537 | −2208 | −2133 | 240 | −1430 | 4106 | 2634 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | −9925 | -894 | −1115 | −1271 | −772 | * | * | | | | | | | | | | | | |
| 30 | −1351 | −2821 | 1219 | 1223 | −3141 | −2325 | −984 | −344 | 1231 | −2837 | −1911 | 611 | 35 | −524 | 366 | 871 | −129 | −206 | −3005 | −2323 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −176 | -8883 | −3149 | -894 | −1115 | −1271 | −772 | * | * | | | | | | | | | | | | |
| 31 | −1425 | −1258 | −3714 | −127 | 1232 | −2967 | −1826 | 1797 | −2690 | 924 | 1589 | −2593 | −3015 | 521 | −2509 | −2049 | −1365 | −669 | 2320 | 1805 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8712 | −9754 | -894 | −1115 | −1177 | -842 | * | * | | | | | | | | | | | | |
| 32 | −114 | −2720 | 1674 | 517 | 249 | −2279 | −941 | −2755 | 1521 | −2727 | −1815 | −923 | −2372 | −488 | −1034 | 1110 | 258 | 176 | −2916 | −2247 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8797 | -9840 | -894 | −1115 | −308 | −2379 | * | * | | | | | | | | | | | | |
| 33 | 415 | −2821 | -87 | -82 | −3118 | −376 | −1052 | −901 | 403 | −4 | 2622 | 1070 | 565 | −600 | 1025 | −1299 | −1347 | −2430 | −3019 | −2352 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 34 | −1744 | −3215 | 1670 | −914 | −3565 | −230 | −1347 | −3321 | 322 | −3261 | −2356 | −1231 | −76 | −903 | 264 | 2561 | −1699 | −2866 | −3427 | −2733 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 35 | 1329 | −2850 | 765 | −740 | −3159 | −2400 | −1066 | −674 | 396 | −2864 | −1951 | −1046 | 840 | −613 | 291 | 1940 | −1365 | −2467 | −3049 | −2379 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 36 | −143 | −2702 | 206 | -835 | 41 | 2448 | −1134 | −2633 | 633 | −73 | −1820 | 450 | −697 | −709 | −1252 | −1380 | −1395 | −2280 | −2943 | −2315 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −213 | -8959 | −2887 | -894 | −1115 | −701 | −1378 | * | * | | | | | | | | | | | | |
| 37 | 166 | −2414 | −4715 | −5003 | −5062 | 3399 | −4318 | −4870 | −4890 | −5128 | −4171 | −3432 | 458 | −4369 | −4612 | −2052 | 396 | −3596 | −5281 | −5222 | 38 |
| — | −149 | −500 | 233 | 43 | −381 | 398 | 105 | −626 | 210 | −466 | −721 | 275 | 394 | 45 | 96 | 359 | 121 | −369 | −295 | −249 | |
| H | −102 | −3892 | −9793 | −983 | −1017 | −268 | −2560 | * | * | | | | | | | | | | | | |
| 38 | −1596 | −1579 | −3159 | −223 | −1532 | −3039 | −1860 | 310 | −2305 | 2337 | 1275 | 1260 | −3096 | −285 | −2369 | −2086 | −1536 | −995 | −2014 | 263 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 39 | 936 | −1541 | −3987 | −3379 | −1508 | 36 | −2149 | −947 | −2993 | 1002 | −761 | −2877 | −3290 | −2630 | −2819 | −2309 | −1647 | 2237 | −2031 | 2169 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 40 | −427 | −1983 | −2019 | −1459 | −2030 | −2699 | 462 | −1613 | −1325 | −479 | −1154 | −1625 | 5 | 1216 | −1689 | 1747 | 1510 | 605 | −2361 | 657 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 41 | 1676 | −1543 | −3171 | −2578 | 383 | 346 | −1844 | −1063 | −2315 | 846 | 914 | −2394 | −3073 | −2070 | 49 | −262 | 1418 | −969 | −1988 | −1623 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 42 | −1894 | −1793 | −3798 | −3120 | −1634 | −3368 | −2136 | 213 | 2065 | 2102 | 1311 | −2819 | −3393 | −2385 | −578 | −2451 | −1824 | −1166 | −2197 | 634 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −1479 | −2958 | 1166 | 898 | −3276 | −2422 | −1102 | −3029 | 1390 | 573 | −2050 | 1786 | −2531 | 1081 | −1207 | 272 | −1420 | −2579 | −3141 | −2453 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 44 | 704 | −2518 | −1559 | −1017 | −2771 | 2206 | −1254 | −2430 | −922 | −2549 | −1723 | 415 | 914 | 659 | −1390 | −78 | −1432 | −313 | 1780 | −2290 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 45 | 409 | −2221 | −4870 | −4267 | 1808 | −4170 | −3081 | 1837 | −3906 | 1595 | 868 | −3820 | −4107 | −3458 | −3700 | −3289 | −2421 | 1369 | −2773 | −2504 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 46 | −148 | −2747 | −1318 | 291 | 163 | −2410 | −1075 | −2725 | 1452 | 422 | −1851 | 1380 | −503 | −635 | −93 | 1005 | −1352 | −219 | −2964 | −2317 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 47 | 940 | −2876 | −1251 | 1392 | −3197 | −371 | −1036 | −693 | 1334 | −2892 | −1965 | 851 | 195 | 818 | 269 | −496 | −181 | −2498 | −3059 | −2377 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −334 | -8959 | −2289 | -894 | −1115 | −701 | −1378 | * | * | | | | | | | | | | | | |
| 48 | 1297 | −2733 | 1535 | 1431 | −3056 | −2202 | -892 | −2807 | −489 | −2754 | −1834 | -841 | −2316 | −437 | 588 | 1066 | 285 | −2358 | −2926 | −2239 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −1424 | -8630 | −679 | -894 | −1115 | −1369 | −706 | * | * | | | | | | | | | | | | |
| 49 | 803 | −1427 | -825 | −268 | −1590 | −1685 | −402 | −1196 | -84 | −1388 | −612 | −497 | −1785 | 1471 | 1155 | −643 | 965 | 1173 | −1775 | −1255 | 52 |
| — | −148 | −500 | 233 | 43 | −381 | 398 | 105 | −626 | 210 | −465 | −721 | 275 | 394 | 45 | 98 | 359 | 117 | −369 | −295 | −250 | |
| . | −2627 | −1417 | −1109 | −95 | −3978 | −3529 | −131 | * | * | | | | | | | | | | | | |
| 50 | −647 | −1874 | 345 | 2351 | −2421 | −1193 | −364 | −2177 | −170 | −2216 | −1421 | 5 | −1573 | 3 | −682 | 1515 | −704 | −1731 | −2422 | −1729 | 54 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −23 | −6571 | −7613 | -894 | −1115 | −3813 | −106 | * | * | | | | | | | | | | | | |
| 51 | -899 | −2032 | −304 | −38 | −2497 | −1533 | −197 | −2187 | 2614 | −2098 | −1325 | 1798 | −1736 | 202 | 407 | −783 | -831 | −1823 | −2144 | −1654 | 55 |
| — | −149 | −500 | 233 | 43 | −381 | 398 | 105 | −624 | 210 | −466 | −721 | 275 | 394 | 48 | 96 | 359 | 118 | −369 | −295 | −250 | |
| . | −1736 | −526 | −7613 | −95 | −3978 | −3813 | −106 | * | * | | | | | | | | | | | | |
| 52 | −1058 | −756 | −3314 | −2780 | 2123 | −2856 | −1783 | 2040 | −2494 | 322 | 455 | −2437 | −2766 | −2117 | −2391 | −2006 | −1010 | 1931 | −1454 | −1041 | 57 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −23 | −6571 | −7613 | -894 | −1115 | −212 | −2869 | * | * | | | | | | | | | | | | |
| 53 | −137 | −2628 | 198 | 380 | 1296 | −391 | −995 | −129 | 216 | −2615 | 539 | −993 | −330 | −560 | 339 | −1242 | 2081 | −2214 | −2853 | −2213 | 58 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8832 | −9874 | -894 | −1115 | −347 | −2225 | * | * | | | | | | | | | | | | |
| 54 | −1404 | −2867 | 133 | 1837 | −3184 | 317 | 797 | −2932 | −621 | -832 | −1958 | −1016 | −788 | 743 | 268 | 7 | 794 | −336 | −3053 | 518 | 59 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 55 | −588 | −1651 | −2743 | −2164 | 1976 | 1343 | 1017 | −1193 | −1959 | −1516 | -843 | −2131 | 684 | −1775 | −306 | −217 | 137 | 1029 | 1859 | −1691 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −2704 | -8959 | −244 | -894 | −1115 | −701 | −1378 | * | * | | | | | | | | | | | | |
| 56 | −656 | −1699 | −141 | 133 | −1449 | −1369 | 2746 | −1700 | 586 | −1661 | −931 | −99 | −1557 | 2522 | 337 | −569 | −593 | −1400 | −1541 | -847 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −28 | −6283 | −7325 | -894 | −1115 | −3178 | −169 | * | * | | | | | | | | | | | | |
| 57 | −514 | −655 | −2362 | −2023 | −1208 | −1770 | −1602 | 643 | −1768 | −621 | −255 | −1663 | −2162 | −1628 | −1860 | −1023 | 1901 | 2468 | −1941 | −1553 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −22 | −6610 | −7652 | -894 | −1115 | −163 | −3225 | * | * | | | | | | | | | | | | |
| 58 | −108 | −1696 | −2389 | −1818 | −1701 | −2777 | −1546 | 616 | −245 | 534 | -881 | −1873 | −2846 | 1589 | 237 | −470 | 1240 | 1453 | −2108 | −1699 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8875 | −9917 | -894 | −1115 | −1319 | −739 | * | * | | | | | | | | | | | | |
| 59 | −5504 | −4447 | −5929 | −6269 | 977 | −5803 | −2007 | −4344 | −5825 | −528 | −3746 | −4425 | −5655 | −4556 | −5194 | −5049 | −5355 | −4523 | 5717 | 2387 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8875 | −9917 | -894 | −1115 | −1319 | −739 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −1665 | −1478 | −4011 | −3385 | 1369 | −340 | −2101 | 1537 | −2988 | −1266 | 1273 | −2876 | −3276 | −2612 | −2794 | −2324 | −1607 | 2489 | −1949 | 1619 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8875 | −9917 | -894 | −1115 | −416 | −1996 | * | * | | | | | | | | | | | | |
| 61 | −31 | −2658 | −4005 | −3959 | −4975 | 3327 | −3824 | −4751 | −20 | −4942 | −4022 | −3241 | −3611 | −3658 | −3959 | 36 | 176 | −3675 | −5120 | −4879 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 62 | −1850 | 1106 | −4529 | −4187 | −2755 | −2972 | −3115 | −2302 | −3816 | −2682 | −2007 | −3266 | −3500 | −3449 | −3647 | 1139 | 1669 | 41 | 5178 | −2895 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 63 | 347 | 1353 | −2513 | −1941 | −1731 | −2855 | −1632 | −1292 | 27 | 894 | 843 | −1978 | 1984 | 473 | −2006 | 420 | 131 | −151 | −2148 | −1744 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 64 | −2265 | −3509 | −2207 | −1558 | −3965 | 2804 | −1544 | −3590 | 631 | −3456 | 1194 | 600 | −3179 | 1479 | 533 | −2148 | −2147 | −3215 | −3516 | −3042 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 65 | −495 | −1628 | -80 | 326 | −1612 | −2946 | −1748 | 1122 | −160 | 549 | 548 | −2195 | −3009 | −1845 | −2198 | −1973 | 644 | 2070 | −2062 | −1680 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 66 | −1405 | −2860 | 394 | 1094 | −3173 | −2382 | 1690 | −279 | −625 | −2872 | −1951 | 883 | 1517 | 377 | −1131 | 800 | 31 | −254 | −3048 | −147 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 67 | −1441 | −2425 | 119 | 263 | −2580 | −488 | −1193 | 825 | -879 | −2368 | 1042 | −1244 | 865 | 661 | −1340 | −187 | 1012 | 1529 | −2718 | −2154 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 68 | −141 | −2886 | 2310 | −67 | −3206 | −474 | −1045 | −2956 | 1001 | −1279 | −1975 | 369 | 1378 | 301 | −1135 | −1293 | 115 | −2507 | −3069 | −2386 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 69 | −79 | −2877 | 713 | 1949 | −3197 | −406 | −1038 | −2947 | 407 | −2892 | −1966 | −1014 | −501 | 744 | −1126 | 792 | 277 | 157 | −3060 | −2378 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 70 | −172 | −2862 | 1694 | 1160 | −3177 | −2381 | −1040 | −687 | 755 | −284 | −1953 | −44 | −2474 | −582 | 368 | 1118 | −1344 | -815 | −3050 | −2371 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 71 | −1485 | −2964 | 990 | 2286 | −3282 | −2426 | −1109 | −3034 | 757 | −2978 | −2056 | −1059 | 1059 | 1038 | −1215 | −64 | −1427 | 259 | −3147 | −2459 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1230 | -8959 | -806 | -894 | −1115 | −701 | −1378 | * | * | | | | | | | | | | | | |
| 72 | 710 | −2243 | −497 | 1091 | −2595 | 1068 | −474 | −2334 | 1141 | −2301 | −1402 | −394 | 1603 | −32 | −579 | −721 | −791 | −1898 | −2487 | −1813 | 77 |
| — | −149 | −500 | 233 | 43 | −381 | 399 | 106 | −626 | 210 | −466 | −720 | 275 | 394 | 45 | 96 | 360 | 117 | −369 | −294 | −249 | |
| — | −2903 | −2766 | −475 | −180 | −3090 | −3378 | −146 | * | * | | | | | | | | | | | | |
| 73 | −566 | −932 | −1095 | −1249 | −2242 | 3220 | −1341 | −2244 | −1466 | −2405 | −1835 | −1106 | −1601 | −1346 | −1558 | −760 | -892 | −1687 | −2022 | −2053 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −1082 | −5917 | −969 | −894 | −1115 | −3081 | −181 | * | * | | | | | | | | | | | | |
| 74 | 2538 | −280 | −978 | −943 | −1445 | −589 | -896 | −706 | -883 | −1230 | −712 | −623 | −1201 | −794 | −1024 | 12 | −73 | −359 | −1779 | −1426 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −960 | −5796 | −1096 | -894 | −1115 | −1449 | −658 | * | * | | | | | | | | | | | | |
| 75 | −1398 | −3053 | 2346 | 1994 | −3303 | −1774 | 2019 | −3123 | −746 | −3042 | −2219 | −379 | 1270 | −454 | −1390 | −1169 | −1396 | −2649 | −3225 | −2398 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −12 | −7483 | -8525 | -894 | −1115 | −2565 | −267 | * | * | | | | | | | | | | | | |
| 76 | −746 | −2129 | 1022 | 1546 | 988 | −1681 | −382 | −2130 | −7 | −2124 | −1234 | 936 | −1801 | 56 | −516 | 625 | −689 | −1727 | −2322 | 1457 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −10 | −7710 | -8752 | -894 | −1115 | −2494 | −282 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | 576 | −1038 | −1759 | −1190 | −1043 | −2133 | −907 | 603 | −1014 | 947 | −224 | 967 | 802 | 1206 | −1270 | −1136 | −756 | 558 | −1455 | −1047 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −9 | −7892 | -8934 | -894 | −1115 | −228 | −2773 | * | * | | | | | | | | | | | | |
| 78 | −79 | 897 | −1226 | 770 | −3071 | −2339 | 1193 | −313 | 1763 | −219 | −1868 | −983 | −2431 | 2074 | −208 | −3 | −1295 | −2382 | −2970 | −2301 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8883 | −9925 | -894 | −1115 | −1271 | −772 | * | * | | | | | | | | | | | | |
| 79 | 670 | −2825 | 1713 | 1005 | −3146 | −2326 | 850 | −2896 | 1069 | −2841 | −1914 | 583 | 27 | 265 | −1073 | −1233 | 561 | −330 | −3008 | −2326 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8883 | −9925 | -894 | −1115 | −433 | −1948 | * | * | | | | | | | | | | | | |
| 80 | 266 | −2872 | 1096 | 374 | −3190 | −2379 | −1037 | −2939 | 1250 | -869 | 979 | 155 | −133 | −578 | 1263 | −34 | 519 | −1130 | −3056 | −2375 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 81 | −1956 | −1755 | −173 | −3624 | −1809 | −3579 | −2507 | 1715 | −3274 | 683 | −989 | −3190 | −3612 | −2939 | −3139 | −325 | 86 | 2605 | −2394 | −2040 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 82 | −226 | −2856 | −1262 | −118 | −3168 | −406 | −1043 | 275 | 1133 | −2868 | −1948 | −124 | 74 | −586 | −158 | 1726 | 1307 | −2473 | −3045 | −2368 | 88 |
| — | −149 | −500 | 236 | 42 | −381 | 398 | 105 | −627 | 210 | −465 | −721 | 275 | 393 | 47 | 97 | 360 | 117 | −370 | −295 | −250 | |
| E | −3078 | −4100 | −281 | −2409 | −301 | −701 | −1378 | * | * | | | | | | | | | | | | |
| 83 | −1266 | −978 | −3328 | −2849 | −488 | −3033 | −2133 | 1056 | −2539 | 1875 | 586 | −2627 | −2925 | −2209 | −2494 | −2241 | −1237 | 2245 | −1750 | −1471 | 95 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −24 | −6467 | −7509 | -894 | −1115 | −151 | −3335 | * | * | | | | | | | | | | | | |
| 84 | −1367 | −2841 | 449 | 678 | −3162 | -879 | 1667 | −2913 | 1173 | −2857 | −1931 | 0 | 1463 | 2326 | 331 | −1247 | −1307 | −2463 | −3024 | −2341 | 96 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | −9925 | -894 | −1115 | −1271 | −772 | * | * | | | | | | | | | | | | |
| 85 | 22 | −2813 | 955 | 980 | −369 | −301 | −986 | −263 | 624 | -885 | −1903 | 10 | −2420 | −528 | 1331 | 489 | 173 | −2432 | −2999 | −2319 | 97 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | −9925 | -894 | −1115 | −1271 | −772 | * | * | | | | | | | | | | | | |
| 86 | -83 | −1385 | −5 | −3126 | 588 | −3073 | −1936 | 392 | −2750 | 2240 | −578 | −2675 | −3123 | 275 | −2596 | −2152 | −1479 | 351 | −1839 | 708 | 98 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | −9925 | -894 | −1115 | −433 | −1948 | * | * | | | | | | | | | | | | |
| 87 | −560 | −2860 | 297 | 1249 | −643 | −354 | −1041 | −396 | 1428 | 168 | −1951 | −1020 | −18 | 1573 | −1130 | −53 | −1344 | −2478 | −3048 | −2369 | 99 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 88 | −1444 | −2919 | 1300 | 2135 | −3238 | 328 | −1072 | −2989 | −660 | −2934 | −2010 | 467 | 82 | 861 | −1170 | −578 | 475 | −343 | −3102 | −2417 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 89 | −1428 | −2898 | −77 | 1613 | −3221 | −2396 | −1054 | −2970 | 1998 | −2913 | 214 | 1409 | −2491 | −595 | 1059 | −1307 | 831 | −2521 | −3079 | −2399 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 90 | −1592 | 1571 | −3825 | −3197 | 2895 | −1068 | 1004 | 927 | −2816 | 411 | −637 | 151 | −3177 | −2460 | −645 | −2206 | −1532 | -850 | −1880 | 1714 | 102 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −101 | -8959 | −3933 | -894 | −1115 | −701 | −1378 | * | * | | | | | | | | | | | | |
| 91 | −1513 | −3004 | 49 | 354 | −3319 | −2410 | −1124 | −3075 | 98 | −3017 | −2100 | 2265 | −2542 | 420 | −1258 | 1536 | 1743 | −2623 | −3186 | −2489 | 103 |
| — | −150 | −501 | 232 | 45 | −382 | 399 | 105 | −627 | 209 | −467 | −721 | 276 | 393 | 47 | 97 | 361 | 118 | −370 | −284 | −250 | |
| E | −191 | −4004 | −4014 | −3112 | −177 | −394 | −2065 | * | * | | | | | | | | | | | | |
| 92 | 252 | 3625 | −3856 | −3221 | 59 | −3072 | −1940 | -847 | −2820 | −143 | −558 | −2712 | −3122 | −2445 | −2625 | 749 | −1467 | 1457 | 1840 | 1618 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8874 | −9917 | -894 | −1115 | −1322 | −737 | * | * | | | | | | | | | | | | |
| 93 | 524 | −1367 | −3725 | −3098 | 244 | −3051 | 2088 | 470 | −2724 | −202 | −569 | −2651 | −3103 | −2373 | 87 | −140 | 148 | 2005 | −1823 | 1042 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8874 | −9917 | -894 | −1115 | −415 | −1999 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 94 | 304 | −1571 | −3113 | −2525 | 570 | −2995 | −1841 | −1101 | −2271 | −344 | −778 | −2364 | 3038 | −2038 | 66 | −350 | 146 | 133 | −2022 | −1654 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 95 | 290 | −2234 | −5012 | −4487 | 321 | −4388 | −3521 | 998 | −4188 | −1907 | −1536 | −4058 | −4373 | −3892 | −4079 | −3548 | 1259 | 3029 | −3321 | −2942 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 96 | −1582 | −1459 | −283 | −3004 | 2433 | −3093 | −1945 | 413 | −2664 | −7 | −660 | 40 | 9 | −2344 | −27 | −2164 | −1522 | 18 | 3152 | 1924 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 97 | −1748 | −1575 | −4028 | −3399 | −1456 | −3300 | −2168 | 454 | −3011 | 2396 | 1325 | −2925 | −129 | 349 | −2832 | −2385 | 486 | 339 | −2026 | −1696 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 98 | −1972 | −3002 | 2302 | −1573 | −3794 | −2773 | −2038 | −3504 | −1825 | −735 | −2752 | −1798 | 1531 | −1667 | −2322 | 1819 | 1388 | −3030 | −3858 | −3248 | 120 |
| — | −149 | −500 | 232 | 44 | −381 | 400 | 105 | −627 | 211 | −467 | −721 | 275 | 395 | 45 | 95 | 360 | 117 | −370 | −295 | −250 | |
| H | −274 | −4100 | −3127 | −2409 | −301 | −701 | −1378 | * | * | | | | | | | | | | | | |
| 99 | −15 | −2789 | 2461 | 1466 | −3108 | −2275 | −943 | −2860 | −529 | −2804 | −1879 | −910 | −399 | 919 | 487 | −266 | 207 | −2410 | −2972 | −2287 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | -8785 | −9827 | -894 | −1115 | −296 | −2430 | * | * | | | | | | | | | | | | |
| 100 | −564 | −2880 | 1170 | 1980 | −3198 | −2386 | −1047 | 403 | −67 | −2895 | −1971 | −1023 | −2481 | 645 | 298 | −1296 | 1743 | −2500 | −3065 | −2384 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 101 | −1452 | −2408 | 1662 | −1008 | −2556 | −2523 | −1208 | 1018 | 935 | 702 | −1546 | −1268 | −2610 | 665 | 316 | −1455 | 834 | −149 | −2705 | −2149 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 102 | 1006 | −1433 | −3778 | −3152 | 1817 | −3114 | 383 | 1009 | −2780 | 183 | −635 | 152 | −3166 | −376 | −2633 | −279 | −1524 | 1374 | −1888 | 855 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 103 | −173 | −2884 | 1895 | 1507 | −3205 | −2382 | 585 | −2956 | 1400 | −2900 | −1973 | 959 | −2476 | 730 | −1132 | −1291 | −260 | −458 | −3067 | −2384 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 104 | 355 | −2873 | −1253 | 1252 | −3192 | 172 | −1037 | −2942 | 910 | −21 | 229 | 472 | −2472 | 1462 | 221 | 638 | −1343 | −2494 | −3057 | −2376 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 105 | 177 | −1647 | −3439 | −2848 | 1416 | −3171 | 2965 | −1163 | −2540 | −264 | -847 | −2584 | −3224 | −2274 | 43 | −2229 | 118 | −1075 | −1887 | 3185 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 106 | −4478 | −4379 | −5338 | −4170 | −1407 | −4948 | −2103 | −4381 | 245 | −3905 | −3642 | −3640 | −4850 | −2669 | 398 | −4304 | −4185 | −4365 | 2169 | 4534 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 107 | −1425 | −2897 | 237 | 288 | −3217 | −2392 | 2636 | −2968 | 672 | −743 | −1987 | 2503 | −2488 | −595 | 299 | 637 | −1364 | −2519 | −3079 | −2397 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 108 | −2244 | −3335 | −1526 | −1406 | −3583 | 2726 | 1138 | 884 | −1497 | −3395 | −2615 | 1510 | −3209 | 1384 | −1895 | −2169 | −2227 | −2995 | −3635 | −3021 | 136 |
| — | −149 | −500 | 233 | 43 | −381 | 398 | 105 | −627 | 210 | −466 | −721 | 275 | 393 | 48 | 98 | 360 | 117 | −370 | −295 | −250 | |
| H | −4123 | −4100 | −177 | −1491 | −634 | −701 | −1378 | * | * | | | | | | | | | | | | |
| 109 | −1566 | −1294 | −2100 | −2001 | 454 | −1834 | −511 | −1219 | −1508 | −1002 | -839 | −1682 | −2130 | −1491 | −1439 | −1793 | −1620 | −1256 | 5487 | 814 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −37 | −5860 | −6902 | -894 | −1115 | −3019 | −190 | * | * | | | | | | | | | | | | |
| 110 | −705 | −948 | −1618 | −1303 | −690 | −1755 | −1020 | −158 | −1010 | 1700 | 117 | −1247 | 2211 | −977 | −1162 | −1032 | −778 | −243 | −1421 | −996 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −25 | −6433 | −7475 | -894 | −1115 | −3841 | −104 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 111 | 1700 | −557 | −1695 | −1297 | −763 | −1420 | −946 | 50 | −1030 | −224 | 3161 | −1099 | −1771 | −916 | −1178 | −626 | −401 | 101 | −1403 | −1029 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −25 | −6433 | −7475 | -894 | −1115 | −64 | −4518 | * | * | | | | | | | | | | | | |
| 112 | −4565 | −3931 | −5739 | −5782 | 3490 | −5425 | −2129 | 141 | −5358 | −3182 | −3080 | −4332 | −5341 | −4368 | −4882 | −4625 | −10 | −3547 | −1410 | 3544 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 113 | 1855 | 4070 | −5342 | −5662 | −5270 | −2885 | −4634 | −5071 | −5293 | −5349 | −4389 | −3719 | −3700 | −4736 | −4907 | 2450 | −2470 | −3788 | −5501 | −5472 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 114 | −3213 | −5100 | 550 | 1018 | −5286 | −3172 | −2476 | −5191 | 2362 | −5049 | −4362 | 3226 | −3686 | −2136 | −3391 | −2878 | −3266 | −4672 | −5228 | −4245 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 115 | 449 | −2880 | −1253 | 325 | −3201 | −2380 | 1383 | −2951 | 403 | −2896 | −1969 | 1663 | 74 | 1692 | 212 | 1362 | −1346 | −2502 | −3063 | −2380 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 116 | −125 | −1430 | −3848 | −3218 | −1386 | −3129 | 574 | 2301 | −2832 | −128 | −632 | −2746 | −3180 | 435 | −2664 | −2210 | 109 | 2053 | −1888 | 297 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 117 | −4650 | −4007 | −7007 | −6424 | 624 | −6837 | −5317 | 1113 | −6231 | 3041 | −796 | −6543 | −5770 | −4901 | −5662 | −6240 | −4476 | −2302 | −3808 | −3932 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 118 | −6136 | −5373 | −6282 | −6179 | −4244 | −5466 | −4668 | −6785 | −4688 | −6196 | −6062 | −5854 | −5831 | −5324 | 236 | −6305 | −6186 | −6637 | 6199 | −3805 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 119 | −3855 | −4453 | 285 | −3128 | 657 | −4033 | −3606 | −5516 | −4486 | −5291 | −4958 | −3318 | 4059 | −3848 | −4972 | −3836 | −4131 | −5058 | −4074 | −3128 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 120 | −421 | −2267 | −5032 | −4491 | −2376 | −4412 | −3487 | 1533 | −4182 | 2108 | −1395 | −4068 | −4370 | −3847 | −4051 | −3564 | 1563 | 1193 | −3244 | −2898 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 121 | −2056 | 1461 | −4340 | −3736 | 3377 | −3593 | −2257 | 315 | −3338 | 1231 | -838 | −3194 | −3607 | 463 | −3123 | −2686 | −1992 | −1214 | −1971 | 829 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 122 | −6595 | −5567 | −6099 | −6438 | −5559 | −5537 | 5463 | −7721 | −6484 | −7100 | −7039 | −6386 | −5985 | −6472 | −6145 | −6901 | −6790 | −7414 | −5292 | −5215 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −263 | -8959 | −2605 | -894 | −1115 | −701 | −1378 | * | * | | | | | | | | | | | | |
| 123 | −5907 | −4878 | −5926 | −6279 | −1901 | −5375 | −3243 | −5538 | −6146 | −4875 | −4948 | −5278 | −5644 | −5409 | −5629 | −5808 | −5948 | −5605 | −2536 | 4916 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8702 | −9744 | -894 | −1115 | −2048 | −399 | * | * | | | | | | | | | | | | |
| 124 | −1596 | −2240 | −1987 | −1365 | −2353 | −2702 | 2791 | 709 | 493 | −179 | 2664 | −1536 | −2766 | 1756 | 1222 | −1691 | −1515 | −1749 | −2532 | −2081 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −5 | -8702 | −9744 | -894 | −1115 | −2048 | −399 | * | * | | | | | | | | | | | | |
| 125 | −1457 | −1290 | −3734 | −3108 | −1165 | −52 | −1830 | 1809 | −2714 | 1473 | −474 | −2615 | 1632 | −2344 | −2534 | −2079 | −1398 | −697 | 2219 | 982 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −5 | -8702 | −9744 | -894 | −1115 | −2048 | −399 | * | * | | | | | | | | | | | | |
| 126 | −1611 | −2691 | 383 | −934 | −2885 | 1234 | −1328 | −2585 | −1072 | −363 | −1893 | 1472 | 2599 | −957 | −1566 | −1564 | −1579 | −2280 | 2067 | −2389 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −1806 | -8702 | −491 | -894 | −1115 | −2048 | −399 | * | * | | | | | | | | | | | | |
| 127 | −493 | −1319 | −931 | −456 | −2029 | −1424 | −515 | −1655 | 27 | −1780 | −995 | −567 | 2227 | −163 | 1245 | −556 | 1707 | −1283 | −2059 | −1589 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −405 | −6914 | −2080 | -894 | −1115 | −3730 | −113 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 128 | −684 | −1624 | −265 | −119 | −2139 | −1361 | −439 | −1943 | 40 | −1961 | −1238 | −332 | 2202 | 2697 | −257 | −660 | −735 | −1573 | −2121 | −1588 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −23 | −6532 | −7574 | -894 | −1115 | −2206 | −352 | * | * | | | | | | | | | | | | |
| 129 | −712 | -857 | −1732 | 1116 | −584 | −2047 | −770 | −273 | −967 | 498 | 3024 | −1192 | −2102 | -817 | −1171 | −1074 | −650 | −235 | −1122 | 1954 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −14 | −7316 | -8358 | -894 | −1115 | −1129 | -882 | * | * | | | | | | | | | | | | |
| 130 | −1059 | 1177 | 2715 | −1059 | 186 | −2245 | −1021 | −1218 | −940 | −1479 | −760 | −1211 | −2351 | -832 | −1301 | 345 | 883 | −1050 | −1912 | 1055 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −7 | -8256 | −9298 | -894 | −1115 | −1466 | −648 | * | * | | | | | | | | | | | | |
| 131 | −1137 | −2290 | −1127 | −578 | 519 | −2162 | -837 | −2176 | −467 | −2261 | −1417 | 1644 | 2036 | 642 | 1335 | 222 | −1077 | 34 | −2549 | −1947 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −6 | -8499 | −9541 | -894 | −1115 | −1634 | −561 | * | * | | | | | | | | | | | | |
| 132 | −235 | −2217 | 982 | −718 | −2383 | −2256 | −943 | 78 | −620 | 350 | −1353 | −986 | 1782 | 975 | −1085 | 821 | 373 | −1754 | −2506 | −1934 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −6 | -8608 | −9650 | -894 | −1115 | −2306 | −326 | * | * | | | | | | | | | | | | |
| 133 | 208 | −2527 | 359 | 527 | −2801 | −2166 | 1508 | 88 | 545 | 6 | −1629 | 1619 | −2258 | 612 | −929 | −1077 | −1112 | −107 | 1991 | −2087 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −6 | -8608 | −9650 | -894 | −1115 | −195 | −2983 | * | * | | | | | | | | | | | | |
| 134 | −560 | −2869 | 989 | 1621 | −3186 | 653 | −1039 | −2934 | 377 | −139 | −1959 | −1017 | −2473 | 743 | −1128 | 752 | −342 | −348 | −3055 | −2374 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 135 | −226 | −2557 | 1239 | −171 | 205 | 798 | −1139 | 228 | 1103 | −2519 | 1535 | −1164 | −56 | −735 | −1265 | −421 | 248 | −338 | −2820 | −2223 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 136 | 675 | −2854 | −1263 | 1286 | −3164 | −2384 | −1043 | −2907 | 456 | −273 | −1946 | 865 | −2477 | 644 | 1415 | −1291 | 808 | −1120 | −3043 | 533 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 137 | −2259 | −2270 | −3464 | −2965 | 3224 | −3571 | −1893 | −1843 | −2741 | −2082 | −1485 | 257 | −3630 | 1354 | −2845 | −129 | −2201 | 119 | −1738 | 2632 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 138 | −1449 | −2891 | 2381 | 1743 | −570 | −470 | 1146 | −2939 | −677 | −1395 | −1986 | −1050 | −2512 | 1358 | −1185 | −1333 | −1389 | −2505 | −3078 | 633 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 139 | −1428 | −2898 | 1337 | 1285 | −3221 | −2396 | 1189 | −2970 | 402 | −1407 | −1988 | −1032 | −2491 | 817 | 2405 | −48 | −1366 | −2522 | −3079 | −2399 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 140 | 249 | −2874 | −1252 | 291 | −3194 | −979 | 2199 | −1080 | 332 | −2890 | −1964 | 1424 | −133 | 727 | −190 | 1357 | −455 | −991 | −3058 | −2376 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 141 | 1264 | −2813 | 236 | 224 | −3095 | −2411 | −1081 | −2820 | −681 | 396 | −1913 | 80 | −2508 | 834 | −1182 | 752 | −1371 | −2414 | 3711 | −2359 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 142 | −4281 | −3793 | −5329 | −95 | 1043 | −5236 | −2232 | −3122 | −4811 | −2646 | 1146 | −4220 | −5168 | −4138 | −4518 | −4449 | −4197 | −3342 | 5852 | −423 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 143 | 1103 | −2879 | 2095 | 309 | −3200 | −2381 | −1039 | −2950 | 846 | −1553 | −1969 | −6 | −2474 | 1247 | 791 | −1288 | −1347 | −2501 | −3062 | 523 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 144 | 1934 | −2789 | 948 | -807 | −281 | 927 | −1128 | −2768 | −744 | −2786 | −1903 | 1627 | −2548 | −693 | 245 | −1375 | −1409 | −2384 | −3012 | 123 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 145 | −5646 | −4569 | −6016 | −6375 | 1745 | −5886 | −2106 | −4537 | −5938 | −3839 | −3938 | −4526 | −5754 | −4667 | −5302 | −5161 | −5502 | −4698 | −1352 | 4689 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 146 | −1540 | −1688 | −2645 | −2069 | 331 | −2894 | −1678 | −351 | 505 | 343 | -877 | −529 | −2960 | 1088 | 258 | −1908 | 987 | 2134 | −2110 | −1716 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 147 | −1410 | −2883 | 197 | 1079 | −3204 | −2382 | 2075 | −2955 | 1787 | −2899 | −1972 | 155 | −2476 | 260 | 1621 | 443 | −244 | −2505 | −3065 | −2383 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 148 | 1731 | −1543 | −4077 | −3446 | 536 | −3293 | −2170 | 411 | −3047 | −404 | 1320 | −2939 | −3331 | −2664 | −2848 | −2382 | −1669 | 2366 | 1932 | −1682 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 149 | −2579 | −3282 | −2806 | −3183 | −5254 | −3212 | −3847 | −5461 | −4198 | −5560 | −4756 | 4258 | −3950 | −3720 | −4479 | −120 | −2996 | −4339 | −5388 | −4932 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 150 | −299 | −3141 | −1636 | 218 | −3514 | −2680 | 1217 | −3221 | 2168 | −3130 | 126 | −1318 | −2756 | 2258 | 1917 | −1621 | −1660 | −2795 | −3251 | −2648 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 151 | 1188 | −1445 | −3736 | −3113 | 427 | −3113 | −1973 | 1215 | 854 | 1306 | 758 | −2693 | −3165 | −2409 | 651 | −2189 | −1528 | -859 | −1899 | 772 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 152 | −5558 | −4518 | −6026 | −6352 | 4341 | −5899 | −2122 | −4219 | −5912 | −696 | −3605 | −4534 | −5738 | −4646 | −5283 | −5151 | −5410 | −4485 | −1366 | 1370 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 153 | 3367 | 823 | −5337 | −5655 | −5281 | 8 | −4633 | −5094 | −5294 | −5360 | −4393 | −3714 | −3696 | −4732 | −4909 | 217 | −2465 | −3795 | −5509 | −5486 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 154 | −1962 | −3493 | 3125 | 1222 | −3797 | −2690 | 1123 | −3566 | 627 | −1632 | −2605 | −1310 | −2899 | 1105 | −1707 | −1801 | −1919 | −3110 | −3662 | −2939 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 155 | 1231 | −2902 | −1311 | 273 | −3224 | −2425 | −1073 | −2965 | 2309 | −2913 | −1995 | 459 | −2517 | −617 | 1101 | −1338 | 751 | −927 | −3081 | −2413 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 156 | 506 | −2757 | −5889 | −5527 | −3311 | −5634 | −5368 | 2953 | −5434 | 258 | −2061 | −5293 | −5414 | −5303 | −5521 | −4956 | −3224 | 2223 | −4851 | −4396 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 157 | 756 | 2465 | −3876 | −1190 | 755 | −417 | −1996 | 433 | −2851 | 93 | 1935 | −524 | −3178 | −2484 | −2671 | −325 | −1526 | 1629 | −1878 | −1534 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 158 | −132 | −2880 | 136 | 1759 | −3201 | −342 | 379 | −2952 | 1060 | −2896 | −1969 | −5 | 718 | −579 | 269 | 1166 | −1346 | −2502 | −3063 | −2380 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 159 | −171 | −2137 | 103 | 1030 | −337 | −2622 | 531 | 919 | −1137 | 59 | −1296 | 1344 | −2704 | −34 | −1545 | −1574 | −1411 | 1536 | −2487 | −1993 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 160 | 791 | −2000 | −4659 | −4077 | −2028 | −3970 | −2930 | 1919 | −3725 | 166 | −1155 | −3614 | −3966 | −3371 | −3563 | −3090 | −2208 | 1271 | −2734 | 3276 | 191 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 161 | −175 | −2891 | 244 | 1153 | −3212 | −2386 | −1047 | −2963 | 1833 | −2906 | −1980 | 1524 | −2481 | 1370 | 1241 | −396 | −1356 | −2513 | −3073 | −2390 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1984 | -8959 | −424 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 162 | -859 | -1515 | -1270 | -663 | -1698 | -1828 | -482 | -1305 | 238 | 199 | -749 | -769 | 2362 | -165 | 1927 | -938 | -809 | -1130 | -1814 | -1381 | 193 |
| — | -149 | -500 | 233 | 45 | -381 | 398 | 105 | -626 | 210 | -466 | -721 | 277 | 394 | 45 | 96 | 359 | 117 | -369 | -295 | -250 | |
| . | -416 | -2019 | -8034 | -984 | -1016 | -71 | -4385 | * | * | | | | | | | | | | | | |
| 163 | -2033 | -3584 | 2285 | 1288 | -3882 | -2720 | 1209 | -3658 | 1355 | -3587 | -2700 | -1337 | 1993 | 565 | -1822 | -1864 | -1995 | -3198 | -3754 | -3017 | 196 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 164 | -3537 | -5628 | 2720 | -276 | -5750 | 2733 | -2719 | -5761 | -3176 | -5583 | -5043 | 1023 | -3849 | -2416 | -4226 | -3132 | -3647 | -5184 | -5789 | -4624 | 197 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 165 | 648 | -3645 | 3812 | -2140 | -5495 | -3092 | -3220 | -5408 | -3669 | -5451 | -4702 | -2348 | -3784 | -2969 | -4389 | -61 | -3036 | -4429 | -5616 | -4875 | 198 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 166 | -1741 | -1557 | -4089 | -3456 | 1103 | -3302 | -2174 | 1276 | -3055 | 1231 | 1700 | -2948 | -3337 | -2666 | -2853 | -2390 | 1104 | 1379 | -2015 | 1445 | 199 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 167 | -3355 | -2845 | -6028 | -5701 | 435 | -5853 | -5693 | 3291 | -5655 | -2119 | -2085 | -5506 | -5576 | -5535 | -5782 | -5222 | -3343 | 2335 | -5008 | -4489 | 200 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 168 | -4269 | -3736 | -6574 | -6008 | -1914 | -6218 | -4637 | 330 | -5712 | 272 | 1546 | -5844 | -5498 | -4661 | -5265 | -5498 | -4129 | -2183 | 5803 | -3317 | 201 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 169 | -3297 | 1813 | -5975 | -5641 | -3434 | -5787 | -5696 | 2800 | -5589 | -332 | -2145 | -5442 | -5535 | -5513 | -5729 | -5143 | -3286 | 2726 | -5108 | -4613 | 202 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 170 | -3529 | -4784 | -1711 | -1950 | -4375 | -3550 | 4845 | -5169 | -1992 | -4896 | -4315 | 338 | -3998 | 2297 | -2205 | -3271 | -3540 | -4754 | -4394 | -3588 | 203 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -4 | -8959 | -10001 | -894 | -1115 | -701 | -1378 | * | * | | | | | | | | | | | | |
| 171 | -6017 | -5649 | 4213 | -4573 | -6837 | -5145 | -5256 | -7689 | -5916 | -7201 | -7011 | -4892 | -5650 | -5366 | -6133 | -5970 | -6182 | -7241 | -5831 | -6504 | 204 |
| — | -149 | -500 | 233 | 43 | -381 | 399 | 106 | -626 | 210 | -466 | -720 | 275 | 394 | 45 | 96 | 359 | 117 | -369 | -294 | -249 | |
| G | -4 | -8959 | -10001 | -894 | -1115 | -701 | -1378 | * | * | | | | | | | | | | | | |
| 172 | -6277 | -5195 | -6255 | -6614 | -2289 | -5655 | -3618 | -5935 | -6505 | -5261 | -5336 | -5643 | -5936 | -5773 | -5970 | -6193 | -6317 | -5996 | -2912 | 4927 | 205 |
| — | -149 | -500 | 233 | 43 | -381 | 399 | 106 | -626 | 210 | -466 | -720 | 275 | 394 | 45 | 96 | 359 | 117 | -369 | -294 | -249 | |
| G | -4 | -8959 | -10001 | -894 | -1115 | -701 | -1378 | * | * | | | | | | | | | | | | |
| 173 | -1844 | -3168 | -1391 | -1055 | -3266 | -2689 | 4433 | -3188 | -1059 | -3180 | -2325 | 470 | -68 | 639 | -1525 | 614 | -1797 | -2799 | -3282 | 636 | 206 |
| — | -149 | -500 | 233 | 43 | -381 | 399 | 106 | -626 | 210 | -466 | -720 | 275 | 394 | 45 | 96 | 359 | 117 | -369 | -294 | -249 | |
| G | -4 | -8959 | -10001 | -894 | -1115 | -701 | -1378 | * | * | | | | | | | | | | | | |
| 174 | -5647 | -4878 | -6611 | -6689 | -3480 | -5830 | -5714 | -3122 | -6613 | 3375 | -2416 | -6629 | -5924 | -5899 | -6106 | -6640 | -5628 | -3921 | -4748 | -4938 | 207 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 175 | -2027 | -1828 | -4333 | -3719 | 1407 | -3574 | -2301 | 241 | -3321 | 872 | 3993 | -3191 | -3585 | 316 | -3104 | -2667 | -1963 | -1184 | 1996 | 925 | 208 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 176 | -3470 | -3092 | -5848 | -5248 | 736 | -5282 | -4109 | 4 | -4934 | 2743 | -834 | -4948 | 915 | -4202 | -4627 | -4458 | -3376 | 720 | -3364 | -3291 | 209 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 177 | -250 | 1699 | -4666 | -4063 | 412 | -3922 | -2856 | -832 | -3693 | 2366 | -920 | -3588 | -3910 | -3276 | -3494 | -3038 | -2226 | 1863 | -2609 | -2306 | 210 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 178 | 605 | -3179 | -5031 | -5380 | -5649 | -3411 | -4875 | -5592 | -5432 | -5785 | -4939 | -4131 | 4094 | -4996 | -5162 | -2880 | -3097 | -4388 | -5593 | -5741 | 211 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 179 | −226 | −2865 | −1257 | 1435 | 220 | −2381 | 1068 | −2927 | 749 | -814 | −1955 | −1018 | −2474 | 2013 | 304 | −6 | 1028 | −2484 | −3051 | −2372 | 212 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 180 | −1685 | 874 | −4002 | 445 | 2042 | −3233 | −2092 | −951 | −2972 | 1058 | 3385 | −2869 | −3274 | −2590 | −2778 | −2319 | −1625 | −244 | −1943 | 1332 | 213 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 181 | −3778 | −3238 | −6374 | −5959 | −2610 | −6194 | −5586 | 2235 | −5860 | 2520 | −1357 | −5873 | −5644 | −5205 | −5707 | −5567 | −3724 | 1252 | −4413 | −4376 | 214 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 182 | −4103 | −4575 | −5214 | −3428 | −5599 | −4469 | −2275 | −4840 | 1347 | −4415 | −3790 | −3200 | −4388 | −1862 | 3932 | −3979 | −3710 | −4648 | −4172 | −4184 | 215 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 183 | −1445 | −2917 | 406 | 1711 | −3240 | −2407 | −1069 | −2989 | 1794 | −2932 | 1851 | 963 | −2505 | 1826 | −192 | −1324 | −1384 | −2541 | −3097 | −2416 | 216 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 184 | −1479 | −2803 | −1392 | 1321 | −3079 | −2469 | −1115 | −2785 | 1517 | 10 | 870 | −1128 | −2558 | 1098 | 2046 | −1387 | −1415 | −672 | −3007 | −125 | 217 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 185 | −1566 | 770 | -817 | −2662 | 1972 | 337 | −1862 | 1464 | −108 | 1236 | −716 | −461 | −3087 | −2124 | −5 | −2082 | −1507 | −250 | −1963 | −1602 | 218 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 186 | −694 | −2802 | 212 | −95 | −3089 | 453 | 1382 | −1062 | −653 | −915 | −1900 | 1506 | 1871 | −610 | −1155 | 670 | −1349 | −429 | −3005 | −2343 | 219 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 187 | −196 | −2885 | 2190 | 244 | -327 | −2383 | −1044 | −2957 | 589 | −2901 | −1975 | 1624 | −2478 | 301 | 1580 | −554 | −1351 | −2507 | −3068 | −2385 | 220 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −1543 | -8959 | −611 | -894 | −1115 | −701 | −1378 | * | * | | | | | | | | | | | | |
| 188 | −543 | −1862 | −440 | 1184 | −2126 | −1533 | −196 | −1834 | 1595 | −624 | 2062 | 822 | −1627 | 241 | −274 | 276 | −481 | −1453 | −2077 | −1437 | 221 |
| — | −148 | −500 | 233 | 43 | −381 | 400 | 105 | −626 | 211 | −466 | −721 | 275 | 394 | 45 | 96 | 360 | 117 | −369 | −295 | −250 | |
| . | −1645 | −1609 | −1504 | −406 | −2028 | −3545 | −129 | * | * | | | | | | | | | | | | |
| 189 | −1167 | −1629 | −1576 | −962 | −1424 | −2102 | −608 | -896 | 2301 | 1658 | −479 | −1024 | −2178 | −313 | 140 | −1299 | −1071 | −929 | −1767 | −1380 | 224 |
| — | −149 | −500 | 234 | 44 | −381 | 398 | 105 | −627 | 212 | −466 | −721 | 276 | 394 | 45 | 96 | 359 | 117 | −370 | −295 | −250 | |
| . | −1972 | −433 | −7850 | −77 | −4269 | −2856 | −214 | * | * | | | | | | | | | | | | |
| 190 | −623 | −1496 | −646 | −685 | −2989 | 666 | −1226 | −2778 | −1137 | −2866 | −2018 | 3108 | −1915 | −909 | −1576 | 1453 | -884 | −2045 | −3062 | −2502 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −15 | −7131 | -8173 | −894 | −1115 | −73 | −4340 | * | * | | | | | | | | | | | | |
| 191 | 1777 | −1612 | −3691 | −3089 | −1613 | −3264 | −2135 | 1748 | −3 | 113 | -825 | 941 | −3313 | −2478 | −2713 | −2338 | −1678 | 1470 | −2134 | −1778 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −101 | -8959 | −3933 | -894 | −1115 | −701 | −1378 | * | * | | | | | | | | | | | | |
| 192 | −1501 | −1969 | −2067 | −1490 | 511 | −2706 | −1414 | 149 | 2707 | −1857 | −1142 | −1640 | 76 | −1209 | 1201 | −1686 | 161 | 70 | −2340 | −1894 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8863 | −9905 | -894 | −1115 | −394 | −2065 | * | * | | | | | | | | | | | | |
| 193 | −3607 | −3077 | −6245 | −5874 | −2873 | −6081 | −5714 | 3505 | −5804 | 1156 | −1606 | −5752 | −5638 | −5357 | −5770 | −5460 | −3573 | 662 | −4673 | −4504 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 194 | −12 | −2598 | −5143 | −5441 | −5217 | 3460 | −4569 | −4977 | −5195 | −5277 | −4333 | −3679 | −3695 | −4653 | −4858 | 47 | −2467 | −115 | −5456 | −5404 | 230 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 195 | −5550 | −4510 | −5995 | −6327 | 4090 | −5863 | 1516 | −589 | −5883 | −3802 | −3874 | −4491 | −5721 | −4625 | −5258 | −5106 | −5404 | −4602 | 2900 | 1385 | 231 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 196 | -5329 | -4446 | -5933 | -6247 | 4361 | -5728 | -2113 | -4364 | -5816 | -3727 | -3796 | -4478 | -5654 | -4615 | -5223 | -4991 | -529 | -4510 | -1366 | 1366 | 232 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 197 | -4197 | -3713 | -6291 | -5791 | -1899 | -5989 | 2805 | 401 | -5286 | 2915 | -905 | -5568 | -5416 | -4535 | -4949 | -5287 | -4076 | -2219 | -3396 | -3073 | 233 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 198 | -6595 | -5567 | -6099 | -6438 | -5559 | -5537 | 5463 | -7721 | -6484 | -7100 | -7039 | -6386 | -5985 | -6472 | -6145 | -6901 | -6790 | -7414 | -5292 | -5215 | 234 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -4 | -8959 | -10001 | -894 | -1115 | -701 | -1378 | * | * | | | | | | | | | | | | |
| 199 | 586 | -1572 | -3544 | -2956 | -1590 | -3074 | 1146 | 2056 | -2650 | -1471 | -821 | -2632 | -3183 | -2360 | -2616 | 749 | 2084 | 548 | -2078 | -1724 | 235 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 200 | -2565 | -3136 | -4632 | -4986 | -5541 | -3345 | -4711 | -5589 | -5217 | -5757 | -4891 | -3960 | 4126 | -4790 | -5030 | 313 | -3031 | -4352 | -5539 | -5556 | 236 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 201 | -5703 | -4637 | -6071 | -6422 | 4247 | -5850 | -2263 | -4601 | -6011 | -3891 | -3997 | -4657 | -5777 | -4789 | -5384 | -5276 | -5579 | -4785 | 3754 | -326 | 237 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 202 | -4004 | 1819 | -6101 | -6452 | -6291 | -4445 | -5640 | -6613 | -6356 | -6594 | -6013 | -5387 | 4217 | -6060 | -5930 | -4283 | -4452 | -5619 | -5713 | -6326 | 238 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 203 | -2055 | -2755 | -3361 | -3367 | -4891 | -2898 | -3513 | -4669 | -3448 | -4824 | -3929 | -2989 | 1088 | 626 | -3651 | 3161 | 980 | -3679 | -5000 | -4666 | 239 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 204 | -193 | -2572 | -2289 | -1802 | -3389 | -2689 | -1973 | -3054 | -1673 | -3195 | -2366 | 391 | -7 | -1619 | 298 | 2877 | -1822 | 681 | -3505 | -2985 | 240 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 205 | -3720 | -5665 | 1799 | 3574 | -5870 | -3397 | -2892 | -5933 | -3362 | -5739 | -5225 | -2010 | -3998 | -2600 | -4392 | -3318 | -3833 | -5362 | -5813 | -4781 | 241 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 206 | -3187 | -2735 | -5771 | -5357 | -2928 | -5425 | -4775 | 3160 | -5193 | -346 | -1817 | -5066 | -5220 | -4927 | -5175 | -4693 | -3161 | 2014 | -4266 | 1730 | 242 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 207 | -425 | -4169 | -5818 | -5963 | 3540 | -5593 | 689 | -3981 | -5531 | -714 | -3475 | -4373 | -5489 | -4453 | -5010 | -4803 | -4826 | -4062 | -1348 | 3430 | 243 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 208 | -3019 | -3434 | -3667 | -2884 | 380 | -3876 | -2081 | -3229 | -1261 | -3138 | 1161 | 1805 | -3948 | -1970 | 3574 | -3099 | -2906 | -3122 | -2846 | -2071 | 244 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 209 | -219 | 3939 | -4124 | -3631 | -2168 | -3133 | -2636 | 2196 | -3268 | -1998 | -1377 | -3062 | -3449 | 362 | -3170 | -2323 | 1989 | -1291 | -2679 | -2340 | 245 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -4 | -8959 | -10001 | -894 | -1115 | -701 | -1378 | * | * | | | | | | | | | | | | |
| 210 | -4729 | -4070 | -7069 | -6474 | 605 | -6916 | -5347 | -1532 | -6280 | 3058 | 2235 | -6629 | -5792 | -4903 | -5682 | -6332 | -4543 | -2432 | -3801 | -3948 | 246 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 211 | 951 | -2633 | -4888 | -5223 | -5307 | -2899 | -4556 | -5134 | -5148 | -5391 | -4430 | -3649 | 3902 | -4616 | -4850 | -36 | -2496 | -3833 | -5522 | -5469 | 247 |
| — | -149 | -500 | 233 | 45 | -381 | 398 | 105 | -626 | 210 | -466 | -721 | 275 | 394 | 45 | 98 | 359 | 117 | -369 | -295 | -250 | |
| T | -96 | -3987 | -10001 | -984 | -1016 | -701 | -1378 | * | * | | | | | | | | | | | | |
| 212 | -1495 | -2002 | -2005 | -1444 | -2051 | -2697 | -1424 | -1636 | 152 | -936 | 1233 | -38 | -2774 | 215 | 945 | -635 | 749 | 2107 | 2763 | -1915 | 250 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 213 | −4303 | −4495 | −4995 | −3753 | −2154 | −4692 | 1241 | −4646 | −1331 | −4154 | −3768 | −3416 | −4635 | −2296 | 3965 | −4140 | −3982 | −4556 | −2596 | 873 | 251 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 214 | 830 | −2879 | 998 | 1610 | −3200 | −2379 | −1038 | −2951 | 1223 | −2895 | −1969 | 545 | −2473 | 1030 | 295 | −34 | 89 | −2501 | −3063 | −2380 | 252 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 215 | 526 | −2939 | 315 | 2774 | −3259 | −2415 | −1087 | −3010 | 147 | −2953 | −2030 | −1049 | −2518 | 1079 | -8 | −1340 | 23 | −2561 | −3120 | −2435 | 253 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 216 | −3774 | −3233 | −6377 | −5972 | −2638 | −6204 | −5637 | 3492 | −5879 | 1426 | −1384 | −5888 | −5660 | −5241 | −5738 | −5586 | −3723 | 8 | −4452 | −4403 | 254 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 217 | −4366 | −3775 | −6802 | −6245 | −2106 | −6588 | −5365 | 1174 | −6063 | 2930 | 1338 | −6301 | −5691 | −4907 | −5598 | −5954 | −4230 | 111 | −3928 | −4124 | 255 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 218 | −1424 | −2894 | 227 | 1737 | −3217 | −284 | −1050 | −2966 | 1433 | −1603 | −1984 | −1029 | −2487 | 1132 | 2024 | −1303 | −394 | −2517 | −3075 | −2395 | 256 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 219 | −518 | −2732 | −3752 | −4015 | −5238 | 3337 | −4093 | −5057 | −4401 | −5263 | −4337 | −3300 | −3689 | 372 | −4433 | 1109 | −2528 | −3851 | −5412 | −5210 | 257 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 220 | −4050 | −3540 | −6473 | −5903 | 76 | −6108 | −4927 | 80 | −5669 | 2372 | 1326 | −5798 | −5450 | −4696 | −5279 | −5383 | −3933 | 2337 | −3774 | −3871 | 258 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 221 | −1859 | 1451 | −4221 | −3607 | −1642 | −3435 | −2372 | 173 | −3221 | 2679 | -835 | −3103 | −3486 | −2847 | −3034 | −432 | −251 | 362 | −2222 | −1885 | 259 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 222 | 1076 | −3179 | 221 | -859 | −3503 | 1800 | 1595 | −3263 | −943 | −3208 | −2299 | 1429 | −2703 | 58 | −1472 | 1118 | −1646 | −2810 | −3381 | −2678 | 260 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 223 | 2382 | 4160 | −4265 | −4067 | −3686 | −2899 | −3505 | −3408 | −3870 | −3708 | −2954 | 453 | −3558 | −3573 | −3874 | −65 | −2269 | −2892 | −4073 | 1623 | 261 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 224 | −3393 | −5135 | 3567 | −1514 | −5677 | −3235 | −2777 | −5681 | −3214 | −5543 | −4967 | 2358 | −3845 | −2479 | −4201 | −3070 | 114 | −5041 | −5725 | −4634 | 262 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 225 | −3026 | −2715 | −5396 | −4787 | 1671 | −4751 | −3603 | 1117 | −4438 | 2460 | -831 | −4406 | −4552 | −3848 | 20 | −3891 | −2946 | 863 | −3077 | −2909 | 263 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 226 | −3291 | 1652 | −5950 | −5596 | −3300 | −5728 | −5502 | 2913 | −5518 | 836 | −2035 | −5383 | −5476 | −5375 | −5611 | −5064 | −3276 | 2254 | −4911 | −4475 | 264 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 227 | −30 | 1774 | −5323 | −5663 | −5339 | 3578 | −4680 | −5153 | −5339 | −5428 | −4470 | −3767 | −3749 | −4786 | −4952 | −2309 | −2531 | −3857 | −5537 | −5537 | 265 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 228 | −5012 | −4348 | −6180 | −6310 | 4410 | −5761 | −2814 | −2957 | −5946 | −2104 | 1335 | −4989 | −5655 | −4846 | −5401 | −5247 | −4977 | −3563 | −2032 | −927 | 266 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 229 | −3530 | −5058 | −1466 | 174 | −5153 | −3457 | 4489 | −5254 | −2091 | −5008 | −4396 | −2075 | −3924 | 3041 | −2386 | −3212 | −3529 | −4827 | −4883 | −4148 | 267 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 230 | −1871 | −2091 | 68 | −2131 | −2160 | −3069 | −2033 | 1465 | −2201 | −453 | −1334 | 294 | −3237 | −1998 | −2464 | −2199 | 3130 | −1332 | −2616 | −2199 | 268 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 231 | −1487 | −2908 | 913 | 1327 | 1312 | −2441 | −1118 | −2940 | 128 | −2911 | −2006 | −1084 | 1355 | −670 | −19 | −1374 | −1428 | −2518 | −3094 | 2726 | 269 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 232 | −1735 | −3247 | 2506 | 1092 | −3556 | −357 | 1103 | −3320 | −973 | −3258 | −2349 | 383 | −2728 | -882 | 1077 | 1091 | −1686 | −2864 | −3427 | −2716 | 270 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 233 | −4978 | −4425 | 926 | −4759 | 1647 | −337 | −2135 | −4407 | −5256 | −3836 | −3839 | −4034 | −5383 | −4255 | −5029 | −4678 | −4938 | −4483 | −1456 | 4397 | 271 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 234 | 2449 | 1598 | −2663 | −2089 | −1702 | −2893 | −1699 | −1258 | −364 | −415 | -899 | −2082 | −2969 | −1721 | −22 | −222 | 531 | 527 | −2132 | −1738 | 272 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 235 | −143 | −3043 | −1773 | 819 | −3340 | −2774 | −1336 | −3011 | −712 | -869 | −2157 | −1443 | −2852 | 661 | 3270 | −1739 | −1740 | −2662 | −3186 | 478 | 273 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 236 | −327 | −3575 | −2094 | −2415 | −4554 | −3206 | 4824 | −5156 | −3160 | −5142 | −4438 | 2290 | −3858 | −2954 | −3502 | −2766 | −3046 | −4315 | −4800 | −4018 | 274 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 237 | −6302 | −5253 | −6400 | −6761 | 4582 | −5634 | −4008 | −5872 | −6718 | −5174 | −5285 | −5914 | −5958 | −6033 | −6150 | −6368 | −6391 | −6027 | −3309 | −2287 | 275 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 238 | −489 | −2739 | −5542 | −4986 | 618 | −4977 | −3961 | 891 | −4689 | 2532 | −1090 | −4635 | −4768 | −4158 | −4480 | −4150 | −3036 | 1545 | −3426 | −3237 | 276 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 239 | −171 | −3125 | 212 | 357 | −3428 | −2542 | −1294 | −262 | −936 | −3141 | −2242 | −1183 | −2696 | 1591 | −1459 | 2693 | −1629 | −2742 | −3331 | −2639 | 277 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 240 | 711 | 4289 | −4221 | −3749 | −2216 | −3019 | −2673 | −1700 | −3397 | −440 | −1446 | −3064 | −3393 | −3042 | −3256 | 932 | 1624 | 140 | −2702 | −2371 | 278 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 241 | −92 | 4907 | −4590 | −4186 | −2494 | −3133 | −3029 | −1643 | −3808 | 230 | −1693 | −3330 | −3569 | −3422 | −3608 | 431 | −2071 | 912 | −3027 | −2705 | 279 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 242 | −1425 | 498 | −1274 | 679 | −3212 | −2397 | −1051 | −2959 | 404 | −2904 | −1980 | 793 | −2489 | 195 | 1434 | 2202 | 242 | −2512 | −3070 | −2393 | 280 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 243 | −2571 | −4077 | 478 | −1336 | −4438 | −3038 | 333 | −4199 | −1538 | −4085 | −3268 | 1254 | −3344 | −1550 | 3561 | −181 | −2541 | −3751 | −4204 | −3509 | 281 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 244 | −3106 | −2752 | −5524 | −427 | −2135 | −4957 | −3914 | 1874 | −4653 | 2204 | 2456 | −4611 | −4743 | −4107 | −4436 | −4124 | −3038 | 1007 | −3374 | −3201 | 282 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 245 | −1766 | −1712 | −3710 | −3139 | −1740 | 516 | −2198 | −1144 | −98 | 2429 | −950 | −2785 | −3320 | −2498 | −2629 | −2306 | 23 | 1085 | −2250 | −1904 | 283 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −177 | −8959 | −3142 | -894 | −1115 | −701 | −1378 | * | * | | | | | | | | | | | | |
| 246 | −307 | −2776 | 1344 | −611 | −3091 | 2102 | −951 | −2837 | 74 | −2790 | 659 | 900 | 606 | −495 | 325 | −1201 | −1259 | −2395 | −2964 | −2285 | 284 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −1808 | −8787 | −490 | −894 | −1115 | −1745 | −511 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 247 | 1293 | -809 | -1315 | -840 | -1256 | -1444 | -748 | -676 | -707 | -1089 | -383 | 924 | -1752 | -583 | -1012 | -562 | 1513 | 1420 | -1612 | -1187 | 285 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -182 | -6996 | -3177 | -894 | -1115 | -3706 | -115 | * | * | | | | | | | | | | | | |
| 248 | -881 | -2428 | 2000 | 1862 | -2710 | -1341 | -383 | -2488 | -246 | -2452 | -1626 | 31 | -1683 | 9 | -859 | -683 | 1617 | -2042 | -2656 | -1872 | 286 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -19 | -6833 | -7875 | -894 | -1115 | -3752 | -111 | * | * | | | | | | | | | | | | |
| 249 | 1391 | -607 | -2105 | -1637 | -964 | -1729 | -1171 | 1909 | -1411 | -612 | -85 | -1401 | -2025 | -1227 | -1540 | -898 | 1630 | 400 | -1525 | -1150 | 287 |
| — | -149 | -500 | 233 | 43 | -381 | 398 | 105 | -627 | 212 | -466 | -721 | 275 | 393 | 45 | 96 | 360 | 119 | -370 | -295 | -250 | |
| . | -1997 | -424 | -7875 | -75 | -4300 | -3752 | -111 | * | * | | | | | | | | | | | | |
| 250 | -1788 | -2524 | -2258 | -1114 | -3297 | -2356 | -348 | -2683 | 2280 | -2382 | -1700 | -1055 | -2327 | 69 | 3087 | -1677 | -1511 | -2440 | -2252 | -2110 | 289 |
| — | -148 | -501 | 234 | 42 | -378 | 397 | 104 | -627 | 209 | -467 | -722 | 274 | 394 | 47 | 97 | 358 | 118 | -364 | -296 | -246 | |
| . | -1031 | -1946 | -1994 | -3249 | -160 | -3752 | -111 | * | * | | | | | | | | | | | | |
| 251 | -1382 | -1651 | -2007 | -2241 | -3135 | 3558 | -2249 | -3310 | -2521 | -3382 | -2848 | -2021 | -2327 | -2362 | -2512 | -1597 | -1742 | -2656 | -2734 | -2979 | 301 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -25 | -6424 | -7466 | -894 | -1115 | -3004 | -192 | * | * | | | | | | | | | | | | |
| 252 | -762 | -830 | -2463 | -2083 | -1101 | -2085 | -1635 | 2007 | -1790 | -447 | -157 | -1819 | -2377 | -1671 | -1883 | -1313 | 2599 | 631 | -1889 | -1499 | 302 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -19 | -6799 | -7841 | -894 | -1115 | -68 | -4438 | * | * | | | | | | | | | | | | |
| 253 | 790 | -1430 | -3900 | -3269 | -1386 | -535 | -2013 | 286 | -2874 | 1961 | -633 | -2774 | -3191 | -2505 | -2689 | -291 | -1538 | 1298 | -1891 | 858 | 303 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 254 | -1406 | -2876 | 1900 | 1982 | -3196 | -406 | -1039 | -2946 | 401 | -817 | -1966 | -120 | -2473 | -579 | -253 | 41 | 421 | -1131 | -3060 | -2378 | 304 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 255 | 526 | -1482 | -3592 | -2983 | -1452 | -247 | -1964 | 964 | -2653 | -1341 | -692 | 167 | -3153 | -2341 | -2576 | -2163 | 2000 | 1508 | -1945 | 1833 | 305 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 256 | -1406 | -2840 | 294 | 1227 | -3144 | -376 | -1047 | -2883 | -633 | -92 | 220 | -1028 | -2479 | 373 | 1378 | 696 | 1332 | -707 | -3033 | -2360 | 306 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 257 | -1835 | -3213 | -1394 | -1073 | -3677 | 546 | 1910 | -3423 | 199 | -3378 | -2485 | 116 | 2249 | -1063 | -1582 | 2067 | -1816 | -2959 | -3548 | -2876 | 307 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 258 | -226 | -2881 | 1603 | 980 | -3202 | -475 | -1039 | -2953 | 1165 | -2897 | -1970 | 1960 | -2474 | 212 | 269 | -595 | 126 | -2503 | -3064 | -2381 | 308 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -574 | -8959 | -1616 | -894 | -1115 | -701 | -1378 | * | * | | | | | | | | | | | | |
| 259 | -1053 | -2420 | -943 | 426 | 478 | 698 | 1566 | -2422 | 694 | -406 | -1520 | -693 | -2132 | -254 | 2029 | 309 | -991 | -2021 | -2624 | -1972 | 309 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -134 | -8391 | -3543 | -894 | -1115 | -2728 | -236 | * | * | | | | | | | | | | | | |
| 260 | -992 | -2412 | 694 | 521 | -2717 | 1945 | -634 | -2454 | -230 | -2425 | -1516 | -603 | -2060 | -183 | 658 | 312 | 591 | 22 | -2615 | -1944 | 310 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -1015 | -8264 | -994 | -894 | -1115 | -2907 | -206 | * | * | | | | | | | | | | | | |
| 261 | -626 | -1575 | -657 | -144 | -1415 | -1646 | 2389 | -1392 | 58 | -1510 | -730 | -389 | -1745 | 1721 | -340 | -616 | 1724 | -1131 | -1637 | 1245 | 311 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -314 | -7263 | -2402 | -894 | -1115 | -3615 | -123 | * | * | | | | | | | | | | | | |
| 262 | -1516 | -1257 | -3227 | -2851 | 145 | -2968 | -1113 | 2926 | -2461 | -342 | -164 | -2349 | -2966 | -2119 | -2359 | -2153 | -1476 | 141 | -633 | 2612 | 312 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -17 | -6966 | -8008 | -894 | -1115 | -462 | -1868 | * | * | | | | | | | | | | | | |
| 263 | 461 | -2082 | -1453 | 92 | -2206 | 2000 | -1071 | 1022 | -810 | -2016 | -1242 | -1153 | -2451 | 1587 | -1244 | -497 | -1204 | -1597 | 2003 | -1888 | 313 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -5 | -8649 | -9691 | -894 | -1115 | -211 | -2878 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 264 | -180 | -1484 | -148 | -3162 | -1451 | -3165 | 1009 | 329 | -2803 | 1454 | -687 | -2745 | -3215 | -2465 | -2676 | -2243 | -429 | 2441 | -1958 | -1610 | 314 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 265 | -1405 | -2876 | 303 | 1453 | -3196 | -2379 | -1037 | -2946 | 1155 | -2891 | -1965 | 454 | -2472 | -578 | 1053 | 970 | 781 | 95 | -3059 | -222 | 315 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 266 | 455 | -1553 | 56 | -2540 | 1476 | -3008 | -1830 | -1071 | -2285 | 357 | -750 | 286 | -3068 | -2045 | -2352 | -250 | -1508 | 223 | -1987 | 3140 | 316 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 267 | -1405 | -2859 | 620 | 238 | 353 | 981 | 797 | -2916 | 393 | -1443 | -1950 | 1276 | -2475 | 1448 | -1131 | -1289 | -1344 | -2476 | 1587 | 1749 | 317 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 268 | -2423 | 1210 | 1728 | -2287 | -5149 | 3119 | -3144 | -4993 | -3380 | -5065 | -4241 | 323 | -3659 | -2873 | -3942 | -163 | -2753 | -4068 | -5252 | -4633 | 318 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 269 | -1945 | -3303 | -1769 | 252 | 232 | -342 | -1380 | -3378 | 1046 | -3278 | -2405 | 1019 | -2921 | -934 | 3173 | -1823 | -1856 | -2969 | -3384 | -2814 | 319 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 270 | -226 | -2759 | 210 | -762 | -744 | -2406 | 515 | 671 | 1017 | -274 | -1861 | -27 | -2498 | 1025 | 292 | -116 | 1441 | -674 | -2973 | -2322 | 320 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -57 | -8959 | -4754 | -894 | -1115 | -701 | -1378 | * | * | | | | | | | | | | | | |
| 271 | -3010 | -2579 | -5603 | -5186 | 1264 | -5216 | -4665 | 2101 | -5014 | -2059 | -1891 | -4875 | -5072 | -4816 | -5019 | -4471 | 1075 | 2862 | -4295 | -3856 | 321 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8906 | -9948 | -894 | -1115 | -1124 | -886 | * | * | | | | | | | | | | | | |
| 272 | -179 | -2570 | 127 | -813 | -527 | -2411 | -1084 | -2462 | 307 | 126 | -1688 | 874 | -2501 | -669 | 1509 | 889 | 555 | 266 | -2821 | -127 | 322 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8906 | -9948 | -894 | -1115 | -1124 | -886 | * | * | | | | | | | | | | | | |
| 273 | -2244 | 649 | -4672 | -4106 | -2144 | -498 | -3013 | 1118 | -3767 | 162 | -1251 | -3646 | -3995 | -3440 | -3622 | -3118 | -21 | 3104 | -2841 | -2477 | 323 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8906 | -9948 | -894 | -1115 | -1124 | -886 | * | * | | | | | | | | | | | | |
| 274 | 6 | -2795 | 984 | 272 | 172 | 1465 | -1012 | -349 | 1377 | -2803 | 577 | -994 | -2444 | -558 | 858 | -520 | -1309 | -2406 | -2990 | -2320 | 324 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8906 | -9948 | -894 | -1115 | -1124 | -886 | * | * | | | | | | | | | | | | |
| 275 | 2342 | -1428 | -3852 | -3227 | 217 | -3126 | -2005 | 937 | -2844 | -1273 | -636 | -2751 | -3182 | -2484 | -2676 | 1099 | -1532 | 873 | -1892 | 418 | 325 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |
| 276 | -403 | -1395 | -3880 | -3247 | 2700 | -3108 | -1972 | 404 | -2849 | 1121 | -592 | -2744 | -3158 | -2476 | -2659 | -244 | -149 | -804 | -1840 | 2352 | 326 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |
| 277 | -116 | -2654 | -3846 | -4018 | -4871 | -2878 | 1379 | -4683 | -4045 | -4907 | -4035 | -3265 | 3912 | -3830 | -4057 | -2253 | 214 | -3657 | -5079 | -4825 | 327 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |
| 278 | -3303 | -2790 | -5999 | -5701 | -3491 | -5835 | -5976 | 3382 | -5683 | -2228 | -2173 | -5520 | -5582 | -5659 | -5871 | -5235 | -3300 | 2407 | -5302 | -4763 | 328 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |
| 279 | -2249 | -2846 | -4590 | -4951 | -5426 | 3363 | -4589 | -5352 | -5175 | -5564 | -4640 | -3742 | -3872 | -4652 | -4946 | 1745 | -2721 | -4062 | -5513 | -5517 | 329 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |
| 280 | -3241 | -2751 | -5935 | -5625 | -3474 | -5690 | -5770 | 3486 | -5582 | -2250 | -2170 | -5404 | -5491 | -5541 | -5743 | -5062 | 33 | 1922 | -5195 | -4666 | 330 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8906 | -9948 | -894 | -1115 | -1124 | -886 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 281 | −3448 | −5532 | 3490 | 967 | −5628 | −3187 | 2135 | −5627 | −3049 | −5455 | −4889 | 1445 | −3776 | −2323 | −4059 | −3048 | −3547 | −5064 | −5657 | −4515 | 331 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8906 | −9948 | -894 | −1115 | −1124 | -886 | * | * | | | | | | | | | | | | |
| 282 | −394 | −1470 | −3470 | −2870 | −1455 | −3022 | −1921 | −993 | −2556 | −1344 | 1974 | −2548 | 2175 | −2260 | −2512 | 628 | 883 | 1718 | −1942 | 403 | 332 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8906 | −9948 | -894 | −1115 | −1124 | -886 | * | * | | | | | | | | | | | | |
| 283 | 513 | −2834 | 983 | 1204 | −289 | 1233 | −1004 | −2899 | 367 | −2849 | −1924 | −16 | 884 | −546 | −1094 | −1252 | 157 | −2454 | −3020 | 134 | 333 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8906 | −9948 | -894 | −1115 | −1124 | -886 | * | * | | | | | | | | | | | | |
| 284 | 486 | −2840 | −39 | 282 | 23 | −2340 | 834 | −2911 | 1004 | −2856 | −1929 | 895 | −2434 | 1241 | 1932 | 45 | −418 | −2462 | −3023 | −2340 | 334 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8906 | −9948 | -894 | −1115 | −488 | −1801 | * | * | | | | | | | | | | | | |
| 285 | −4008 | −3514 | −6417 | −5837 | 2692 | −6018 | −4818 | 2407 | −5587 | 1525 | 1534 | −5706 | −5394 | −4631 | −5199 | −5276 | −3890 | 108 | −3713 | −3793 | 335 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 286 | 418 | −2708 | 854 | 1407 | −2958 | −2420 | −1087 | 993 | −700 | 35 | −1816 | −1087 | −2512 | 979 | 294 | −1334 | 621 | −2291 | −2935 | 550 | 336 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 287 | −134 | −2892 | −350 | 1468 | −3214 | −2388 | 1143 | −2964 | 948 | −2908 | −1982 | −108 | −2483 | −589 | 1680 | 1612 | −1358 | −2515 | −3075 | −2392 | 337 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 288 | 599 | 1293 | 58 | −1387 | 210 | 942 | −1398 | 986 | −1259 | −1930 | −1199 | −1569 | −2751 | 1501 | 177 | −162 | 204 | 58 | −2401 | −1931 | 338 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 289 | 1342 | 2126 | −3821 | −3212 | −1494 | −3120 | −2066 | −997 | −680 | 1883 | −735 | −2759 | −3210 | −2502 | −2704 | −278 | −1584 | 1224 | −1995 | −1650 | 339 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 290 | 1145 | −2875 | −1258 | 412 | 120 | −375 | −1042 | −2942 | 1881 | −2890 | −1965 | 1273 | −2477 | −583 | 807 | 383 | −1349 | −2496 | −3060 | −2379 | 340 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | -80 | -8959 | −4259 | -894 | −1115 | −701 | −1378 | * | * | | | | | | | | | | | | |
| 291 | −1353 | −2813 | 796 | −657 | −3128 | −2329 | −988 | −2875 | 1414 | −148 | −1903 | 1044 | −2422 | 251 | −148 | 1470 | 920 | -872 | −2999 | −2320 | 341 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −5 | -8883 | −9925 | -894 | −1115 | −433 | −1948 | * | * | | | | | | | | | | | | |
| 292 | −229 | −2893 | 1240 | 967 | −3213 | 626 | −1054 | −2962 | 996 | −2908 | −1984 | −1026 | 2006 | −595 | 267 | −1303 | −1363 | −348 | −3077 | −2395 | 342 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 293 | 587 | −2907 | 237 | 756 | −3227 | −2395 | −1062 | −2978 | 763 | −2923 | −1998 | 430 | 1305 | −604 | −1157 | 1755 | 189 | −2529 | −3091 | −2406 | 343 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 294 | −2879 | −2497 | −5404 | −4919 | 539 | −4908 | −4120 | 1305 | −4674 | −407 | −1654 | −4557 | −4798 | −4384 | −4596 | −4105 | 1558 | 2976 | −3800 | −3432 | 344 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 295 | 370 | −2871 | 226 | 241 | −3190 | −2379 | −1038 | −1100 | 804 | −1200 | 1709 | 368 | −133 | 1903 | 269 | 598 | −1343 | −1080 | −3056 | −2375 | 345 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 296 | −592 | −2876 | −1251 | 1909 | −3197 | −2378 | 1064 | −2948 | 736 | -828 | −1966 | −156 | −133 | 1553 | 269 | 793 | −258 | −2498 | −3060 | −2377 | 346 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 297 | −3595 | −4303 | −4315 | −2919 | −5108 | −4155 | 1508 | −4451 | 2972 | −4110 | −3432 | −2818 | −4080 | −1612 | 2163 | −3472 | −138 | −4221 | 3248 | −3839 | 347 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 298 | 493 | −1459 | −60 | −3180 | −1420 | −3147 | −2014 | 1814 | −2811 | 629 | 1455 | −2742 | −3197 | −2464 | 431 | −2226 | −411 | 1756 | −1925 | −1579 | 348 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 299 | 1357 | −3099 | −1577 | 923 | −3460 | −2638 | −1219 | −3172 | 2211 | -807 | −2193 | −1276 | −2718 | 1902 | 370 | −1576 | −1616 | −2746 | −3223 | −2609 | 349 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 300 | −1420 | −2694 | −1352 | 2197 | 254 | −2426 | −1094 | −2636 | 291 | −394 | 92 | −1097 | −2517 | 2016 | -86 | 268 | −1359 | −393 | −2924 | −2292 | 350 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 301 | −518 | −2939 | −5981 | −5545 | −2710 | −5637 | −4996 | 2462 | −5381 | 2406 | −1502 | −5313 | −5327 | −4934 | −5285 | −4922 | −3367 | 590 | −4257 | −4057 | 351 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 302 | −2088 | −3418 | −1984 | 484 | −3852 | −2968 | −1443 | −3512 | 2417 | −3379 | −2517 | 405 | −3034 | 1740 | 2285 | −704 | −1983 | −3108 | −3450 | −2924 | 352 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 303 | −231 | −2905 | 993 | 1943 | −3225 | −2392 | −1059 | −2977 | 1029 | −2921 | −1995 | −158 | −2491 | 1884 | −1153 | 300 | 492 | −2527 | −3088 | −2403 | 353 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 304 | −146 | −2883 | 241 | 842 | −3204 | −2385 | −1043 | −2954 | 1210 | 36 | −1973 | −1021 | −2479 | 877 | 2258 | 233 | −1352 | −2505 | −3066 | −2385 | 354 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 305 | −3120 | −2804 | −5031 | −4657 | 3180 | −4449 | −2105 | 15 | −28 | 830 | −1933 | −3763 | −4437 | −3626 | −3947 | −3573 | −3048 | −2303 | 2608 | 2671 | 355 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −712 | -8959 | −1367 | -894 | −1115 | −701 | −1378 | * | * | | | | | | | | | | | | |
| 306 | −1289 | −2731 | -888 | 1373 | −3077 | 1791 | -833 | −2809 | −344 | −2738 | −1843 | −784 | 563 | 1766 | 1336 | −1157 | −1228 | −2373 | −2885 | −2232 | 356 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −7 | -8254 | -9296 | -894 | −1115 | −124 | −3597 | * | * | | | | | | | | | | | | |
| 307 | −565 | −2880 | −1267 | −717 | −3199 | 783 | −1046 | −2947 | 1767 | −1296 | −1970 | 2225 | −2483 | 655 | 660 | −54 | −345 | −2501 | −3063 | −2384 | 357 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −282 | -8959 | −2508 | -894 | −1115 | −701 | −1378 | * | * | | | | | | | | | | | | |
| 308 | −1559 | −3051 | 1811 | −700 | −3373 | 1724 | −1132 | −3127 | 1766 | −3061 | −2157 | 583 | 211 | −688 | 388 | −1417 | −1506 | −2677 | −3222 | −2528 | 358 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −641 | -8682 | −1488 | -894 | −1115 | −2108 | −381 | * | * | | | | | | | | | | | | |
| 309 | -873 | 1938 | −976 | −420 | −1997 | −1939 | −618 | −157 | 1581 | −1782 | −979 | 596 | −2025 | 865 | 975 | -872 | 86 | 1093 | −2133 | −1576 | 359 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −3213 | -8048 | −171 | -894 | −1115 | −962 | −1039 | * | * | | | | | | | | | | | | |
| 310 | −1504 | −2255 | −1920 | −994 | −2666 | −2307 | −492 | −2161 | 1922 | −2083 | 3560 | −1035 | −2307 | −98 | 1976 | −1470 | −1316 | −1949 | −2211 | −1929 | 360 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −15 | −7173 | -8215 | -894 | −1115 | −74 | −4325 | * | * | | | | | | | | | | | | |
| 311 | −1843 | −3098 | −1811 | −1197 | 321 | −2791 | 1110 | −705 | 3142 | −3061 | −2206 | −1451 | −2860 | 606 | 449 | −243 | −1755 | −2731 | −3219 | −2663 | 361 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 312 | −3094 | −2676 | −5638 | −5185 | −2803 | −5221 | −4524 | 2052 | −4976 | 2077 | −1660 | 40 | −5047 | −4668 | −4915 | −4455 | −3062 | 2055 | −4078 | −3746 | 362 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 313 | −3722 | −3199 | −6300 | −5866 | −2572 | −6072 | −5389 | 3404 | −5740 | 395 | 2641 | −5746 | −5563 | −5098 | −5576 | −5413 | −3666 | 496 | −4313 | −4261 | 363 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 314 | −2928 | −2609 | −5320 | −4741 | 433 | −4690 | −3543 | 1586 | −4407 | 1948 | −985 | −4332 | −4532 | −3876 | −4179 | −3835 | −2859 | 2174 | −3067 | 855 | 364 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 315 | –2015 | 2237 | –4968 | –5073 | –5157 | 3142 | –4333 | –4949 | –4502 | –5185 | –4255 | –3605 | –3695 | –4321 | 261 | 1434 | –2475 | –3759 | –5337 | –5246 | 365 |
| — | –149 | –500 | 233 | 43 | –381 | 399 | 106 | –626 | 210 | –466 | –720 | 275 | 394 | 45 | 96 | 359 | 117 | –369 | –294 | –249 | |
| E | –4 | -8959 | –10001 | -894 | –1115 | –701 | –1378 | * | * | | | | | | | | | | | | |
| 316 | –141 | –1651 | –3278 | –2671 | –1654 | –3093 | 1024 | –180 | –2267 | –1517 | -868 | –2482 | –3166 | –2130 | 1986 | –2156 | 207 | 2664 | –2123 | –1760 | 366 |
| — | –149 | –500 | 233 | 43 | –381 | 399 | 106 | –626 | 210 | –466 | –720 | 275 | 394 | 45 | 96 | 359 | 117 | –369 | –294 | –249 | |
| — | –4 | -8959 | –10001 | -894 | –1115 | –701 | –1378 | * | * | | | | | | | | | | | | |
| 317 | –3588 | –5621 | 3927 | 164 | –5802 | –166 | –2778 | –5830 | –3251 | –5648 | –5120 | –1886 | –3894 | –2480 | –4304 | –3187 | –3705 | –5245 | –5820 | –4685 | 367 |
| — | –149 | –500 | 233 | 43 | –381 | 399 | 106 | –626 | 210 | –466 | –720 | 275 | 394 | 45 | 96 | 359 | 117 | –369 | –294 | –249 | |
| — | –4 | -8959 | –10001 | -894 | –1115 | –701 | –1378 | * | * | | | | | | | | | | | | |
| 318 | –3384 | –4365 | 1274 | –2368 | –5088 | –3832 | –2062 | –4518 | 410 | –4205 | –3505 | –2468 | –3919 | 1755 | 3500 | –3211 | –3162 | –4226 | –4097 | –3856 | 368 |
| — | –149 | –500 | 233 | 43 | –381 | 399 | 106 | –626 | 210 | –466 | –720 | 275 | 394 | 45 | 96 | 359 | 117 | –369 | –294 | –249 | |
| B | –4 | -8959 | –10001 | -894 | –1115 | –701 | –1378 | * | * | | | | | | | | | | | | |
| 319 | –309 | –3178 | –5913 | –5296 | 1008 | –5336 | –4124 | –1352 | –4974 | 2767 | 2097 | –5008 | –4954 | –4189 | –4637 | –4510 | –3452 | 71 | –3336 | –3303 | 369 |
| — | –149 | –500 | 233 | 43 | –381 | 399 | 106 | –626 | 210 | –466 | –720 | 275 | 394 | 45 | 96 | 359 | 117 | –369 | –294 | –249 | |
| — | –4 | -8959 | –10001 | -894 | –1115 | –701 | –1378 | * | * | | | | | | | | | | | | |
| 320 | –3574 | –4646 | 4049 | –2255 | –5845 | –3598 | –3418 | –5940 | –3891 | –5875 | –5307 | –2580 | –4233 | –3178 | –4704 | –3428 | 56 | –5196 | –5710 | –5088 | 370 |
| — | –149 | –500 | 233 | 43 | –381 | 399 | 106 | –626 | 210 | –466 | –720 | 275 | 394 | 45 | 96 | 359 | 117 | –369 | –294 | –249 | |
| G | –4 | -8959 | –10001 | -894 | –1115 | –701 | –1378 | * | * | | | | | | | | | | | | |
| 321 | –1502 | –1954 | –2080 | 10 | –1993 | –2723 | –1458 | 670 | 131 | –393 | 1861 | –1670 | –138 | –1269 | 530 | –174 | –1441 | –1418 | –2336 | 3174 | 371 |
| — | –149 | –500 | 233 | 43 | –381 | 399 | 106 | –626 | 210 | –466 | –720 | 275 | 394 | 45 | 96 | 359 | 117 | –369 | –294 | –249 | |
| G | –4 | -8959 | –10001 | -894 | –1115 | –701 | –1378 | * | * | | | | | | | | | | | | |
| 322 | –151 | –1495 | –4010 | –3381 | 1550 | –3238 | –2122 | 2448 | –2986 | –203 | –703 | –2880 | –3285 | –2617 | –2797 | 974 | 95 | 964 | –1989 | –1645 | 372 |
| — | –149 | –500 | 233 | 43 | –381 | 399 | 106 | –626 | 210 | –466 | –720 | 275 | 394 | 45 | 96 | 359 | 117 | –369 | –294 | –249 | |
| G | –4 | -8959 | –10001 | -894 | –1115 | –701 | –1378 | * | * | | | | | | | | | | | | |
| 323 | –3766 | 1634 | –4758 | –3140 | –5020 | –4275 | –2098 | –4501 | 3383 | –4156 | –3507 | –2965 | –4191 | –1690 | 1978 | –3657 | –3419 | –4299 | –3950 | 744 | 373 |
| — | –149 | –500 | 233 | 43 | –381 | 399 | 106 | –626 | 210 | –466 | –720 | 275 | 394 | 45 | 96 | 359 | 117 | –369 | –294 | –249 | |
| — | –4 | -8959 | –10001 | -894 | –1115 | –701 | –1378 | * | * | | | | | | | | | | | | |
| 324 | –3425 | –3945 | –3781 | –4164 | –5971 | 3711 | –4650 | –6240 | –5119 | –6240 | –5534 | 517 | –4617 | –4644 | –5247 | –3601 | –3843 | –5153 | –5649 | –5756 | 374 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 325 | –3261 | –2780 | –5900 | –5526 | –3201 | –5637 | –5297 | 2641 | –5421 | 1245 | –1961 | –5294 | –5400 | –5236 | –5477 | –4952 | –14 | 2333 | –4739 | –4333 | 375 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 326 | –1407 | –2840 | 191 | –721 | –3144 | –2387 | 796 | –173 | 407 | –2848 | –1933 | –1029 | 2321 | 444 | 204 | 780 | 782 | –334 | –3033 | –2361 | 376 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 327 | –1451 | –2887 | –1314 | 860 | –3203 | –2425 | 1192 | –2940 | 679 | 212 | –1980 | –1065 | –2516 | 2928 | 385 | –153 | –1388 | –371 | –3068 | –2403 | 377 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 328 | –3719 | –4356 | –4571 | –3066 | –5272 | –210 | –2088 | –4546 | 3433 | –4182 | 1204 | –2918 | –4159 | –1668 | 1768 | –3602 | –3385 | –4326 | –4014 | –3944 | 378 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 329 | –4633 | –4000 | –6997 | –6392 | 1848 | –6803 | –5359 | 1123 | –6191 | 2794 | 1093 | –6529 | –5743 | –4869 | –5622 | –6188 | –4455 | –2358 | –3832 | –4061 | 379 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 330 | –1597 | –1859 | –2475 | –178 | –1873 | –2884 | 2558 | 535 | 48 | 1278 | 1220 | –1949 | –2950 | –1530 | 1877 | –1889 | –1532 | –1309 | 1286 | –1848 | 380 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |
| 331 | 3358 | 1792 | –5345 | –5669 | –5272 | –2886 | –4637 | –5072 | –5298 | –5352 | –4392 | –3721 | –3701 | –4740 | –4910 | 731 | –2470 | –3789 | –5504 | –5476 | 381 |
| — | –149 | –500 | 233 | 43 | –381 | 399 | 106 | –626 | 210 | –466 | –720 | 275 | 394 | 45 | 96 | 359 | 117 | –369 | –294 | –249 | |
| H | –4 | -8959 | –10001 | -894 | –1115 | –701 | –1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 332 | −4982 | −4198 | −6050 | −6138 | 3630 | −5838 | −2373 | −3072 | −5737 | 19 | 2124 | −4659 | −5589 | −4573 | −5178 | −5073 | −4846 | −3590 | −1609 | 3021 | 382 |
| — | −149 | −500 | 233 | 43 | −381 | 399 | 106 | −626 | 210 | −466 | −720 | 275 | 394 | 45 | 96 | 360 | 117 | −369 | −294 | −249 | |
| H | -86 | −4140 | −10001 | −197 | −2973 | −701 | −1378 | * | * | | | | | | | | | | | | |
| 333 | −3108 | −4583 | −1489 | 3539 | −5033 | −768 | −2258 | −4749 | −1698 | −4558 | −3832 | −1938 | −3688 | 621 | 323 | −2859 | −3075 | −4319 | −4606 | −3978 | 384 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 334 | −227 | −2709 | −1346 | 280 | −2959 | −2425 | 1269 | −989 | 896 | 47 | −1818 | −1092 | −2516 | 940 | 1984 | −1339 | 121 | 757 | −2936 | −2301 | 385 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 335 | −4913 | −4208 | −6635 | −6424 | 3785 | −6383 | −3682 | −1998 | −6156 | 2018 | −1271 | −5698 | −5762 | −4885 | −5572 | −5848 | −4761 | −2825 | −2728 | −1859 | 386 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 336 | −488 | −3682 | −6571 | −5984 | −99 | −6181 | −4896 | 254 | −5734 | 3084 | -809 | −5890 | −5476 | −4672 | −5290 | −5461 | −4066 | −2080 | −3694 | −3776 | 387 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 337 | −144 | −2792 | −1293 | 2073 | −3076 | −1083 | −1061 | 417 | −656 | −912 | −1891 | −136 | −2490 | 1062 | 1039 | 270 | −259 | −688 | −2998 | −2338 | 388 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 338 | 151 | −2877 | 654 | 1516 | −3198 | −406 | 1186 | −2948 | 898 | −2893 | 959 | −1013 | −2471 | 1553 | 699 | −1284 | 545 | −2499 | −3060 | −2377 | 389 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 339 | −4671 | −4277 | −4945 | −4712 | 954 | −5276 | 3348 | −4193 | −4050 | −3690 | −3597 | 2461 | −5218 | −3787 | 1089 | −4442 | −4551 | −4238 | −1417 | 3179 | 390 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 340 | −619 | −2226 | −2773 | −548 | −2674 | −2881 | −2296 | −2257 | −2343 | −2554 | −1845 | −2367 | 3717 | −2197 | −2597 | −685 | −1914 | −57 | 1145 | −2635 | 391 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 341 | −255 | −3030 | −1257 | 2981 | −3351 | −2472 | 535 | −3102 | 980 | −3042 | −2124 | −20 | −2589 | 628 | −1245 | −549 | −1493 | −2653 | −3207 | −2521 | 392 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 342 | −1650 | −1627 | −3232 | −2636 | 604 | −3087 | 1032 | −1147 | −579 | 478 | 651 | −2447 | −3143 | 282 | 18 | −2136 | −1589 | −1055 | 4638 | 1812 | 393 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 343 | −1507 | −2587 | 128 | −981 | −2781 | −2541 | 2027 | 1085 | −77 | −1285 | −1715 | −1251 | −2626 | 688 | 2630 | −1472 | −1442 | 318 | −2845 | −2269 | 394 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 344 | −3441 | −5465 | 1837 | 1202 | −5604 | 2991 | −2647 | −5577 | 10 | −5413 | −4818 | −1811 | −3803 | −2333 | −3943 | −3058 | −3532 | −5023 | −5609 | −4508 | 395 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 345 | −1827 | −3214 | −1717 | 213 | −3602 | −2751 | 1239 | −3298 | 3017 | −3197 | −2308 | 321 | −2825 | 712 | 859 | −1705 | 45 | −2876 | −3305 | −2719 | 396 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 346 | −2945 | −2617 | −5600 | −5244 | −3257 | −4895 | −4760 | 1559 | −5066 | −2289 | −2091 | −4796 | −4972 | −4881 | −5068 | -882 | −132 | 3385 | −4492 | −4053 | 397 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | -86 | -8959 | −4166 | -894 | −1115 | −701 | −1378 | * | * | | | | | | | | | | | | |
| 347 | −1621 | −1704 | −2921 | −2315 | −1722 | −2989 | −1783 | 224 | 144 | −1574 | −915 | −2240 | −3061 | −1841 | 76 | −170 | 699 | 2926 | −2158 | −1782 | 398 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −5 | -8878 | −9920 | -894 | −1115 | −422 | −1979 | * | * | | | | | | | | | | | | |
| 348 | −4262 | −3725 | −6207 | −5849 | 811 | −5836 | −3335 | −1845 | −5524 | 2927 | −1196 | −5133 | −5378 | −4503 | −5069 | −5063 | −4134 | −76 | −2498 | 1711 | 399 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 349 | −3266 | −2781 | −5912 | −5545 | −3248 | −5663 | −5365 | 2486 | −5450 | 1067 | −1999 | −5318 | −5424 | −5286 | −5521 | −4984 | −160 | 2605 | −4805 | −4383 | 400 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 350 | −166 | −3350 | −2812 | −2418 | −4236 | −3351 | −2264 | −3674 | −178 | −3789 | −3075 | −2460 | −3650 | 4157 | −1438 | −2633 | −2637 | −170 | −3975 | −3627 | 401 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 351 | −2918 | −2521 | −5469 | −5014 | −2935 | −5010 | −4338 | 3060 | −4797 | −412 | −1831 | −4668 | 70 | −4566 | −4762 | −4230 | 86 | 2167 | −4040 | −3633 | 402 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 352 | 2480 | 2217 | −4919 | −4844 | −4012 | −25 | −3922 | −3635 | −4514 | −3965 | −3196 | −3508 | −3615 | −4091 | −4314 | −61 | 1821 | 890 | −4393 | −4161 | 403 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 353 | −127 | −2015 | −2003 | −1445 | −2077 | −2691 | −1435 | 1048 | 216 | −1920 | −1195 | 1330 | 1291 | −1215 | −1684 | 561 | 99 | 1560 | −2399 | −1936 | 404 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −4 | -8959 | −10001 | -894 | −1115 | −701 | −1378 | * | * | | | | | | | | | | | | |
| 354 | −1503 | −2856 | −1346 | 199 | −3168 | 39 | −1161 | −2889 | 944 | −789 | −1992 | −1136 | 3015 | −720 | −1243 | -82 | 21 | −2483 | −3093 | −2440 | 405 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 355 | 1385 | −2639 | −3275 | −2921 | −4408 | −2800 | −2991 | −4145 | −392 | −4281 | −3387 | −2694 | 215 | −2687 | −3109 | 2640 | 1651 | −3340 | −4501 | −4086 | 406 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 356 | 1135 | −2226 | −3200 | −2637 | −2644 | −2989 | −2268 | −2138 | −2059 | −630 | −1789 | −2503 | −3297 | −2163 | 3297 | 222 | −1949 | 6 | −2992 | −2618 | 407 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 357 | −1410 | −2878 | −1253 | 897 | 115 | 1658 | −1043 | −2945 | 165 | −2893 | −1968 | 458 | −642 | 1824 | −1133 | 968 | −344 | −2499 | −3063 | −2381 | 408 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 358 | −1418 | −2892 | 2458 | 243 | −3213 | −351 | −1048 | −2964 | 396 | −1467 | −1982 | 465 | −2482 | 797 | 1306 | 451 | −1357 | −2514 | −3075 | −2391 | 409 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 359 | −1558 | −1587 | −2991 | −2407 | −1567 | 693 | 1135 | 346 | −2170 | −1449 | 1281 | 1075 | −443 | −1952 | −2281 | −350 | −1500 | 2447 | −2027 | −1653 | 410 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 360 | −1439 | −2899 | −1291 | 2180 | −3223 | −2410 | −1060 | −2968 | 1173 | −1404 | −1990 | −1046 | 1131 | 644 | 1066 | −65 | −1376 | −2523 | −3077 | 538 | 411 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −304 | -8959 | −2411 | -894 | −1115 | −701 | −1378 | * | * | | | | | | | | | | | | |
| 361 | −54 | −2903 | 1448 | 2434 | −3214 | −2318 | −1073 | 17 | −715 | −2926 | −2025 | −962 | 253 | −631 | −1239 | 817 | −1406 | −2525 | −3114 | −2421 | 412 |
| — | −149 | −500 | 233 | 43 | −381 | 399 | 106 | −626 | 210 | −466 | −720 | 275 | 394 | 48 | 96 | 359 | 117 | −369 | −294 | −249 | |
| H | −223 | −3795 | −3812 | −192 | −3008 | −2170 | −363 | * | * | | | | | | | | | | | | |
| 362 | −2413 | −2410 | −4487 | −4279 | −1248 | −3607 | −2402 | −1491 | −3881 | −2285 | −1934 | −3459 | −3947 | −3513 | −3714 | −2873 | 415 | 1488 | −1954 | 4259 | 414 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −6 | -8556 | −9598 | -894 | −1115 | −1519 | −619 | * | * | | | | | | | | | | | | |
| 363 | −1726 | −3082 | −1465 | 775 | −3453 | −2596 | −1177 | 38 | −528 | −3057 | −2188 | 666 | −2698 | 3418 | 1421 | −1603 | −1643 | −2737 | −3178 | −2597 | 415 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | -8660 | −9702 | -894 | −1115 | −1270 | −772 | * | * | | | | | | | | | | | | |
| 364 | -87 | −2739 | 808 | 1361 | −3060 | −2240 | -899 | −2811 | 905 | −2755 | −1828 | 1992 | −2333 | −439 | 438 | 64 | 684 | −2361 | −2923 | −193 | 416 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | -8757 | −9799 | -894 | −1115 | −272 | −2539 | * | * | | | | | | | | | | | | |
| 365 | 624 | −1429 | −3849 | −322 | −1382 | −3129 | 1002 | 283 | −2833 | 2003 | 1213 | −2746 | −3179 | −2472 | −2664 | −2210 | −1530 | 504 | −1885 | 1469 | 417 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 366 | −1515 | −2947 | −1380 | 1348 | −3274 | −2480 | −1112 | −3006 | 27 | 486 | −2040 | −1120 | −2569 | 1694 | 2231 | −14 | 236 | −2574 | −3113 | −2459 | 418 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 367 | 488 | −2881 | −1255 | 371 | −3202 | −2382 | 1069 | −2953 | 1089 | −2896 | −1970 | 1162 | −136 | 730 | 1414 | 1306 | −1347 | −2503 | −3063 | −2381 | 419 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 368 | −649 | −2877 | 197 | 1594 | −3197 | −2380 | 1065 | −2947 | 406 | −2893 | −1967 | −1016 | −2474 | 2517 | −1128 | −61 | 440 | 441 | −3061 | −2379 | 420 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 369 | −3249 | −2761 | −5908 | −5556 | −3372 | −5675 | −5467 | 2599 | −5475 | −509 | −2109 | −5331 | −5449 | −5372 | −5583 | −5006 | 1312 | 2654 | −4945 | −4467 | 421 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 370 | −227 | −2865 | −1260 | 1794 | −3179 | −2384 | 1330 | −2925 | 1029 | −2878 | 1400 | 2029 | −2478 | −587 | −1132 | 231 | −1348 | −2483 | −3052 | 627 | 422 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 371 | −487 | −2866 | 1211 | 2235 | −3182 | −2382 | −1041 | −688 | 397 | −1274 | −1957 | 1121 | −2475 | −583 | 991 | −1289 | −1345 | −717 | −3053 | −2373 | 423 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 372 | −1710 | −1591 | −3668 | −410 | −1543 | −3230 | −2088 | 1383 | −2738 | 1876 | −754 | −2740 | −3275 | 1164 | −2678 | −2302 | 1305 | 592 | −2073 | −1724 | 424 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 373 | 1594 | −2759 | −5429 | −5530 | −4215 | −3610 | −4931 | −1477 | −5326 | −3330 | −3093 | −4247 | −4281 | −4983 | −5140 | −2993 | −2846 | 3419 | −5241 | −4942 | 425 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 374 | −143 | −2903 | 984 | 371 | −3223 | 2258 | −1057 | −2974 | 523 | −2918 | −1993 | 460 | −2490 | 724 | −198 | −1306 | 25 | −2524 | −3086 | −2401 | 426 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 375 | −201 | −3100 | −1551 | 738 | −3462 | −2624 | 1176 | −3178 | 452 | −3095 | −2193 | −1261 | −2706 | 724 | 3108 | −113 | −1606 | −2747 | −3225 | −2605 | 427 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 376 | −3377 | −2887 | −6050 | −5764 | −3432 | −5781 | −5900 | 3877 | −5721 | −2168 | −2149 | −5546 | −5585 | −5630 | −5857 | −5194 | −3384 | 633 | −5198 | −4712 | 428 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 377 | −3445 | −3927 | −3531 | −3854 | −4319 | −3947 | −4080 | −720 | −4336 | −4917 | −4613 | 4329 | −4588 | −4187 | −4465 | −3614 | −3797 | −4144 | −4687 | −4031 | 429 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 378 | −2893 | −4364 | −1230 | 1405 | −5063 | 2595 | −2483 | −4925 | −2543 | −4840 | −4090 | −1836 | −3609 | 591 | −3217 | 1892 | −3003 | −4336 | −5017 | −4152 | 430 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 379 | 410 | −2951 | −1423 | 1787 | −3276 | −2510 | −1132 | −2999 | 1635 | −415 | 1195 | −1152 | −2596 | 162 | 1788 | −1431 | −1475 | −2576 | −3115 | −2473 | 431 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 380 | −5166 | −4310 | −5900 | −6122 | 3460 | −5702 | −2092 | −4121 | −5688 | -88 | −3578 | −4435 | −5587 | −4535 | −5123 | 124 | −5049 | −4253 | −1351 | 3454 | 432 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 381 | −11 | −2606 | −5124 | −5443 | −5306 | 3437 | −4598 | −5126 | −5228 | −5385 | −4415 | −3680 | −3697 | −4674 | −4887 | 523 | −225 | −3813 | −5527 | −5494 | 433 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −4 | -8959 | −10001 | -894 | −1115 | −701 | −1378 | * | * | | | | | | | | | | | | |
| 382 | −228 | −2885 | −1260 | 288 | −3207 | −2387 | −1045 | −2956 | 414 | −2900 | −1975 | 1770 | −2481 | 646 | 543 | 658 | 2210 | −2508 | −3067 | −2387 | 434 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 383 | −708 | −1484 | 835 | −2873 | −1447 | −3073 | 391 | 1172 | −2560 | 1457 | −684 | −2566 | 319 | −2265 | −2516 | -857 | −1520 | 1762 | −1936 | −1582 | 435 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 384 | −306 | −3357 | 2056 | 1588 | −3675 | 1144 | −1428 | −3445 | −1103 | −3382 | −2481 | 484 | −2812 | −989 | −1646 | 845 | 222 | −2985 | −3554 | −2832 | 436 |
| — | −149 | −500 | 233 | 43 | −381 | 399 | 106 | −626 | 210 | −466 | −720 | 275 | 394 | 45 | 96 | 360 | 117 | −369 | −294 | −249 | |
| B | −2524 | −4236 | −371 | −207 | −2902 | −701 | −1378 | * | * | | | | | | | | | | | | |
| 385 | −514 | −928 | −1238 | −693 | −1113 | 635 | −490 | 1955 | −109 | -893 | −236 | −751 | −1799 | −293 | 1620 | −730 | −498 | −370 | −1421 | −1004 | 438 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −19 | −6826 | −7868 | -894 | −1115 | −166 | −3202 | * | * | | | | | | | | | | | | |
| 386 | −149 | −3783 | −5474 | −5433 | 2448 | −5229 | 1338 | −3536 | −5043 | −3287 | −3082 | −4131 | −5161 | −4148 | −4649 | 200 | −4264 | −3561 | 4174 | 3240 | 439 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8878 | −9920 | -894 | −1115 | −422 | −1979 | * | * | | | | | | | | | | | | |
| 387 | −1425 | −2718 | −1348 | −121 | −2970 | −2427 | 1139 | −2672 | 1106 | −2703 | 881 | −1094 | −2518 | 1419 | −1188 | −74 | 1808 | 1544 | −2943 | −2307 | 440 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 388 | −6266 | −5465 | −6390 | −6767 | −6968 | −5461 | −6137 | −7956 | −6975 | −7412 | −7278 | −6614 | 4329 | −6836 | −6484 | −6639 | −6570 | −7422 | −5831 | −6936 | 441 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 389 | −3403 | −2891 | −6064 | −5714 | −3187 | −5884 | −5676 | 2672 | −5653 | −402 | 1138 | −5540 | −5565 | −5436 | −5728 | −5244 | −3383 | 2880 | −4910 | −4557 | 442 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 390 | −1546 | −1684 | −2675 | −56 | −1675 | −2904 | 3309 | 885 | −1881 | −1550 | 1252 | −2086 | −2970 | 446 | −22 | −1921 | −1486 | 1832 | −2106 | 596 | 443 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 391 | −5497 | −4483 | −5986 | −6299 | 2732 | −5848 | 3660 | −4370 | −5855 | 1135 | −3784 | −4490 | −5706 | −4614 | −5239 | −5090 | −5354 | −4534 | −1335 | 2732 | 444 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 392 | −2905 | −2619 | −5258 | −4635 | 1447 | −4572 | −3392 | 2059 | −4273 | 1864 | 1876 | −4226 | −4403 | −3684 | −4006 | −3699 | −2822 | 115 | −2903 | 1667 | 445 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 393 | −1431 | −2879 | 1369 | 305 | −3187 | −2399 | 3324 | −2931 | −652 | -861 | −1971 | 1416 | −2496 | −610 | 202 | −1314 | 132 | −2494 | −3068 | 1485 | 446 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 394 | −1424 | −2891 | −1274 | 305 | −3213 | -809 | 1144 | −2961 | 946 | −2905 | 963 | −1032 | −2489 | 2282 | 2175 | −48 | −263 | −2514 | −3070 | −2393 | 447 |
| — | −149 | −500 | 233 | 43 | −381 | 399 | 106 | −626 | 210 | −466 | −720 | 275 | 394 | 45 | 98 | 359 | 117 | −369 | −294 | −249 | |
| — | −182 | −4140 | −4010 | −197 | −2973 | −701 | −1378 | * | * | | | | | | | | | | | | |
| 395 | −1359 | −2821 | 626 | −659 | −3140 | −2331 | 1134 | −2886 | 393 | −263 | −1911 | −968 | 1775 | 788 | 366 | 1719 | −1298 | −2442 | −3003 | −2326 | 449 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8868 | −9910 | -894 | −1115 | −403 | −2036 | * | * | | | | | | | | | | | | |
| 396 | 560 | −2285 | −4952 | −4355 | 413 | −4267 | −3187 | 1147 | −4001 | 1938 | 750 | −3918 | −4190 | −3548 | −3796 | −3391 | −2496 | 1966 | −2861 | −2598 | 450 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 397 | −152 | −3018 | 2235 | 307 | −3334 | 348 | −1149 | −3090 | −16 | −3032 | −2112 | 421 | 1820 | 347 | −1270 | 17 | −1475 | −2638 | −3200 | −2507 | 451 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 398 | −2076 | −2543 | −2654 | −1997 | 2824 | −3191 | −1678 | −2220 | 272 | −2415 | −1722 | −2086 | 980 | −1503 | 1935 | −2223 | −371 | −2062 | −2556 | 2190 | 452 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 399 | 807 | −2876 | 1888 | 951 | 334 | −2378 | 585 | −2947 | 332 | −1278 | −1965 | −52 | −642 | 712 | 211 | 134 | −1343 | −2498 | −3060 | −2377 | 453 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 400 | −633 | −2962 | 785 | 2589 | −3221 | −2525 | −1254 | −2928 | -897 | 37 | −2075 | −1179 | −2661 | 1579 | −1407 | −1510 | −1561 | 489 | −3182 | −2521 | 454 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 401 | −1786 | −1636 | −3906 | −3278 | 464 | −3296 | −2045 | −1096 | 539 | 2055 | −782 | −2845 | −3337 | −2533 | −492 | −2379 | −1724 | 296 | −1919 | 2710 | 455 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 402 | 562 | 1721 | −3932 | −3296 | 536 | −3136 | −2007 | 2243 | −2892 | 970 | 1217 | −2781 | −3186 | −2515 | −2692 | -886 | −402 | −3 | −1873 | 778 | 456 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 403 | 3192 | −2676 | −4054 | −4120 | −5090 | −226 | −3971 | −4878 | −168 | −5077 | −4153 | −3316 | −3649 | −3839 | −4103 | 1046 | −2459 | −3745 | −5240 | −5036 | 457 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 404 | −188 | −2079 | −4642 | −4018 | 533 | −3899 | −2724 | 279 | −3632 | 2578 | −739 | −3541 | −3859 | −3167 | −3407 | −3001 | −2234 | −361 | −2427 | 1901 | 458 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 405 | −2378 | −2160 | −4466 | −3948 | 2382 | −3826 | −2052 | −1667 | −3557 | 867 | 1168 | −228 | −3853 | −3092 | −3342 | −729 | −2315 | −1614 | −1631 | 3546 | 459 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 406 | 1562 | 2126 | −1700 | −1145 | −2355 | −2577 | −1281 | −1971 | 304 | −2170 | 963 | −282 | −2663 | −961 | 1378 | 699 | 123 | 385 | −2579 | −2060 | 460 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 407 | 1214 | −1531 | −3214 | 167 | −1501 | −3023 | −1852 | 1735 | −2347 | 71 | −728 | 280 | −3081 | −2096 | 32 | −2073 | −1507 | 1506 | −1975 | 630 | 461 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 408 | 2422 | −2546 | −4325 | −4169 | −4490 | −234 | −3797 | −4204 | −4009 | −4459 | −3610 | −3301 | −3582 | −3719 | −4062 | 2307 | 341 | −3375 | −4757 | 898 | 462 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 409 | −3498 | −5578 | 3733 | 929 | −5682 | −3239 | −2680 | −5674 | −116 | −5500 | −4934 | 542 | −3827 | −2371 | −4073 | −3099 | −3596 | −5112 | −5702 | −4566 | 463 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 410 | 978 | 3347 | −5396 | −4926 | −2861 | −4901 | −4180 | 1351 | −4693 | 189 | −1783 | −4560 | −4814 | −4447 | −4639 | −4107 | −2825 | 2544 | −3903 | −3501 | 464 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 411 | 869 | 3896 | −3951 | −3318 | 920 | 344 | −2042 | −916 | −2917 | 1056 | 1286 | −2809 | −3215 | −2541 | −2723 | −2250 | −1561 | −10 | −1908 | −1568 | 465 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 412 | −2190 | 1597 | −4548 | −3924 | 1051 | −3797 | −2667 | 1556 | −3539 | 2128 | −761 | −3445 | −3776 | −3103 | −3325 | −2899 | −2126 | 1092 | 1992 | −2118 | 466 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 413 | −3286 | −2802 | −194 | −5516 | −3515 | −5693 | −5695 | 1810 | −5557 | −2310 | −2224 | −5344 | −5511 | −5492 | −5733 | −5074 | −3286 | 3417 | −5200 | −4661 | 467 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 414 | −2602 | −3716 | 52 | −1795 | −5026 | −3028 | −2726 | −4876 | −2853 | −4872 | −4078 | 2506 | −3601 | −2403 | −3505 | 1815 | 2614 | −4134 | −5060 | −4298 | 468 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 415 | 1318 | −2621 | −4968 | −5275 | −5295 | −2891 | −4553 | −5118 | −5140 | −5374 | −4410 | −3653 | 2467 | −4612 | −4842 | 2769 | −2482 | −3819 | −5511 | −5461 | 469 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 416 | −3197 | −2757 | −5769 | −5329 | −2832 | −5385 | −4745 | 1360 | −5146 | 2065 | −1656 | −5046 | −5170 | −4817 | −5090 | −4640 | 1402 | 2039 | −4213 | −3909 | 470 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 417 | −156 | −3805 | −4986 | −4361 | −5616 | −3936 | −3474 | −5380 | −2289 | −5218 | −4553 | −3860 | −4444 | −3180 | 4087 | −3480 | −3561 | −4683 | −4923 | −4969 | 471 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −4 | -8959 | −10001 | -894 | −1115 | −701 | −1378 | * | * | | | | | | | | | | | | |
| 418 | −3714 | −5676 | 3799 | 1651 | −5870 | −3388 | −2883 | −5933 | −3358 | −5739 | −5227 | −1998 | −3990 | −2591 | −4397 | −3309 | −3827 | −5360 | −5823 | −4776 | 472 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 419 | −2415 | −3002 | −4640 | −5006 | −5541 | 3690 | −4691 | −5502 | −5275 | −5698 | −4792 | −3872 | −4012 | −4763 | −5056 | -88 | −2886 | −4224 | −5577 | −5613 | 473 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 420 | −3047 | −2717 | −5410 | −4824 | −2082 | −4846 | −3767 | 389 | −319 | 60 | 4775 | −4479 | −4653 | −3964 | −4242 | −4003 | −2977 | 284 | −3280 | −3100 | 474 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 421 | −2522 | −3221 | −2846 | −3220 | −5260 | −3176 | −3861 | −5424 | −4219 | −5535 | −4717 | 4172 | −3919 | −3735 | −4485 | 683 | −2943 | −4287 | −5400 | −4960 | 475 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 422 | −2564 | −2404 | −4686 | −4197 | −1983 | −4085 | −3182 | 461 | −3830 | 2811 | −1004 | 197 | −4131 | −3457 | −3683 | −3253 | 909 | −1287 | −2930 | −2670 | 476 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 423 | −2985 | −2585 | −5523 | −5052 | −2774 | −5065 | −4323 | 409 | −4827 | −295 | 1280 | −4716 | −4924 | −4528 | −4758 | −4280 | 1575 | 3149 | −3946 | −3598 | 477 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 424 | 2470 | 2243 | −5284 | −5553 | −5220 | −2881 | −4581 | −5019 | −5203 | −5287 | −4334 | −3695 | 1977 | −4669 | −4855 | 1864 | −2459 | −3765 | −5454 | −5410 | 478 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 425 | −4250 | −3838 | −5154 | −4879 | 267 | −5124 | 2520 | −3572 | 2147 | 858 | −3089 | −3986 | −5068 | −3816 | −3988 | −4282 | −4145 | −3595 | −1429 | 3428 | 479 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 426 | −3450 | −4892 | −1603 | 3560 | −5376 | −3485 | −2387 | −5045 | 871 | −4784 | −4128 | −2092 | −3878 | 500 | −1903 | −3157 | −3393 | −4650 | −4766 | −4210 | 480 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 427 | −317 | −4460 | −5948 | −6272 | 2394 | −5742 | −2102 | −4420 | −5845 | −3777 | −3846 | −4478 | −5664 | −4621 | −5239 | −5002 | −5282 | −4554 | −1354 | 4424 | 481 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 428 | −273 | −2719 | −5833 | −5488 | −3406 | −5443 | −5318 | 2482 | −5387 | −2293 | −2159 | −5192 | −5330 | −5284 | −5478 | −4766 | 203 | 2953 | −4896 | −4405 | 482 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 429 | 2214 | −1537 | −3967 | −3354 | −1535 | −3222 | −2158 | 906 | −2976 | −1394 | −768 | −2873 | −3295 | −2621 | −2814 | −1005 | 129 | 2030 | −2054 | 643 | 483 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 430 | 1055 | 4610 | −4356 | −3854 | −2108 | −3184 | −2686 | 395 | −3481 | −1935 | −1320 | −3173 | −3486 | −3111 | −3303 | −597 | 655 | 883 | −2635 | −2299 | 484 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −4 | -8959 | −10001 | -894 | −1115 | −701 | −1378 | * | * | | | | | | | | | | | | |
| 431 | −2827 | −3916 | −2902 | −2099 | −4531 | −3569 | −1786 | −4046 | 1196 | −3808 | −3032 | 466 | −3585 | 3466 | 1909 | 148 | −2644 | −3712 | −3764 | −3440 | 485 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 432 | −1406 | −2879 | 832 | 784 | −328 | −2379 | −1038 | −2951 | 423 | −2895 | −1969 | 473 | −2473 | 2442 | 1463 | 580 | −389 | −2501 | −3063 | −2380 | 486 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 433 | −664 | −3212 | 1946 | 1299 | −3522 | 1201 | 1216 | −3284 | 1359 | −3223 | −2313 | −1174 | 794 | -854 | −1470 | −1564 | −1655 | −2830 | −3392 | −2684 | 487 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −1281 | -8959 | −770 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 434 | −654 | −1977 | 897 | 1071 | −2237 | −1646 | −316 | −1948 | 74 | −46 | 1762 | 830 | −1741 | 121 | −423 | 376 | 972 | −1566 | −2197 | −1552 | 488 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −740 | −7689 | −1335 | -894 | −1115 | −3409 | −143 | * | * | | | | | | | | | | | | |
| 435 | −497 | −1377 | -889 | −488 | −2291 | −1387 | −621 | −1978 | −106 | −2058 | −1240 | −594 | 2470 | −257 | 1165 | 1397 | −612 | −1510 | −2276 | −1782 | 489 |
| — | −147 | −502 | 233 | 42 | −380 | 400 | 103 | −626 | 211 | −463 | −718 | 277 | 392 | 43 | 94 | 360 | 116 | −368 | −297 | −251 | |
| . | −1141 | -882 | -8008 | −2967 | −197 | −3715 | −114 | * | * | | | | | | | | | | | | |
| 436 | −1069 | −2728 | 2095 | 1448 | −2981 | −1429 | −514 | −2801 | −430 | −2721 | −1902 | 2043 | 1093 | −126 | −1082 | -837 | −1070 | −2326 | −2907 | −2075 | 499 |
| — | −149 | −500 | 233 | 43 | −381 | 399 | 106 | −626 | 210 | −466 | −720 | 275 | 394 | 45 | 96 | 359 | 117 | −369 | −294 | −249 | |
| . | −17 | −6966 | -8008 | -894 | −1115 | −3715 | −114 | * | * | | | | | | | | | | | | |
| 437 | −647 | −1559 | 1891 | −76 | 1806 | −1472 | −432 | −1517 | −336 | −1659 | −922 | −328 | −1740 | −168 | -816 | 1443 | −663 | −1233 | −1729 | −988 | 500 |
| — | −148 | −500 | 234 | 43 | −381 | 398 | 105 | −627 | 210 | −464 | −721 | 275 | 393 | 45 | 96 | 360 | 117 | −370 | −295 | −250 | |
| . | −2130 | −381 | -8008 | −67 | −4459 | −2877 | −211 | * | * | | | | | | | | | | | | |
| 438 | 1808 | 3097 | −2604 | −2203 | −1479 | −1551 | −1567 | -825 | −1947 | −1330 | −664 | −1639 | 1687 | −1687 | −1981 | −793 | −663 | 1013 | −1930 | −1594 | 502 |
| — | −149 | −500 | 233 | 43 | −381 | 399 | 106 | −626 | 210 | −466 | −720 | 275 | 394 | 45 | 96 | 359 | 117 | −369 | −294 | −249 | |
| S | −14 | −7234 | -8276 | -894 | −1115 | −447 | −1909 | * | * | | | | | | | | | | | | |
| 439 | −1869 | −3221 | 296 | −1096 | −3622 | −2717 | −1251 | −3306 | 2147 | −3187 | −2324 | 1389 | −2811 | -808 | 2638 | −1739 | −1775 | −2899 | −3270 | 849 | 503 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8685 | −9727 | -894 | −1115 | −227 | −2777 | * | * | | | | | | | | | | | | |
| 440 | −1418 | −2892 | 304 | 326 | −3212 | 422 | 1950 | −2963 | 2087 | −2907 | −1982 | 795 | 721 | −590 | −1140 | −1298 | 194 | −2513 | −3075 | 520 | 504 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 441 | 311 | −2747 | −3274 | −3175 | −4824 | 3111 | −3329 | −4598 | −3189 | −4726 | −3818 | 392 | −3534 | −3060 | 35 | 979 | −2377 | −3630 | −4895 | −4526 | 505 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 442 | 959 | −1799 | −3772 | −3251 | −2028 | −3000 | −2389 | −1544 | −2956 | −1916 | 1885 | −2811 | 1713 | −2664 | −2928 | 637 | 660 | 2112 | −2503 | −2156 | 506 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 443 | −4356 | −3760 | −6817 | −6287 | −2155 | −6626 | −5475 | 26 | −6120 | 3151 | −917 | −6354 | −5733 | −4978 | −5673 | −6021 | −4232 | 122 | −3998 | −4184 | 507 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 444 | −3421 | −2900 | −6099 | −5768 | −3269 | −5952 | −5868 | 3092 | −5731 | 636 | −1974 | −5610 | −5624 | −5554 | −5841 | −5335 | −3404 | 2336 | −5059 | −4676 | 508 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 445 | −4365 | −3822 | −6755 | −6286 | −2172 | −6368 | −5383 | −1340 | −6078 | 3142 | −958 | −6256 | −5681 | −4973 | −5626 | −5823 | −4272 | 786 | −3976 | −4104 | 509 |
| — | −149 | −500 | 233 | 43 | −381 | 399 | 106 | −626 | 210 | −466 | −720 | 275 | 394 | 45 | 96 | 359 | 117 | −369 | −294 | −249 | |
| E | −4 | -8959 | −10001 | -894 | −1115 | −701 | −1378 | * | * | | | | | | | | | | | | |
| 446 | −3394 | −3819 | −5347 | −5705 | −5881 | −4005 | −5224 | −6253 | −5855 | −6292 | −5576 | −4737 | −4729 | −5485 | −5568 | 3744 | −3850 | −5118 | −5593 | −5835 | 510 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 447 | −3523 | −4810 | −1835 | 3642 | −5378 | −3600 | −2386 | −5009 | −1539 | −4724 | −4074 | −2229 | −3950 | 510 | 296 | −3255 | −3436 | −4643 | −4657 | −4202 | 511 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 448 | −5422 | −4815 | −5974 | −6079 | 4459 | −5417 | −3157 | −5084 | −5052 | −4431 | −4484 | −5079 | −5664 | −4979 | 298 | −5391 | −5492 | −5208 | −2514 | −1401 | 512 |
| — | −149 | −500 | 233 | 43 | −381 | 399 | 106 | −626 | 210 | −466 | −720 | 275 | 394 | 45 | 96 | 359 | 117 | −369 | −294 | −249 | |
| B | −4 | -8959 | −10001 | -894 | −1115 | −701 | −1378 | * | * | | | | | | | | | | | | |
| 449 | 2274 | −2044 | −4328 | −3901 | −2530 | −3115 | −2951 | 1252 | −3582 | −2339 | −1721 | −3215 | −3539 | −3251 | −3483 | 658 | 2014 | 66 | −3046 | −2713 | 513 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |
| 450 | −120 | −3074 | −4990 | −5351 | −5637 | 3698 | −4839 | −5566 | −5454 | −5769 | −4876 | −4040 | −4097 | −4951 | −5167 | −2759 | −2980 | −4302 | −5612 | −5753 | 514 |
| — | −149 | −500 | 233 | 43 | −381 | 399 | 106 | −626 | 210 | −466 | −720 | 275 | 394 | 45 | 96 | 359 | 117 | −369 | −294 | −249 | |
| G | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 451 | 2387 | 3873 | -5315 | -5584 | -5170 | -2881 | -4575 | -4951 | -5214 | -5230 | -4288 | -3699 | -3690 | -4674 | -4855 | 1451 | 1070 | -3735 | -5415 | -5365 | 515 |
| — | -149 | -500 | 233 | 43 | -381 | 399 | 106 | -626 | 210 | -466 | -720 | 275 | 394 | 45 | 96 | 359 | 117 | -369 | -294 | -249 | |
| G | -4 | -8959 | -10001 | -894 | -1115 | -701 | -1378 | * | * | | | | | | | | | | | | |
| 452 | 2968 | -2644 | -4650 | -4839 | -4299 | -2939 | -4140 | -4687 | -4743 | -4916 | -4079 | -3562 | -3717 | -4320 | -4573 | 2017 | -2501 | -3667 | -4716 | 929 | 516 |
| — | -149 | -500 | 233 | 43 | -381 | 399 | 106 | -626 | 210 | -466 | -720 | 275 | 394 | 45 | 96 | 359 | 117 | -369 | -294 | -249 | |
| G | -4 | -8959 | -10001 | -894 | -1115 | -701 | -1378 | * | * | | | | | | | | | | | | |
| 453 | 498 | -2879 | 300 | 319 | -3200 | -2380 | -1040 | -2950 | -621 | -2895 | -1969 | 1118 | 1070 | 2227 | 210 | 752 | -1347 | -328 | -3063 | -2380 | 517 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 454 | -1723 | -1660 | -3423 | 1825 | -1619 | -3209 | -2054 | 279 | -2560 | 249 | 1282 | -2622 | -3257 | -2301 | -2590 | 2048 | -1665 | 761 | -2145 | -1787 | 518 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 455 | -5647 | -4878 | -6611 | -6689 | -3480 | -5830 | -5714 | -3122 | -6613 | 3375 | -2416 | -6629 | -5924 | -5899 | -6106 | -6640 | -5628 | -3921 | -4748 | -4938 | 519 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 456 | -79 | -2873 | -1253 | -704 | -3193 | -226 | 1173 | -2942 | 842 | -827 | -1963 | 2159 | 1 | 647 | 269 | 781 | 31 | -2495 | -3058 | -2376 | 520 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -519 | -8959 | -1737 | -894 | -1115 | -701 | -1378 | * | * | | | | | | | | | | | | |
| 457 | 306 | -3147 | 2543 | 1240 | -3449 | -2 | 1604 | -3225 | -884 | -3162 | -2275 | -926 | -2533 | -737 | -1445 | 971 | -1572 | -2765 | -3337 | -2597 | 521 |
| — | -149 | -500 | 233 | 43 | -381 | 399 | 106 | -626 | 210 | -466 | -720 | 275 | 394 | 45 | 96 | 359 | 117 | -369 | -294 | -249 | |
| S | -6 | -8447 | -9489 | -894 | -1115 | -153 | -3314 | * | * | | | | | | | | | | | | |
| 458 | 2092 | -2633 | -3029 | -2908 | -4004 | 2611 | 1399 | -3683 | -3022 | -3911 | -3114 | 254 | -3465 | -2828 | -3303 | -2165 | -2274 | -132 | -4249 | -3841 | 522 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -707 | -8959 | -1376 | -894 | -1115 | -701 | -1378 | * | * | | | | | | | | | | | | |
| 459 | 3124 | -1891 | -4246 | -4339 | -4026 | -2240 | -3598 | -3426 | -4087 | -3963 | -3160 | -2920 | -3011 | -3665 | -3890 | 1080 | -1761 | 672 | -4357 | -4185 | 523 |
| — | -149 | -500 | 233 | 43 | -381 | 399 | 106 | -626 | 210 | -466 | -720 | 275 | 394 | 45 | 96 | 359 | 117 | -369 | -294 | -249 | |
| . | -7 | -8259 | -9301 | -894 | -1115 | -125 | -3590 | * | * | | | | | | | | | | | | |
| 460 | -2403 | -2144 | -4784 | -4191 | -1909 | -4092 | -3003 | 2986 | -3831 | 1239 | -1000 | -3736 | 32 | -3418 | -3642 | -3211 | -2345 | 393 | -2731 | 1645 | 524 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 461 | -2065 | -1855 | -4382 | -3770 | -1797 | -309 | -2603 | 2073 | -3348 | 1894 | -942 | -3315 | -3703 | -3026 | 1162 | -2792 | -2011 | 993 | -2449 | -2117 | 525 |
| — | -149 | -500 | 233 | 43 | -381 | 399 | 106 | -626 | 210 | -466 | -720 | 275 | 394 | 45 | 96 | 359 | 117 | -369 | -294 | -249 | |
| E | -4 | -8959 | -10001 | -894 | -1115 | -701 | -1378 | * | * | | | | | | | | | | | | |
| 462 | -3291 | -2799 | -5988 | -5680 | -3536 | -5753 | -5848 | 1958 | -5641 | -2310 | -2228 | -5463 | -5549 | -5609 | -5809 | -5127 | -15 | 3361 | -5269 | -4732 | 526 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 463 | -5484 | -5242 | -4990 | -5367 | -6389 | -5108 | -5499 | -7466 | -6086 | -7077 | -6801 | 4440 | -5645 | -5816 | -5991 | -5668 | -5796 | -6829 | -5673 | -6139 | 527 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 464 | -6266 | -5465 | -6390 | -6767 | -6968 | -5461 | -6137 | -7956 | -6975 | -7412 | -7278 | -6614 | 4329 | -6836 | -6484 | -6639 | -6570 | -7422 | -5831 | -6936 | 528 |
| — | -149 | -500 | 233 | 43 | -381 | 399 | 106 | -626 | 210 | -466 | -720 | 275 | 394 | 45 | 96 | 359 | 117 | -369 | -294 | -249 | |
| T | -4 | -8959 | -10001 | -894 | -1115 | -701 | -1378 | * | * | | | | | | | | | | | | |
| 465 | -5648 | -4559 | -6016 | -6375 | 1072 | -5900 | 1373 | -4533 | -5929 | -3838 | -3935 | -4506 | -5753 | -4647 | -5290 | -5148 | -5496 | -4689 | 5559 | 2896 | 529 |
| — | -149 | -500 | 233 | 43 | -381 | 399 | 106 | -626 | 210 | -466 | -720 | 275 | 394 | 45 | 96 | 359 | 117 | -369 | -294 | -249 | |
| — | -4 | -8959 | -10001 | -894 | -1115 | -701 | -1378 | * | * | | | | | | | | | | | | |
| 466 | -302 | -5045 | 3423 | -1534 | -5682 | -3229 | -2795 | -5683 | -3241 | -5551 | -4969 | 2706 | -3844 | -2499 | -4230 | -3057 | -3529 | -5022 | -5734 | -4652 | 530 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |
| 467 | -1594 | -1441 | -3800 | -3173 | -1399 | -3127 | -1992 | 2143 | -2797 | -218 | -643 | -2727 | -3178 | -2449 | -115 | 516 | 1624 | 357 | -1900 | 2101 | 531 |
| — | -149 | -500 | 233 | 43 | -381 | 399 | 106 | -626 | 210 | -466 | -720 | 275 | 394 | 45 | 96 | 359 | 117 | -369 | -294 | -249 | |
| H | -4 | -8959 | -10001 | -894 | -1115 | -701 | -1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 468 | −1416 | −2883 | 1702 | 1735 | −3201 | −2386 | −1049 | −924 | 883 | −2898 | −1974 | 993 | −2482 | −590 | −1140 | 1018 | −345 | −343 | −3068 | −2387 | 532 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 469 | 1114 | −2918 | 643 | 2045 | −3238 | 368 | 799 | −2990 | 318 | −2934 | −2009 | 155 | −2501 | −611 | 1017 | −1320 | −1382 | −2540 | −3101 | −2416 | 533 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 470 | −1614 | 1551 | −3956 | −3321 | 1146 | −3165 | −2039 | -895 | −2919 | 610 | 1814 | −2810 | −3213 | −2543 | −2721 | -849 | 1343 | 2302 | −1903 | −1562 | 534 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 471 | 2865 | −2999 | 274 | −1499 | −3908 | −2709 | −1926 | −3655 | 139 | −3670 | −2783 | −1724 | −3050 | −1520 | −2120 | 820 | 408 | −3100 | −3870 | −3238 | 535 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 472 | 203 | −3055 | 1299 | 2392 | −3371 | −1124 | −1178 | −3128 | 354 | −3069 | −2150 | 1275 | −2597 | 1043 | −1308 | −658 | −1509 | −2675 | −3237 | −2541 | 536 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 473 | 2799 | −2525 | −4780 | −4732 | −4532 | −148 | −4066 | −4 | −4480 | −4507 | −3671 | −3488 | −3629 | −4100 | −4369 | 1790 | 193 | −3373 | −4837 | −4637 | 537 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 474 | −2979 | −2677 | −5343 | −4730 | 456 | −4679 | −3508 | 3189 | −4377 | 700 | 2370 | −4333 | −4493 | −3784 | −4113 | −3814 | −2898 | −388 | −2995 | 638 | 538 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 475 | 209 | −2876 | 1227 | 291 | −3197 | −933 | 379 | −2948 | 534 | −1202 | −1966 | 1659 | −2471 | 168 | 208 | 398 | −1343 | −2498 | −3060 | 1803 | 539 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 476 | −1404 | −2876 | 321 | 1444 | −3197 | −2378 | −1036 | −2948 | 168 | −2892 | 959 | 454 | −2471 | 1163 | 1263 | 972 | 28 | −2498 | −3060 | 1162 | 540 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 477 | 3146 | 1780 | −5333 | −5642 | −5273 | 138 | −4626 | −5084 | −5281 | −5350 | −4384 | −3712 | −3695 | −4723 | −4902 | 1148 | −2464 | −3791 | −5502 | −5475 | 541 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 478 | −4523 | −3907 | −6924 | −6340 | −2047 | −6727 | −5392 | −203 | −6149 | 3019 | 2126 | −6452 | −5729 | −4893 | −5624 | −6108 | −4365 | −66 | −3885 | −4119 | 542 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −4 | -8959 | −10001 | -894 | −1115 | −701 | −1378 | * | * | | | | | | | | | | | | |
| 479 | −133 | −2849 | −1274 | 579 | −3156 | −2395 | −1059 | −113 | 1266 | −2861 | −1946 | 1695 | −2490 | −605 | −1149 | 775 | 1943 | −2464 | −3045 | −2373 | 543 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 480 | −2144 | −1946 | −4419 | −3792 | -88 | −3720 | −2577 | −1077 | −3411 | 318 | 4544 | −3345 | −3703 | 315 | −3218 | −2814 | 60 | 308 | −2348 | −2061 | 544 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | -8959 | −10001 | -894 | −1115 | −701 | −1378 | * | * | | | | | | | | | | | | |
| 481 | −2322 | −3171 | 1166 | −2407 | −5061 | −2965 | −3158 | −4889 | −3321 | −4974 | −4125 | −2481 | 2189 | −2882 | −3821 | 2590 | 1331 | −3957 | −5155 | −4587 | 545 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 482 | −578 | −2867 | 1016 | 2165 | −304 | −2419 | −1094 | −2893 | 992 | 435 | −1965 | −1064 | 1054 | −645 | −1198 | −1344 | −1395 | −2474 | −3066 | −2397 | 546 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 483 | 250 | −2985 | 1077 | 2695 | −628 | −267 | −1135 | −3051 | 803 | −2999 | −2080 | −1077 | −2558 | −681 | −1251 | −1387 | −411 | −2604 | −3171 | −2483 | 547 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 484 | −269 | −3283 | −1808 | 2886 | −3682 | −2830 | −1354 | −3365 | 1786 | −1638 | −2380 | −1469 | −2904 | 53 | 453 | −1801 | −1830 | −2952 | −3357 | −2793 | 548 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 485 | −3531 | 1467 | −4180 | −2861 | −5129 | −361 | −2026 | −4452 | 2201 | −4111 | −3424 | −2778 | −4046 | 693 | 3270 | −3409 | −3231 | −4207 | −3964 | −3845 | 549 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 486 | 482 | −2886 | −1265 | 1183 | −3208 | −2390 | −1045 | −395 | 1448 | −2900 | −1975 | 92 | −2482 | 2060 | 1423 | −60 | −1355 | −2508 | −3067 | −2387 | 550 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 487 | −660 | −2861 | −1259 | 909 | −778 | −1061 | −1041 | −2920 | 1604 | 99 | 1593 | 456 | −417 | 164 | 1336 | −138 | −1344 | −2479 | −3048 | −2370 | 551 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 488 | −2812 | −3649 | −3151 | −2252 | −4095 | −3624 | −1819 | −101 | −9 | 234 | −2780 | 1510 | −3622 | 300 | 3320 | −2756 | −2627 | −3354 | −3592 | −3292 | 552 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 489 | −1588 | −2127 | −2027 | 763 | 1713 | −2765 | 3285 | −1776 | −1356 | −2015 | 1992 | 218 | −2845 | −1260 | −1731 | −97 | −1527 | −1607 | 3276 | −1739 | 553 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 490 | −228 | −2885 | −1261 | 1396 | −3207 | −353 | −1044 | −2957 | 1533 | −2900 | −1975 | −1023 | −2480 | 850 | 1711 | 823 | 29 | −2508 | −3067 | −2386 | 554 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 491 | −232 | −2887 | −1266 | 856 | −3209 | −285 | 1332 | −2957 | 2542 | −2902 | −1977 | −1026 | −2484 | −588 | 317 | 583 | 29 | −2510 | −3068 | −2389 | 555 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 492 | −1742 | −1748 | −3165 | −2664 | −1655 | −3123 | 2320 | −1268 | −2335 | 2042 | 3095 | 383 | −3217 | −2180 | −2391 | −264 | −1696 | −1188 | −2149 | −1743 | 556 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 493 | −1581 | 1408 | −1091 | −2782 | 2171 | −3060 | 1464 | −1014 | −51 | −305 | 1835 | −2515 | −3116 | −2205 | −12 | −2119 | −1522 | −927 | 2847 | 2340 | 557 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 494 | −132 | −2876 | 832 | −707 | −3196 | −2381 | 1777 | −2946 | 2609 | −2892 | 286 | 365 | −2474 | −580 | 270 | 7 | −456 | −2498 | −3060 | −2379 | 558 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 495 | −131 | −2820 | -87 | 303 | −3116 | −2392 | 1329 | −2849 | −643 | −925 | −1916 | −1037 | −2484 | 2170 | 364 | −331 | −1347 | −435 | −3019 | 2762 | 559 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 496 | −376 | −2786 | −5960 | −5625 | −3437 | −5761 | −5662 | 2937 | −5568 | −516 | −2151 | −5419 | −5519 | −5494 | −5706 | −5114 | −3275 | 2642 | −5094 | −4595 | 560 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 497 | −1477 | −2099 | −1860 | −458 | −2169 | −2641 | −1358 | 389 | 627 | 967 | −1262 | −376 | −15 | −1094 | −1578 | 1490 | 1153 | −139 | −2456 | −1971 | 561 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | -89 | -8959 | −4120 | -894 | −1115 | −701 | −1378 | * | * | | | | | | | | | | | | |
| 498 | −119 | −2839 | −1219 | 759 | −3163 | −2344 | −998 | −2910 | 2043 | −2854 | −1930 | 209 | −2437 | −540 | 1024 | 463 | 1681 | −2463 | −3019 | −2342 | 562 |
| — | −149 | −500 | 233 | 43 | −381 | 399 | 106 | −626 | 210 | −466 | −720 | 275 | 394 | 45 | 96 | 359 | 117 | −369 | −294 | −249 | |
| T | −5 | -8875 | −9917 | -894 | −1115 | −1319 | −739 | * | * | | | | | | | | | | | | |
| 499 | −2872 | −3842 | −2701 | −2108 | −3054 | −3571 | 4240 | −3893 | -861 | −3684 | −2989 | 1048 | −3628 | 734 | 679 | −2747 | −2710 | −3613 | −3125 | 2722 | 563 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | -8875 | −9917 | -894 | −1115 | −416 | −1996 | * | * | | | | | | | | | | | | |
| 500 | −2964 | −4295 | 3033 | −1635 | −5349 | −3128 | −2754 | −5257 | −3044 | −5197 | −4490 | 19 | −3722 | −2445 | −3852 | 372 | 2615 | −4548 | −5391 | −4478 | 564 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 501 | 850 | −1950 | −4542 | −3976 | −2096 | −3820 | −2884 | 1642 | −3633 | −1721 | 1270 | −3507 | −3877 | −3303 | −3495 | 1712 | −2136 | 2168 | −2747 | −2389 | 565 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 502 | 1190 | −2893 | 754 | −730 | −3210 | 151 | −1072 | −2957 | −661 | −2910 | −1990 | 368 | −2501 | 2665 | −1169 | 239 | −188 | −2514 | −3085 | 629 | 566 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 503 | −1406 | −2859 | 224 | −44 | 964 | −2382 | 2312 | −2917 | −625 | −2872 | −1950 | 791 | −2475 | 1416 | 928 | 542 | −1345 | −923 | −3047 | 1912 | 567 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 504 | −7105 | −5660 | −6607 | −6980 | −5351 | −5674 | −5723 | −7746 | −7072 | −7049 | −7086 | −6845 | −6098 | −6903 | −6523 | −7533 | −7247 | −7591 | 6305 | −5006 | 568 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 505 | 2121 | 1495 | −3613 | −3109 | −2193 | 1111 | −2414 | 1685 | −2847 | −2081 | −1408 | −2743 | −3282 | 311 | −2892 | −2124 | 958 | −1563 | −2649 | −2296 | 569 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 506 | −1407 | −2877 | −1256 | 1660 | −3197 | −2381 | −1039 | −2947 | 843 | −2892 | −1966 | 1685 | −2474 | 1057 | 1363 | −61 | −182 | −458 | −3060 | 531 | 570 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 507 | −602 | 1178 | 138 | 371 | −3197 | −2380 | 1196 | −2947 | 1303 | −2893 | −1967 | 438 | −2474 | −581 | −1129 | 1837 | 1200 | −2499 | −3061 | −2379 | 571 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 508 | −2039 | 1144 | −4191 | −3620 | 3634 | −3526 | −2039 | −1352 | −3230 | 871 | −1043 | −3067 | −3568 | 478 | −3046 | −696 | −1979 | −1289 | −1735 | 526 | 572 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 509 | −1607 | −1438 | −732 | −3281 | 1196 | −3153 | −2022 | 1874 | −2885 | 1356 | 721 | −2786 | −3201 | 206 | −2699 | -890 | −1547 | 1530 | −1897 | −1555 | 573 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | -86 | -8959 | −4166 | -894 | −1115 | −701 | −1378 | * | * | | | | | | | | | | | | |
| 510 | −636 | −2822 | 356 | 137 | −3143 | −2322 | 486 | −2894 | 443 | −2838 | −1911 | 1178 | −2415 | 1950 | 1064 | 1584 | −435 | −2444 | −3005 | −2322 | 574 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −5 | -8878 | −9920 | -894 | −1115 | −422 | −1979 | * | * | | | | | | | | | | | | |
| 511 | −1606 | −3066 | 2566 | 1977 | −3365 | −2501 | −1219 | −3116 | -837 | −930 | −2167 | −1136 | −2635 | −772 | 277 | 604 | −1551 | −2680 | −3253 | 129 | 575 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 512 | 1061 | −3281 | −6068 | −5476 | 677 | −5538 | −4342 | 1298 | −5179 | 2630 | -831 | −5220 | −5107 | −4359 | −4837 | −4740 | −3591 | −1795 | −3471 | −3431 | 576 |
| — | −149 | −500 | 233 | 43 | −381 | 399 | 106 | −626 | 210 | −466 | −720 | 275 | 394 | 45 | 96 | 359 | 117 | −369 | −294 | −249 | |
| H | −4 | -8959 | −10001 | -894 | −1115 | −701 | −1378 | * | * | | | | | | | | | | | | |
| 513 | 519 | −2869 | −1255 | 1249 | −3186 | −2380 | 797 | −2934 | 1531 | -868 | −1959 | 1081 | −2473 | 393 | −1127 | −594 | 749 | −2489 | −3054 | 1412 | 577 |
| — | −149 | −500 | 233 | 43 | −381 | 399 | 106 | −626 | 210 | −466 | −720 | 275 | 394 | 45 | 96 | 359 | 117 | −369 | −294 | −249 | |
| C | −4 | -8959 | −10001 | -894 | −1115 | −701 | −1378 | * | * | | | | | | | | | | | | |
| 514 | 926 | −2877 | 1061 | 858 | −3198 | −2380 | −1038 | −692 | 359 | −2893 | −1967 | 992 | −2473 | 647 | 1930 | −1287 | −1345 | −2499 | −3061 | 531 | 578 |
| — | * | * | * | * | * | * | * | * | * | * | * | * | * | * | * | * | * | * | * | * | |
| S | * | * | * | * | * | * | * | * | 0 | | | | | | | | | | | | |
| // | | | | | | | | | | | | | | | | | | | | | |

HMMER2.0 [2.3.2]
NAME Trehalose_PPase
ACC PF02358.8
DESC Trehalose-phosphatase
LENG 251
ALPH Amino
RF no
CS no
MAP yes
COM hmmbuild -F HMM_ls.ann SEED.ann
COM hmmcalibrate --seed 0 HMM_ls.ann
NSEQ 24
DATE Thu Jun 26 16:41:21 2008
CKSUM 7747
GA −49.4000 −49.4000;
TC −48.9000 −48.9000;
NC −49.9000 −49.9000;
XT −8455 −4 −1000 −1000 −8455 −4 −8455 −4
NULT −4 −8455
NULE 595 −1558 85 338 −294 453 −1158 197 249 902 −1085 −142 −21 −313 45 531 201 384 −1998 −644
EVD −147.909348 0.162078

| HMM | A | C | D | E | F | G | H | I | K | L | M | N | P | Q | R | S | T | V | W | Y | |
|---|---|---|---|---|---|---|---|---|---|---|---|---|---|---|---|---|---|---|---|---|---|
| | m->m | m->i | m->d | i->m | i->i | d->m | d->d | b->m | m->e | | | | | | | | | | | | |
| | −70 | * | −4393 | | | | | | | | | | | | | | | | | | |
| 1 | −2140 | 1327 | −4484 | −3849 | 3068 | −3695 | −2564 | 239 | −3447 | 1159 | 2286 | −3341 | −479 | −142 | −3244 | −2782 | −2079 | 103 | −2407 | −2077 | 1 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | −70 | * | | | | | | | | | | | | |
| 2 | −438 | −1920 | −4415 | −568 | 2013 | −3645 | −2515 | −1349 | −3385 | 2153 | 1899 | −3283 | −3687 | −3005 | −3192 | −2730 | 44 | 456 | −2373 | −2038 | 2 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 3 | −4124 | −6144 | 3996 | −283 | −5790 | −3813 | −3270 | −6309 | −3762 | −6106 | −5606 | −2405 | −4415 | −2996 | −4801 | −3716 | −4236 | −5752 | −5983 | 778 | 3 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 4 | −776 | −2648 | −5022 | −4510 | 1875 | −4337 | −2551 | 1253 | −4108 | −616 | −1816 | −290 | −4360 | −3623 | −3870 | −3441 | −2817 | −2055 | −2111 | 3979 | 4 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −59 | −9479 | −4702 | −894 | −1115 | −701 | −1378 | * | * | | | | | | | | | | | | |
| 5 | −3856 | −5872 | 3808 | 205 | −6005 | −3659 | −3059 | −5966 | −231 | −5801 | −5195 | −2240 | −308 | 340 | −4272 | −3476 | −3939 | −5420 | −5994 | −4911 | 5 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9423 | −10465 | −894 | −1115 | −424 | −1974 | * | * | | | | | | | | | | | | |
| 6 | −432 | −3354 | −4002 | −4018 | −5608 | 3495 | −4002 | −5358 | −3563 | −5459 | −4585 | −3584 | −4182 | −27 | −344 | −417 | −3057 | −4331 | −5564 | −5314 | 6 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 7 | −2520 | −3134 | −5531 | −5881 | −5842 | 236 | −5112 | −5673 | −5746 | −5929 | −4959 | −4187 | −4219 | −5188 | −5409 | 472 | 3771 | −4348 | −6055 | −6023 | 7 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 8 | −3572 | −3348 | −5680 | −4780 | −2488 | −5081 | −3646 | 1010 | 586 | 2663 | 1656 | −4480 | −4902 | −3633 | 528 | −4255 | −3457 | −2357 | −3568 | −3433 | 8 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 9 | 237 | −1955 | −3556 | −2963 | −1927 | −3419 | −2244 | 1 | 498 | 20 | 744 | −2789 | −3478 | −2461 | −421 | 1893 | 1431 | 706 | −2397 | −2031 | 9 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 10 | −1869 | −3350 | 1514 | 1185 | −3668 | −798 | 966 | −3422 | −1086 | −3365 | −2441 | 1002 | 2409 | 262 | 35 | −1744 | 72 | −2971 | −3532 | −2844 | 10 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 11 | −1936 | −2137 | 363 | 2 | −2136 | −3264 | −2040 | 2807 | −2173 | 450 | 977 | −2388 | −517 | −64 | −2417 | −495 | −1876 | −1577 | 1926 | −2149 | 11 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 12 | 1119 | −2839 | −345 | −1360 | 911 | 257 | −1581 | −2649 | 60 | −2787 | −1976 | −1627 | −2983 | 931 | −1725 | −681 | −471 | 2220 | −3130 | −2561 | 12 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 13 | −270 | −3249 | 339 | 1402 | −3565 | −2765 | −1424 | 794 | 605 | −3263 | −2340 | −1402 | 1253 | −966 | 683 | 983 | −366 | −563 | −3436 | −2756 | 13 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −212 | −9479 | −2888 | −894 | −1115 | −701 | −1378 | * | * | | | | | | | | | | | | |
| 14 | −1638 | −3110 | 2129 | 8 | 1018 | −2609 | 1164 | −3181 | 143 | −3126 | −2200 | 351 | −2704 | 827 | 1336 | −1518 | 1263 | −2732 | −3293 | −2611 | 14 |
| — | −149 | −500 | 233 | 43 | −381 | 398 | 106 | −626 | 210 | −466 | −721 | 275 | 394 | 45 | 96 | 359 | 117 | −369 | −294 | −243 | |
| — | −100 | −3913 | −10313 | −144 | −3395 | −2198 | −355 | * | * | | | | | | | | | | | | |
| 15 | −2630 | −4183 | −1487 | 652 | −4497 | −3170 | 1464 | −4271 | 92 | −4182 | −3334 | 384 | 3520 | −1678 | −2279 | −305 | −2601 | −3814 | −4336 | −3600 | 16 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9270 | −10313 | −894 | −1115 | −211 | −2875 | * | * | | | | | | | | | | | | |
| 16 | −530 | −3117 | 2210 | 644 | −3369 | −2813 | −1483 | 1729 | −1097 | −1286 | 1437 | 995 | −48 | 309 | −1592 | −1730 | −1755 | −2701 | −3342 | −2702 | 17 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 17 | 1624 | 776 | 1026 | 177 | −3555 | −2766 | −1426 | −3300 | 533 | −3255 | 948 | −1405 | −2859 | 507 | 523 | 611 | −1729 | 628 | −3431 | −2753 | 18 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 18 | 2409 | −2131 | −2940 | 447 | −2130 | −3269 | −2047 | 519 | 175 | −792 | 1220 | −2399 | −3337 | −188 | −2425 | −2276 | −347 | 528 | −2549 | −2147 | 19 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 19 | 344 | −2330 | 171 | −345 | 676 | −3129 | −1868 | 444 | −1801 | −2218 | −1504 | −147 | 671 | −1691 | 853 | −2104 | 1059 | 1359 | 994 | 127 | 20 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 20 | −2459 | −2250 | −4814 | −4201 | −2140 | −4068 | −2981 | −68 | −3820 | 684 | 1595 | −3718 | 3049 | −3433 | −3632 | −358 | −2403 | 1519 | −2797 | −2473 | 21 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 21 | −797 | −2679 | 65 | −1553 | −2814 | −2974 | 1579 | −2433 | −1449 | −646 | −1854 | −1787 | 1154 | −1376 | −1883 | 1974 | 1704 | 23 | −3029 | −2506 | 22 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 22 | 23 | −3266 | 2027 | −31 | −3587 | −2765 | 670 | −3338 | 9 | −3282 | −2355 | −128 | 1524 | 1381 | 524 | 738 | −1732 | −2888 | −3449 | −2766 | 23 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 23 | 103 | −3301 | −252 | 1964 | −3621 | 284 | −1453 | −3373 | 557 | −3316 | −2391 | 248 | −2885 | −994 | 2146 | 216 | −1765 | −2923 | −3483 | −2799 | 24 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 24 | 320 | −2430 | −5073 | −4476 | −2361 | −4360 | −3300 | 1361 | −4113 | 1535 | 3281 | −4008 | −4350 | −3732 | −3933 | −3474 | 651 | 874 | −3089 | −2764 | 25 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 25 | −614 | −1910 | −3809 | −3203 | −1875 | −3470 | −2309 | 1729 | 934 | 1292 | −1109 | −2931 | 560 | −2619 | 1434 | −2530 | −569 | −333 | −2358 | 343 | 26 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 26 | −489 | −3280 | 1589 | 1324 | −3601 | 63 | −1436 | −3352 | −1019 | −3296 | −2370 | 419 | −2869 | 507 | 1104 | 1445 | −264 | −2902 | −3464 | −2780 | 27 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 27 | 1002 | −1934 | −3661 | −3064 | −1902 | −599 | −2272 | 1406 | −2788 | 968 | −1132 | −241 | −479 | 30 | −2818 | −621 | 983 | 935 | −2378 | −2016 | 28 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 28 | −4933 | −4368 | −7319 | −6848 | −2656 | −6944 | −5947 | −1861 | −6662 | 3175 | −1437 | −6857 | −6209 | −5493 | −6178 | −6436 | −4831 | 784 | −4480 | −4641 | 29 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 29 | −539 | −3266 | −110 | −1093 | −3587 | −2767 | 854 | −301 | 1748 | −3281 | −2355 | 1994 | −2860 | 1988 | 1175 | −319 | −1733 | −2888 | −3448 | −2766 | 30 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 30 | 762 | −3254 | 1195 | 39 | −3572 | −2763 | 853 | −3320 | 1157 | −1012 | 1025 | 680 | −2857 | −963 | 1567 | −1670 | 435 | −778 | −3439 | −2758 | 31 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 31 | −5136 | −4492 | −7524 | −6936 | −2514 | −7360 | −5975 | −1937 | −6750 | 3164 | 1158 | −7112 | −6271 | −5412 | −6180 | −6781 | −4965 | 221 | −4381 | −4641 | 32 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 32 | 2513 | 3637 | −5874 | −6184 | −5779 | −230 | −5141 | −5590 | −5804 | −5856 | −4890 | −4225 | −4203 | −5241 | −5417 | 1259 | 899 | −4297 | −6009 | −5985 | 33 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 33 | 1129 | −3393 | −235 | −249 | −3713 | −2839 | −1534 | −3467 | 1126 | −3411 | −2490 | 780 | −2957 | −1079 | −1650 | 2307 | 406 | −3016 | −3579 | −2889 | 34 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 34 | −370 | 807 | 2715 | −1095 | −3565 | −2767 | 447 | −299 | 1120 | −3263 | −2341 | 814 | −2860 | 286 | 672 | −1674 | −1730 | −2869 | −3436 | 1 | 35 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −70 | −9479 | −4434 | −894 | −1115 | −701 | −1378 | * | * | | | | | | | | | | | | |
| 35 | −2032 | 2972 | −4267 | −3662 | 1367 | −578 | −2421 | −1429 | −3285 | 98 | −1134 | −3172 | 2786 | −2925 | −3126 | 354 | −1991 | −1344 | −2297 | 811 | 36 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −392 | −2072 | * | * | | | | | | | | | | | | |
| 36 | −1838 | −3311 | 22 | −1122 | −3633 | 126 | 801 | −3383 | 1438 | −3325 | −2401 | 1596 | 1730 | −1003 | 1691 | 128 | −1777 | −2934 | −3491 | −2809 | 37 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −535 | −9479 | −1696 | −894 | −1115 | −701 | −1378 | * | * | | | | | | | | | | | | |
| 37 | −2066 | −2660 | −3310 | −3399 | −4245 | 1448 | −3490 | 1167 | −3669 | −4147 | −3393 | 3425 | −3611 | −3386 | −3831 | −2291 | 983 | −3131 | −4557 | −4209 | 38 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −8948 | −9990 | −894 | −1115 | −1938 | −436 | * | * | | | | | | | | | | | | |
| 38 | 1426 | −1707 | −4035 | −3427 | −1713 | −3437 | −2334 | 1054 | −3077 | −404 | −922 | −3020 | −3482 | 1170 | −2961 | −2524 | 1971 | 1574 | −2256 | −1906 | 39 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −9057 | −10099 | −894 | −1115 | −131 | −3528 | * | * | | | | | | | | | | | | |
| 39 | −3081 | −2755 | −5552 | −5018 | −2886 | −4955 | −4031 | 1713 | −4717 | 992 | −1899 | −4603 | −4897 | −4389 | −4591 | −4112 | 834 | 2595 | −3775 | 1403 | 40 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 40 | 2198 | −2170 | −4649 | −4056 | 1257 | −3889 | −2504 | 19 | −3653 | −1968 | −1367 | −3481 | −3929 | −3239 | −3440 | −2981 | −2306 | 1399 | 3509 | 1495 | 41 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 41 | −4388 | −3868 | −6886 | −6379 | 469 | −6590 | −5608 | 3047 | −6194 | 1327 | 1101 | −6273 | −5987 | −5345 | −5894 | −5897 | −4300 | 1362 | −4469 | −4516 | 42 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 42 | −2288 | −2084 | −4649 | −4032 | 491 | −3892 | −2796 | 2255 | −3647 | 923 | −1279 | −86 | −3926 | −3280 | −3462 | 360 | −2232 | 2081 | −2646 | −2300 | 43 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 43 | −2584 | −3193 | −5527 | −5874 | −5845 | −3460 | −5130 | −5709 | −5730 | −5962 | −5009 | −4233 | −4270 | −5211 | −5408 | 3441 | 1609 | −4402 | −6040 | −5997 | 44 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 44 | −180 | −3316 | −5562 | −5906 | 1164 | 3558 | −4947 | −5613 | −5826 | −5782 | −4975 | −4334 | −4390 | −5269 | −5497 | −2987 | −3205 | −4462 | −5347 | −4758 | 45 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 45 | −3270 | −4151 | −3646 | −2760 | −4767 | −4059 | −2336 | −4271 | −13 | −735 | −3393 | −2819 | −156 | −1923 | 3666 | 78 | −261 | −3977 | −4171 | −3878 | 46 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 46 | −2120 | 871 | 2061 | −149 | −3940 | 851 | −1730 | −3701 | 721 | −3644 | −2735 | −1604 | 26 | −1285 | −1900 | 2085 | −2074 | −3244 | −3815 | −3110 | 47 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 47 | −1954 | 1551 | −3165 | −2586 | −2045 | −3330 | −2124 | 428 | 147 | 857 | 1041 | −13 | −236 | 1811 | 1581 | −2352 | −1894 | 758 | −2485 | −2099 | 48 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 48 | 1056 | −3257 | 967 | 1246 | −3576 | −2763 | −1422 | −484 | 675 | −3272 | −2346 | −1399 | −2856 | 1226 | 773 | −477 | −128 | 600 | −3441 | −2760 | 49 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 49 | −567 | −3115 | 1297 | 1252 | 2020 | −2800 | −1466 | −3081 | 902 | −1014 | −2221 | −1463 | −536 | −1029 | −1570 | −29 | −337 | −731 | −3337 | 1118 | 50 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2001 | −9479 | −417 | −894 | −1115 | −701 | −1378 | * | * | | | | | | | | | | | | |
| 50 | −3442 | −2950 | −4783 | −4700 | −1462 | −4258 | −3722 | −1007 | −4386 | 3221 | −434 | −4546 | −4247 | −3835 | −4064 | −4342 | −3434 | −1668 | −2849 | −2749 | 51 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −378 | −7490 | −2151 | −894 | −1115 | −4179 | −82 | * | * | | | | | | | | | | | | |
| 51 | −527 | −1805 | 1364 | 180 | −2056 | −1450 | −166 | 831 | 220 | −1791 | −932 | 1573 | −1581 | 256 | 1388 | −438 | −472 | −1386 | −2033 | −1397 | 52 |
| — | −149 | −500 | 232 | 42 | −378 | 398 | 105 | −624 | 210 | −465 | −714 | 275 | 393 | 45 | 95 | 359 | 120 | −368 | −295 | −250 | |
| — | −2291 | −2385 | −727 | −2605 | −259 | −1967 | −426 | * | * | | | | | | | | | | | | |
| 52 | −2207 | −1984 | −3847 | −3267 | −757 | −3786 | −2505 | −273 | −2747 | 2477 | 2763 | −3174 | −3530 | 1478 | −2686 | −2931 | −2110 | −832 | −2099 | −1986 | 60 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −12 | −7521 | −8563 | −894 | −1115 | −151 | −3331 | * | * | | | | | | | | | | | | |
| 53 | 829 | −2899 | −1757 | 1770 | −3100 | −2791 | −1469 | −2771 | 7 | 274 | −2024 | 81 | −2882 | −1062 | −1593 | 496 | −279 | 1428 | −3162 | −2562 | 61 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −366 | −2156 | * | * | | | | | | | | | | | | |
| 54 | −1789 | 1327 | 1732 | 884 | −3557 | −2766 | −1425 | −1033 | −66 | −854 | −2335 | 759 | −2859 | 667 | 517 | −319 | −539 | −2862 | 2880 | 906 | 62 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 55 | 262 | −3252 | 124 | 446 | −3568 | −2764 | −1423 | −3316 | 447 | 723 | 1463 | 699 | −2857 | 897 | 218 | −532 | −1728 | −2871 | 3480 | −2757 | 63 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 56 | −1945 | −2086 | −478 | −2489 | 2296 | 50 | −2090 | −1633 | −111 | 956 | 1935 | −224 | −3368 | −2120 | 734 | −2317 | −1885 | −289 | −2509 | 1349 | 64 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −121 | −9479 | −3667 | −894 | −1115 | −701 | −1378 | * | * | | | | | | | | | | | | |
| 57 | 235 | −2306 | −379 | −1749 | 2207 | 234 | −1733 | −540 | −1619 | −2201 | −1477 | 167 | −3079 | 620 | −1987 | 674 | −1739 | 1701 | −2682 | −2221 | 65 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9362 | −10404 | −894 | −1115 | −299 | −2419 | * | * | | | | | | | | | | | | |
| 58 | −1790 | −3263 | 626 | −1088 | 116 | 1473 | 782 | −3334 | 1642 | −3279 | −2352 | −27 | 168 | 252 | 907 | 610 | −1729 | −2885 | −3446 | −2763 | 66 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 59 | −2621 | 2828 | −5004 | 122 | −2468 | −4323 | −3293 | 1249 | −4070 | 624 | −1600 | −3963 | 1719 | −3731 | −3917 | −3439 | −2572 | 2192 | −3130 | −2775 | 67 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 60 | −485 | −3253 | 474 | 307 | 667 | −2764 | −1423 | −3319 | 760 | −1055 | −2343 | −28 | 2187 | 474 | −1511 | 227 | −345 | −2873 | −3439 | 1140 | 68 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 61 | −509 | −3380 | 992 | 1803 | −3698 | 1203 | −1517 | −3452 | 271 | −3394 | −2473 | 2132 | −2943 | 329 | 69 | −1770 | −1839 | −3001 | −3562 | −2872 | 69 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 62 | −491 | −4065 | −6924 | −6315 | 1663 | −6493 | −5217 | 2044 | −6045 | 2449 | 934 | −6184 | −5846 | −5040 | −5621 | −5737 | −4421 | −2570 | −4104 | −4203 | 70 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 63 | −2402 | −2560 | −3201 | −212 | −2107 | 2518 | −2397 | −2191 | −2793 | −2476 | −1829 | −2834 | 1250 | −2600 | −2976 | −2735 | −2380 | −58 | 3581 | 1659 | 71 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 64 | −3197 | −2894 | −5609 | −5031 | −2512 | −4964 | −3901 | 1804 | −4696 | 2219 | −1511 | −4614 | −4857 | −4235 | −4498 | −4104 | −389 | 167 | −3522 | 2642 | 72 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 65 | 2395 | −2078 | −4516 | −3948 | 420 | −881 | −2759 | 770 | −3572 | −2046 | −1409 | −3381 | −3760 | −3208 | −3403 | 1514 | −2159 | 859 | −2682 | −2341 | 73 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 66 | 2816 | −3122 | −5655 | −6008 | −5846 | 2494 | −5141 | −5675 | −5804 | −5934 | −4959 | −4205 | −4213 | −5228 | −5436 | −403 | −2991 | −4341 | −6062 | −6042 | 74 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 67 | −2493 | −3573 | −1890 | 3040 | −3911 | −3256 | −2254 | −3547 | −2041 | −224 | −2905 | 367 | −3530 | −1892 | −2543 | 1389 | −2501 | −429 | −4023 | −3401 | 75 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 68 | −4985 | −5441 | −3662 | −4015 | −4757 | −4920 | 5051 | −6871 | −4741 | −6507 | −6149 | 2326 | −5470 | −4577 | −4987 | −4920 | −5209 | −6329 | −5040 | −4257 | 76 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 69 | −6706 | −5971 | −6982 | −7366 | −7600 | 3860 | −6711 | −8550 | −7592 | −8009 | −7846 | −7163 | −6477 | −7420 | −7070 | −7077 | −7029 | −7946 | −6398 | −7600 | 77 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 70 | 1704 | 2777 | −4347 | −3714 | 1142 | −3563 | −2428 | −1341 | −3313 | −339 | 2784 | −3204 | −3615 | −2938 | −3119 | 165 | −1962 | −1264 | −2293 | 1905 | 78 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 71 | −525 | 1488 | 951 | 2016 | 3054 | −3439 | −2160 | −2717 | −2244 | −2921 | −2233 | −2295 | −3607 | −2069 | −2651 | −2542 | −2406 | −2542 | −2906 | 1426 | 79 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 72 | −2003 | −1832 | −4325 | −3690 | −1786 | −3548 | 1093 | 2240 | −3290 | 642 | 908 | −3186 | −3598 | −2918 | 625 | −1029 | 285 | 1476 | −2290 | 731 | 80 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 73 | −1937 | −2900 | −2049 | −316 | −3064 | −2995 | −1652 | −138 | 518 | −2837 | 524 | −1735 | −3077 | −1280 | 3302 | −386 | 98 | −654 | −3177 | −2632 | 81 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 74 | 338 | −2583 | 1101 | −1593 | −2674 | −72 | 715 | 752 | −186 | −179 | 688 | 15 | 509 | −1401 | −1898 | 335 | −1800 | −340 | 2663 | −2418 | 82 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 75 | −494 | −3027 | 96 | −1276 | −3252 | −2863 | −1556 | −355 | −231 | −3009 | −2161 | 2218 | 2777 | −1144 | −1681 | −1796 | 402 | −638 | −3294 | −2684 | 83 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 76 | 105 | −3261 | 1502 | −133 | −3582 | 1254 | 782 | −3333 | −139 | −1079 | −2350 | 873 | 25 | 309 | −95 | 537 | −365 | −2883 | −3444 | −2761 | 84 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 77 | −422 | 960 | −1757 | −1213 | −3528 | 2143 | −1524 | −3252 | 1212 | −3247 | −2347 | 1332 | −2930 | 237 | −1616 | 991 | −1788 | −536 | −3453 | −2799 | 85 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −209 | −9479 | −2906 | −894 | −1115 | −701 | −1378 | * | * | | | | | | | | | | | | |
| 78 | −1632 | −3104 | 587 | 1330 | −3425 | 916 | −1265 | −3175 | 314 | −3120 | −2193 | −1242 | −2699 | 506 | 118 | 664 | 1219 | −2726 | 1901 | 699 | 86 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9273 | −10315 | −894 | −1115 | −1248 | −788 | * | * | | | | | | | | | | | | |
| 79 | −1683 | −3153 | 1540 | −122 | −3472 | −2657 | 1963 | −3222 | 351 | −3168 | 746 | 826 | −428 | 742 | −1404 | 744 | 656 | −566 | 2354 | −2655 | 87 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9341 | −10383 | −894 | −1115 | −272 | −2539 | * | * | | | | | | | | | | | | |
| 80 | −216 | −3157 | −1726 | 128 | −3427 | −2815 | 2750 | −3139 | −72 | −1297 | 1434 | −1473 | −2906 | 371 | 214 | −552 | −1759 | −2752 | 4599 | −2724 | 88 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 81 | −1803 | −3088 | −1730 | 1066 | 178 | −431 | −1475 | 371 | 19 | −3072 | −2197 | 650 | −2899 | 1613 | −1582 | −350 | 1400 | −670 | −3317 | 1699 | 89 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −246 | −9479 | −2688 | −894 | −1115 | −701 | −1378 | * | * | | | | | | | | | | | | |
| 82 | −1736 | −2472 | −2078 | −1541 | −2667 | −222 | 834 | −2280 | −1432 | −2490 | 1331 | 2706 | −2974 | −1354 | −1849 | 640 | 1890 | −125 | −2907 | −2401 | 90 |
| — | −150 | −501 | 231 | 43 | −382 | 397 | 108 | −628 | 211 | −467 | −722 | 274 | 395 | 44 | 96 | 362 | 117 | −364 | −296 | −247 | |
| — | −4401 | −3189 | −246 | −2488 | −283 | −967 | −1034 | * | * | | | | | | | | | | | | |
| 83 | −993 | −2427 | −97 | 2130 | −2791 | 888 | −461 | −2526 | 1919 | −2451 | −1605 | −271 | −1868 | −45 | −436 | −832 | −952 | −2095 | −2595 | −1931 | 100 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7191 | −8233 | −894 | −1115 | −4259 | −77 | * | * | | | | | | | | | | | | |
| 84 | −1448 | −2899 | 32 | 2032 | −3208 | −1763 | −792 | −3020 | −456 | −2921 | −2171 | −413 | −2133 | 3341 | −875 | −1232 | −1440 | −2599 | −3029 | −2332 | 101 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7191 | −8233 | −894 | −1115 | −4259 | −77 | * | * | | | | | | | | | | | | |
| 85 | −600 | −1497 | 1370 | −163 | −1837 | 806 | −504 | 1596 | −297 | −1645 | −866 | −405 | −1755 | −168 | −764 | 982 | −613 | −1155 | −2020 | −1460 | 102 |
| — | −147 | −500 | 233 | 43 | −381 | 398 | 105 | −627 | 211 | −466 | −721 | 277 | 393 | 45 | 96 | 360 | 117 | −370 | −295 | −250 | |
| — | −2355 | −320 | −8233 | −56 | −4723 | −4259 | −77 | * | * | | | | | | | | | | | | |
| 86 | −1225 | −2874 | 1754 | 2546 | −3136 | −1592 | −653 | −2949 | 1423 | −2860 | −2042 | −197 | −1957 | −262 | −1128 | −994 | −1221 | −2476 | −3034 | −2219 | 104 |
| — | −149 | −500 | 233 | 43 | −381 | 398 | 105 | −627 | 210 | −464 | −721 | 275 | 393 | 45 | 97 | 360 | 117 | −368 | −295 | −250 | |
| — | −2355 | −320 | −8233 | −56 | −4723 | −4259 | −77 | * | * | | | | | | | | | | | | |
| 87 | −612 | −574 | −2213 | −1638 | −343 | −2050 | −820 | 22 | −1330 | 858 | 280 | 1251 | −2109 | −1106 | −1372 | −1113 | −556 | 1296 | 3597 | −406 | 106 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7191 | −8233 | −894 | −1115 | −4259 | −77 | * | * | | | | | | | | | | | | |
| 88 | −1657 | −1964 | −2208 | −1585 | −1553 | −2586 | −1091 | −1035 | 2087 | 2229 | −594 | −1589 | −2650 | −823 | −265 | −1857 | −1558 | −1189 | −2072 | −1733 | 107 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7191 | −8233 | −894 | −1115 | −4259 | −77 | * | * | | | | | | | | | | | | |
| 89 | −870 | 2936 | −2298 | −1911 | 2741 | −2033 | −923 | −771 | −1688 | −1040 | −478 | 2169 | −2313 | −1445 | −1766 | −1211 | −945 | −643 | −830 | 11 | 108 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −15 | −7191 | −8233 | −894 | −1115 | −763 | −1283 | * | * | | | | | | | | | | | | |
| 90 | −162 | 2293 | 597 | −874 | −2663 | −2438 | −1117 | −2323 | 657 | 595 | 1887 | −1150 | −2527 | 1764 | −1248 | 919 | −1334 | −2026 | −2752 | −2165 | 109 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −8904 | −9946 | −894 | −1115 | −3148 | −173 | * | * | | | | | | | | | | | | |
| 91 | 1804 | −2250 | −1696 | 79 | −2413 | −577 | −1298 | −2033 | −1045 | −2226 | −1451 | −1378 | 2063 | −972 | −1478 | −149 | 173 | 288 | −2626 | 378 | 110 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −8904 | −9946 | −894 | −1115 | −1077 | −927 | * | * | | | | | | | | | | | | |
| 92 | 1547 | −2050 | −2951 | 2259 | −2095 | −3201 | −2131 | 957 | −2338 | 976 | −1273 | −2457 | −3330 | −2156 | −2539 | −642 | −1868 | −1398 | −2559 | −2170 | 111 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −9187 | −10229 | −894 | −1115 | −547 | −1663 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 93 | 73 | −3160 | −1596 | −234 | −3462 | −299 | 2265 | −3200 | 73 | −1157 | −2254 | 248 | 303 | −919 | −129 | 98 | 915 | 1540 | −3354 | −2683 | 112 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −366 | −2156 | * | * | | | | | | | | | | | | |
| 94 | 1046 | −2932 | 507 | 1805 | −3122 | −2903 | −1609 | −2777 | −1282 | 914 | −2078 | −1629 | −3006 | −1220 | −1755 | −562 | 1460 | −602 | −3225 | −2642 | 113 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 95 | 473 | −3347 | 2325 | 1146 | 1656 | −836 | −1496 | −3415 | −1092 | −3361 | −2440 | 745 | −172 | 461 | −1605 | −1748 | −562 | −2967 | −3531 | −2844 | 114 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 96 | −2011 | −1839 | −343 | −3711 | 41 | −3558 | −2429 | 816 | −3309 | 1653 | 2862 | −3201 | −47 | −2933 | −3112 | −2642 | 932 | −1 | −2296 | 731 | 115 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −81 | −9479 | −4226 | −894 | −1115 | −701 | −1378 | * | * | | | | | | | | | | | | |
| 97 | 767 | −3223 | 1528 | 1165 | −3543 | −701 | −1425 | −192 | −1020 | −3247 | −2331 | −1390 | 1516 | −972 | −1527 | 1076 | 136 | −2848 | −3428 | −2750 | 116 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −366 | −2156 | * | * | | | | | | | | | | | | |
| 98 | −1906 | −2341 | −310 | −343 | −2377 | −873 | −1873 | 405 | −1805 | −2229 | 1993 | −2088 | −13 | 445 | −2151 | −2109 | −1846 | −645 | 5065 | −2279 | 117 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 99 | −381 | −1883 | −3990 | −3376 | 971 | −3503 | −2354 | 940 | 1785 | 960 | 2010 | −3028 | −3556 | 817 | 443 | −2571 | −1937 | −179 | −2334 | −1983 | 118 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 100 | −585 | −3261 | 1737 | 1152 | −3582 | −2762 | −1421 | −268 | 2028 | −3277 | −2350 | 211 | −2856 | 1008 | 86 | −620 | −1728 | −726 | −3444 | −2762 | 119 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 101 | −485 | −3245 | 745 | 1523 | −3559 | −2765 | −1425 | 95 | 1085 | −886 | 296 | −1403 | −2858 | 691 | 648 | 166 | 729 | −973 | −3433 | −2754 | 120 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 102 | 1441 | −2809 | −5616 | −5106 | −3104 | −5078 | −4240 | 395 | −225 | −14 | −2086 | −4722 | −5025 | −4552 | −4729 | −4252 | −3116 | 3041 | −4020 | −3638 | 121 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 103 | 1132 | 1372 | −1696 | 739 | −3417 | −2792 | −1456 | −3133 | 1332 | −1299 | 580 | 63 | −2884 | 290 | 678 | 503 | −1737 | −814 | 1751 | 40 | 122 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 104 | 956 | 775 | −39 | 1082 | −3574 | −2763 | 2122 | −3323 | 753 | −1266 | −2345 | −27 | 1168 | −963 | 788 | −1670 | −539 | −520 | −3440 | −2759 | 123 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 105 | −504 | −1933 | −3670 | 45 | 225 | −3443 | −2275 | 2409 | −637 | −385 | −1131 | −2855 | −3501 | 1309 | −2822 | −790 | −1920 | 1649 | −2379 | −2017 | 124 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 106 | −2406 | −2220 | −4637 | −324 | 2536 | −457 | −2648 | −1589 | −3650 | 1920 | 2762 | −3531 | −3960 | −3243 | −3458 | −3028 | −2343 | −1596 | −2405 | 400 | 125 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 107 | −585 | −3258 | 619 | 1394 | −3577 | −2762 | 1005 | −797 | −14 | −858 | −2347 | −29 | −2856 | 1958 | 1432 | −1669 | −216 | 78 | −3442 | −2760 | 126 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 108 | −485 | −3225 | 956 | 1732 | 121 | −2771 | 1553 | −3269 | −1018 | −582 | −2318 | −1412 | −2864 | 84 | 215 | −624 | −91 | −2838 | −3418 | 2421 | 127 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 109 | 127 | −3164 | 141 | −54 | 2010 | −2790 | −1454 | −3162 | 1381 | −3161 | −2265 | −1443 | −2883 | 681 | −1553 | −543 | −1739 | −493 | −3374 | 2766 | 128 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 110 | 396 | 1084 | −4359 | −3726 | −1816 | −3582 | −2455 | 126 | −224 | 690 | 1497 | −3222 | −3631 | −2955 | −3135 | −2667 | 2489 | 1108 | −2325 | −1982 | 129 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 111 | 800 | −3269 | −166 | 2674 | −3587 | −328 | −1433 | −265 | 915 | −3284 | −2359 | −1408 | −2867 | −975 | −149 | −1682 | −263 | −2890 | −3453 | −2772 | 130 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 112 | −42 | −3260 | 701 | −119 | −3580 | −2763 | 853 | −3330 | −1002 | −3276 | −2350 | −1399 | 55 | 509 | 2789 | 196 | 280 | −2882 | 1184 | −2762 | 131 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 113 | −2091 | −1918 | −4383 | −340 | −178 | −3629 | −2444 | 1241 | −3362 | 160 | −1105 | −3251 | −3676 | −2984 | −3173 | −2713 | 2957 | −1328 | 1575 | 1376 | 132 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 114 | 109 | −3729 | 1285 | 158 | −4036 | −3015 | −1797 | −3802 | −220 | −3740 | −2836 | −1640 | 3156 | 1003 | −1991 | −2066 | 48 | −3346 | −3910 | −3195 | 133 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 115 | −3516 | −4183 | −3603 | −3801 | −6130 | 3582 | −4039 | −6038 | −3385 | −5951 | −5222 | 326 | −4689 | −3784 | 615 | −3629 | −3840 | −5130 | −5730 | −5552 | 134 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 116 | 1547 | −3079 | −5782 | −6029 | −5507 | −3403 | −5033 | −4985 | −5679 | −5494 | −4625 | −4203 | −4203 | −5147 | −5329 | 2749 | −592 | 1813 | −5803 | −5718 | 135 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 117 | −1943 | −2092 | −3044 | 554 | 1704 | −3296 | 682 | 123 | −537 | −29 | 1388 | −427 | −3363 | −57 | −2487 | −9 | −347 | 218 | −2514 | 2352 | 136 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 118 | −3487 | −3118 | −5928 | −5415 | 1144 | −5388 | −4257 | 2699 | −5129 | 325 | −1791 | −5008 | −5230 | −4671 | −4957 | −4567 | −3435 | 2186 | −3767 | 1432 | 137 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 119 | −4735 | −5859 | −2610 | 3771 | −6551 | −4479 | −3727 | −6512 | 691 | −6208 | −5677 | −3253 | −4970 | −3428 | −3564 | −4433 | −4760 | −6070 | −5892 | −5530 | 138 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 120 | 132 | −3241 | 1504 | 944 | −554 | −2769 | 1858 | 415 | −1014 | −3252 | −2332 | 1352 | −2862 | −973 | 1214 | −1677 | 854 | −2857 | −3430 | −2753 | 139 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 121 | −690 | −4863 | −4765 | −3505 | −5836 | −4677 | −2596 | −5105 | 3490 | −4724 | −4065 | 1698 | −4641 | −2176 | 858 | −4077 | −3886 | −4868 | −4544 | −4473 | 140 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 122 | −2914 | −4463 | 1405 | 1760 | −4789 | 1324 | −2316 | −4550 | 2176 | −4439 | −3602 | −2037 | −3710 | −1905 | 1324 | −2715 | −2877 | −4098 | −4570 | −3859 | 141 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 123 | 826 | 1125 | −4318 | −3684 | 2126 | −3546 | 878 | 240 | −3285 | −1682 | 1104 | −3183 | −3597 | −2914 | −3096 | 1219 | 1395 | 503 | −2291 | −1948 | 142 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 124 | 2482 | 3224 | −5595 | −5649 | −4986 | 733 | −4708 | −4669 | −5307 | −4973 | 1934 | −4098 | −4153 | −4843 | −5052 | 824 | 117 | −3855 | −5321 | −5146 | 143 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | |
|---|---|---|---|---|---|---|---|---|---|---|---|---|---|---|---|---|---|---|---|---|
| 125 | −3388 | −3089 | −5760 | −5149 | 324 | −5094 | −3945 | 1605 | −4798 | 1681 | 1706 | −4749 | −4922 | −4224 | −4542 | −4227 | −3310 | 2005 | −3457 | 1647 | 144 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 126 | 1703 | −2174 | −2959 | −2388 | −2193 | −3277 | −2079 | 710 | −241 | −2061 | −1377 | −2419 | −3359 | −2048 | −140 | 1338 | 954 | 1310 | −2607 | −2204 | 145 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 127 | 173 | −2299 | −4874 | −4256 | 1719 | −4121 | −2993 | 285 | −3870 | 360 | −1246 | −3766 | −4122 | −3461 | −3667 | −3221 | −2453 | 1613 | 4694 | −2440 | 146 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 128 | −3534 | 1422 | −4289 | −4564 | −4269 | −4171 | 5154 | −5976 | −4550 | −5888 | −5292 | 1328 | −4853 | −4581 | −4578 | −3708 | −3928 | −5096 | −4698 | −3849 | 147 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 129 | −5701 | −4824 | −6403 | −6629 | 1772 | −6218 | 2142 | −4685 | −6188 | −647 | −4146 | −4932 | −6098 | −5035 | −5622 | −5443 | 643 | −4795 | −1841 | 4209 | 148 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 130 | −4364 | −4966 | −5068 | 522 | −5928 | −4791 | −2597 | −5149 | 718 | −4743 | −4098 | −3448 | −4708 | 2137 | 3535 | −4221 | −3986 | −4946 | −4545 | −4504 | 149 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 131 | −1793 | −3260 | 307 | 665 | −368 | −2767 | −1426 | −3327 | 9 | −337 | −2350 | 2539 | −2860 | 1301 | 1379 | −1675 | −1732 | −2881 | −3444 | 980 | 150 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 132 | 3070 | 1688 | −5853 | −6024 | −5047 | −3510 | −4990 | −3529 | −5652 | −4737 | −4110 | −4276 | −4277 | −5145 | −5314 | −2865 | −329 | 1794 | −5544 | −5378 | 151 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 133 | 328 | −3406 | 2678 | 1115 | −3727 | −2855 | −1560 | −3479 | −1167 | −3428 | −2510 | 191 | 1160 | −1107 | −1683 | −206 | 32 | −724 | −3600 | −2911 | 152 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 134 | −1796 | −3256 | 2139 | 1191 | −3570 | −2770 | 667 | −712 | −1014 | −3269 | −2346 | −1407 | 2129 | 507 | 276 | −1679 | −147 | −776 | −3442 | −2763 | 153 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 135 | −1788 | −3261 | 1985 | 1502 | −3582 | −2762 | 1005 | −3333 | 504 | −890 | −2350 | −7 | −17 | 1180 | −38 | −532 | −146 | −2883 | −3444 | 203 | 154 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −846 | −9479 | −1177 | −894 | −1115 | −701 | −1378 | * | * | | | | | | | | | | | | |
| 136 | −1901 | −1780 | 1351 | −3078 | 2990 | −3321 | −1715 | 792 | −2791 | −76 | −972 | 477 | −3363 | −2441 | −2741 | −2397 | −1839 | −1218 | −1457 | 2135 | 155 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8638 | −9680 | −894 | −1115 | −3505 | −133 | * | * | | | | | | | | | | | | |
| 137 | −1976 | −2618 | −3596 | −3612 | −4922 | 3271 | −3366 | −4711 | −2789 | −4799 | −3943 | −3007 | −3494 | −3154 | 1664 | 357 | −2377 | −3654 | −4820 | −4652 | 156 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8638 | −9680 | −894 | −1115 | −1728 | −519 | * | * | | | | | | | | | | | | |
| 138 | 553 | −2817 | −1296 | 1634 | −3122 | −2399 | −1055 | −2847 | 534 | −2823 | −1920 | −1049 | −2493 | −606 | 1012 | 1246 | −1361 | 1334 | −3014 | −2358 | 157 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −8898 | −9940 | −894 | −1115 | −3158 | −171 | * | * | | | | | | | | | | | | |
| 139 | 907 | 2815 | −3807 | −3177 | 2302 | −3079 | −1946 | −871 | 209 | 630 | −580 | −2699 | 224 | −2427 | −2617 | −2160 | −1481 | 305 | 1801 | −1490 | 158 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −8898 | −9940 | −894 | −1115 | −299 | −2419 | * | * | | | | | | | | | | | | |
| 140 | −161 | −3220 | −1590 | 19 | −3541 | −2720 | 853 | −3291 | −957 | −3235 | −2310 | 730 | −2815 | 3181 | 856 | 884 | −76 | −2842 | −3403 | −2721 | 159 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9409 | −10451 | −894 | −1115 | −385 | −2093 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 141 | 2117 | −2168 | −2851 | −300 | −2173 | −3243 | −2012 | −1735 | −323 | −730 | 1212 | −2337 | −3313 | −1960 | 63 | −489 | −1872 | 1394 | 2821 | −2170 | 160 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 142 | −1790 | −3230 | 629 | −38 | −3537 | −1086 | −1429 | 416 | 1793 | −323 | −2323 | −207 | −532 | −974 | 1514 | −516 | −365 | −663 | 1831 | −2747 | 161 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 143 | 1197 | −3500 | 1016 | 2308 | −3810 | 273 | −1627 | −3565 | −1249 | 151 | −2600 | 2 | −3041 | −1178 | 190 | −1885 | −1963 | −3118 | −3686 | −2989 | 162 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 144 | 396 | 2649 | −388 | 289 | −1828 | −3575 | −2444 | 246 | −3275 | 1909 | 1540 | −3190 | −3624 | −2916 | −3109 | −2657 | −1973 | 680 | −2336 | −1992 | 163 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 145 | 1549 | −2881 | −174 | −178 | 180 | −2874 | −1555 | −608 | 756 | 1034 | 1599 | −1593 | −2962 | 1087 | −149 | −1799 | −1763 | −2423 | −3159 | −2579 | 164 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 146 | 443 | −3256 | 807 | 1661 | −3575 | −2763 | −1422 | 412 | 776 | −1160 | −2346 | −7 | −2856 | 1401 | −38 | −1669 | 624 | −1071 | −3441 | −2759 | 165 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 147 | 345 | 2182 | −2627 | −2062 | −2287 | −3171 | 2964 | −1859 | −318 | 510 | 1680 | 984 | −3245 | 841 | −2227 | −2155 | 636 | −437 | −2661 | −2229 | 166 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 148 | −389 | 1592 | −4258 | −673 | −1861 | −3578 | 2353 | −1348 | −3264 | 2192 | −1100 | −3191 | −3637 | −2919 | −3113 | −2663 | −1995 | 1573 | −2371 | −2026 | 167 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 149 | −1796 | −3219 | −267 | 2104 | −3520 | −2777 | 852 | 419 | −71 | −1200 | 952 | −1420 | −2870 | 1299 | 1205 | −1686 | −1735 | −2830 | 2875 | −2744 | 168 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 150 | −488 | −3277 | 577 | 1063 | −3596 | −2773 | −1436 | −3347 | −1019 | −3292 | −2367 | 955 | −2869 | −977 | 1267 | 1683 | 1331 | −2898 | −3461 | 206 | 169 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −61 | −9479 | −4634 | −894 | −1115 | −701 | −1378 | * | * | | | | | | | | | | | | |
| 151 | 462 | −1793 | −4292 | −3658 | −1749 | 44 | 750 | 950 | −3258 | 482 | 1088 | −3152 | −3562 | −2885 | −3065 | −2597 | 700 | 2330 | −2254 | −1912 | 170 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9420 | −10463 | −894 | −1115 | −416 | −1998 | * | * | | | | | | | | | | | | |
| 152 | −2001 | 1510 | −4292 | −3 | 127 | −189 | −2411 | −141 | −3266 | 1385 | 809 | 181 | 1175 | −2900 | −3086 | −2625 | −87 | 990 | −2292 | 414 | 171 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 153 | −714 | 928 | −1726 | 148 | 876 | −2806 | 711 | 698 | 1149 | −1109 | −2203 | 402 | −2897 | 1327 | 577 | −467 | 850 | −916 | −3322 | −2684 | 172 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 154 | 602 | −3239 | 2013 | −1098 | 200 | −2768 | 938 | −432 | 6 | −3250 | −2331 | 1418 | −2860 | −971 | 275 | 1084 | −365 | −2855 | −3428 | −2752 | 173 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 155 | −586 | −3262 | 1067 | 739 | −3582 | 119 | 1554 | −3332 | 775 | −3278 | −2352 | 1639 | −2859 | −965 | −1513 | −1672 | −275 | −2884 | 1594 | 2346 | 174 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −695 | −9479 | −1392 | −894 | −1115 | −701 | −1378 | * | * | | | | | | | | | | | | |
| 156 | 647 | −1395 | −3406 | −2800 | 669 | −2986 | −1795 | −900 | −2475 | −1244 | −596 | −2477 | 2574 | −2178 | 1220 | −2052 | −1436 | 686 | 2025 | 901 | 175 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8788 | −9830 | −894 | −1115 | −284 | −2485 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 157 | 399 | −3350 | 2084 | −1103 | −3669 | 848 | −1485 | −3424 | 970 | −3367 | −2447 | 182 | 1739 | 551 | −1605 | −448 | −1810 | −2972 | −3535 | −2843 | 176 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −1479 | −641 | * | * | | | | | | | | | | | | |
| 158 | −2877 | 1696 | −5267 | −4665 | −2279 | −4568 | −3482 | 934 | −4305 | 1720 | 1187 | −4219 | −4504 | −3858 | −4100 | −3688 | −2815 | 2365 | 2655 | −2903 | 177 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −1479 | −641 | * | * | | | | | | | | | | | | |
| 159 | 760 | −3196 | 567 | 1356 | −3515 | −2704 | 1875 | −874 | 794 | −3211 | −2286 | −1340 | −2797 | −903 | 1563 | 443 | −1668 | −52 | −3381 | −2700 | 178 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −366 | −2156 | * | * | | | | | | | | | | | | |
| 160 | 898 | −3258 | −6400 | −6040 | −3744 | −6154 | −5901 | 1388 | −5953 | 1065 | −2488 | −5817 | −5915 | −5799 | −6035 | −5483 | −3730 | 2910 | −5328 | −4899 | 179 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 161 | −1796 | −3184 | 143 | −1128 | −3470 | −2783 | −1445 | −3197 | 1333 | −3185 | 2026 | −140 | −2875 | 1591 | −1541 | −341 | 1913 | 58 | −3388 | 1239 | 180 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 162 | −539 | −3166 | −169 | −1136 | −3445 | −2787 | 2292 | −202 | 229 | −1132 | −2266 | −1439 | −252 | 2084 | 1264 | −1697 | 1045 | 299 | −3375 | −2718 | 181 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 163 | −571 | −3918 | −2622 | −2731 | −3648 | 3409 | 1029 | −4572 | −2884 | −4592 | −3927 | −2872 | −4209 | 532 | −3156 | −3148 | −3296 | −4130 | −4058 | 540 | 182 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 164 | −2571 | −3879 | −2518 | −1863 | −4329 | −828 | 554 | −3976 | 2588 | −3835 | −2979 | 1196 | −3508 | 1356 | 2214 | −665 | −2460 | −3579 | −3895 | −3389 | 183 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 165 | 579 | 1177 | 850 | 230 | −3582 | −2762 | 2167 | −3332 | 1515 | −3277 | 2232 | 211 | −2855 | 861 | −125 | −334 | −1727 | −2883 | −3444 | −2761 | 184 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 166 | −2120 | −1936 | −4466 | −3837 | 247 | −3688 | −2570 | 1331 | −3440 | 154 | 1291 | 1185 | −3731 | −3066 | −3247 | 29 | −2062 | 2573 | −2430 | −2087 | 185 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 167 | −4110 | −3586 | −6719 | −6316 | 73 | −6518 | −5973 | 1542 | −6217 | 1353 | −1958 | −6184 | −6057 | −5688 | −6124 | −5871 | −4066 | 3015 | −4949 | −4815 | 186 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 168 | −2997 | −3657 | −2625 | 3614 | 182 | −3673 | −3259 | −3744 | −3558 | −4153 | −3602 | −2945 | −4203 | −3204 | −3974 | −489 | −3207 | −150 | −4181 | −3357 | 187 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 169 | −3812 | 1649 | −6488 | −6153 | −3826 | −6310 | −6206 | 1666 | −6103 | 1027 | −2536 | −5966 | −6031 | −5983 | −6227 | −5673 | −3798 | 3073 | −5538 | −5092 | 188 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 170 | −4473 | −4994 | −5700 | −3778 | −6003 | −4887 | 1029 | −5183 | 2069 | −4760 | −4126 | −3548 | −4770 | 1233 | 3478 | −4337 | −4059 | −4998 | −4547 | −4540 | 189 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 171 | −614 | −3250 | −4284 | −4565 | −5778 | −3431 | −4617 | −5603 | −4857 | −5804 | −4881 | −3828 | 3842 | 1175 | −4862 | 690 | −3052 | −4382 | −5939 | −5749 | 190 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 172 | 189 | −3227 | 760 | −1104 | −3533 | −2770 | −1431 | −759 | −1017 | −3237 | −2320 | 1068 | −17 | 1629 | 1162 | 374 | 475 | 995 | −3420 | −2746 | 191 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 173 | −1990 | −1889 | −3920 | −3309 | 900 | 2098 | −2335 | 1514 | 709 | −364 | −1089 | −2989 | −3542 | −2688 | 544 | −700 | −1931 | −384 | −2339 | 490 | 192 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 174 | 139 | −2235 | 645 | −2122 | −2252 | −3191 | 1143 | −265 | 956 | 489 | −1416 | −2223 | −3264 | −1837 | −2268 | −547 | −88 | 2191 | −2636 | −2211 | 193 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 175 | −415 | −2816 | −3196 | −2757 | −3153 | −3302 | −2669 | −3023 | −2646 | −3262 | −2529 | 2293 | −3661 | −2521 | −2965 | 2288 | −359 | −2731 | 3854 | 718 | 194 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −1761 | −9479 | −507 | −894 | −1115 | −701 | −1378 | * | * | | | | | | | | | | | | |
| 176 | −2392 | −4185 | 3598 | −443 | −4470 | −2197 | −1676 | −4544 | −2069 | −4397 | −3823 | 2029 | −2784 | −1379 | −3009 | −2044 | −2512 | −3969 | −4482 | −3460 | 195 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −10 | −7728 | −8770 | −894 | −1115 | −362 | −2172 | * | * | | | | | | | | | | | | |
| 177 | −6468 | −5794 | −6279 | −6066 | −7061 | −5716 | −5298 | −7572 | 4053 | −7055 | −6716 | −5990 | −6075 | −5251 | −4350 | −6634 | −6440 | −7266 | −5880 | −6603 | 196 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −9255 | −10297 | −894 | −1115 | −673 | −1424 | * | * | | | | | | | | | | | | |
| 178 | −3792 | −4239 | −5211 | −4992 | −5479 | 3549 | −4320 | −5529 | −3435 | 76 | −4851 | −4502 | −4984 | −4149 | 309 | −3994 | −4098 | −5024 | −5353 | −5222 | 197 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −1479 | −641 | * | * | | | | | | | | | | | | |
| 179 | 252 | −3189 | 676 | 676 | 950 | −706 | −1367 | −3249 | 1698 | 535 | −2280 | −1345 | −2801 | 310 | −1457 | 813 | −1671 | −2807 | −3376 | −2698 | 198 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9401 | −10443 | −894 | −1115 | −366 | −2156 | * | * | | | | | | | | | | | | |
| 180 | 2697 | 1569 | −5768 | −5354 | −3407 | −4841 | −4534 | 1989 | −5093 | −2673 | −2364 | −4791 | −5009 | −4818 | −5002 | −4087 | 31 | 992 | −4353 | −3963 | 199 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 181 | 1917 | −2949 | −5877 | −5407 | −3308 | −5379 | −4662 | 1338 | −5174 | 1131 | −2224 | −5043 | −5289 | −4920 | −5117 | −4587 | −747 | 2210 | −4370 | −3978 | 200 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 182 | 262 | −3261 | 970 | 1972 | −3582 | −995 | 448 | −3333 | 607 | −1554 | 946 | −27 | −2855 | 475 | 875 | −1668 | 380 | −2883 | −3444 | −2761 | 201 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 183 | 262 | −3264 | 185 | 154 | 1942 | −2775 | 668 | −3330 | 1017 | −3278 | −2354 | −1412 | −2868 | 335 | 2173 | −1683 | −1740 | −2885 | 2567 | −2769 | 202 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 184 | −3564 | −3209 | −5994 | −5429 | 1624 | −5419 | −4374 | 2530 | −254 | 1907 | −1515 | −5075 | −5209 | −4580 | −4903 | −4588 | −3497 | 676 | −3836 | −3647 | 203 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 185 | −2333 | −2140 | −4680 | −4047 | 1061 | −927 | −2765 | 1366 | −3649 | 2180 | 1938 | −3548 | −3916 | −3238 | −3439 | −2992 | −2270 | 479 | −2570 | 769 | 204 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 186 | −622 | −3261 | 212 | 1633 | −3582 | 554 | −1421 | −3333 | 1094 | −3277 | −2350 | −1397 | −2855 | 1571 | 590 | 738 | −336 | −2883 | 1343 | −2762 | 205 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 187 | 336 | −3260 | 153 | 1586 | 858 | −2763 | 1449 | −3329 | −1003 | −3275 | −2349 | −1399 | −2857 | 391 | 1307 | 1213 | 340 | −2881 | −3444 | −2762 | 206 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 188 | −375 | −2328 | −315 | −1946 | −2363 | −450 | −1870 | 397 | −1805 | 956 | 2300 | 295 | −350 | 135 | −2149 | 412 | −1839 | −1789 | −2714 | 2154 | 207 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −81 | −9479 | −4226 | −894 | −1115 | −701 | −1378 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 189 | −1737 | −3201 | 214 | −20 | −3517 | 1601 | 1510 | −3265 | −953 | −1399 | −2291 | 1013 | 1762 | 336 | −129 | −1619 | −1676 | 550 | −3386 | −2706 | 208 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −128 | −9401 | −3589 | −894 | −1115 | −1479 | −641 | * | * | | | | | | | | | | | | |
| 190 | −1697 | −2479 | −1933 | 822 | 1579 | 458 | 2479 | −2199 | −1268 | −937 | −1631 | 18 | −334 | −1196 | −1699 | 967 | −1636 | −22 | −2809 | 1118 | 209 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −265 | −9276 | −2587 | −894 | −1115 | −2172 | −362 | * | * | | | | | | | | | | | | |
| 191 | 1497 | −2916 | 533 | 194 | −3234 | −249 | −1082 | −91 | 981 | −2931 | −2006 | 317 | −2516 | −624 | −1172 | 1352 | −22 | −2536 | −3101 | −2419 | 210 |
| — | −151 | −502 | 232 | 44 | −383 | 398 | 107 | −626 | 214 | −465 | −715 | 273 | 397 | 47 | 93 | 360 | 118 | −369 | −297 | −252 | |
| — | −2585 | −1672 | −945 | −2074 | −391 | −646 | −1469 | * | * | | | | | | | | | | | | |
| 192 | −1144 | −2583 | 1670 | 573 | −2891 | −2120 | −780 | −2632 | 1620 | −2593 | 2083 | −760 | −2213 | −325 | 373 | 337 | −1083 | 535 | −2774 | −2100 | 224 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −6 | −8553 | −9595 | −894 | −1115 | −1598 | −578 | * | * | | | | | | | | | | | | |
| 193 | −3050 | −4533 | 1905 | −1492 | −5391 | 2488 | −2666 | −5325 | −3002 | −5233 | −4566 | 2321 | −3688 | −2358 | −3873 | −2820 | 964 | −4649 | −5428 | −4446 | 225 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8883 | −9925 | −894 | −1115 | −3182 | −168 | * | * | | | | | | | | | | | | |
| 194 | −1382 | 2214 | −1352 | 822 | −2818 | −2399 | −1079 | 546 | 1376 | −2569 | −1713 | −1091 | 969 | −661 | −1189 | 1591 | 135 | −2161 | −2842 | −2227 | 226 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8883 | −9925 | −894 | −1115 | −3182 | −168 | * | * | | | | | | | | | | | | |
| 195 | 711 | −2383 | 858 | 170 | −2541 | −2449 | −1134 | −2187 | −816 | 662 | 1099 | −1183 | 1314 | −757 | 1059 | −1377 | 97 | −147 | −2673 | −2107 | 227 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8883 | −9925 | −894 | −1115 | −575 | −1606 | * | * | | | | | | | | | | | | |
| 196 | −1808 | −2005 | 1430 | −2230 | −2005 | 342 | −1916 | 1148 | −2054 | −45 | −1192 | 33 | 2175 | −1896 | −2295 | −787 | −1749 | −35 | −2422 | 850 | 228 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9316 | −10358 | −894 | −1115 | −1993 | −417 | * | * | | | | | | | | | | | | |
| 197 | −1707 | −3057 | 2449 | 521 | −3330 | −2689 | −1362 | −3046 | −966 | −634 | −2163 | −1345 | −2787 | −921 | 1645 | 407 | −7 | 634 | −3272 | −2620 | 229 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9316 | −10358 | −894 | −1115 | −247 | −2671 | * | * | | | | | | | | | | | | |
| 198 | −2003 | 1205 | −4337 | −3702 | 3106 | −3549 | −2420 | −1323 | −3299 | 438 | 1377 | −3192 | −3599 | −2924 | −354 | 382 | −87 | 302 | −2288 | 1144 | 230 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 199 | 360 | −2261 | −4825 | −4245 | −2365 | −4046 | −3092 | 1606 | −3883 | −825 | −1536 | −3748 | 2368 | −3538 | −3725 | 271 | −2420 | 2052 | −2964 | −2612 | 231 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −70 | −9479 | −4434 | −894 | −1115 | −701 | −1378 | * | * | | | | | | | | | | | | |
| 200 | −2963 | −2695 | −5347 | −4742 | 1763 | −602 | −3552 | 1946 | −4382 | 1808 | 721 | −4303 | −4569 | −3910 | −4166 | −3772 | −2898 | 1467 | −3210 | −2959 | 232 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −1395 | −690 | * | * | | | | | | | | | | | | |
| 201 | 468 | 4606 | −4324 | −3769 | 408 | −3609 | −2525 | −1728 | −3408 | −2058 | −1423 | −3278 | −3760 | 191 | −3290 | −2731 | −199 | −1631 | −2385 | 2737 | 233 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −1395 | −690 | * | * | | | | | | | | | | | | |
| 202 | 1324 | −2593 | −5347 | −4810 | −2779 | −4674 | −3791 | 2850 | −4495 | 1134 | −1825 | −4361 | −4674 | −4173 | −4364 | −805 | −2849 | 675 | −3584 | −3224 | 234 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −1395 | −690 | * | * | | | | | | | | | | | | |
| 203 | −2462 | −3077 | −5365 | −5721 | −5783 | 3619 | −5031 | −5618 | −5660 | −5871 | −4903 | −4105 | −4156 | −5100 | −5339 | −72 | −79 | −4291 | −5993 | −5956 | 235 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −1395 | −690 | * | * | | | | | | | | | | | | |
| 204 | −4007 | −6051 | 3830 | −1896 | −6072 | −3708 | 1799 | −6236 | −3650 | −6048 | −5526 | 1291 | −4312 | −2891 | −4685 | −3603 | −4122 | −5658 | −6151 | −5002 | 236 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −1395 | −690 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 205 | −4542 | −4679 | 3932 | −3772 | 1064 | −4893 | −3337 | −154 | −5033 | −3463 | −3538 | −3865 | −5286 | −4265 | −5370 | −4589 | −4649 | −3612 | −3028 | −1921 | 237 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −392 | −2072 | * | * | | | | | | | | | | | | |
| 206 | −2014 | −1909 | −3967 | −3346 | 901 | −3512 | −2351 | 990 | −414 | 1054 | −1104 | −3016 | 35 | 124 | 2420 | −2580 | −1954 | 672 | −2358 | −2007 | 238 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 207 | −237 | −3242 | 123 | −4313 | −5704 | −663 | −4493 | −5522 | −4837 | −5720 | −4791 | −3716 | −4168 | −4367 | −4955 | 1303 | 3455 | −4336 | −5881 | −5635 | 239 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −2634 | −9479 | −256 | −894 | −1115 | −701 | −1378 | * | * | | | | | | | | | | | | |
| 208 | −1191 | −2088 | −994 | −631 | −2776 | −1843 | −609 | −2439 | 2770 | −2372 | −1636 | −776 | 2113 | −229 | 126 | −1147 | −1167 | −2074 | −2390 | −2024 | 240 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −19 | −6863 | −7905 | −894 | −1115 | −46 | −5004 | * | * | | | | | | | | | | | | |
| 209 | −3953 | −5105 | 4019 | −2597 | −6313 | −3984 | −3790 | −6453 | −4284 | −6345 | −5751 | −2927 | −4626 | −3538 | −5155 | 387 | −4207 | −5651 | −6238 | −5503 | 241 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 210 | −409 | −5583 | 424 | 3530 | −5788 | −3645 | −2986 | −5709 | −3214 | −5575 | −4891 | −2239 | −4171 | 295 | −4062 | −531 | −3759 | −5175 | −5769 | −4756 | 242 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 211 | −596 | −3897 | 3228 | −311 | −4201 | −735 | −1926 | −3975 | −1624 | −3910 | −3015 | 192 | −3304 | 397 | −2178 | 846 | 39 | −3515 | −4081 | −3348 | 243 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 212 | 1641 | −2074 | −4428 | −3857 | −2143 | −569 | −2725 | −114 | −3497 | −1993 | 4152 | −59 | −3773 | −3152 | −3356 | −2748 | −2158 | 691 | −2659 | −2315 | 244 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −70 | −9479 | −4434 | −894 | −1115 | −701 | −1378 | * | * | | | | | | | | | | | | |
| 213 | −5917 | −4919 | −6429 | −6742 | 4268 | −6285 | −2543 | −4715 | −6301 | −1039 | −4118 | −4942 | −64 | −5060 | −5686 | −5532 | −5781 | −4924 | −1791 | 1614 | 245 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9411 | −10454 | −894 | −1115 | −392 | −2072 | * | * | | | | | | | | | | | | |
| 214 | 262 | −3263 | 1575 | 1158 | −279 | −2764 | −1424 | −3333 | 916 | −3278 | −2352 | −1400 | −2858 | −964 | 1568 | 919 | 397 | −2884 | −3446 | −2764 | 246 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 215 | −55 | −2670 | −122 | 42 | 683 | −2955 | −1653 | −394 | −1393 | −2594 | −1818 | −242 | −422 | 234 | −1830 | 509 | −218 | 2202 | 1871 | −2466 | 247 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 216 | −506 | 1512 | −4348 | −3712 | 1816 | −653 | −2422 | 1643 | −3307 | 708 | 1296 | −3197 | −3601 | 95 | −3107 | −2635 | −1944 | 1456 | −2288 | 254 | 248 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 217 | −1790 | −3242 | −1646 | 962 | −3554 | −1086 | 782 | −3298 | 936 | 82 | 479 | 2021 | −2860 | −969 | 1680 | −623 | −345 | −849 | −3430 | −2753 | 249 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −101 | −9479 | −3916 | −894 | −1115 | −701 | −1378 | * | * | | | | | | | | | | | | |
| 218 | 231 | −3186 | −183 | 501 | −3507 | −353 | 523 | −3258 | 1193 | −3202 | −2275 | 1155 | 1092 | 550 | 827 | 132 | 405 | −2808 | −3369 | −2686 | 250 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −87 | −9381 | −4128 | −894 | −1115 | −1618 | −569 | * | * | | | | | | | | | | | | |
| 219 | −457 | −3043 | −1538 | 606 | 1019 | −738 | 803 | −495 | 251 | 514 | −2141 | 193 | −2736 | 602 | 721 | −1553 | 1552 | −2646 | −3248 | −2587 | 251 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −655 | −9297 | −1461 | −894 | −1115 | −2081 | −389 | * | * | | | | | | | | | | | | |
| 220 | 176 | −2637 | 158 | 772 | −2943 | −2177 | −838 | −2683 | 1795 | 586 | −1730 | −818 | 1092 | 842 | −929 | −1086 | −1139 | −370 | −2829 | −2155 | 252 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −511 | −8648 | −1757 | −894 | −1115 | −3495 | −134 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 221 | −1114 | −2129 | 1507 | −688 | 1061 | −2044 | −1014 | −2244 | −741 | −2362 | −1540 | −932 | 2169 | −640 | −1217 | 1341 | 496 | −1891 | −2664 | −2073 | 253 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −153 | −8144 | −3368 | −894 | −1115 | −3899 | −100 | * | * | | | | | | | | | | | | |
| 222 | 1156 | −2163 | −756 | 1169 | −2523 | 211 | −586 | −2238 | −208 | −2255 | −1369 | 869 | −1969 | −152 | −706 | 1299 | −833 | 227 | −2480 | −1835 | 254 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −8 | −8000 | −9042 | −894 | −1115 | −3978 | −95 | * | * | | | | | | | | | | | | |
| 223 | −887 | −2361 | 843 | −140 | −2680 | −1819 | −507 | −2431 | −100 | −2376 | −1457 | 1212 | 1306 | 1149 | 1228 | 1255 | −829 | −1983 | −2545 | −1859 | 255 |
| — | −149 | −500 | 233 | 43 | −381 | 400 | 105 | −627 | 210 | −466 | −721 | 275 | 395 | 45 | 96 | 359 | 119 | −370 | −295 | −250 | |
| — | −758 | −1826 | −2982 | −572 | −1612 | −1197 | −827 | * | * | | | | | | | | | | | | |
| 224 | −27 | −2471 | −1189 | 282 | 260 | −312 | 1525 | −2390 | −547 | −2447 | 2274 | 510 | −201 | 1212 | −1035 | 595 | −1177 | 639 | −2711 | −2089 | 258 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8694 | −9736 | −894 | −1115 | −398 | −2053 | * | * | | | | | | | | | | | | |
| 225 | −1695 | −3018 | −1604 | 6 | 52 | 1067 | 1472 | −646 | 349 | −453 | −2123 | −1354 | 532 | 334 | −1461 | 1485 | 510 | −2608 | −3238 | −2593 | 259 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −62 | −9342 | −4629 | −894 | −1115 | −1856 | −467 | * | * | | | | | | | | | | | | |
| 226 | −417 | −3097 | −1496 | −947 | −3411 | 2105 | 1087 | −3156 | 943 | −1308 | 909 | 530 | −2711 | 621 | 52 | 205 | −112 | −2715 | −3285 | −2606 | 260 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9284 | −10326 | −894 | −1115 | −220 | −2819 | * | * | | | | | | | | | | | | |
| 227 | −2003 | 1144 | −4341 | −3705 | 9 | −3550 | −2420 | 943 | −182 | 1048 | 1701 | 827 | −527 | −2926 | −3104 | −2634 | −1943 | 1518 | −2288 | 1794 | 261 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 228 | −566 | −3210 | −1661 | 660 | −3508 | 823 | 959 | −494 | −1025 | −1251 | −2305 | 58 | 919 | 990 | −101 | 1033 | 17 | −802 | 1347 | −2738 | 262 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −55 | −9479 | −4800 | −894 | −1115 | −701 | −1378 | * | * | | | | | | | | | | | | |
| 229 | −565 | −2594 | 590 | −1507 | −2697 | −2937 | 798 | 2406 | 544 | −2513 | −1746 | −1739 | −640 | −1321 | −186 | −1881 | −434 | 1614 | −2925 | −2408 | 263 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9427 | −10469 | −894 | −1115 | −435 | −1941 | * | * | | | | | | | | | | | | |
| 230 | −1829 | −3261 | 725 | 2041 | −3568 | −2800 | −1461 | −3306 | 848 | 532 | −2356 | −1442 | −2896 | −1007 | 1118 | −491 | −1768 | 949 | −3451 | −2781 | 264 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 231 | −632 | −1875 | −624 | −3388 | 1087 | −3501 | −2354 | 1716 | −578 | −629 | −1076 | −3032 | 32 | −2739 | −453 | −2571 | −283 | 2381 | −2328 | −1977 | 265 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 232 | −412 | −2247 | −256 | −2096 | 1989 | 1180 | −1936 | −1836 | −1942 | 46 | −1426 | −2203 | −471 | −1816 | 750 | 899 | −354 | −200 | −2646 | 277 | 266 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 233 | 1308 | 2124 | 61 | −1379 | 655 | −2901 | 1861 | −2600 | −187 | −1069 | −1943 | −1642 | 504 | −1217 | −1737 | 1122 | 770 | −2335 | −3101 | −2540 | 267 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 234 | −542 | 2664 | −224 | −1328 | 260 | −561 | −1559 | −469 | 190 | −2819 | −2000 | −49 | −344 | 556 | −1698 | 120 | 1450 | 1090 | −3150 | −2572 | 268 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −197 | −9479 | −2987 | −894 | −1115 | −701 | −1378 | * | * | | | | | | | | | | | | |
| 235 | −1692 | −3161 | 528 | 1467 | −3480 | 192 | −1321 | −3230 | −912 | −3178 | −2255 | −1283 | 474 | 487 | −1422 | 1673 | 1232 | −521 | −3348 | −2664 | 269 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −473 | −9285 | −1846 | −894 | −1115 | −2134 | −373 | * | * | | | | | | | | | | | | |
| 236 | −1334 | −2427 | 659 | −807 | −2613 | 727 | 1193 | 316 | 425 | −2384 | −1554 | 471 | −2465 | −657 | −1186 | −29 | −1274 | 1790 | −2698 | 822 | 270 |
| — | −149 | −487 | 233 | 43 | −381 | 398 | 105 | −627 | 210 | −466 | −721 | 275 | 396 | 45 | 96 | 360 | 117 | −370 | −295 | −250 | |
| — | −412 | −2015 | −9859 | −58 | −4659 | −3283 | −156 | * | * | | | | | | | | | | | | |

-continued

| | | | | | | | | | | | | | | | | | | | | | |
|---|---|---|---|---|---|---|---|---|---|---|---|---|---|---|---|---|---|---|---|---|---|
| 237 | −1865 | −2518 | −3579 | −3587 | −4612 | 2963 | −3582 | −4353 | −3739 | −4574 | −3697 | 522 | 801 | −3431 | −3891 | 1092 | −2267 | 467 | −4819 | −4529 | 272 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8817 | −9859 | −894 | −1115 | −3283 | −156 | * | * | | | | | | | | | | | | |
| 238 | −84 | −2785 | 839 | 664 | −3106 | −318 | −943 | −2857 | −525 | −2801 | −1875 | 281 | −2377 | 1890 | 853 | 1396 | 355 | −2407 | −2969 | −2285 | 273 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −5 | −8817 | −9859 | −894 | −1115 | −910 | −1096 | * | * | | | | | | | | | | | | |
| 239 | −271 | −3004 | −1447 | 415 | −3305 | −2561 | 1152 | −3042 | 2267 | −3011 | 686 | −1204 | −126 | −768 | 1032 | 580 | −1519 | −138 | 1561 | −2529 | 274 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −4 | −9196 | −10238 | −894 | −1115 | −1442 | −662 | * | * | | | | | | | | | | | | |
| 240 | 993 | −3126 | 592 | 18 | −3446 | −595 | 2102 | −3197 | 418 | −3142 | −2216 | −1255 | 2458 | −824 | 4 | −327 | −1592 | −2748 | −3309 | −2626 | 275 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9276 | −10319 | −894 | −1115 | −215 | −2850 | * | * | | | | | | | | | | | | |
| 241 | −1987 | −1920 | −3774 | −3173 | −1889 | −387 | −2308 | 38 | −2880 | −680 | −1122 | 877 | −3521 | −2605 | −2876 | 1966 | 2065 | 548 | −2371 | 325 | 276 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 242 | 327 | 999 | −41 | −35 | −3550 | −803 | −1427 | 268 | 1168 | −312 | −2331 | 1344 | −2860 | 507 | −1517 | 897 | −274 | −2856 | −3428 | 145 | 277 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 243 | 2567 | −3362 | −17 | 1028 | −3682 | 563 | −1572 | −653 | −1183 | −3391 | −2483 | −1512 | −2986 | −1124 | −133 | −148 | −1880 | −2990 | −3578 | −2899 | 278 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 244 | −270 | −3136 | −219 | −1152 | 603 | −770 | −1459 | −728 | 1447 | −95 | −2239 | 178 | 652 | −1019 | 207 | 256 | 1080 | −2728 | −3352 | 137 | 279 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 245 | −2021 | −1881 | −4143 | −3524 | 1724 | −765 | −2381 | −1379 | −3166 | 530 | −1083 | 189 | −3593 | −2828 | −460 | 678 | −1962 | −149 | 2517 | 2993 | 280 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 246 | 215 | −2954 | 602 | −1288 | 2040 | −2860 | −1545 | −2829 | −1194 | −2925 | −2087 | −1567 | 985 | −1141 | 1847 | 924 | −547 | −2516 | −3225 | 938 | 281 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 247 | −437 | 1122 | −109 | −3580 | −1811 | −3538 | −2402 | 622 | 941 | 1904 | 804 | −3136 | −482 | −2858 | −3059 | −2617 | −1946 | 1185 | −2312 | −1966 | 282 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 248 | 431 | −3258 | 1875 | −119 | −3578 | −2762 | −1421 | −3328 | 760 | 240 | 464 | 193 | 467 | 253 | −184 | −398 | −261 | −2879 | −3442 | 543 | 283 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 249 | −1793 | 837 | 1857 | 1010 | −3538 | 372 | −1432 | −3278 | 107 | −1221 | −2324 | −1412 | −2864 | −976 | 542 | 1152 | −1732 | 757 | −3423 | −2749 | 284 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 250 | 117 | −3186 | −1675 | 402 | −3474 | −753 | −1444 | −249 | 1047 | −3188 | −2284 | 203 | 1831 | −995 | −1540 | 828 | 341 | 688 | −3390 | −2728 | 285 |
| — | −149 | −500 | 233 | 43 | −381 | 399 | 106 | −626 | 210 | −466 | −720 | 275 | 394 | 45 | 96 | 359 | 117 | −369 | −294 | −249 | |
| — | −3 | −9479 | −10521 | −894 | −1115 | −701 | −1378 | * | * | | | | | | | | | | | | |
| 251 | 770 | −3155 | −34 | 1110 | −3429 | −2791 | −1456 | 730 | −1057 | −3151 | 206 | −1446 | 522 | 459 | −1556 | 1934 | −1739 | −2752 | −3368 | 65 | 286 |
| — | * | * | * | * | * | * | * | * | * | * | * | * | * | * | * | * | * | * | * | * | |
| — | * | * | * | * | * | * | * | * | 0 | | | | | | | | | | | | |
| // | | | | | | | | | | | | | | | | | | | | | |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08410336B2). An electronic copy of the "Sequence Listing" will also be available from the USPTO upon request and payment of the fee set forth in 37 CFR 1.19(b)(3).

What is claimed is:

1. A transgenic plant cell having recombinant DNA in its chromosomal DNA wherein said recombinant DNA comprises (a) a promoter that is functional in a plant cell and that is operably linked to a polynucleotide that encodes a protein having an amino acid sequence having at least 95% identity over at least 95% of the length of SEQ NO:13 and having trehalose phosphate synthase activity and (b) a promoter that is functional in a plant cell and that is operably linked to a polynucleotide that encodes a protein having an amino acid sequence having at least 95% identity over at least 95% of the length of SEQ ID NO:14 and having trehalose phosphatase activity.

2. A transgenic plant cell comprising the recombinant DNA of claim 1 wherein said plant cell is in a plant selected by screening a population of transgenic plants that have been transformed with said recombinant DNA for an enhanced trait as compared to control plants that do not comprise the recombinant DNA; and wherein said enhanced trait is increased yield.

3. The plant cell of claim 2 further comprising DNA expressing a protein that provides tolerance from exposure to an herbicide comprising an agent applied at levels that are lethal to a wild type of said plant cell.

4. The plant cell of claim 3 wherein the agent of said herbicide is a glyphosate, dicamba, or glufosinate compound.

5. A transgenic plant comprising a plurality of plant cells of claim 2.

6. The transgenic plant of claim 5 which is homozygous for said recombinant DNA.

7. A transgenic seed comprising a plurality of plant cells of claim 2.

8. The transgenic seed of claim 7 from a corn, soybean, cotton, canola, alfalfa, wheat, rice, sugarcane, or sugar beet plant.

9. Grain comprising transgenic seed identifiable by the recombinant DNA in the transgenic plant cell of claim 1.

10. Seed meal produced from transgenic seed identifiable by the recombinant DNA in the transgenic plant cell of claim 1.

11. A transgenic pollen grain comprising a haploid gamete of a plant cell nucleus having a chromosome comprising the recombinant DNA in the transgenic plant cell of claim 1.

12. A method for manufacturing non-natural, transgenic seed that can be used to produce a crop of transgenic plants with an enhanced trait resulting from expression of a stably-integrated, recombinant DNA, said method comprising:

(a) screening a population of plants for an enhanced trait, wherein plants in the population comprise the transgenic plant cell of claim 1, wherein individual plants in said population that have the recombinant DNA in the transgenic plant cell exhibit said trait at a level less than, the same as or greater than the level that said trait is exhibited in control plants which do not contain said recombinant DNA, wherein said enhanced trait is increased yield;

(b) selecting from said population one or more plants that exhibit said trait at a level greater than the level that said trait is exhibited in control plants, and (c) collecting seed from selected plant from step b.

13. The method of claim 12 wherein said method for manufacturing said transgenic seed further comprises:

(a) verifying that said recombinant DNA is stably integrated in said selected plants, and (b) analyzing tissue of said selected plant to determine the expression of a protein having the function of a protein having an amino acid sequence selected from the group consisting SEQ ID NO:13 and SEQ ID NO:14.

14. The method of claim 13 wherein said seed is corn, soybean, cotton, canola, alfalfa, wheat, rice, sugarcane, or sugar beet seed.

15. A method of producing hybrid corn seed, said method comprising:

(a) acquiring hybrid corn seed from an herbicide tolerant corn plant, wherein the chromosomal DNA of said corn seed comprises recombinant DNA comprising:

(i) a promoter that is functional in a plant cell operably linked to a polynucleotide that encodes a protein having an amino acid sequence having at least 95% identity over at least 95% of the length of SEQ ID NO: 13 and having trehalose phosphate synthase activity; and (ii) a promoter that is functional in a plant cell operably linked to a polynucleotide that encodes a protein having an amino acid sequence having at least 95% identity over at least 95% of the length of SEQ ID NO: 14 and having trehalose synthase activity;

(b) producing corn plants from said hybrid corn seed, wherein a fraction of the plants produced from said hybrid corn seed are homozygous for said recombinant DNA, a fraction of the plants produced from said hybrid corn seed are hemizygous for said recombinant DNA, and a fraction of the plants produced from said hybrid corn seed has none of said recombinant DNA;

(c) selecting corn plants which are homozygous and hemizygous for said recombinant DNA by treating with a herbicide;

(d) collecting seed from herbicide-treated-surviving corn plants and planting said seed to produce further progeny corn plants;

(e) repeating steps (c) and (d) at least once to produce an inbred corn line; and (f) crossing said inbred corn line with a second corn line to produce hybrid seed.

* * * * *